(12) United States Patent
McCarthy et al.

(10) Patent No.: US 12,037,336 B2
(45) Date of Patent: Jul. 16, 2024

(54) COMPOUNDS WITH ACTIVITY AS INHIBITORS OF THE EPITHELIAL SODIUM CHANNEL (ENaC)

(71) Applicant: Enterprise Therapeutics Limited, Brighton (GB)

(72) Inventors: Clive McCarthy, Abingdon (GB); Duncan Alexander Hay, Abingdon (GB); Thomas Beauregard Schofield, Abingdon (GB)

(73) Assignee: Enterprise Therapeutics Limited, Brighton (GB)

( * ) Notice: Subject to any disclaimer, the term of this patent is extended or adjusted under 35 U.S.C. 154(b) by 861 days.

(21) Appl. No.: 17/056,370

(22) PCT Filed: May 17, 2019

(86) PCT No.: PCT/GB2019/051383
§ 371 (c)(1),
(2) Date: Nov. 17, 2020

(87) PCT Pub. No.: WO2019/220147
PCT Pub. Date: Nov. 21, 2019

(65) Prior Publication Data
US 2021/0188855 A1 Jun. 24, 2021

(30) Foreign Application Priority Data
May 18, 2018 (GB) ..................................... 1808093

(51) Int. Cl.
| C07D 487/04 | (2006.01) |
| A61K 45/06 | (2006.01) |
| C07C 53/06 | (2006.01) |
| C07C 53/18 | (2006.01) |
| C07D 235/08 | (2006.01) |
| C07D 401/12 | (2006.01) |

(52) U.S. Cl.
CPC ............ *C07D 487/04* (2013.01); *A61K 45/06* (2013.01); *C07C 53/06* (2013.01); *C07C 53/18* (2013.01); *C07D 235/08* (2013.01); *C07D 401/12* (2013.01)

(58) Field of Classification Search
None
See application file for complete search history.

(56) References Cited

U.S. PATENT DOCUMENTS

| 2015/0018313 A1 | 1/2015 | Kley et al. |
| 2015/0018314 A1 | 1/2015 | Kley et al. |

FOREIGN PATENT DOCUMENTS

| EP | 3022198 A1 | 5/2016 |
| WO | WO 03/070182 | 8/2003 |
| WO | WO 03/070184 | 8/2003 |
| WO | WO 2004/073629 | 9/2004 |
| WO | WO 2005/016879 | 2/2005 |
| WO | WO 2005/018644 | 3/2005 |
| WO | WO 2005/025496 | 3/2005 |
| WO | WO 2005/034847 | 4/2005 |
| WO | WO 2005/044180 | 5/2005 |
| WO | WO 2006/022935 | 3/2006 |
| WO | WO 2007/018640 | 2/2007 |
| WO | WO 2007/071396 | 6/2007 |
| WO | WO 2007/071400 | 6/2007 |
| WO | WO 2008/124491 | 10/2008 |
| WO | WO 2008/135557 | 11/2008 |
| WO | WO 2009/019506 | 2/2009 |
| WO | WO 2009/074575 | 6/2009 |
| WO | WO 2009/138378 | 11/2009 |
| WO | WO 2009/139948 | 11/2009 |
| WO | WO 2009/150137 | 12/2009 |
| WO | WO 2011/028740 | 3/2011 |
| WO | WO 2011/079087 | 6/2011 |
| WO | WO 2011/113894 | 9/2011 |
| WO | WO 2012/035158 | 3/2012 |
| WO | WO 2013/003386 | 1/2013 |
| WO | WO 2013/064450 | 5/2013 |
| WO | WO 2013/092674 | 6/2013 |
| WO | WO 2013/181232 | 12/2013 |
| WO | WO 2014/044849 | 3/2014 |

(Continued)

OTHER PUBLICATIONS

Beasley. Lancet, 2015, 386, 1075-1085 (Year: 2015).*
Basel. Tetrahedron Letters, 2002, 43, 2529-2533 (Year: 2002).*
International Search Report in PCT/GB2018/051383 dated Jul. 9, 2019 (3 pages).
App et al., "Acute and Long-term Amiloride Inhalation in Cystic Fibrosis Lung Disease. A Rational Approach to Cystic Fibrosis Therapy," *Am Rev Respir Dis.*, 1990, 141(3):605-12.
Botero-Velez et al., "Brief Report: Liddle's Syndrome Revisited—A Disorder of Sodium Reabsorption in The Distal Tubule," *The New England Journal of Medicine*, 1994, 330(3):178-81.
Boucher, "Evidence for Airway Surface Dehydration as The Initiating Event in CF Airway Disease," *Journal of Internal Medicine*, 2007, 261(1):5-16.

(Continued)

*Primary Examiner* — Noble E Jarrell
(74) *Attorney, Agent, or Firm* — Bookoff McAndrews, PLLC

(57) ABSTRACT

Compounds of general formula (I) wherein $R^1$, $R^2$, $R^3$, $R^4$ and X are as defined herein are inhibitors of the epithelial sodium channel (ENaC) and are useful for the treatment or prevention respiratory diseases and conditions, skin conditions and ocular conditions.

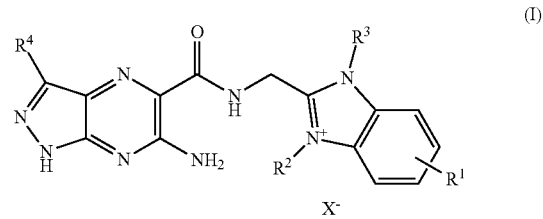

30 Claims, No Drawings

(56) References Cited

FOREIGN PATENT DOCUMENTS

| WO | WO 2014/099673 | 6/2014 |
|---|---|---|
| WO | WO 2014/099676 | 6/2014 |
| WO | WO 2014/099705 | 6/2014 |
| WO | WO 2014/177469 | 11/2014 |
| WO | WO 2015/003083 | 1/2015 |
| WO | WO 2015/003958 | 1/2015 |
| WO | WO 2015/007516 | 1/2015 |
| WO | WO 2015/007517 | 1/2015 |
| WO | WO 2015/007519 | 1/2015 |
| WO | WO 2015/018754 | 2/2015 |
| WO | WO 2016/113167 | 7/2016 |
| WO | WO 2016/113168 | 7/2016 |
| WO | WO 2016/113169 | 7/2016 |
| WO | WO 2016/113170 | 7/2016 |
| WO | WO 2017/028926 | 2/2017 |
| WO | WO 2017/028927 | 2/2017 |
| WO | WO 2017/221008 | 12/2017 |
| WO | WO 2018/096325 | 5/2018 |

OTHER PUBLICATIONS

Bowler et al., "Nebulised Amiloride in Respiratory Exacerbations of Cystic Fibrosis: A Randomised Controlled Trial," *Archives of Disease In Childhood*, 1995, 73(3):427-30.

Chang et al., "Mutations in Subunits of The Epithelial Sodium Channel Cause Salt Wasting With Hyperkalaemic Acidosis, Pseudohypoaldosteronism Type 1," *The Nature Publishing Group, Nature Genetics*, 1996, 12(3):248-53.

Coote et al., "Camostat Attenuates Airway Epithelial Sodium Channel Function in Vivo Through The Inhibition of A Channel-Activating Protease," *The Journal Of Pharmacology And Experimental Therapeutics*, 2009, 329(2):764-74.

Coote et al., "The Guinea-Pig Tracheal Potential Difference as an In Vivo Model for The Study Of Epithelial Sodium Channel Function in The Airways," *British Journal of Pharmacology*, 2008, 155(7):1025-33.

Dörwald, FZ, "Side Reactions In Organic Synthesis: A Guide To Successful Synthesis Design", *John Wiley & Sons*, 2006.

Fajac et al., "Nasal Airway Ion Transport Is Linked To The Cystic Fibrosis Phenotype In Adult Patients," *Thorax*, 2004, 59(11):971-76.

Frateschi et al., "The Epithelial Sodium Channel ENaC And Its Regulators in The Epidermal Permeability Barrier Function," *The Open Dermatology Journal*, 2010, 4: 27-35.

Graham et al., "No Added Benefit From Nebulized Amiloride in Patients With Cystic Fibrosis," *Eur Respir J.*, 1993, 6(9):1243-48.

Hirsh et al., "Pharmacological Properties of N-(3,5-diamino-6-chloropyrazine-2-carbonyl)-N'-4-[4-(2,3-dihydroxypropoxy)phenyl]butyl-guanidine Methanesulfonate (552-02), A Novel Epithelial Sodium Channel Blocker With Potential Clinical Efficacy for Cystic Fibrosis Lung Disease," *The Journal Of Pharmacology And Experimental Therapeutics*, Apr. 2008; 325(1):77-88.

Howsham, C. et al., "The Discovery of Novel Inhaled ENaC Blockers for the Treatment of Cystic Fibrosis Lung Disease," *The Royal Society of Chemistry*, Sep. 18, 2014.

Jordan v. Tamoxifen: "A Most Unlikely Pioneering Medicine," *Nat Rev Drug Discov 2*, pp. 205-213 (2003).

Kellenberger, "Epithelial Sodium Channel/Degenerin Family of Ion Channels: A Variety of Functions For A Shared Structure," *Physiol Rev.*, 2002 82(3):735-67.

Kerem et al., "Pulmonary Epithelial Sodium-Channel Dysfunction And Excess Airway Liquid In Pseudohypoaldosteronism," *The New England Journal of Medicine*, 1999, 341(3):156-62.

Knowles et al., "A Pilot Study Of Aerosolized Amiloride For The Treatment Of Lung Disease In Cystic Fibrosis.", *The New England Journal of Medicine*, 1990, 322(17): 1189-94.

Knowles et al., "Abnormal Ion Permeation Through Cystic Fibrosis Respiratory Epithelium," *Science*, 1983, 221(4615):1067-70.

Leal et al., "Airway Ion Transport Impacts on Disease Presentation and Severity in Cystic Fibrosis," *Science Direct, Clinical Biochemistry*, 2008, 41(10-11):764-72.

Matsui et al., "Evidence for Periciliary Liquid Layer Depletion, Not Abnormal Ion Composition, in the Pathogenesis of Cystic Fibrosis Airways Disease," *Cell*, 1998, 95(7):1005-15.

Middleton et al., "Effect Of Amiloride and Saline on Nasal Mucociliary Clearance and Potential Difference in Cystic Fibrosis and Normal Subjects," *Thorax*, 1993, 48(8):812-6.

Noone et al., "Airway Deposition and Clearance and Systemic Pharmacokinetics of Amiloride Following Aerosolization With an Ultrasonic Nebulizer to Normal Airways," *Chest*, 1997, 112(5):1283-90.

Paulekuhn et al., "Trends in Active Pharmaceutical Ingredient Salt Selection based on Analysis of the Orange Book Database," *J. Med. Chem.*, 2007, 50: 6665-6672.

Perazella, "Drug-Induced Hyperkalemia: Old Culprits and New Offenders," *Am J Med.*, 2000, 109(4):307-14.

Pons et al., "French Multicenter Randomized Double-Blind Placebo-Controlled Trial on Nebulized Amiloride in Cystic Fibrosis Patients," *Pediatric Pulmonology*, 2000, 30(1):25-31.

Schoenberger et al., "Novel Small Molecule Epithelial Sodium Channel Inhibitors as Potential Therapeutics in Cystic Fibrosis—A Patent Evaluation," *Expert Opinion Ther. Patents*, 2013, 23(10), 1383-89.

Thelin et al., "Effect of Topically Applied Epithelial Sodium Channel Inhibitors on Tear Production in Normal Mice and in Mice With Induced Aqueous Tear Deficiency," Journal of Ocular Pharmacology And Therapeutics, 2012, 28(4): 433-38.

\* cited by examiner

COMPOUNDS WITH ACTIVITY AS INHIBITORS OF THE EPITHELIAL SODIUM CHANNEL (ENaC)

This application is a the U.S. national stage entry under 35 U.S.C. § 371 of International Application No. PCT/GB2019/051383, filed on May 17, 2019, which claims priority to GB Application No. 1808093.7, filed on May 18, 2018.

The present invention relates to novel compounds which have activity as inhibitors of the epithelial sodium channel (ENaC). The invention also relates to the use of these compounds in treating diseases and conditions modulated by ENaC, particularly respiratory diseases and conditions, methods of preparing the compounds and pharmaceutical compositions containing them.

Humans can inhale up to 12,000 L of air each day and with it comes the potential for airborne pathogens (bacteria, viruses, fungal spores). To protect against these airborne pathogens, the lung has evolved innate defence mechanisms to minimise the potential for infection and colonisation of the airways. One such mechanism is the mucus clearance system, whereby secreted mucus is propelled up and out of the airways by the coordinated beating of cilia together with cough clearance. This ongoing 'cleansing' of the lung constantly removes inhaled particles and microbes thereby reducing the risk of infection.

In recent years it has become clear that the hydration of the mucus gel is critical to enable mucus clearance (Boucher 2007; Matsui et al, 1998). In a normal, healthy airway, the mucus gel is typically 97% water and 3% solids under which conditions the mucus is cleared by mucociliary action. The hydration of the airway mucosa is regulated by the coordinated activity of a number of ion channels and transporters. The balance of anion ($Cl^-/HCO_3^-$) secretion mediated via the Cystic Fibrosis Transmembrane Conductance Regulator (CFTR) and the Calcium Activated Chloride Conductance (CaCC; TMEM16A, also known as Ano1) and $Na^+$ absorption through the epithelial $Na^+$ channel (ENaC) determine the hydration status of the airway mucosa. As ions are transported across the epithelium, water is osmotically obliged to follow and thus fluid is either secreted or absorbed. As ions are transported across the epithelium, water is osmotically obliged to follow and thus fluid is either secreted or absorbed.

In respiratory diseases such as chronic bronchitis and cystic fibrosis, the % solids of the mucus gel is increased as the hydration is reduced and mucus clearance is reduced (Boucher, 2007). In cystic fibrosis, where loss of function mutations in CFTR attenuates ability of the airway to secrete fluid, the % solids can be increased to 15% which is believed to contribute towards the plugging of small airways and failure of mucus clearance. Furthermore, in cystic fibrosis an increase in ENaC activity has been reported by several groups (Knowles et al, 1983; Middleton et al, 1993) and this increase in ENaC function has been shown to correlate with disease severity (Fajac et al, 2004; Leal et al, 2008). Strategies to increase the hydration of the airway mucus include either the stimulation of anion and thereby fluid secretion or the inhibition of $Na^+$ absorption. To this end, blocking the activity of ENaC will inhibit $Na^+$ absorption and therefore increase fluid accumulation in the airway mucosa, hydrate mucus and enhance mucus clearance mechanisms.

ENaC is expressed in renal, colonic, corneal, sweat duct and respiratory epithelia where it forms a low conductance channel (~4 pS) with a selectivity for $Na^+$ over $K^+$ of approximately 10-fold (Kellenberger 2002). Loss and gain of function mutations in the channel can cause human disease including pseudohypoaldosteronism type 1 (PHA1), a salt wasting disease (Chang et al, 1996), and Liddles's syndrome, a disease associated with salt retention and hypertension (Botero-Velez et al, 1994). Of particular note to lung physiology is the observation that patients with PHA1 loss-of-function mutations in ENaC have an enhanced rate of airway mucociliary clearance (MCC) compared with the normal healthy population, typically 3-4 fold faster (Kerem et al, 1999). Furthermore the upper airways of these patients appear to be 'wet' and have extra-hydration compared to normal. These observations further support the salient role that ENaC plays in the human airway in the regulation of hydration and the therapeutic benefit that blocking ENaC in the airway could deliver in terms of enhancing MCC and innate defence.

Amiloride, a small compound blocker of ENaC, has been demonstrated to increase MCC in both healthy controls and also patients with CF, further supporting the physiological significance of this mechanism (App et al, 1990). However, the lack of a robust effect of inhaled amiloride on clinical endpoints (Bowler et al, 1995; Graham et al, 1993; Knowles et al, 1990; Pons et al, 2000) was ascribed to the short duration of action of this compound in the lungs (Noone et al., 1997). Novel ENaC blockers, specifically designed for a long duration of action in the airway are therefore predicted to acutely provide an extended enhancement of MCC with resulting clinical benefit in the longer term.

A challenge with the design of inhaled ENaC blockers for the treatment of respiratory diseases has been the potential for the renal-based side effect of hyperkalaemia (Perazela et al., 2000). ENaC is expressed in the cortical collecting duct of the kidney epithelium and block of the channel here can lead to a systemic accumulation of $K^+$. For this reason, it is desirable that an inhaled ENaC blocker avoids renal exposure following absorption from the lung. This could be achieved through either a high lung retention of ENaC blocker therefore enabling only a low dose to be administered or through the design of a compound that will be rapidly transformed to an inactive metabolite before it reaches the kidney.

ENaC blockers have also been implicated in the hydration of skin and the surface of the eye (Frateschi et al, 2010; Thelin et al, 2012).

Several ENaC blockers are known. For example, WO 2011/113894 relates to compounds which are said to be of use for treating inflammatory or obstructive diseases of the airways or for promoting mucosal hydration. The compounds are of the formula:

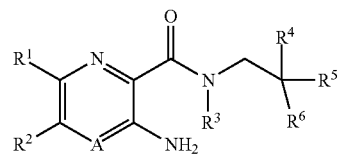

where A is N or $CR^{4a}$ and $R^2$ is haloalkyl. None of the compounds exemplified in this document contain a benzimidazole moiety.

WO 2011/079087 relates to compounds of the formula:

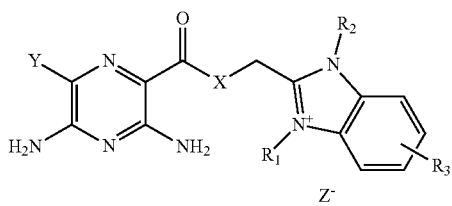

WO 2015/007516, WO 2015/007517 and WO 2015/007519 all relate to compounds of the formula:

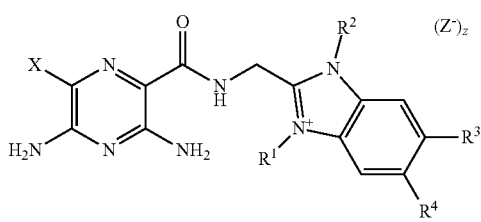

WO 2016/113168, WO 2016/113167 and WO 2016/113169 relate to compounds of the formula:

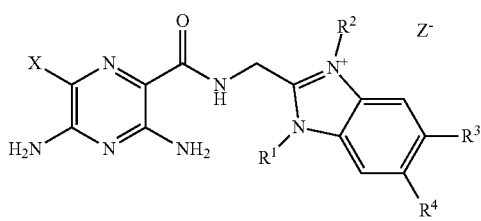

WO 2016/113170 relates to compounds of the formula:

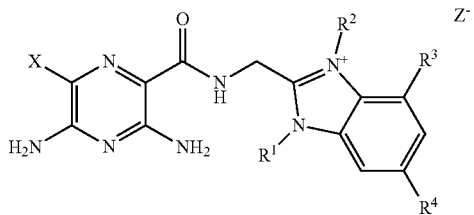

The compounds described in these documents all contain a 6-halo-3,5-diaminopyrazine group and this group is also a structural feature of the ENaC inhibitors disclosed in numerous other documents including WO2013/0664450, WO2013/092674, WO2014/044849, WO 2014/177469, WO 2015/003958, WO2015/018754, WO 2011/028740, WO 2007/071396, WO 2007/071400, WO 2008/135557, WO 2009/074575, WO 2009/138378, WO 2009/150137 and WO 2012/035158 Other documents relating to pyrazine derivatives with ENaC inhibitor activity include WO 2015/003083, WO 2004/073629, WO 03/070184, WO 03/070182, WO 2006/022935, WO 2007/018640, WO 2008/124491, WO 2009/139948, WO 2005/044180, WO 2005/016879, WO 2005/018644, WO 2005/025496, WO 2005/034847 and WO 2013/181232. However, every compound exemplified in these documents contains a 6-halo-3,5-diaminopyrazine group and it is therefore clear that a pyrazine ring with amino substituents at the 3- and 5-positions and 6-halo substituent was, until recently, considered essential for ENaC blocking activity.

Some more recent documents relate to ENaC blocking compounds in which the 5-amino group is not present. For example, WO 2017/028926 relates to ENaC inhibiting compounds of the formula:

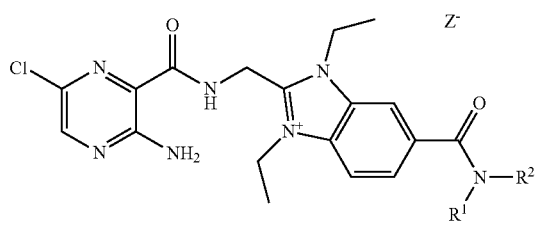

and WO 2017/028927 relates to ENaC inhibiting compounds of the formula:

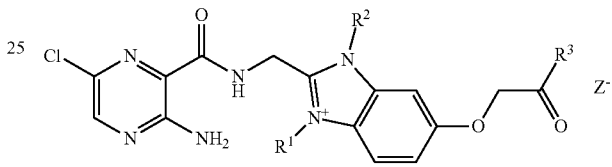

Our earlier application WO 2017/221008 also relates to compounds comprising a pyrazine group with a single amino substituent at the 3-position, with most of these compounds also having a substituent at the pyrazine 6-position.

The present inventors have surprisingly discovered that compounds with alternative structures to the 6-halo-3,5-diamino pyrazine or 6-substituted-3-aminopyrazine also have ENaC blocking activity and may have beneficial properties compared with the known compounds, particularly in relation to the ADME (Absorption, Excretion, Distribution and Metabolism) properties. For example, our application PCT/GB2017/053499 relates to pyrrolopyrazine compounds having ENaC blocking activity.

In the present invention there is provided a compound of general formula (I) including all tautomeric forms, all enantiomers and isotopic variants and salts thereof:

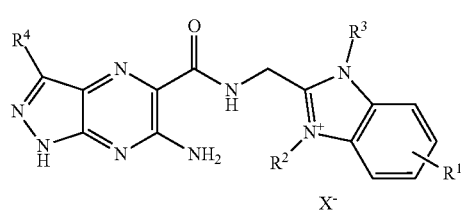

(I)

wherein
  $X^-$ is an anion;
  $R^1$ is:
    i. H or halo; or
    ii. $-L^1R^{10}$, wherein
      $L^1$ is:
        $-Z^1-$, $-Q^1-$, $-Z^1Q^1-$, $-Q^1Z^1-$, $-Z^1Q^1Z^2-$, $-Q^1Q^2-$, $-Q^1Q^2Z^1-$, $-Q^1Q^2Z^1Q^3Z^2-$, $-Z^1Q^1OQ^2OQ^3-$;

OZ$^1$—, —OQ$^1$-, —OZ$^1$Q$^1$-, —OQ$^1$Z$^1$—, —OZ$^1$Q$^1$Z$^2$—, —OQ$^1$Q$^2$-, —OQ$^1$Q$^2$Z$^1$—, —OQ$^1$Q$^2$Z$^1$Q$^3$Z$^2$—, —OZ$^1$Q$^1$OQ$^2$OQ$^3$-;

—Z$^1$N(R$^7$)Z$^2$—, -Q$^1$Z$^1$N(R$^7$)Z$^2$—, —Z$^1$N(R$^7$)Z$^2$Q$^1$-, -Q$^1$Z$^1$N(R$^7$)Z$^2$Q$^2$Z$^3$—;

Z$^1$O(CH$_2$CH$_2$O)$_n$Z$^2$—, —Z$^1$O(CH$_2$CH$_2$O)$_n$Q$^1$-, —Z$^1$O(CH$_2$CH$_2$O)$_n$Z$^2$Q$^1$, —Z$^1$O(CH$_2$CH$_2$O)$_n$Q$^1$Z$^2$—, -Q$^1$Z$^1$O(CH$_2$CH$_2$O)$_n$Z$^2$—, -Q$^1$Z$^1$O(CH$_2$CH$_2$O)$_n$Q$^1$-, -Q$^1$Z$^1$O(CH$_2$CH$_2$O)$_n$Z$^2$Q$^1$, —Z$^1$O(CH$_2$CH$_2$O)$_n$Z$^2$Q$^1$Z$^3$—;

—C(O)Z$^1$—, —C(O)Q$^1$-, —C(O)Z$^1$Q$^1$-, —C(O)Z$^1$Q$^1$Z$^2$—, —C(O)Q$^1$Z$^1$—, —C(O)Q$^1$Q$^2$-, —C(O)Q$^1$Q$^2$Z$^1$—, —C(O)Q$^1$N(R$^7$)C(O)Z$^1$—, —C(O)Q$^1$N(R$^7$)C(O)Z$^1$Q$^2$-, —C(O)Q$^1$N(R$^7$)C(O)Z$^1$Q$^2$Q$^3$-, —C(O)Q$^1$N(R$^7$)C(O)Z$^1$Q$^2$Z$^2$—, —C(O)Z$^1$Q$^1$OQ$^2$OQ$^3$-;

—C(O)N(R$^7$)Z$^1$—, —C(O)N(R$^7$)Q$^1$-, —C(O)N(R$^7$)Z$^1$Q$^1$-, —C(O)N(R$^7$)Z$^1$Q$^1$Z$^2$—, —C(O)N(R$^7$)Q$^1$Z$^1$—, —C(O)N(R$^7$)Q$^1$Q$^2$-, —C(O)N(R$^7$)Q$^1$Q$^2$Z$^1$—, —C(O)N(R$^7$)Z$^1$Q$^1$Q$^2$Z$^2$—, —C(O)N(R$^7$)Z$^1$O(CH$_2$CH$_2$O)$_n$Z$^2$—, —C(O)N(R$^7$)Z$^1$O(CH$_2$O)$_n$Z$^2$—, —C(O)N(R$^7$)Z$^1$Q$^1$Z$^2$N(R$^8$)Z$^3$—, —C(O)N(R$^7$)Z$^1$N(R$^8$)Z$^2$—, —C(O)N(R$^7$)Q$^1$Z$^1$N(R$^8$)Z$^2$—, —C(O)N(R$^7$)Z$^1$Q$^1$OQ$^2$OQ$^3$-, —C(O)N(R$^7$)Z$^1$Q$^1$OQ$^2$OQ$^3$Z$^2$—;

Z$^1$C(O)N(R$^7$)Z$^2$—, —Z$^1$C(O)N(R$^7$)Q$^1$-, —Z$^1$C(O)N(R$^7$)Z$^2$Q$^1$-, —Z$^1$C(O)N(R$^7$)Q$^1$Z$^2$—, —Z$^1$C(O)N(R$^7$)Q$^1$Q$^2$-, —Z$^1$C(O)Q$^1$-, —Z$^1$C(O)Q$^1$Z$^2$—, —Z$^1$C(O)Q$^1$Q$^2$-, —Z$^1$C(O)N(R$^7$)Q$^1$Q$^2$Z$^2$—;

—C(O)OZ$^1$—, —C(O)OQ$^1$-, —C(O)OZ$^1$Q$^1$-, —C(O)OZ$^1$Q$^1$Z$^2$—, —C(O)OQ$^1$Z$^1$—, —C(O)OQ$^1$Q$^2$-, —C(O)OQ$^1$Q$^2$Z$^1$—;

Q$^1$C(O)Q$^2$-, Q$^1$C(O)Z$^1$—, -Q$^1$C(O)Q$^2$Z$^1$—, Q$^1$C(O)Q$^2$Q$^3$-, Q$^1$C(O)Z$^1$Q$^2$-, Q$^1$C(O)Q$^2$Q$^3$Z$^1$—;

—C(=NR$^9$)N(R$^7$)Z$^1$—, —C(=NR$^9$)N(R$^7$)Q$^1$-, —C(=NR$^9$)N(R$^7$)Z$^1$Q$^1$-, —C(=NR$^9$)N(R$^7$)Z$^1$Q$^1$Z$^2$—, —C(=NR$^9$)N(R$^7$)Q$^1$Z$^1$—, —C(=NR$^9$)N(R$^7$)Q$^1$Q$^2$- or C(=NR$^9$)N(R$^7$)Q$^1$Q$^2$Z$^1$—; wherein

- each of $Z^1$, $Z^2$ and $Z^3$ is independently $C_{1-12}$ alkylene, $C_{2-12}$ alkenylene, $C_{2-12}$ alkynylene any of which is optionally substituted by one or more substituents selected from halo, OH, C(O)NR$^{15}$R$^{16}$, C(O)OR$^{15}$ and NR$^{15}$R$^{16}$;
- each R$^{15}$ and R$^{16}$ is independently H or $C_{1-6}$ alkyl or R$^{15}$ and R$^{16}$ together with the nitrogen atom to which they are attached may form a 5- or 6-membered heterocyclic ring optionally containing one or more further heteroatoms selected from N, O and S;
- each of $Q^1$, $Q^2$ and $Q^3$ is independently carbocyclyl, heterocyclyl, aryl or heteroaryl any of which is optionally substituted with one or more substituents selected from halo, OH, $C_{1-4}$ alkyl, $C_{1-4}$ haloalkyl, C(O)NR$^{15}$R$^{16}$, C(O)OR$^{15}$ and NR$^{15}$R$^{16}$, and, for cycloalkyl and heterocyclyl groups, oxo, wherein R$^{15}$ and R$^{16}$ are as defined above; n is 1 to 6;
- each R$^7$ and R$^8$ is independently selected from H or $C_{1-12}$ alkyl optionally substituted with one or more halo or OH groups, or
- when an R$^7$ and an R$^8$ or two R$^8$ groups are attached to a nitrogen atom they may, together with the nitrogen atom combine to form a 5- or 6-membered heterocyclic ring optionally comprising one or more further heteroatoms selected from N, O and S;
- R$^9$ is H or $C_{1-6}$ alkyl;
- R$^{10}$ is H, —N(R$^7$)R$^8$, —N(R$^7$)C(=NR$^9$)N(R$^8$)$_2$, —N(R$^7$)—C(O)OR$^8$, OR$^7$ or —C(O)OR$^7$; or a cationic group selected from —N(R$^7$)—C(O)—(C$_{1-3}$ alkylene)-N$^+$(R$^8$)$_3$ and —N$^+$(R$^8$)$_3$, in which case, an additional anion X$^-$ will be required; and R$^7$, R$^8$ and R$^9$ are as defined above; or iii. —R$^{12}$, —OR$^{12}$ —SO$_2$R$^{12}$, —C(O)OR$^{12}$, —C(O)NR$^{12}$R$^{13}$, —C(=NR$^9$)NR$^{12}$R$^{13}$, -Q$^1$R$^{12}$—, -Q$^1$OR$^{12}$-Q$^1$SO$_2$R$^{12}$, -Q$^1$C(O)OR$^{12}$, -Q$^1$C(O)NR$^{12}$R$^{13}$, -Q$^1$C(=NR$^7$)NR$^{12}$R$^{13}$, -Q$^1$Q$^2$OR$^{12}$, -Q$^1$SO$_2$R$^{12}$, -Q$^1$Q$^2$C(O)OR$^{12}$, -Q$^1$Q$^2$C(O)NR$^{12}$R$^{13}$ or -Q$^1$Q$^2$C(=NR$^9$)NR$^{12}$R$^{13}$; wherein Q$^1$ and Q$^2$ are defined as above; and each R$^{12}$ and R$^{13}$ is independently H, $C_{1-6}$ alkyl, $C_{2-6}$ alkenyl, $C_{2-6}$ alkynyl, $C_{3-8}$ cycloalkyl or $C_{3-8}$ heterocyclyl, any of which is optionally substituted by one or more substituents selected from halo, OR$^7$, C(O)OR$^7$, —N(R$^7$)R$^8$ and C(O)N(R$^7$)R$^8$ and, in the case of cycloalkyl or heterocyclyl groups, oxo; wherein R$^7$, R$^8$ and R$^9$ are as defined above;

each of R$^2$ and R$^3$ is independently $C_{1-10}$ alkyl, wherein one or more —CH$_2$— groups is optionally replaced by —O—, —S— or —NR$^7$— provided that adjacent —CH$_2$— groups are not so replaced and which is optionally substituted with one or more substituents selected from halo, OH, SH, N(R$^7$)R$^8$, aryl, heteroaryl, cycloalkyl, heterocyclyl, —C(O)OR$^7$, —C(O)N(R$^7$)R$^8$, OR$^7$ and N(R$^7$)R$^8$, wherein R$^7$ and R$^8$ are as defined above;

R$^4$ is H, halo, cyano, $C_{1-6}$ alkyl, C(O)OR$^{16}$ or C(O)N(R$^{16}$)R$^{17}$;

wherein alkyl groups are optionally substituted with one or more substituents selected from halo, —OR$^7$ and N(R$^7$)R$^8$, wherein R$^7$ and R$^8$ are as defined above;

each R$^{16}$ and R$^{17}$ is independently H or $C_{1-6}$ alkyl or R$^{16}$ and R$^{17}$ together with the nitrogen atom to which they are attached may form a 5- or 6-membered heterocyclic ring optionally containing one or more further heteroatoms selected from O, N and S.

The compounds of general formula (I) have ENaC blocking activity and, furthermore, are expected to have one or both of the following advantageous properties.

Effective mucocilliary clearance in vivo.

Prolonged lung retention so reducing the dose required to give adequate inhibition of ENaC commensurate with b.i.d. or q.d. dosing without leading to hyperkalaemia.

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

In the present specification, references to "pharmaceutical use" refer to use for administration to a human or an animal, in particular a human or a mammal, for example a domesticated or livestock mammal, for the treatment or prophylaxis of a disease or medical condition. The term "pharmaceutical composition" refers to a composition which is suitable for pharmaceutical use and "pharmaceutically acceptable" refers to an agent which is suitable for use in a pharmaceutical composition. Other similar terms should be construed accordingly.

In the context of the present specification, the term "plurality" refers to two or more.

The anion X$^-$ can have any negative charge and will be balanced by the appropriate number of cations. Thus, for example, a compound of general formula (I) in which X$^-$ is an anion having a single negative charge will have a 1:1 ratio of cation:anion whereas if the anion X⁻ has a charge of −2, the ratio of cation:anion in the compound of general formula (I) will be 2:1. The anion X⁻ is suitably a pharmacologically acceptable anion, although other anions may also be useful, particularly in synthetic precursors to the compounds of general formula (I). Suitable anions, X⁻ include halide, sulfate, nitrate, phosphate, formate, acetate, trifluoroacetate, fumarate, citrate, tartrate, oxalate, succinate, mandelate, methane sulfonate and p-toluene sulfonate. An additional anion X or an anion with additional negative charge, e.g. a charge of −2, will be required if the $R^1$ substituent contains a moiety $R^{10}$ which is cationic such that the charge in the compound of general formula (I) is balanced.

All of the compounds of general formula (I) are salts. In the present specification, references to salts of the compounds of formula (I) may refer to salts of an additional basic nitrogen atom, for example a nitrogen atom to which $R^7$ and $R^8$ moieties are attached. Counter ions for such salts are as defined for X⁻.

Alternatively, when $R^1$, $R^2$ or $R^3$ comprises a carboxyl group C(O)OH, salts may be formed. Suitable counter ions for such salts include sodium, potassium, lithium calcium, aluminium, zinc, magnesium and other metal ions as well as choline, diethanolamine, ethanolamine, ethyl diamine, megulmine and other well-known basic addition salts as summarised in Paulekuhn et al., (2007) J. Med. Chem. 50: 6665-6672 and/or known to those skilled in the art. In some cases, $R^2$ or $R^3$ may comprise an anionic group, for example C(O)O⁻, which may act as counter ion to the N⁺ moiety in the benzimidazolium ring.

In the present specification, the term "$C_{1-6}$" alkyl refers to a straight or branched fully saturated hydrocarbon group having from 1 to 6 carbon atoms. The term encompasses methyl, ethyl, n-propyl, isopropyl, n-butyl, isobutyl and t-butyl. Other alkyl groups, for example $C_{1-12}$ alkyl and $C_{1-4}$ alkyl are as defined above but contain different numbers of carbon atoms.

The term "$C_{2-6}$ alkenyl" refers to a straight or branched hydrocarbon group having from 2 to 6 carbon atoms and at least one carbon-carbon double bond. Examples include ethenyl, prop-1-enyl, hex-2-enyl etc. Other alkenyl groups, for example $C_{1-12}$ alkenyl are as defined above except that they contain the specified number (e.g. 1 to 12) carbon atoms.

The term "$C_{2-6}$ alkynyl" refers to a straight or branched hydrocarbon group having from 2 to 6 carbon atoms and at least one carbon-carbon triple bond. Examples include ethynyl, prop-1-ynyl, hex-2-ynyl etc. Other alkynyl groups, for example $C_{2-12}$ alkynyl are as defined above except that they contain the specified number (e.g. 2 to 12) carbon atoms.

The term "$C_{1-6}$ alkylene" refers to a straight or branched fully saturated hydrocarbon chain having from 1 to 6 carbon atoms. Examples of alkylene groups include —CH₂—, —CH₂CH₂—, CH(CH₃)—CH₂—, CH₂CH(CH₃)—, —CH₂CH₂CH₂—, —CH₂CH(CH₂CH₃)— and —CH₂CH(CH₂CH₃)CH₂—. Other alkylene groups, for example $C_{1-12}$ alkylene are as defined above except that they contain the specified number (e.g. 1 to 12) carbon atoms.

The term "$C_{2-6}$ alkenylene" refers to a straight or branched hydrocarbon chain containing from 2 to 6 carbon atoms and at least one carbon-carbon double bond. Examples of alkenylene groups include —CH═CH—, —CH═C(CH₃)—, —CH₂CH═CH—, —CH═CHCH₂—, CH₂CH₂CH═CH—, CH₂CH═C(CH₃)— and —CH₂CH═C(CH₂CH₃)—. Other alkenylene groups, for example $C_{2-12}$ alkenylene, are as defined above except that they contain the specified number (e.g. 2 to 12) carbon atoms.

The term "$C_{2-6}$ alkynylene" refers to a straight or branched hydrocarbon chain containing from 2 to 6 carbon atoms and at least one carbon-carbon triple bond. Examples of alkenylene groups include —C≡C—, —CH₂C≡C—, —C≡C—CH₂—, CH₂CH₂C≡C—, CH₂C≡CCH₂— and —CH₂CH≡C—CH₂CH₂—)—. Other alkynylene groups, for example $C_{2-12}$ alkynylene, are as defined above except that they contain the specified number (e.g. 2 to 12) carbon atoms.

The terms "carbocyclic" and "carbocyclyl" refer to a non-aromatic hydrocarbon ring system containing from 3 to 10 ring carbon atoms, unless otherwise indicated, and optionally one or more double bond. The carbocyclic group may be a single ring or may contain two or three rings which may be fused or bridged. Examples include cyclopropyl, cyclobutyl, cyclopentyl, cyclohexyl, cyclopentenyl and cyclohexenyl.

In the context of the present specification, the terms "heterocyclic" and "heterocyclyl" refer to a non-aromatic ring system containing 3 to 10 ring atoms including at least one heteroatom selected from N, O and S. The heterocyclic group may be a single ring or may contain two or three rings which may be fused or bridged. Examples include tetrahydrofuranyl, tetrahydroypranyl, pyrrolidine, piperidinyl, morpholinyl, piperazinyl and thiomorpholinyl.

The terms "aryl" and "aromatic" in the context of the present specification refer to a ring system with aromatic character having from 5 to 14 ring carbon atoms and containing up to three rings. Where an aryl group contains more than one ring, not all rings must be fully aromatic in character. Examples of aromatic moieties are benzene, naphthalene, fluorene, indane and indene.

The terms "heteroaryl" and "heteroaromatic" in the context of the specification refer to a ring system with aromatic character having from 5 to 14 ring atoms, at least one of which is a heteroatom selected from N, O and S, and containing up to three rings. Where a heteroaryl group contains more than one ring, not all rings must be fully aromatic in character. Examples of heteroaryl groups include pyridine, pyrimidine, indole, benzofuran, benzimidazole and indolene.

The term "halogen" refers to fluorine, chlorine, bromine or iodine, the term "halo" to fluoro, chloro, bromo or iodo groups and "halide" to fluoride, chloride, bromide or iodide.

The term "$C_{1-6}$ haloalkyl" as used herein refers to a $C_{1-6}$ alkyl group as defined above in which one or more of the hydrogen atoms is replaced by a halo group. Any number of hydrogen atoms may be replaced, up to perhalo substitution. Examples include trifluoromethyl, chloroethyl and 1,1-difluoroethyl. Other haloalkyl groups, for example $C_{1-12}$ haloalkyl are as defined above except that they contain the specified number (e.g. 1 to 12) carbon atoms.

The term "isotopic variant" refers to isotopically-labelled compounds which are identical to those recited in formula (I) but for the fact that one or more atoms are replaced by an atom having an atomic mass or mass number different from the atomic mass or mass number most commonly found in nature, or in which the proportion of an atom having an atomic mass or mass number found less commonly in nature has been increased (the latter concept being referred to as "isotopic enrichment"). Examples of isotopes that can be incorporated into compounds of the invention include isotopes of hydrogen, carbon, nitrogen, oxygen, fluorine, iodine and chlorine such as 2H (deuterium), 3H, 11C, 13C, 14C, 18F, 123I or 125I (e.g. 3H, 11C, 14C, 18F, 123I or 125I), which may be naturally occurring or non-naturally occurring isotopes.

The concept of canonical forms is well understood by the person of skill in the art. Thus, a compound of general formula (I) can have canonical forms as follows:

[Chemical structure showing two canonical forms of the compound with substituents $R^1$, $R^2$, $R^3$, $R^4$, $R^6$, $NH_2$ and counterion $X^-$]

Both of these canonical forms are included within the scope of the invention.

The $R^1$ substituent is suitably at the 5- or the 6-position and thus the compound of general formula (I) can be a compound of general formula (IA):

[Chemical structure of formula (IA)]

wherein $R^1$, $R^2$, $R^3$, $R^4$ and $X^-$ are as defined for general formula (I);
or a compound of general formula (IB):

[Chemical structure of formula (IB)]

wherein $R^1$, $R^2$, $R^3$, $R^4$ and $X^-$ are as defined for general formula (I).

It should be noted that, because the compound of general formula (I) can have different canonical forms as discussed above, if $R^2$ and $R^3$ are the same then the 5- and 6-positions are equivalent.

In some suitable compounds of general formula (I), $R^1$ is:
H, halo, —$R^{12}$, —C(O)O$R^{12}$ or —O$R^{12}$; in particular, H, halo, C(O)OH, C(O)O$C_{1-6}$ alkyl), $C_{1-6}$ alkyl, $C_{2-6}$ alkenyl, $C_{2-6}$ alkynyl, —O($C_{1-6}$ alkyl), —O($C_{2-6}$ alkenyl) or —O($C_{2-6}$ alkynyl), any of which is optionally substituted by one or more halo substituents.

More suitably in these compounds, $R^1$ is H, halo, C(O)OH, C(O)O($C_{1-6}$ alkyl), $C_{1-6}$ alkyl, 6 haloalkyl, $C_{1-6}$ alkoxy or $C_{1-6}$ haloalkoxy.

Examples of such $R^1$ groups include H, chloro, C(O)OH, methyl, trifluoromethyl, methoxy and trifluoromethoxy.

In other suitable compounds of general formula (I), $R^1$ is -$L^1R^{10}$.

Suitably in such compounds, $L^1$ is:
—$Z^1$—, -$Q^1$-, —$Z^1Q^1$-, -$Q^1Z^1$—, —$Z^1Q^1Z^2$—, -$Q^1Q^2$-, -$Q^1Q^2Z^1$—, -$Q^1Q^2Z^1Q^3Z^2$—;
—O$Z^1$—, —O$Z^1Q^1$-, —O$Z^1Q^1Z^2$—;
—$Z^1$N($R^7$)$Z^2$—, -$Q^1Z^1$N($R^7$)$Z^2$—;
—C(O)$Q^1$-, —C(O)$Q^1Z^1$—, —C(O)$Q^1Q^2$-, —C(O)$Q^1Q^2Z^1$—, —C(O)$Q^1$N($R^7$)C(O)$Z^1$—, —C(O)$Q^1$N($R^7$)C(O)$Z^1Q^2$-;
—C(O)N($R^7$)$Z^1$—, —C(O)N($R^7$)$Q^1$-, —C(O)N($R^7$)$Z^1Q^1$-, —C(O)N($R^7$)$Z^1Q^1Z^2$—, —C(O)N($R^7$)$Q^1Z^1$—, —C(O)N($R^7$)$Q^1Q^2$-, —C(O)N($R^7$)$Q^1Q^2Z^1$—, —C(O)N($R^7$)$Z^1Q^1Q^2Z^2$—, —C(O)N($R^7$)$Z^1$O(CH$_2$CH$_2$O)$_n$$Z^2$—, —C(O)N($R^7$)$Z^1$O(CH$_2$O)$_n$$Z^2$—, —C(O)N($R^7$)$Z^1Q^1Z^2$N($R^8$)$Z^3$—, —C(O)N($R^7$)$Z^1$N($R^8$)$Z^2$—, —C(O)N($R^7$)$Q^1Z^1$N($R^8$)$Z^2$—, —C(O)N($R^7$)$Z^1Q^1$O$Q^2$O$Q^3$-, —C(O) N($R^7$)$Z^1Q^1$O$Q^{20}Q^3Z^2$—;
—C(O)O$Z^1$—, —C(O)O$Z^1Q^1$-, C(O)O$Z^1Q^1Z^2$—;
$Q^1$C(O)$Q^2$-, $Q^1$C(O)$Z^1$—, -$Q^1$C(O)$Q^2Z^1$—, $Q^1$C(O)$Q^2Q^3$-, $Q^1$C(O)$Z^1Q^2$- or $Q^1$C(O)$Q^2Q^3Z^1$—.

In some more suitable compounds, $L^1$ is:
—$Z^1$—, -$Q^1$-, -$Q^1Z^1$—, -$Q^1Q^2$-, -$Q^1Q^2Z^1$—, -$Q^1Q^2Z^1Q^3Z^2$—;
—O$Z^1$—;
—$Z^1$N($R^7$)$Z^2$—, -$Q^1Z^1$N($R^7$)$Z^2$—;
—C(O)$Q^1$-, —C(O)$Q^1Z^1$—, —C(O)$Q^1Q^2$-, —C(O)$Q^1$N($R^7$)C(O)$Z^1$—;
—C(O)N($R^7$)$Z^1$—, —C(O)N($R^7$)$Q^1$-, —C(O)N($R^7$)$Z^1Q^1$-, —C(O)N($R^7$)$Z^1Q^1Z^2$—, —C(O)N($R^7$)$Q^1Z^1$—, —C(O)N($R^7$)$Q^1Q^2$-, —C(O)N($R^7$)$Q^1Q^2Z^1$—, —C(O)N($R^7$)$Z^1Q^1Q^2Z^2$—, —C(O)N($R^7$)$Z^1$O(CH$_2$CH$_2$O)$_n$$Z^2$—, —C(O)N($R^7$)$Z^1$N($R^8$)$Z^2$—, —C(O)N($R^7$)$Z^1Q^1$O$Q^2$O$Q^3Z^2$—; or
—$Q^1$C(O)$Q^2$-.

In other more suitable compounds, $L^1$ is:
—$Z^1$—, -$Q^1$, -$Q^1Z^1$—, -$Q^1Q^2Z^1$—;
—O$Z^1$—;
—C(O)$Q^1$-, —C(O)$Q^1Z^1$—;
—C(O)N($R^7$)$Z^1$—, C(O)N($R^7$)$Q^1$-, —C(O)N($R^7$)$Z^1Q^1$-, —C(O)N($R^7$)$Q^1Z^1$—, —C(O)N($R^7$)$Z^1Q^1Q^2Z^2$—, —C(O)N($R^7$)$Z^1$O(CH$_2$CH$_2$O)$_n$$Z^2$— or —C(O)N($R^7$)$Z^1Q^1Z^2$N($R^8$)$Z^3$—.

In some suitable compounds where $R^1$ is -L$R^{10}$, the cyclic groups $Q^1$, $Q^2$ and $Q^3$ are independently selected from 5- and 6-membered aryl and heteroaryl groups and 4 to 8-membered carbocyclyl and heterocyclyl groups.

More suitably, $Q^1$, $Q^2$ and $Q^3$ are selected from phenyl, 5- and 6-membered heteroaryl groups and 4- to 7-membered and heterocyclyl groups, still more suitably phenyl, 5- and 6-membered nitrogen-containing heteroaryl and 4- to 7-membered nitrogen-containing heterocyclyl groups.

Examples of such heteroaryl $Q^1$, $Q^2$ and $Q^3$ groups include pyridyl, pyrimidinyl, pyrazolyl, imidazolyl and oxazolyl groups, with 5-membered rings such as imidazolyl and oxazolyl and especially pyrazolyl being particularly suitable. When $Q^1$, $Q^2$ or $Q^3$ is pyrazolyl, it may have the following regiochemistry:

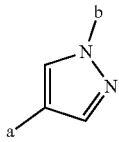

Where a and b show the links to the remainder of the molecule.

Examples of heterocyclyl $Q^1$, $Q^2$ and Cr groups include azetidinyl, piperidinyl, piperazinyl, and aziridinyl, with 6-membered rings such as piperazinyl and piperidinyl being more suitable. Piperidinyl is a particularly suitable heterocyclyl group, especially 1,4-piperidinyl.

Other more suitable $Q^1$, $Q^2$ and $Q^3$ groups include cyclohexyl and tetrohydropyran groups, either or which may be substituted with one or more substituents selected from OH, or $NR^{15}R^{16}$, especially OH, $NH_2$ or $NHCH_3$.

When $L^1$ comprises a C(O) moiety linked to a Q moiety, the Q moiety may be a nitrogen containing heterocyclyl ring in which C(O) is linked to the nitrogen atom.

For example, in —C(O)$Q^1$-, —C(O)$Q^1Z^1$—, —C(O)$Q^1Q^2$-, —C(O)$Q^1Q^2Z^1$—, —C(O)$Q^1N(R^7)C(O)Z^1$—, —C(O)$Q^1N(R^7)C(O)Z^1Q^2$-, —C(O)$Q^1N(R^7)C(O)Z^1Q^2Q^3$-, —C(O)$Q^1N(R^7)C(O)Z^1Q^2Z^2$—, $Q^1$ is suitably a 5- or 6-membered heterocyclyl ring which is linked to the —C(O) moiety via a ring nitrogen atom. Suitably, $Q^1$ is a 5- or 6-membered nitrogen-containing heterocyclyl ring such as piperidin-1-yl or pyrrolidine-1-yl, more suitably piperidin-1yl. Suitably, when $Q^1$ is piperidin-1-yl the remainder of the molecule is linked to the 4-position of the piperidine ring. When $Q^1$ is pyrrolidine-1-yl, the remainder of the molecule may be linked to the 3-position of the pyrrolidine ring.

When $L^1$ is -$Q^1$C(O)$Q^2$-, -$Q^1$C(O)$Q^2Z^1$—, $Q^1$C(O)$Q^2Q^3$-, $Q^1$C(O)$Q^2Q^3Z^1$—, $Q^2$ is suitably a 5- or 6-membered heterocyclyl ring which is linked to the —C(O) moiety via a ring nitrogen atom. Suitably, $Q^2$ is piperidin-1-yl or pyrrolidine-1-yl, more suitably piperidin-1yl. Suitably, when $Q^1$ is piperidin-1-yl the remainder of the molecule is linked to the 4-position of the piperidine ring. When $Q^1$ is pyrrolidine-1-yl, the remainder of the molecule may be linked to the 3-position of the pyrrolidine ring.

In other cases, however, when $L^1$ comprises a C(O) moiety linked to a Q moiety, the Q moiety may be a heterocyclyl group which is linked to the C(O) moiety via a ring carbon atom. Examples of heterocyclyl groups include 5- and 6-membered rings, suitably nitrogen-containing rings such as piperidinyl or pyrrolidinyl. Suitably, in this case, when $Q^1$ is a piperidine ring it is a piperidin-4-yl group such that the piperidine 4-position is linked to the C(O) moiety. Suitably, the piperidine nitrogen atom is linked to the remainder of the molecule. Examples of $L^1$ moieties of this type include C(O)$Q^1Z^1$, in which $Q^1$ may be a piperidine ring in which the 4-position is linked to C(O) and the 1-position is linked to $Z^1$.

When $L^1$ comprises a —C(O)N($R^7$)— moiety linked to a Q moiety, the Q moiety is suitably a heterocyclyl ring, e.g. a 5- or 6-membered nitrogen-containing heterocyclyl ring, which is linked to the —C(O)N($R^7$)— moiety via a ring carbon atom.

For example, when $L^1$ is —C(O)N($R^7$)$Q^1$-, —C(O)N($R^7$)$Q^1Z^1$—, —C(O)N($R^7$)$Q^1Q^2$-, —C(O)N($R^7$)$Q^1Q^2Z^1$—, —C(O)N($R^7$)$Q^1Z^1$—, —C(O)N($R^7$)$Q^1Z^1N(R^8)Z^2$—, —$Z^1$C(O)N($R^7$)$Q^1$-, —$Z^1$C(O)N($R^7$)$Q^1Z^2$— or —$Z^1$C(O)N($R^7$)$Q^1Q^2$-, $Q^1$ is suitably a 5- or 6-membered heterocyclyl ring which is linked to the —C(O)N($R^7$)— moiety via a ring carbon atom, with the remainder of the molecule being linked to a ring nitrogen atom. Suitably, $Q^1$ is piperidin-4-yl or pyrrolidinyl. When $Q^1$ is piperidin-4-yl, the remainder of the molecule is suitably linked to the 1-position of the piperidine ring.

For other $L^1$ groups in which $Q^1$ and/or $Q^2$ and/or $Q^2$ is piperidinyl, they are suitably either piperidin-1-yl or piperidin-4-yl.

When the $L^1$ comprises a -$Q^1Q^2$- or -$Q^2Q^3$- moiety, this may be, for example:

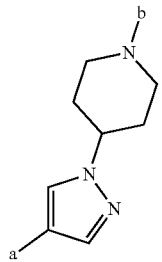

Where a and b show the links to the remainder of the molecule.

Other examples of -$Q^1Q^2$- and -$Q^2Q^3$- moieties include biphenyl, suitably a 1,1'-biphenyl-4-yl moiety. This type of -$Q^1Q^2$- or -$Q^2Q^3$- moiety is suitably linked at each side to a Z moiety, for example as in —C(O)N($R^7$)$Z^1Q^1Q^2Z^2$—

In some suitable compounds where $R^1$ is -$L^1R^{10}$, and $L^1$ contains $Z^1$ and optionally $Z^2$ and $Z^3$, each of $Z^1$, $Z^2$ and $Z^3$ is independently $C_{1-12}$ alkylene, optionally substituted by one or more halo or OH groups.

In some compounds of the invention, $R^1$ is $L^1R^{10}$ and $L^1$ comprises a $Z^1$, and optionally a $Z^2$ and optionally a $Z^3$ moiety.

In compounds where $L^1$ is:

—$Z^1$—, —$Z^1Q^1$-, -$Q^1Z^1$—, —$Z^1Q^1Z^2$—, -$Q^1Q^2Z^1$—, -$Q^1Q^2Z^1Q^3Z^2$—, —$Z^1Q^1OQ^2OQ^3$-;

—O$Z^1$—, —O$Z^1Q^1$-, —O$Q^1Z^1$—, —O$Z^1Q^1Z^2$—, —O$Q^1Q^2Z^1$—, —O$Q^1Q^2Z^1Q^3Z^2$—, —O$Z^1Q^1OQ^2OQ^3$-;

—$Z^1$N($R^7$)$Z^2$—, -$Q^1Z^1$N($R^7$)$Z^2$—, —$Z^1$N($R^7$)$Z^2Q^1$-, -$Q^1Z^1$N($R^7$)$Z^2Q^2Z^3$—;

—$Z^1$O(CH$_2$CH$_2$O)$_n$$Z^2$—, —$Z^1$O(CH$_2$CH$_2$O)$_n$$Q^1$-, —$Z^1$O(CH$_2$CH$_2$O)$_n$$Q^2Q^1$, —$Z^1$O(CH$_2$CH$_2$O)$_n$$Q^1Z^2$—, -$Q^1Z^1$O(CH$_2$CH$_2$O)$_n$$Z^2$—, -$Q^1Z^1$O(CH$_2$CH$_2$O)$_n$$Q^1$-, -$Q^1Z^1$O(CH$_2$CH$_2$O)$_n$$Z^2Q^1$, —$Z^1$O(CH$_2$CH$_2$O)$_n$$Z^2Q^1Z^3$—;

—C(O)$Z^1$—, —C(O)$Z^1Q^1$-, —C(O)$Z^1Q^1Z^2$—, —C(O)$Q^1Z^1$—, —C(O)$Q^1Q^2Z^1$—, —C(O)$Q^1$N($R^7$)C(O)$Z^1$—, —C(O)$Q^1$N($R^7$)C(O)$Z^1Q^2$-, —C(O)$Q^1$N($R^7$)C(O)$Z^1Q^2Q^3$-—C(O)$Q^1$N($R^7$)C(O)$Z^1Q^2Z^2$—, —C(O)$Z^1Q^1OQ^2OQ^3$-;

—C(O)N($R^7$)$Z^1$—, —C(O)N($R^7$)$Z^1Q^1$-, —C(O)N($R^7$)$Z^1Q^1Z^2$—, —C(O)N($R^7$)$Q^1Z^1$—, —C(O)N($R^7$)$Q^1Q^2Z^1$—, —C(O)N($R^7$)$Z^1Q^1Q^2Z^2$—, —C(O)N($R^7$)$Z^1$O(CH$_2$CH$_2$O)$_n$$Z^2$—, —C(O)N($R^7$)$Z^1$O(CH$_2$O)$_n$$Z^2$—, —C(O)N($R^7$)$Z^1Q^1Z^2$N($R^8$)$Z^3$—, —C(O)N($R^7$)$Z^1$N($R^8$)$Z^2$—, —C(O)N($R^7$)$Q^1Z^1$N($R^8$)$Z^2$—, —C(O)N($R^7$)$Z^1Q^1OQ^2OQ^3$-, —C(O)N($R^7$)$Z^1Q^1OQ^2OQ^3Z^2$—;

—Z¹C(O)N(R⁷)Z²—, —Z¹C(O)N(R⁷)Q¹-, —Z¹C(O)N(R⁷)Z²Q¹-, —Z¹C(O)N(R⁷)Q¹Z²—, Z¹C(O)N(R⁷)Q¹Q²-, —Z¹C(O)Q¹-, —Z¹C(O)Q¹Z²—, —Z¹C(O)Q¹Q²-, —Z¹C(O)N(R⁷)Q¹Q²Z²—;

—C(O)OZ¹—, —C(O)OZ¹Q¹-, —C(O)OZ¹Q¹Z²—, —C(O)OQ¹Z¹—, —C(O)OQ¹Q²-, —C(O)OQ¹Q²Z¹—;

Q¹C(O)Z¹—, -Q¹C(O)Q²Z¹—, -Q¹C(O)Z¹Q²-, Q¹C(O)Q²Q³Z¹—;

—C(=NR⁹)N(R⁷)Z¹—, —C(=NR⁹)N(R⁷)Q¹-, —C(=NR⁹)N(R⁷)Z¹Q¹-, —C(=NR⁹)N(R⁷)Z¹Q¹Z²—, —C(=NR⁹)N(R⁷)Q¹Z¹—, —C(=NR⁹)N(R⁷)Q¹Q²-, C(=NR⁹)N(R⁷)Q¹Q²Z¹—;

the groups Z¹ and, where present, Z² and Z³ suitably comprise $C_{1-8}$ alkylene, $C_{2-8}$ alkenylene, $C_{2-8}$ alkynylene any of which is optionally substituted by one or more halo, OH, C(O)NR¹⁵R¹⁶, C(O)OR¹⁵ or NR¹⁵R¹⁶; wherein R¹⁵ and R¹⁶ are as defined above.

In some more suitable compounds, the groups Z¹ and, where present, Z² and Z³ comprise $C_{1-6}$ alkylene optionally substituted by one or more halo, OH, C(O)NR¹⁵R¹⁶, C(O)OR¹⁵ or NR¹⁵R¹⁶; wherein R¹⁵ and R¹⁶ are as defined above.

Still more suitably, the groups Z¹ and, where present, Z² and Z³ comprise $C_{1-4}$ alkylene which is unsubstituted or substituted by one or more halo, OH, C(O)NR¹⁵R¹⁶, C(O)OR¹⁵ or NR¹⁵R¹⁶, wherein each R¹⁵ and R¹⁶ is H. Typically, Z¹ and where present, Z² and Z³ comprise $C_{1-4}$ alkylene which is unsubstituted or substituted with one or more OH, halo, C(O)NH₂ or C(O)OH.

In some particularly suitable compounds, Z¹ and, where present, Z² and Z³ are unsubstituted $C_{1-4}$ alkylene.

In other particularly suitable compounds Z¹ is $C_{1-4}$ alkylene substituted with one or more halo, C(O)NH₂ or C(O)OH.

These Z¹, Z² and Z³ moieties are particularly suitable when L¹ is:
—Z¹—, -Q¹Z¹— where Q¹ is linked via a ring carbon atom to Z¹, -Q¹Q²Z¹— where Q² is linked via a ring carbon atom to Z¹;
—OZ¹—;
—C(O)Q¹Z¹—, where Q¹ is linked via a ring nitrogen atom to C(O) and via a ring carbon atom to Z¹;
—C(O)N(R⁷)Z¹—, —C(O)N(R⁷)Q¹Z¹—, —C(O)N(R⁷)Z¹Q¹Q²Z²—, —C(O)N(R⁷)Z¹O(CH₂CH₂O)ₙZ²——C(O)N(R⁷)Z¹Q¹Z²N(R⁸)Z³—.

In some compounds of general formula (I), Z¹, Z² or Z³ may be directly linked to a cyclic group via a ring nitrogen atom. This may occur, for example, in compounds where R¹ is L¹R¹⁰ and L¹ is:
Q¹Z¹—, —Z¹Q¹Z²—, -Q¹Q²Z¹—, —OQ¹Z¹—, —OZ¹Q¹Z²—, —OQ¹Q²Z¹—, —Z¹O(CH₂CH₂O)ₙQ¹Z²—, -Q¹Z¹O(CH₂CH₂O)ₙZ²—, —Z¹O(CH₂CH₂O)ₙQ²Q¹Z³—, —C(O)Z¹Q¹Z²—, —C(O)Q¹Z¹—, —C(O)Q¹Q²Z¹—, —C(O)Q¹N(R⁷)C(O)Z¹Q²Z²—, —C(O)N(R⁷)Z¹Q¹Z²—, —C(O)N(R⁷)Q¹Z¹—, —C(O)N(R⁷)Q¹Q²Z¹—, —C(O)N(R⁷)Z¹Q¹Q²Z²—, —C(O)N(R⁷)Z¹Q¹OQ²OQ³Z²—, Z¹C(O)N(R⁷)Q¹Z²—, —Z¹C(O)Q¹Z²—, Z¹C(O)N(R⁷)Q¹Q²Z²—, —C(O)OZ¹Q¹Z²—, —C(O)OQ¹Z¹—, —C(O)OQ¹Q²Z¹—; Q¹C(O)Q²Z¹—, Q¹C(O)Q²Q³Z¹—, —C(=NR⁹)N(R⁷)Z¹Q¹Z²—, —C(=NR⁹)N(R⁷)Q¹Z¹—, —C(=NR⁹)N(R⁷)Q¹Q²Z¹—.

In some such compounds, the Z¹ or Z² or Z³ group is also linked to R¹⁰. Where this is the case, the Z¹ or Z² or Z³ group may be $C_{1-12}$ alkylene substituted with one or more OH group, suitably by a plurality of OH groups, for example 2-11 OH groups. Typically, the number of OH groups will be one less than the number of carbon atoms in the alkylene group;

More suitably in this case, Z¹ is a $C_{1-8}$ alkylene group substituted with 2-7 OH groups, for example 5-7 OH groups.

Examples of suitable Z¹ or Z² or Z³ groups of this type include —CH₂[CH(OH)]ₙ—, where n is suitably 3-7. Most suitably, Z¹ or Z² or Z³ where appropriate is —CH₂—CH(OH)—CH(OH)—CH(OH)—CH(OH)—CH(OH)—.

In such compounds, R¹⁰ is suitably H such that the Z¹R¹⁰, Z²R¹⁰, Z²R¹⁰ or Z³R¹⁰ moiety is —CH₂[CH(OH)]n-H, where n is suitably 3-7, for example —CH₂—[CH(OH)]4-CH₂OH.

In compounds where R¹ is -L¹R¹⁰, suitable R¹⁰ groups include H, —N(R⁷)R⁸, —N(R⁷)C(=NR⁹)N(R⁸)₂, —N(R⁷)C(O)OR⁸, —N(R⁷)—C(O)—($C_{1-3}$ alkylene)-N⁺(R⁸)₃, —N⁺(R⁸)₃, OR⁷ or —C(O)OR⁷.

More suitably, R¹⁰ is H, —N(R⁷)R⁸, —N(R⁷)C(=NR⁹)N(R⁸)₂, —N(R⁷)C(O)OR⁸ or —C(O)OR⁷.

When R¹⁰ is H, L¹ is suitably —Z¹—, Q¹, -Q¹Z¹—, —Z¹Q¹Z²—, -Q¹Q², -Q¹Q²Z¹—;
—OZ¹—, —OQ¹Z¹—, —OZ¹Q¹Z²—, —OQ¹Q²Z¹—;
—Z¹O(CH₂CH₂O)ₙQ¹Z²—, -Q¹Z¹O(CH₂CH₂O)ₙZ²—, —Z¹O(CH₂CH₂O)ₙZ²Q¹Z³—, —C(O)Z¹—, —C(O)Z¹Q¹Z²—, —C(O)Q¹Z¹—, —C(O)Q¹Q²Z¹—;
—C(O)N(R⁷)Z¹—, —C(O)N(R⁷)Q¹-, —C(O)Q¹N(R⁷)C(O)Z¹Q²Z²—, —C(O)N(R⁷)Z¹Q¹Z²—, —C(O)N(R⁷)Q¹Z¹—, —C(O)N(R⁷)Q¹Q²Z¹—, —C(O)N(R⁷)Z¹Q¹Q²Z²—, —C(O)N(R⁷)Z¹Q¹OQ²OQ³Z²—, Z¹C(O)N(R⁷)Q¹Z²—;
—C(O)N(R⁷)Q¹Q²Z¹—, —Z¹C(O)Q¹Z²—, Z¹C(O)N(R⁷)Q¹Q²Z²—;
—C(O)OZ¹—, —C(O)OZ¹Q¹Z²—, —C(O)OQ¹Z¹—, —C(O)OQ¹Q²-, C(O)OQ¹Q²Z¹—;
—C(O)OQ¹Z¹—, —C(O)OQ¹Q²Z¹—; Q¹C(O)Q²Z¹—, Q¹C(O)Q²Q³Z¹—, —C(=NR⁹)N(R⁷)Z¹—, C(=NR⁹)N(R⁷)Z¹Q¹Z², —C(=NR⁹)N(R⁷)Q¹Z¹—, C(=NR⁹)N(R⁷)Q¹Q²Z¹—.

In some more suitable compounds, when R¹⁰ is H, L¹ is —OZ¹, where Z¹ is as defined above but is suitably $C_{1-8}$ alkylene optionally substituted as described above. More suitably in these compounds, Z¹ is $C_{1-4}$ alkylene such that the group —OZ¹R¹⁰ is —O($C_{1-4}$ alkyl), for example methoxy, ethyoxy isopropoxy or t-butyloxy. In one embodiment (e.g. as used in Compounds 1, 7, 10-16, 61, 64 and 67-73), R¹ is methoxy.

In other more suitable compounds, when R¹⁰ is H, L¹ is -Q¹-, -Q¹Q²- or —C(O)N(R⁷)Q¹-, where the Q¹ group or, for -Q¹Q²-, the Q² group, is a nitrogen-containing heterocyclyl group which is linked to the R¹⁰ group via a ring nitrogen atom. Examples of such groups Q¹R¹⁰ or Q²R¹⁰ groups include:

where * indicates the point at which the group is joined to the remainder of the molecule.

In an embodiment (e.g. as used in Compounds 29 and 86), R¹ is -Q¹-H.

In an embodiment (e.g. as used in Compounds 30 and 87), R¹ is -Q¹Q²-H.

In an embodiment (e.g. as used in Compounds 39 and 96), R¹ is —C(O)N(R⁷)Q¹-H.

In still other more suitable compounds, when $R^{10}$ is H, $L^1$ is:
- —$Z^1$—, $Q^1$, -$Q^1Z^1$—, -$Q^1Q^2$, -$Q^1Q^2Z^1$—;
- —$OZ^1$—, —$OQ^1Z^1$—, —$OQ^1Q^2Z^1$—;
- —$C(O)Z^1$—, —$C(O)Q^1Z^1$—, —$C(O)Q^1Q^2Z^1$—;
- —$C(O)N(R^7)Z^1$—, —$C(O)N(R^7)Q^1Z^1$—, —$C(O)N(R^7)Q^1Q^2Z^1$—;
- —$C(O)OZ^1$—, —$C(O)OQ^1Z^1$—, —$C(O)OQ^1Q^2$-, $C(O)OQ^1Q^2Z^1$—;
- —$C(=NR^9)N(R^7)Z^1$—, —$C(=NR^9)N(R^7)Q^1Z^1$— or $C(=NR^9)N(R^7)Q^1Q^2Z^1$—.

In still other more suitable compounds, when $R^{10}$ is H, and which contain a cyclic group $Q^1$, $Q^2$ or $Q^3$ linked to $Z^1$ or $Z^2$ or $Z^3$, the cyclic group may be a nitrogen containing heterocyclyl group linked to $Z^1$ or $Z^2$ or $Z^3$ via a ring nitrogen atom. This may occur, for example, in compounds where $R^1$ is $L^1R^{10}$ and $L^1$ is:
- $Q^1Z^1$—, —$Z^1Q^1Z^2$—, -$Q^1Q^2Z^1$—;
- —$OQ^1Z^1$—, —$OZ^1Q^1Z^2$—, —$OQ^1Q^2Z^1$—;
- —$Z^1O(CH_2CH_2O)_nQ^1Z^2$—, -$Q^1Z^1O(CH_2CH_2O)_nZ^2$—, —$Z^1O(CH_2CH_2O)_nZ^2Q^1Z^3$—;
- —$C(O)Z^1Q^1Z^2$—, —$C(O)Q^1Z^1$—, —$C(O)Q^1Q^2Z^1$—, —$C(O)Q^1N(R^7)C(O)Z^1Q^2Z^2$—, —$C(O)N(R^7)Z^1Q^1Z^2$—, —$C(O)N(R^7)Q^1Z^1$—;
- —$C(O)N(R^7)Q^1Q^2Z^1$—, —$C(O)N(R^7)Z^1Q^1Q^2Z^2$—, $C(O)N(R^7)Z^1Q^1OQ^2OQ^3Z^2$—;
- $Z^1C(O)N(R^7)Q^1Z^2$—, —$Z^1C(O)Q^1Z^2$—, $Z^1C(O)N(R^7)Q^1Q^2Z^2$—;
- —$C(O)OZ^1Q^1Z^2$—, —$C(O)OQ^1Z^1$—, —$C(O)OQ^1Q^2Z^1$—;
- $Q^1C(O)Q^2Z^1$—, $Q^1C(O)Q^2Q^3Z^1$—;
- —$C(=NR^9)N(R^7)Z^1Q^1Z^2$—, —$C(=NR^9)N(R^7)Q^1Z^1$— or —$C(=NR^9)N(R^7)Q^1Q^2Z^1$—.

Particularly suitable compounds of this type are those in which $R^{10}$ is H and $L^1$ is -$Q^1Z^1$—, $Q^1Q^2Z^1$—, —$C(O)N(R^7)Q^1Z^1$—, or —$C(O)Q^1Z^1$—; or, still more suitably, -$Q^1Q^2Z^1$— or —$C(O)N(R^7)Q^1Z^1$—.

In compounds where $R^{10}$ is H and in which $L^1$ contains a moiety $Z^1$, $Z^2$ or $Z^3$ linked directly to $R^{10}$, the $Z^1$, $Z^2$ or $Z^3$ moiety is suitably a $C_{1-12}$ alkylene group substituted by a plurality of OH groups, for example 2 to 11 OH groups. Typically, the number of OH groups will be one less than the number of carbon atoms in the alkylene group;

More suitably in this case, $Z^1$ is a $C_{1-8}$ alkylene group substituted with 2-7 OH groups, for example 5-7 OH groups.

Examples of suitable $Z^1$ groups of this type include —$CH_2[CH(OH)]_n$—, where n is suitably 3-7. Most suitably, n is 5 and in this case, $Z^1$ is —$CH_2[CH(OH)]_4$—$CH(OH)$— such that the group $Z^1R^{10}$, $Z^2R^{10}$ or $Z^3R^{10}$ is a moiety —$CH_2[CH(OH)]_4$—$CH_2OH$.

Examples of compounds where the group $Z^1R^{10}$ is a moiety —$CH_2[CH(OH)]4$-$CH_2OH$ include those in which $R^1$ is:
- piperidinyl-4-yl-$CH_2$—$CH(OH)$—$CH(OH)$—$CH(OH)$—$CH(OH)$—$CH_2(OH)$.
- pyrazol-4-yl-piperidin-4-yl-$CH_2$—$CH(OH)$—$CH(OH)$—$CH(OH)$—$CH(OH)$—$CH_2(OH)$.
- —$C(O)NH$-piperidin-4-yl-$CH_2$—$CH(OH)$—$CH(OH)$—$CH(OH)$—$CH(OH)$—$CH_2(OH)$.

In an embodiment, $R^1$ is -$Q^1Z^1$—H.

In an embodiment (e.g. as used in Compounds 45 and 102), $R^1$ is -$Q^1Q^2Z^1$—H.

In an embodiment (e.g. as used in Compounds 47 and 104), $R^1$ is $C(O)N(R^7)Q^1Z^1$—H.

Other suitable compounds in which $R^{10}$ is H include those in which $R^{10}$ is attached to a ring nitrogen atom of a moiety $Q^1$, $Q^2$ or $Q^3$ or the $L^1$ group.

When $R^{10}$ is other than H, $Z^1$, $Z^2$ and $Z^3$, where present, may be —$(CH_2)_n$— where n is 1 to 6 or —$O(CH_2)_m$—, where m is 1 to 5.

In compounds where $R^{10}$ is —$C(O)OR^7$, $L^1$ is suitably:
- -$Q^1$- or -$Q^1Q^2$- where $Q^1$ or, for -$Q^1Q^2$-, $Q^2$ is a carbocyclyl or heterocyclyl group and is linked to $R^{10}$ via a ring carbon atom; or
- $C(O)N(R^7)Q^1$, where $Q^1$ is a is a carbocyclyl or heterocyclyl group and is linked to $R^{10}$ via a ring nitrogen atom.

In these compounds, $R^7$ is suitably $C_{1-6}$ alkyl, still more suitably $C_{1-4}$ alkyl, for example t-butyl.

In an embodiment (e.g. as used in Compounds 24 and 81), $R^1$ is -$Q^1C(O)OR^7$, where $Q^1$ is piperidin-4-yl and $R^7$ is t-butyl.

In an embodiment (e.g. as used in Compounds 25 and 82), $R^1$ is -$Q^1Q^2C(O)OR^7$, where $Q^1$ is pyrazol-4-yl, $Q^2$ is piperidin-4-yl and $R^7$ is t-butyl.

In an embodiment (e.g. as used in Compounds 35 and 91), $R^1$ is $C(O)NHQ^1C(O)OR^7$, where $Q^1$ is piperidin-1-yl and $R^7$ is When $R^{10}$ is —$N(R^7)R^8$, —$N(R^7)C(=NR^9)N(R^8)_2$ or —$N(R^7)C(O)OR^8$—, $L^1$ is suitably:
- —$Z^1$—,
- —$OZ^1$—;
- —$C(O)N(R^7)Z^1$—, —$C(O)N(R^7)Z^1Q^1Q^2Z^2$—, —$C(O)N(R^7)Z^1Q^1Z^2N(R^8)Z^3$, —$C(O)N(R^7)Z^1O(CH_2CH_2O)_nZ^2$;
- —$C(O)N(R^7)Q^1$-, —$C(O)N(R^7)Z^1Q^1$- or —$C(O)Q^1$-, where $Q^1$ is a carbocyclyl or heterocyclyl group and is linked to $R^{10}$ via a ring carbon atom; or
- $C(O)Q^1Z^1$—.

Compounds in which $R^{10}$ is —$N(R^7)R^8$ are particularly suitable.

Typically, when $R^{10}$ is —$N(R^7)R^8$, each of $R^7$ and $R^8$ is independently either H or $C_{1-8}$ alkyl optionally substituted with one or more OH groups. In some cases, both $R^7$ and $R^8$ are H.

In the case where either or both of $R^7$ and $R^8$ is $C_{1-8}$ alkyl, it may be substituted with a plurality of OH groups, for example 2-7 OH groups. Typically, the number of OH groups will be one less than the number of carbon atoms in the alkyl group. More suitably in compounds of this type, one or preferably both, of $R^7$ and $R^8$ may be —$CH_2[CH(OH)]_mCH_2OH$, where m is suitably 2-6. Most suitably, m is 4 and in this case, the $R^7$ and/or $R^8$ group is a moiety —$CH_2[CH(OH)]_4$—$CH_2OH$.

In particularly suitable compounds $R^{10}$ is —$N\{CH_2[CH(OH)]_4$—$CH_2OH\}_2$.

In an embodiment (e.g. as used in Compounds 28 and 85), $L^1$ is —$Z^1$— and $R^{10}$ is $NH_2$.

In an embodiment (e.g. as used in Compounds 26, 27, 83 and 84), $L^1$ is —$OZ^1$— and $R^{10}$ is $NH_2$.

In an embodiment (e.g. as used in Compounds 38 and 95), $L^1$ is —$C(O)N(R^7)Z^1$— and $R^{10}$ is $NH_2$.

In an embodiment (e.g. as used in Compounds 40 and 97), $L^1$ is —$C(O)Q^1$ and $R^{10}$ is $NH_2$.

In an embodiment (e.g. as used in Compounds 41 and 98), $L^1$ is —$C(O)N(R^7)Z^1Q^1$ and $R^{10}$ is $NH_2$.

In an embodiment (e.g. as used in Compounds 42, 43, 99 and 100), $L^1$ is —$OZ^1$— and $R^{10}$ is —$N\{CH_2[CH(OH)]4$-$CH_2OH\}_2$.

In an embodiment (e.g. as used in Compounds 44 and 101), $L^1$ is —$Z^1$— and $R^{10}$ is —$N\{CH_2[CH(OH)]4$-$CH_2OH\}_2$.

In an embodiment (e.g. as used in Compounds 46, 55, 56, 59, 103, 111, 112 and 115), $L^1$ is —C(O)N($R^7$)$Z^1$— and $R^{10}$ is —N{$CH_2$[CH(OH)]$_4$—$CH_2$OH}$_2$.

In an embodiment (e.g. as used in Compounds 4 48, 51, 52, 107 and 108), $L^1$ is —C(O)$Q^1$ and $R^{10}$ is —N{$CH_2$[CH(OH)]$_4$—$CH_2$OH}$_2$.

In an embodiment (e.g. as used in Compounds 49 and 105), $L^1$ is —C(O)N($R^7$)$Z^1Q^1$ and $R^{10}$ is —N{$CH_2$[CH(OH)]$_4$—$CH_2$OH}$_2$.

In an embodiment (e.g. as used in Compounds 53, 54, 109 and 110), $L^1$ is —C(O)N($R^7$)$Q^1$ and $R^{10}$ is —N{$CH_2$[CH(OH)]$_4$—$CH_2$OH}$_2$.

In an embodiment (e.g. as used in Compounds 57 and 113), $L^1$ is —C(O)N($R^7$)$Z^1$O($CH_2CH_2$O)$_n Z^2$— and $R^{10}$ is —N{$CH_2$[CH(OH)]$_4$—$CH_2$OH}$_2$.

In an embodiment (e.g. as used in Compounds 58 and 114), $L^1$ is —C(O)N($R^7$)$Z^1Q^1Q^2Z^2$— and $R^{10}$ is —N{$CH_2$[CH(OH)]$_4$—$CH_2$OH}$_2$.

In an embodiment (e.g. as used in Compounds 60 and 116), $L^1$ is —C(O)N($R^7$)$Z^1Q^1Z^2$N($R^8$)$Z^3$— and $R^{10}$ is —N{$CH_2$[CH(OH)]$_4$—$CH_2$OH}$_2$.

When $R^{10}$ is —N($R^7$)C(=N$R^9$)N($R^8$)$_2$, each of $R^7$ and $R^9$ is suitably H or $C_{1-4}$ alkyl, particularly H or methyl and especially H; and each $R^8$ is independently either H or $C_{1-8}$ alkyl optionally substituted with one or more OH groups. In the case where either or both $R^8$ groups is a $C_{1-8}$ alkyl group, it may be substituted with a plurality of OH groups, for example 2-7 OH groups. Typically, the number of OH groups will be one less than the number of carbon atoms in the alkyl group. More suitably in compounds of this type, one or preferably both, $R^8$ groups may be —$CH_2$[CH(OH)]$_m$$CH_2$OH, where m is suitably 2-6. Most suitably, m is 4 and in this case, one or preferably both the $R^8$ groups is a moiety —$CH_2$[CH(OH)]$_4$—$CH_2$OH.

In particularly suitable compounds —N($R^7$)C(=N$R^9$)N($R^8$)$_2$ is:

—NHC(=NH)—N{$CH_2$[CH(OH)]$_4$—$CH_2$OH}$_2$.

When $R^{10}$ is —N($R^7$)C(O)O$R^8$, each of $R^7$ and $R^8$ is suitably H or $C_{1-6}$ alkyl. More suitably, $R^7$ is H and $R^8$ is $C_{1-6}$ alkyl, still more suitably $C_{1-4}$ alkyl, for example t-butyl.

In still other compounds of general formula (I), $R^1$ is —O$R^{12}$ —SO$_2R^{12}$, —C(O)O$R^{12}$, —C(O)N$R^{12}R^{13}$, —C(=N$R^9$)N$R^{12}R^{13}$, -$Q^1$O$R^{12}$-$Q^1$SO$_2R^{12}$, -$Q^1$C(O)O$R^{12}$, -$Q^1$C(O)N$R^{12}R^{13}$, -$Q^1$C(=N$R^7$)N$R^{12}R^{14}$, -$Q^1Q^2$O$R^{12}$, -$Q^1$SO$_2R^{12}$, -$Q^1Q^2$C(O)O$R^{12}$, -$Q^1Q^2$C(O)N$R^{12}R^{13}$ or -$Q^1Q^2$C(=N$R^9$)N$R^{12}R^{13}$;

Suitable groups $Q^1$ and $Q^2$ are as set out above.

Suitable $R^{12}$ and $R^{13}$ groups include H and $C_{1-6}$ alkyl optionally substituted with one or more substituents selected from halo and O$R^7$.

As mentioned above, each of $R^2$ and $R^3$ is independently $C_{1-10}$ alkyl in which one or more —$CH_2$— groups is optionally replaced by —O—, —S— or —N$R^7$— and which is optionally substituted as defined above. There may, for example, be no such substituents or a single substituent.

Suitably, each of $R^2$ and $R^3$ is independently $C_{1-10}$ alkyl in which one or more —$CH_2$— groups is optionally replaced by —O— or —S— and which is optionally substituted as defined above.

Examples of $R^2$ and $R^3$ groups include —($CH_2$)$_s$$CH_3$ or ($CH_2CH_2$O)$_t$-H, either of which is optionally substituted as defined above; and wherein s is 0-9, more suitably 0-6 and still more suitably 0-3; and t is 1-3, especially 2 or 3.

Particularly suitable compounds of general formula (I) are those in which $R^2$ and $R^3$ are the same or different and are both unsubstituted $C_{1-4}$ alkyl, for example methyl or ethyl. In some such compounds $R^2$ and $R^3$ are the same and are both methyl or both ethyl. In other such compounds, one of $R^2$ and $R^3$ is methyl and the other of $R^2$ and $R^3$ is ethyl.

Suitable substituents for $R^2$ and $R^3$ include OH, SH, halo, N($R^7$)$R^8$, C(O)O$R^7$, C(O)N($R^7$)$R^8$, phenyl or pyridyl, where $R^7$ and $R^8$ are as defined above. Particularly suitable substituents for $R^2$ include OH, SH, phenyl or pyridyl, particularly OH, phenyl, pyridyl, C(O)O—$C_{1-6}$ alkyl, C(O)OH, C(O)NH$_2$ or C(O)N($R^7$)$R^8$, where each of $R^7$ and $R^8$ is $C_{1-3}$ alkyl or $R^7$ and $R^8$ together with the nitrogen atom to which they are attached form a pyrrolidine, piperidine, piperazine or morpholine ring.

In some compounds of general formula (I), at least one of $R^2$ and $R^3$ is —($CH_2$)$_s$$CH_3$, wherein s is as defined above, and is optionally substituted with a single substituent as defined above.

In some such compounds of general formula (I) at least one of $R^2$ and $R^3$ is methyl, ethyl, benzyl, pyridylmethyl, —$CH_2$OH, —$CH_2$NH$_2$, —$CH_2CH_2$OH or $CH_2CH_2$NH$_2$.

In other particularly suitable compounds, at least one of $R^2$ and $R^3$ is —$CH_2CH_2$O$CH_2CH_2$OH or —$CH_2CH_2$O$CH_2CH_2$O$CH_2CH_2$OH In suitable compounds of general formula (I), $R^4$ is H, halo, cyano or $C_{1-3}$ alkyl. In more suitable compounds of general formula (I), $R^4$ is H, chloro, bromo, cyano or methyl. In particularly suitable compounds of general formula (I), $R^4$ is H or methyl.

In other compounds of general formula (I), $R^4$ is H.

In other compounds of general formula (I), $R^4$ is methyl.

Some particularly suitable compounds of the present invention include those having a cation selected from:

2-[({6-amino-3-methyl-1H-pyrazolo[3,4-b]pyrazin-5-yl}formamido)methyl]-1,3-diethyl-6-methoxy-1H-1,3-benzodiazol-3-ium;

2-[({6-amino-3-methyl-1H-pyrazolo[3,4-b]pyrazin-5-yl}formamido)methyl]-6-carboxy-1,3-diethyl-1H-1,3-benzodiazol-3-ium;

2-[({6-amino-1H-pyrazolo[3,4-b]pyrazin-5-yl}formamido)methyl]-6-carboxy-1,3-diethyl-1H-1,3-benzodiazol-3-ium; and 2-[({6-amino-1H-pyrazolo[3,4-b]pyrazin-5-yl}formamido)methyl]-6-(4-{bis[(2S,3R,4R,5R)-2,3,4,5,6-pentahydroxyhexyl]amino}piperidine-1-carbonyl)-1,3-diethyl-1H-1,3-benzodiazol-3-ium trifluoroacetic acid;

and an anion X⁻ as defined for general formula (I).

Compounds of general formula (I) may be prepared by reacting a compound of general formula (II) or a salt or activated derivative thereof:

(II)

wherein $R^4$ and $R^5$ are as defined for general formula (I); with a salt of general formula (III):

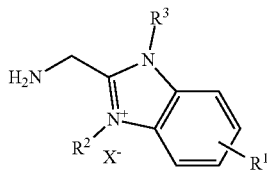

(III)

wherein $R^1$, $R^2$ and $R^3$ are as defined for general formula (I); and $X^-$ is as defined for general formula (I) and which may be the same or different from the $X^-$ of the product of general formula (I).

Suitably the reaction is carried out under basic conditions in the presence of a coupling reagent, which may generate an activated acid as an intermediate. The basic conditions may be supplied by a non-nucleophilic base such as N,N-diisopropylethylamine (DIPEA) or trimethylamine. Suitable coupling reagents include O-(7-Azabenzotriazol-1-yl)-N,N,N',N'-tetramethyluronium hexafluorophosphate (HATU), O-(Benzotriazol-1-yl)-N,N,N',N'-tetramethyluronium tetrafluoroborate (TBTU), N,N,N',N'-tetramethyl-O-(1H-benzothazol-1-yl)uronium hexafluorophosphate (HBTU) or a combination of 1-ethyl-3-(3-dimethylaminopropyl)carbodiimide (EDC) with 1-hydroxy-7-azabenzotriazole (HOAt) or hydroxybenzotriazole (HOBt).

In some cases, carbonyldiimidazole (CDI) may be used as a coupling agent.

In other cases, imidazole or a salt thereof (e.g. imidazole hydrochloride) may be used.

The reaction may be conducted at a temperature of about 10 to 50° C., more usually at 15 to 30° C., or room temperature and in an organic solvent such as N,N-dimethylformamide.

When a CDI coupling agent is used, a compound of general formula (I) may be prepared by reacting a compound of general formula (III) as defined above with an activated derivative of a compound of general formula (II), which is a compound of general formula (IVa) or (IVb):

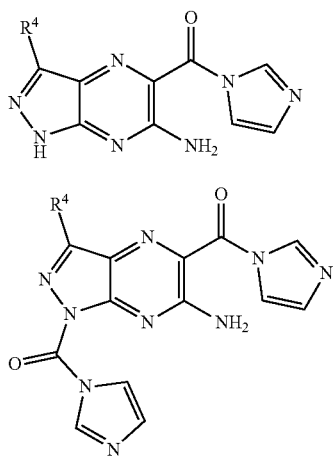

(IVa)

(IVb)

wherein $R^4$ and $R^5$ are as defined for general formula (I).

As discussed above, the reaction is suitably conducted at a temperature of about 10 to 50° C., more usually at 15 to 30° C., or room temperature and in an organic solvent such as N,N-dimethylformamide.

The activated compounds of general formula (IVa) are prepared by reacting a compound of general formula (II) as defined above or a salt thereof with carbonyl diimidazole (CDI). Suitably the reaction takes place in an organic solvent such as N,N-dimethylformamide and at a temperature of from about 10 to 30° C., more usually 15 to 25° C. or room temperature.

The activated compounds of general formula (IVb) are prepared by reacting a compound of general formula (II) as defined above, or a salt thereof, with carbonyl diimidazole (CDI) under basic conditions. Suitably the reaction takes place in an organic solvent such as N,N-dimethylformamide and at a temperature of from about 10 to 30° C., more usually 15 to 25° C. or room temperature.

In cases where the target compound of general formula (I) has an $R^1$, $R^2$, $R^3$ and/or $R^4$ substituent which is sensitive to the conditions used when the compound of general formula (III) is reacted with a compound of general formula (II) or an activated derivative thereof, for example a compound of general formula (IVa) or (IVb), the compounds of general formulae (III) may comprise a protected $R^1$, $R^2$ and/or $R^3$ substituent and/or the compounds of general formulae (II) and (IVa) or (IVb) may comprise a protected $R^4$ substituent.

Compounds of general formula (II) may be prepared by hydrolysis of a compound of general formula (V):

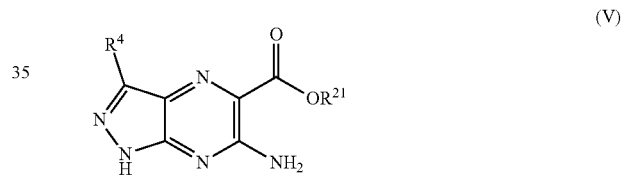

(V)

wherein $R^4$ is as defined for general formula (I) and $R^{21}$ is $C_{1-6}$ alkyl or benzyl.

Suitably, the hydrolysis is base hydrolysis such that the compound of general formula (V) is reacted with a base, suitably a strong aqueous base such as lithium hydroxide, potassium hydroxide or sodium hydroxide.

Compounds of general formula (V) wherein $R^4$ is $C_{1-6}$ alkyl and $R^{21}$ is $C_{1-6}$ alkyl or benzyl. may be prepared by reaction of a compound of general formula (XIX):

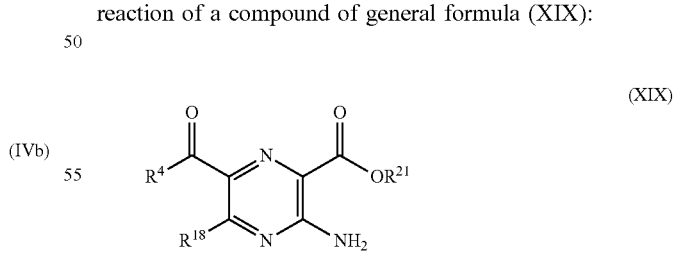

(XIX)

wherein $R^4$ is $C_{1-6}$ alkyl, $R^{21}$ is $C_{1-6}$ alkyl or benzyl and $R^{18}$ is a leaving group, for example halo such as chloro; with hydrazine hydrate.

Suitably, the reaction is carried out at elevated temperature such as 50° C.

Compounds of general formula (XIX) may be prepared by palladium catalysed reaction of of a compound of general formula (XX)

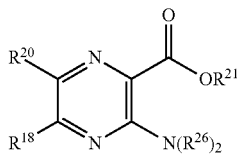

(XX)

wherein $R^{18}$ and $R^{21}$ are as defined above for general formula (XIX), $R^{20}$ is halo, for example bromo and $R^{26}$ is an amine protecting group, for example butyloxycarbonyl (Boc), fluorenylmethyloxycarbonyl (Fmoc) or benzyloxycarbonyl (Cbz);
with a stannane of general formula (XXVI):

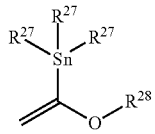

(XXVI)

wherein each $R^{27}$ is independently $C_{1-6}$ alkyl and $R^{28}$ is $C_{1-6}$ alkyl;
under reducing conditions, for example in the presence of a copper (I) salt, followed by treatment with an acid, for example hydrochloric acid, to catalyse protonation of the alkene with subsequent removal of $OR^{28}$ to give the ketone product. Treatment with the acid may also result in the by removal of the amine protecting groups $R^{26}$. This reaction is described below for the preparation of Intermediate 4.

Compounds of general formula (XX) may be prepared by protecting a compound of general formula (XXa):

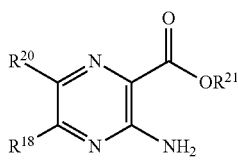

(XXa)

wherein $R^{18}$ and $R^{21}$ are as defined above for general formula (XIX) and $R^{20}$ is as defined for general formula (XX) with a suitable protecting group using standard methods.

Compounds of general formula (XIX) may be prepared directly from the compounds of general formula (XXa) using the same conditions as described above for the reaction with general formula (XX) but without the protecting groups $R^{26}$, the reaction is less selective.

Compounds of general formula (XXa) may be prepared from compounds of general formula (XXI):

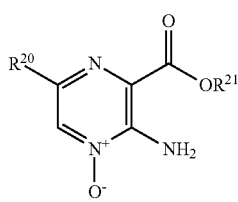

(XXI)

wherein $R^{21}$ is as defined above for general formula (XIX) and $R^{20}$ is as defined for general formula (XX) by reaction of a compound of general formula (XXIa) with a suitable halogenating agent. For example, when $R^{18}$ is chloro, the halogenating agent may be phosphorous oxychloride as described for the synthesis of Intermediate 2 below.

Compounds of general formula (XXI) may be prepared from a compound of general formula (XXII):

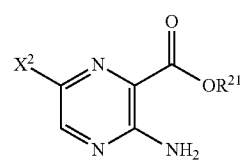

(XXII)

wherein $R^{21}$ is as defined above for general formula (XIX) and $X^2$ is as defined for general formula (XX) by oxidation, for example with metachloroperbenzoic acid (mCPBA) as described for the preparation of Intermediate 1 below.

Compounds of general formula (XXII) are well known and are commercially available or may be prepared by methods familiar to those of skill in the art.

Some compounds of general formula (V) may be converted to other compounds of general formula (V). For example, compounds of general formula (V) in which $R^4$ is halo may be prepared from compounds of general formula (V) in which $R^4$ is H by reaction with a halogenating agent such as N-chlorosuccinimide, N-bromosuccinimide or N-iodosuccinimide.

Compounds of general formula (V) in which $R^4$ is halo may be converted into compounds of general formula (V) in which $R^4$ is alkyl or cyano. Compounds in which $R^4$ is alkyl may be prepared from compounds in which $R^4$ is halo by reaction with an organometallic reagent, for example dialkyl zinc.

Compounds of general formula (V) in which $R^4$ is cyano may be prepared from compounds of general formula (V) in which $R^4$ is halo by reaction with potassium ferrocyanide. For this reaction, the nitrogen at the 5-position of the pyrrazolopyrazine ring should be protected, for example with a trimethylsilylethoxymethyl protecting group.

An alternative method for the preparation of a compound of general formula (II) is by deprotection of a compound of general formula (XXIII):

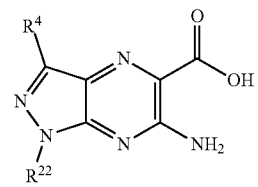

(XXIII)

wherein $R^4$ is as defined for general formula (I) and $R^{22}$ is a protecting group, for example $C_{1-8}$ alkyl, or benzyl optionally substituted with OH, halo, $C_{1-6}$ alkyl, $C_{1-6}$ alkoxy, $C_{1-6}$ haloalkyl or $C_{1-6}$ haloalkoxy.

Deprotection may be achieved by heating under acidic conditions, typically also with microwave irradiation as described for the synthesis of Intermediate 11.

A compound of general formula (XXIII) may be prepared from a compound of general formula (XXIV):

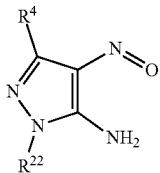
(XXIV)

wherein $R^4$ is as defined for general formula (I) and $R^{22}$ is as defined for general formula (XXIII);
by reaction with 2-cyanoacetic acid under basic conditions as described for the preparation of Intermediate 10. Suitably, the reaction is carried out at a temperature of 110-160° C., more usually 130-150° C., with microwave irradiation.

A compound of general formula (XXIV) may be prepared from a compound of general formula (XXV):

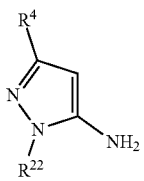
(XXV)

wherein $R^4$ is as defined for general formula (I) and $R^{22}$ is as defined for general formula (XXIII);
by reaction with amyl nitrite. Typically, the reaction is carried out with cooling, for example to −5 to 5° C., usually about 0° C. as described for the preparation of Intermediate 9.

Compounds of general formula (III) may be prepared by deprotection of compounds of general formula (VII)

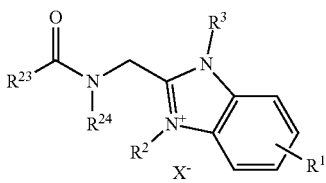
(VII)

wherein $R^1$, $R^2$ and $R^3$ are as defined for general formula (I) and $X^-$ is as defined for general formula (I) and which may be the same or different from the $X^-$ of the product of general formula (III); $R^{23}$ is $O(C_{1-6})$ alkyl optionally substituted with aryl; or aryl optionally substituted with C(O)OH; and
$R^{24}$ is H; or
$R^{23}$ and $R^{24}$ together with the carbon and nitrogen atoms to which they are attached form a heterocyclic ring, optionally fused to an aryl or heteroaryl ring and optionally containing a further =O substituent.

Alternatively, when the group $R^1$ requires protection at an earlier stage of the synthesis, the compound of general formula (III) may be prepared by deprotection of a compound of general formula (VIIa):

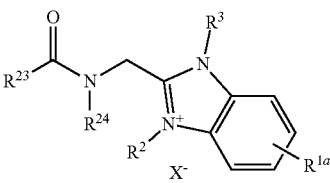
(VIIa)

wherein $R^2$ and $R^3$ are as defined for general formula (I) and $X^-$ is as defined for general formula (I) and may be the same or different from the $X^-$ of the product of general formula (III); $R^{23}$ and $R^{24}$ are as defined for general formula (VII); and $R^{1a}$ is a protected group $R^1$, for example when $R^1$ is a carboxylic acid, $R^{1a}$ may be a $C_{1-8}$ alkyl or benzyl carboxylic ester.

In some cases, the removal of the protecting group $C(O)R^{23}$ may be achieved by reaction with an acid. This is appropriate for alkyloxycarbonyl protecting groups, for example when $R^{23}$ is $^t$butyloxy. Acid deprotection is also appropriate for use with compounds of general formula (VIIa) when the protecting group $R^{1a}$ is acid sensitive as in the case of carboxylic esters.

Reaction with an acid may result in a change in the anion $X^-$. Furthermore, following reaction with an acid, the compound of formula (III) will usually be present in the form of its acid addition salt.

Other protecting groups, for example Fmoc (i.e. when $R^{23}$ is fluorenylmethyloxy), can be removed by treatment with a base, for example piperidine or morpholine.

In some suitable compounds of general formula (VIIa), $R^{23}$ is benzyloxy or fluoren-9-ylmethyloxy and $R^{1a}$ comprises another protecting group, for example $^t$butyloxycarbonyl (Boc), such that the two protecting groups are stable under different conditions. Removal of the protecting group $R^{23}$ will then result in production of a protected compound of general formula (IIIa):

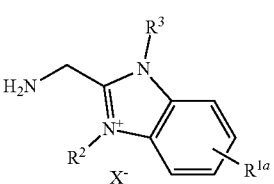
(IIIa)

wherein $R^2$, $R^3$ are described for general formula (I), $R^{1a}$ is as defined for general formula (VIIa) and $X^-$ is as defined for general formula (I) and which may be the same or different from the $X^-$ of the product of general formula (VIIa)

Examples of cyclic $N(R^{24})C(O)R^{23}$ groups include 1,3-dioxo-2,3-dihydro-1H-isoindol-2-yl.

Examples of individual $R^{23}$ groups include methoxy, ethoxy, $^n$propoxy, $^i$propoxy, $^n$butyloxy, $^s$butyloxy, $^t$butyloxy, benzyloxy, fluorenylmethyloxy and phenyl optionally substituted with C(O)OH.

When $R^{23}$ and $R^{24}$ together with the carbon and nitrogen atoms to which they are attached form a heterocyclic ring of this type, the compound of general formula (III) or (IIIa) may be synthesised by reacting the compound of general formula (VII) or (VIIa) with hydrazine hydrate. Suitably, this reaction is carried out in an alcoholic solvent such as methanol and at elevated temperature, for example about 60-90° C., typically about 75° C. as described for the synthesis of Intermediate 14 below.

Some compounds of general formula (VII) are known. For example, Intermediate 64 may be synthesised according to the procedure described in US 2015/0018313).

Other compounds of general formula (VII) and (VIIa) may be prepared from compounds of general formula (VIII) and (VIIIa):

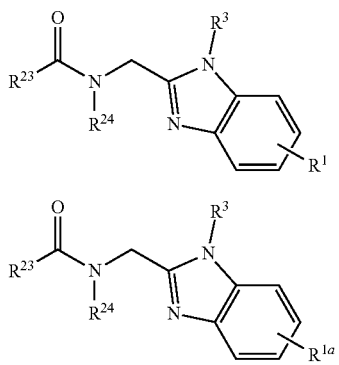

wherein $R^1$ and $R^3$ are as defined for general formula (I); $R^{1a}$ is as defined for general formula (VIIa) and $R^{23}$ and $R^{24}$ are as defined for general formula (VII);
by reaction with a compound of general formula (IX):

wherein $R^2$ is as defined for general formula (I) and $X^1$ is a leaving group such as halo; or with a compound of general formula (IXa):

wherein $X^1$ is as defined above for general formula (IX) and $R^{2a}$ is a protected $R^2$ group. For example, when the desired $R^2$ group contains one or more OH moieties, these may be protected using standard protecting groups, for example silyl protecting groups such as trimethylsilyl (TMS), ᵗbutyldimethylsilyl (TBDMS) etc.

When the route via the compound of general formula (IXa) is used, the compound of general formula (VIII) is suitably one in which $R^{23}$ is —O(C$_{1-6}$) alkyl optionally substituted with aryl, or $R^{23}$ is aryl optionally substituted with C(O)OH; and $R^{24}$ is H; because, in this case, the silyl and carbonyloxy protecting groups can be removed using an acid such as hydrogen chloride solution.

In some cases, when a compound of general formula (IX) is reacted with a compound of general formula (VIII) in which N(R$^{24}$)C(O)R$^{23}$ is a cyclic group such as 1,3-dioxo-2,3-dihydro-1H-isoindol-2-yl, the reaction may be accompanied by ring opening. Thus a compound of general formula (VIII) in which N(R$^{24}$)C(O)R$^{23}$ is 1,3-dioxo-2,3-dihydro-1H-isoindol-2-yl may give rise to a product of general formula (VII) in which N(R$^{24}$)C(O)R$^{23}$ is:

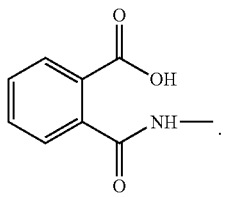

Some compounds of general formula (VIII) are known. For example, Intermediate 13 (see examples below) may be synthesised by the route set out in US 2015/0018314 A1.

Some compounds of general formulae (VII) and (VIII) may be synthesised from other compounds of general formulae (VII) and (VIII). For example, a compound of general formula (VIII) in which $R^1$ is C(O)OR$^5$, where $R^5$ is other than H may be converted to a compound of general formula (VIII) in which $R^1$ is C(O)OH by hydrolysis, for example with a base, suitably an alkali metal hydroxide such as lithium hydroxide. The compound in which $R^1$ is C(O)OH may then be converted to a compound in which $R^1$ is C(O)OR$^{12}$, where $R^{12}$ is other than H by reaction with a compound of general formula (X):

(X)

wherein $R^{12}$ is as defined for general formula (I) except that it is not H and $R^{25}$ is C$_{1-4}$ alkyl.

This type of conversion is exemplified below in the synthesis of Intermediate 20.

Compounds of general formula (VIII) can also be converted to other compounds of general formula (VIII) with a different $R^{23}$ and/or $R^{24}$ groups. For example, when $R^{23}$ is O(C$_{1-6}$) alkyl optionally substituted with aryl, or $R^{23}$ is aryl optionally substituted with C(O)OH; and $R^{24}$ is H, the compound of general formula (VIII) may be hydrolysed, for example by reaction with HCl in a solvent such as dioxane, to give a compound of general formula (XI):

(XI)

wherein $R^1$ and $R^3$ are as defined in general formula (I). This is exemplified by the synthesis of Intermediate 18 from Intermediate 17.

The compound of general formula (XI) may be re-protected to obtain a new compound of general formula (VIII), for example by reaction with a compound of general formula (XII):

(XII)

wherein $R^{23}$ is as defined above for general formula (VII). The reaction may be conducted in the presence of a base such as trimethylamine in a polar organic solvent, for example dichloromethane and at a temperature of from 10 to 30° C., more usually 15 to 25° C., typically at room temperature. An example of this type of process is the synthesis of Intermediate 19 from Intermediate 18.

Compounds of general formula (VII) and (VIII) may also be synthesised from other compounds of general formula (VII) and (VIII) using the methods described for the preparation of Intermediates 20, 72, 73, 76, 77, 80, 83, 84, 87, 88, 93 and 94 below.

Thus, for example a compound of general formula (VII) or (VIII) in which $R^1$ is halo, particularly bromo, may be reacted with an alkyne to give a compound of general formula (VII) in which $R^1$ is -$L^1R^{10}$, where $L^1$ comprises an alkynylene group. The reaction may be catalysed with a copper (I) salt, for example copper (I) iodide. This is illustrated in the synthesis of Intermediate 72.

A compound of general formula (VII) or (VIII) in which $R^1$ is halo, particularly bromo, may also be reacted with a compound of general formula (XX):

$R^{1a}$—$X^2$ (XX)

where $R^{1a}$ is as defined above for $R^1$ except that it is not halo and $X^2$ is an organoborane group, for example 4,4,5,5-tetramethyl-1,3,2-dioxaborolan-2-yl. A reaction of this type is used in the preparation of Intermediate 76.

Compounds of general formulae (VII) and (VIII) in which $R^1$ is -$L^1R^{10}$, where $L^1$ comprises an alkenylene, alkynylene or partially saturated carbocyclyl or heterocyclyl moiety may be reduced, suitably by catalytic hydrogenation, to give compounds of formula (VII) in which $L^1$ comprises an alkylene or saturated carbocyclyl or heterocyclyl moiety. Examples of this are shown in the synthesis of Intermediate 73 below.

Compounds of general formulae (VII) and (VIII) in which $R^1$ is C(O)OH may be esterified to give compounds of general formulae (VII) and (VIII) in which $R^1$ is $C(O)OR^{12}$, where $R^{12}$ is as defined above except that it is not H. An example of this is the preparation of Intermediate 20, in which the carboxylic acid derivative Intermediate 19 is reacted with 1,1-di-tert-butoxy-N,N-dimethylmethanamine.

Compounds of general formulae (VII) and (VIII) in which $R^1$ or $R^3$ (for compounds of general formula (VIII)) comprises a —$C(O)OR^{12}$ or —$C(O)OR^7$ group in which $R^{12}$ or $R^7$ is other than H; or a —$C(O)N(R^7)R^8$ group can be converted to compounds in which $R^1$ or $R^3$ comprises a —C(O)OH group by hydrolysis. In some cases, base hydrolysis may be used, for example using a base such as lithium hydroxide, sodium hydroxide or potassium hydroxide. Alternatively, the hydrolysis may be acid hydrolysis using an acid such as hydrochloric acid. This is particularly suitable when the $R^{12}$ or $R^7$ group is an alkyl group such as tert-butyl.

Compounds of general formulae (VII) and (VIII) in which $R^1$ is C(O)OH may be converted to compounds in which $R^1$ is —$C(O)NR^{12}R^{13}$, wherein $R^{12}$ and $R^{13}$ are as defined above, or in which $R^1$ is -$L^1R^{10}$, wherein $L^1$ is
—$C(O)N(R^7)Z^1$—, —$C(O)N(R^7)Q^1$-, —$C(O)N(R^7)$ $Z^1Q^1$-, —$C(O)N(R^7)Z^1Q^1Z^2$—, —$C(O)N(R^7)Q^1Z^1$—, —$C(O)N(R^7)Q^1Q^2$-, —$C(O)N(R^7)Q^1Q^2Z^1$—, —$C(O)$ $N(R^7)Z^1Q^1Q^2Z^2$—, —$C(O)N(R^7)Z^1O(CH_2CH_2O)_n$ $Z^2$—, —$C(O)N(R^7)Z^1O(CH_2O)_nZ^2$—, —$C(O)N(R^7)$ $Z^1Q^1Z^2N(R^8)Z^3$—, —$C(O)N(R^7)Z^1N(R^8)Z^2$—, —$C(O)N(R^7)Q^1Z^1N(R^8)Z^2$—, —$C(O)N(R^7)$ $Z^1Q^1OQ^2OQ^3$- or —$C(O)N(R^7)Z^1Q^1OQ^2OQ^3Z^2$—;

especially
—$C(O)N(R^7)Z^1$—, —$C(O)N(R^7)Q^1$-, —$C(O)N(R^7)$ $Z^1Q^1$-, —$C(O)N(R^7)Z^1Q^1Z^2$—, —$C(O)N(R^7)Q^1Z^1$—, —$C(O)N(R^7)Q^1Q^2$- or —$C(O)N(R^7)Q^1Q^2Z^1$—;

by reaction with an appropriate amine or ammonium salt.

Compounds of general formulae (VII) and (VIII) in which $R^1$ is $L^1R^{10}$ where $R^{10}$ is —$N(R^7)$—$C(O)OR^8$ can be converted to compounds of general formulae (VII) and (VIII) in which $R^1$ is $L^1R^{10}$ where $R^{10}$ is —$NH_2$ by hydrolysis, for example acid hydrolysis using hydrochloric acid in a solvent such as dioxane. An example of this is the synthesis of Intermediate 83.

These compounds can in turn be converted to compounds of general formulae (VII) and (VIII) in which $R^{10}$ is N(H)$R^7$ or $N(R^7)R^8$ where $R^7$ is $CH_2$—$R^{7a}$ and $R^8$ is $CH_2$—$R^{8a}$ and each $R^{7a}$ and $R^{8a}$ is independently selected from H or $C_{1-11}$ alkyl optionally substituted with one or more halo or OH groups or protected OH groups. The conversion can be achieved by reductive amination using a reducing agent such as a hydride, for example sodium cyanoborohydride, with an aldehyde or acetal as shown below:

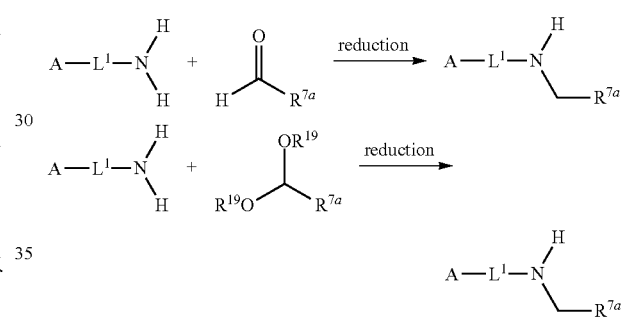

where $L^1$ is as defined for general formula (I);
$R^7$ is —$CH_2R^{7a}$, where $R^{7a}$ is H or $C_{1-11}$ alkyl optionally substituted with one or more halo or OH groups; and
$R^{19}$ is $C_{1-12}$ alkyl; and
A is a fragment of a compound of general formula (VII) or (VIII) not including $R^1$ as follows:

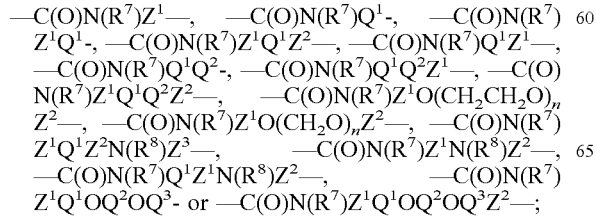

In other cases, a cyclic hemiacetal can be used in place of the aldehyde or acetal. The scheme below shows an example where a 6-membered hemiacetal is used to give a compound in which $R^1$ is $L^1$-$NHR^7$ where $R^7$ is $(CH_2)_4CH_2OH$:

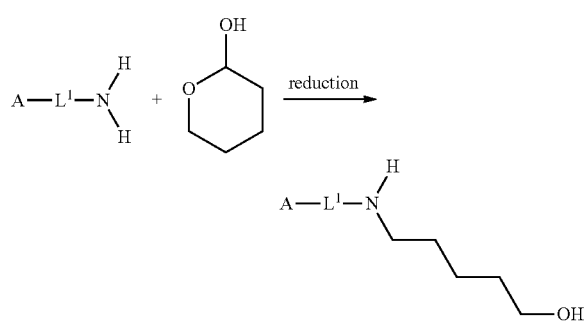

wherein A and $L^1$ are as defined above.

If a large excess of the aldehyde, acetal or cyclic hemiacetal is used, both of the amine hydrogen atoms will be replaced. In some cases, it may be possible to react successively with different aldehydes, acetals or hemiacetals to yield compounds in which $R^7$ and $R^8$ are different.

More suitably in these product compounds of general formulae (VII) or (VIII) both $R^{7a}$ and $R^{8a}$ are $C_{1-11}$ alkyl optionally substituted with one or more halo or OH or protected OH groups; and most suitably each $R^7$ and $R^8$ is $CH_2[CH(OH)]_4CH_2OH$, wherein OH groups are optionally protected, for example as acetals, such as benzylidene acetals.

Examples of this type of reaction include the conversion of Intermediate 83 to Intermediate 84 and the conversion of Intermediate 87 to Intermediate 88.

Similarly, compounds of general formulae (VII) and (VIII) in which $R^1$ is $L^1R^{10}$ where:

Similarly, compounds of general formulae (VII) and (VIII) in which $L^1$ comprises a moiety $Q^1$, $Q^2$ or $Q^3$ linked to $R^{10}$ via a ring nitrogen atom and in which $R^{10}$ is $C(O)OR^7$;

may be converted to compounds in which $R^{10}$ is H by hydrolysis, for example acid hydrolysis using hydrochloric acid in a solvent such as dioxane.

An example of a reaction of this type is the preparation of Intermediate 93 from Intermediate 92.

Compounds of general formulae (VII) and (VIII) in which $L^1$ comprises a moiety $Q^1$, $Q^2$ or $Q^3$ linked to $R^{10}$ via a ring nitrogen atom and in which $R^{10}$ is H can be converted to compounds of general formula (I) in which the $Q^1$, $Q^2$ or $Q^3$ moiety is linked is linked to a $Z^1$, $Z^2$ or $Z^3$ moiety, wherein $Z^1$, $Z^2$ or $Z^3$ is:

$CH_2$—$C_{1-11}$ alkylene, $CH_2$—$C_{2-11}$ alkenylene, $CH_2$—$C_{2-11}$ alkynylene any of which is optionally substituted by one or more halo, OH, $C(O)NR^{15}R^{16}$, $C(O)OR^{15}$ or $NR^{15}R^{16}$; and each $R^{15}$ and $R^{16}$ is independently H or $C_{1-6}$ alkyl;
and $R^{10}$ is H;

by reductive amination with an aldehyde, acetal or cyclic hemiacetal equivalent compound using a method similar to that described above for the conversion of compounds of general formulae (VII) and (VIII) in which $R^1$ is $L^1NH_2$ to compounds of general formulae (VII) and (VIII) in which $R^1$ is $L^1N(R^7)R^8$ where $R^7$ is $CH_2$—$R^{7a}$ and $R^8$ is $CH_2$—$R^{8a}$ and each $R^{7a}$ and $R^{8a}$ is independently selected from H or $C_{1-11}$ alkyl optionally substituted with one or more halo or OH groups.

More suitably in these product compounds of general formulae (VII) or (VIII) $Z^1$, $Z^2$ or $Z^3$ is $CH_2$—$C_{1-11}$ alkyl optionally substituted with one or more halo or OH groups; and most suitably is $CH_2[CH(OH)]_4CH_2OH$, wherein OH groups are optionally protected, for example as acetals, such as benzylidene acetals.

An example of this process is shown in the preparation of Intermediate 94.

Compounds of general formulae (VII) and (VIII) in which $R^1$ is $L^1R^{10}$ and $R^{10}$ is $NH_2$ can be converted into compounds in which $R^{10}$ is —$NHC(=NR^9)N(R^8)_2$ by reaction with a carboximidamide or a salt thereof, for example 1,2,4-triazole carboximidamide hydrochloride.

Compounds of general formula (VIII) may also be prepared from compounds of general formula (XIII):

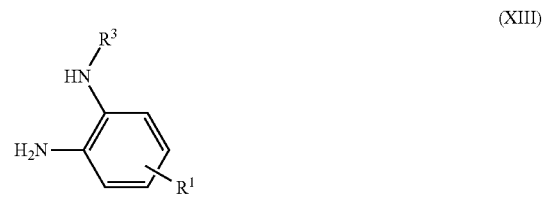

wherein $R^1$ and $R^3$ are as defined for general formula (I);
by reaction with a compound of general formula (XIV):

wherein $R^{23}$ is as defined above for general formula (VII).

The reaction suitably takes place in the presence of a base, typically a non-nucleophilic base, for example an amine such as N,N-diisopropylethylamine (DIPEA) or triethylamine and a peptide coupling agent, for example HATU, TBTU, HBTU or a combination of EDC with HOAt or HOBt. The reaction is suitably conducted at a temperature of about 10 to 30° C., usually 15 to 25° C., for example at room temperature. Suitable reaction solvents include organic solvents such as N,N-dimethylformamide (DMF).

Compounds of general formulae (XIII) and (XIV) are known and are readily available or may be prepared by methods known to those of skill in the art.

Alternatively, compounds of general formula (XIII) may be prepared from compounds of general formula (XV):

wherein $R^1$ and $R^3$ are as defined for general formula (I);
by catalytic hydrogenation, suitably using a palladium catalyst.

The hydrogenation is suitably carried out at 1 atmosphere pressure and at a temperature of about 10 to 30° C., usually 15 to 25° C., for example at room temperature.

The product of general formula (XIII) can be reacted directly with a compound of general formula (XIV) as described above without further isolation or purification steps.

Compounds of general formula (XV) may be prepared from compounds of general formula (XVI):

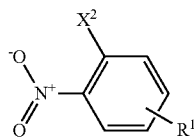

(XVI)

wherein $R^1$ is as defined for general formula (I) and $X^2$ is a leaving group, particularly a halo group such as chloro or fluoro;

by reaction with a compound of general formula (XVII): $R^3$—$NH_2$ (XVII) wherein $R^3$ is as defined for general formula (I).

The reaction is suitably carried out under pressure, at a temperature of about 30-70° C., more usually about 40-60° C., typically about 50° C. and in an organic solvent such as tetrahydrofuran.

Compounds of general formulae (XVI) and (XVII) are known and are readily available or may be prepared by methods known to those of skill in the art.

An alternative method for the preparation of a compound of general formula (I) is by reaction of a compound of general formula (XVIII):

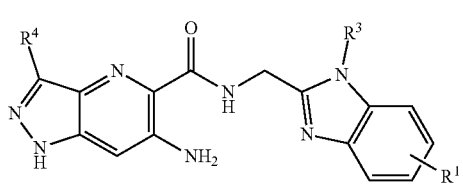

(XVIII)

wherein $R^1$, $R^3$ and $R^4$ are as defined for general formula (I); with a compound of general formula (IX) or (IXA) as defined above under conditions similar to those described above for the reaction of the compound of general formula (VIII) with the compound of general formula (IX) or (IXA).

Compounds of general formula (I) may also be synthesised from other compounds of general formula (I), for example using the method described in Example 4 below. In general, methods of converting compounds of general formulae (VI) and (VIII) to other compounds of general formulae (VI) and (VIII) may also be applied to compound of general formula (I) and vice versa.

Thus, for example, compounds of general formula (I) in which $R^3$ comprises a —C(O)$OR^7$ group in which $R^7$ is other than H or a —C(O)N($R^7$)$R^8$ group can be converted to compounds in which $R^3$ comprises a —C(O)OH or C(O)O$^-$ group by hydrolysis. In some cases the hydrolysis may be base hydrolysis, for example using a base such as lithium hydroxide, sodium hydroxide or potassium hydroxide. Alternatively, acid hydrolysis may be employed, for example using hydrochloric acid.

Compounds of general formula (I) in which $R^1$ is $L^1R^{10}$ where $R^{10}$ is —N($R^7$)—C(O)$OR^8$ can be converted to compounds of general formula (I) in which $R^1$ is $L^1R^{10}$ where $R^{10}$ is —NH$R^7$ by hydrolysis, for example acid hydrolysis using hydrochloric acid in a solvent such as dioxane. Suitably $R^7$ is H such that in the product compound of general formula (I) $R^{10}$ is $NH_2$.

Compounds of general formula (I) in which $R^1$ is $LR^{10}$, wherein $L^1$ comprises a moiety $Q^1$, $Q^2$ or $Q^3$ which is linked to $R^{10}$ via a ring nitrogen atom and in which $R^{10}$ is C(O)$OR^7$ can be converted to compounds of formula (I) in which $R^{10}$ is H by a similar method, i.e. by hydrolysis, for example acid hydrolysis using hydrochloric acid in a solvent such as dioxane.

The compounds of formula (I) in which $R^1$ is $LR^{10}$, and $R^{10}$ is $NH_2$ can in turn be converted to compounds of general formula (I) in which $R^{10}$ is N($R^7$)$R^8$ where $R^7$ is $CH_2$—$R^{7a}$ and $R^8$ is $CH_2$—$R^{8a}$ and one of $R^{7a}$ and $R^{8a}$ is $C_{1-11}$ alkyl optionally substituted with one or more halo or OH groups; and the other of $R^{7a}$ and $R^{8a}$ is H or $C_{1-11}$ alkyl optionally substituted with one or more halo or OH groups. Similarly, the compounds of general formula (I) in which $R^1$ is $LR^{10}$, and $L^1$ comprises a moiety $Q^1Q^2$ or $Q^3$ linked to $R^{10}$ via a ring nitrogen atom and in which $R^{10}$ is H can be converted to compounds of general formula (I) in which $Q^1$, $Q^2$ or $Q^3$ is linked to a $Z^1$, $Z^2$ or $Z^3$ moiety via a ring nitrogen atom, wherein $Z^1$, $Z^2$ or $Z^3$ is $CH_2$—$C_{1-11}$ alkyl optionally substituted with one or more halo or OH groups; and $R^{10}$ is H. These conversions can be achieved by reductive amination with an aldehyde, acetal or cyclic hemiacetal equivalent compound using a similar method to that described above for the compounds of general formulae (VII) and (VIII). Examples of this type of reaction include the methods in which:

a compound in which $L^1$ is a moiety —$Z^1$— and $R^{10}$ is $NH_2$ is reacted with 4,6-O-benzylidene-D-glucopyranose to give a product where $R^{10}$ is —N{$CH_2$[CH(OH)]$_4$—$CH_2$OH}2; and a compound where $L^1$ is a moiety -$Q^1Q^2$- in which $Q^2$ is linked to $R^{10}$ via a ring nitrogen atom and $R^{10}$ is H is reacted with 4,6-O-benzylidene-D-glucopyranose to give a product in which $L^1$ is $Q^1Q^2Z^1$, where $Z^1$ is $CH_2$[CH (OH)]$_4CH_2$O—; and $R^{10}$ is H.

Compounds in which $R^1$ is $L^1R^{10}$ and $R^{10}$ is $NH_2$ can be converted into compounds in which $R^{10}$ is —NHC(=$NR^9$)N($R^8$)$_2$ by reaction with a carboximidamide or a salt thereof, for example 1,2,4-triazole carboximidamide hydrochloride.

Compounds in which $R^1$ is C(O)OH may be converted to compounds in which $R^1$ is —C(O)N$R^{12}R^{13}$, wherein $R^{12}$ and $R^{13}$ are as defined above, or in which $R^1$ is -$L^1R^{10}$, wherein $L^1$ is —C(O)N($R^7$)$Z^1$—, —C(O)N($R^7$)$Q^1$-, —C(O)N($R^7$) $Z^1Q^1$-, —C(O)N($R^7$)$Z^1Q^1Z^2$—, —C(O)N($R^7$)$Q^1Z^1$—, —C(O)N($R^7$)$Q^1Q^2$-, —C(O)N($R^7$)$Q^1Q^2$-$L^1$-, —C(O) N($R^7$)$Z^1Q^1Q^2Z^2$—, —C(O)N($R^7$)$Z^1$O($CH_2CH_2$O)$_n$ $Z^2$— —C(O)N($R^7$)$Z^1$O($CH_2$O)$_n$$Z^2$—, —C(O)N($R^7$) $Z^1Q^1Z^2$N($R^8$)$Z^3$—, —C(O)N($R^7$)$Z^1$N($R^8$)$Z^2$—, —C(O)N($R^7$)$Q^1Z^1$N($R^8$)$Z^2$—, —C(O)N($R^7$) $Z^1Q^1$O$Q^2$O$Q^3$-, —C(O) N($R^7$)$Z^1Q^1$O$Q^2$O$Q^3Z^2$—; or $L^1$ is —C(O)$Q^1$-, —C(O)$Q^1Z^1$—, —C(O)$Q^1Q^2$-, —C(O) $Q^1Q^2Z^1$—, —C(O)$Q^1$N($R^7$)C(O)$Z^1$—, —C(O)$Q^1$N ($R^7$)C(O)$Z^1Q^2$-, —C(O)$Q^1$N($R^7$)C(O)$Z^1Q^2Q^3$- or —C(O)$Q^1$N$R^7$)C(O)$Z^1Q^2Z^2$—, wherein $Q^1$ is a heterocyclyl ring linked to the —C(O) moiety via a ring nitrogen atom;

by reaction with an appropriate amine or ammonium salt.

Suitably the reaction is carried out under basic conditions in the presence of a coupling reagent. The basic conditions may be supplied by a non-nucleophilic base such as N,N-diisopropylethylamine (DIPEA) or trimethylamine. Suitable coupling reagents include O-(7-Azabenzotriazol-1-yl)-N,N, N',N'-tetramethyluronium hexafluorophosphate (HATU), O-(Benzotriazol-1-yl)-N,N,N',N'-tetramethyluronium tetrafluoroborate (TBTU), N,N,N',N'-tetramethyl-O-(1H-benzotriazol-1-yl)uronium hexafluorophosphate (HBTU) or a combination of 1-ethyl-3-(3-dimethylaminopropyl)carbodiimide (EDC) with 1-hydroxy-7-azabenzotriazole (HOAt) or hydroxybenzotriazole (HOBt).

In some compounds of the invention, $L^1$ is —C(O)N($R^7$) $Z^1$— where $R^7$ is H and $Z^1$ is as defined above; $R^{10}$ is —N($R^7$)—C(O)O$R^8$; $R^7$ is H and $R^8$ is as defined above.

In some compounds of the invention, $L^1$ is —C(O)N($R^7$) $Q^1$- where $R^7$ is H and $Q^1$ is heterocyclyl linked to $R^{10}$ via a ring nitrogen atom; $R^{10}$ is —C(O)O$R^7$ where $R^7$ is as defined above.

In some compounds of the invention, $L^1$ is —C(O)$Q^1$- where $Q^1$ is heterocyclyl linked to C(O) via a ring nitrogen atom and to $R^{10}$ via a ring carbon atom; $R^{10}$ is —N($R^7$)—C(O)O$R^8$; $R^7$ is H and $R^8$ is as defined above.

In some compounds of the invention, $L^1$ is —C(O)N($R^7$) $Z^1Q^1$- where $R^7$ is H, $Z^1$ is as defined above, $Q^1$ is heterocyclyl linked to $R^{10}$ via a ring carbon atom; $R^{10}$ is —N($R^7$)—C(O)O$R^8$; $R^7$ is H and $R^8$ is as defined above.

In some compounds of the invention, $L^1$ is C(O)N($R^7$)$Z^1$ where $R^7$ is H or methyl and $Z^1$ is as defined above; $R^{10}$ is N($R^7$)$R^8$, where $R^7$ and $R^8$ are both $C_{1-12}$ alkyl substituted with one or more OH groups.

In some compounds of the invention, $L^1$ is C(O)N($R^7$) $Q^1Z^1$ where $R^7$ is H, $Q^1$ is linked to —C(O)N($R^7$)— via a ring carbon atom and to $Z^1$ via a ring nitrogen, $Z^1$ is $C_{1-12}$ alkylene substituted with one or more OH; $R^{10}$ is H.

In some compounds of the invention, $L^1$ is C(O)$Q^1$, where $Q^1$ is linked to C(O) via a ring nitrogen atom; $R^{10}$ is N($R^7$)$R^8$, where $R^7$ and $R^8$ are both $C_{1-12}$ alkyl substituted with one or more OH groups.

In some compounds of the invention, $L^1$ is —C(O)N($R^7$) $Z^1Q^1$- where $R^7$ is H; $Z^1$ is as defined above, $Q^1$ is linked to $R^{10}$ via a ring carbon atom, $R^{10}$ is N($R^7$)$R^8$, where $R^7$ and $R^8$ are both $C_{1-12}$ alkyl substituted with one or more OH groups.

In some compounds of the invention, $L^1$ is —C(O) $Q^1Z^1$— where $Q^1$ is linked to the C(O) moiety via a ring nitrogen atom and $Z^1$ as defined above; $R^{10}$ is N($R^7$)$R^8$, where $R^7$ and $R^8$ are both $C_{1-12}$ alkyl substituted with one or more OH groups.

In some compounds of the invention, $L^1$ is —C(O)N($R^7$) $Q^1$- where $R^7$ is H, $Q^1$ is linked to —C(O)N($R^7$)— via a ring carbon atom and to $R^{10}$ via a ring nitrogen atom; $R^{10}$ is N($R^7$)$R^8$, where $R^7$ and $R^8$ are both $C_{1-12}$ alkyl substituted with one or more OH groups.

In some compounds of the invention, $L^1$ is —C(O)N($R^7$) $Z^1O(CH_2CH_2O)_nZ^2$, where $R^7$ is H, $Z^1$, n and $Z^2$ are as defined above; $R^{10}$ is N($R^7$)$R^8$, where $R^7$ and $R^8$ are both $C_{1-12}$ alkyl substituted with one or more OH groups.

In some compounds of the invention, $L^1$ is —C(O)N($R^7$) $Z^1Q^1Q^2Z^2$—, where $R^7$ is H, $Z^1$, $Q^1$, $Q^2$ and $Z^2$ are as defined above; $R^{10}$ is N($R^7$)$R^8$, where $R^7$ and $R^8$ are both $C_{1-12}$ alkyl substituted with one or more OH groups.

The amines or ammonium salts which react with the compounds of general formulae (I), (VII) or (VIII) in which $R^1$ is C(O)OH are described below. For example, an amine of general formula (XXX):

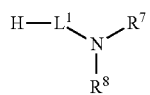

(XXX)

wherein $R^7$ and $R^8$ are as defined for general formula (I); $L^1$ is as defined for general formula (I) and is linked to H via an amine of a $Z^1$ moiety or a ring nitrogen atom of a $Q^1$ moiety;

may be prepared from a protected compound of general formula (XXXI):

(XXXI)

wherein $R^7$ and $R^8$ are as defined for general formula (I), $L^1$ is as defined for general formula (XXX) and $R^{30}$ is an amine protecting group such as fluorenylmethyloxycarbonyl (Fmoc), butyloxycarbonyl (Boc) or benzyloxycarbonyl (Cbz). Deprotection may be by hydrogenation for compounds where $R^{30}$ is Cbz or by reaction with an acid such as hydrochloric or hydrobromic acid in the case where $R^{30}$ is a protecting group such as Boc or Cbz or with a weak base such as morpholine or piperidine when $R^{30}$ is a protecting group such as Fmoc.

When $R^7$ and/or $R^8$ is a group —$CH_2[CH(OH)]_4CH_2OH$, this may be protected in the compound of general formula (XXXI), for example as a benzylidene acetal.

An amine of general formula (XXXI) in which $R^7$ and/or $R^8$ is a group —$CH_2[CH(OH)]_4CH_2OH$, protected as a benzylidene acetal may be reacted with a compound of general formula (VII) or (VIII). In the resulting product, when the protecting group $R^{23}$ is an acid labile group such as Boc, the protecting group $R^{23}$ and the benzylidene acetal protecting groups can be removed simultaneously using an acid. In some cases, however, a two step deprotection process may be used wherein the $R^{23}$ group is removed by hydrogenation and the benzylidene acetal is subsequently removed by treatment with an acid. When the protecting group $R^{23}$ is a group such as Fmoc it may be removed by treatment with a base as described above. Treatment with an acid will then be required to remove the benzylidene acetal protection.

The preparation of other intermediates which can be used to react with compounds of general formulae (I), (VII) or (VIII) to convert them to other compounds of general formulae (I), (VII) or (VIII) is described below.

The compounds of general formula (I) are ENaC blockers and are therefore useful in the treatment or prevention of respiratory diseases and conditions.

Therefore in a further aspect of the invention there is provided a compound of general formula (I) for use in medicine.

Suitably, the compound of general formula (I) is for use in the treatment or prophylaxis of a disease or condition mediated by ENaC.

There is also provided:

A compound of general formula (I) for use in the treatment or prophylaxis of respiratory diseases and conditions.

A compound of general formula (I) for use in the treatment or prophylaxis of skin conditions or ocular conditions.

The invention further provides:

The use of a compound of general formula (I) in the preparation of a medicament for the treatment or prophylaxis of respiratory diseases and conditions.

The use of a compound of general formula (I) in the preparation of a medicament for the treatment or prophylaxis of skin conditions or ocular conditions There is also provided:

A method for the treatment or prophylaxis of respiratory diseases and conditions, the method comprising administering to a patient in need of such treatment an effective amount of a compound of general formula (I).

A method for the treatment or prophylaxis of skin conditions and ocular conditions, the method comprising administering to a patient in need of such treatment an effective amount of a compound of general formula (I).

Respiratory diseases and conditions which may be treated by the compounds of general formula (I) include cystic fibrosis, chronic obstructive pulmonary disease (COPD), chronic bronchitis, emphysema, bronchiectasis, including non-cystic fibrosis bronchiectasis, asthma and primary ciliary dyskinesia.

Skin conditions which may be treated by the compounds of the present invention include psoriasis, atopic dermatitis and ichthyosis.

Ocular conditions which may be treated by the compounds of the present invention included dry eye disease.

Compounds of the present invention have good ENaC blocking activity. They are particularly suitable for treating respiratory diseases because they have a prolonged retention time in the lungs.

The patient to be treated is suitably a mammal and more suitably a human.

The compounds of general formula (I) may be administered in a pharmaceutical composition and therefore in a further aspect of the invention there is provided a pharmaceutical composition comprising a compound of general formula (I) and a pharmaceutically acceptable excipient. Other pharmacologically active materials may also be present, as considered appropriate or advisable for the disease or condition being treated or prevented.

The carrier, or, if more than one be present, each of the carriers, must be acceptable in the sense of being compatible with the other ingredients of the formulation and not deleterious to the recipient.

The formulations include those suitable for oral, rectal, nasal, bronchial (inhaled), topical (including dermal, transdermal, eye drops, buccal and sublingual), vaginal or parenteral (including subcutaneous, intramuscular, intravenous and intradermal) administration and may be prepared by any methods well known in the art of pharmacy.

The route of administration will depend upon the condition to be treated but preferred compositions are formulated for oral, nasal, bronchial or topical administration.

The composition may be prepared by bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate, stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

More suitably a compound of formula (I) is administered topically to the lung, eye or skin. Hence there is provided according to the invention a pharmaceutical composition comprising a compound of the general formula (I) optionally in combination with one or more topically acceptable diluents or carriers.

For topical application to the skin, compounds of general formula (I) may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40%-99.5% e.g. 40%-90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a non-pressurised formulation such as an aqueous solution or suspension. These may be administered by means of a nebuliser e.g. one that can be hand-held and portable or for home or hospital use (ie non-portable). The formulation may comprise excipients such as water, buffers, tonicity adjusting agents, pH adjusting agents, surfactants and co-solvents. Suspension liquid and aerosol formulations (whether pressurised or unpressurised) will typically contain the compound of the invention in finely divided form, for example with a $D_{50}$ of 0.5-10 μm e.g. around 1-5 μm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

Topical administration to the lung may also be achieved by use of a dry-powder formulation. A dry powder formulation will contain the compound of the disclosure in finely divided form, typically with a mass mean diameter (MMAD) of 1-10 μm or a $D_{50}$ of 0.5-10 μm e.g. around 1-5 μm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of comparatively large particle size e.g. a mass mean diameter (MMAD) of 50 μm or more, e.g. 100 μm or more or a $D_{50}$ of 40-150 μm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac®70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients. Thus in one embodiment a dry powder formulation according the present disclosure comprises magnesium or calcium stearate. Such formulations may have superior chemical and/or physical stability especially when such formulations also contain lactose.

A dry powder formulation is typically delivered using a dry powder inhaler (DPI) device. Example dry powder delivery systems include SPINHALER®, DISKHALER®, TURBOHALER®, DISKUS®, SKYEHALER®, ACCUHALER® and CLICKHALER®. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

In one embodiment a compound of general formula (I) is provided as a micronized dry powder formulation, for example comprising lactose of a suitable grade.

Thus, as an aspect of the invention there is provided a pharmaceutical composition comprising a compound of general formula (I) in particulate form in combination with particulate lactose, said composition optionally comprising magnesium stearate.

In one embodiment a compound of general formula (I) is provided as a micronized dry powder formulation, comprising lactose of a suitable grade and magnesium stearate, filled into a device such as DISKUS. Suitably, such a device is a multidose device, for example the formulation is filled into blisters for use in a multi-unit dose device such as DISKUS.

In another embodiment a compound of general formula (I) is provided as a micronized dry powder formulation, for example comprising lactose of a suitable grade, filled into hard shell capsules for use in a single dose device such as AEROLISER.

In another embodiment a compound of general formula (I) is provided as a micronized dry powder formulation, comprising lactose of a suitable grade and magnesium stearate, filled into hard shell capsules for use in a single dose device such as AEROLISER.

In another embodiment a compound of general formula (I) is provided as a fine powder for use in an inhalation dosage form wherein the powder is in fine particles with a $D_{50}$ of 0.5-10 μm e.g. around 1-5 μm, that have been produced by a size reduction process other than jet mill micronisation e.g. spray drying, spray freezing, microfluidisation, high pressure homogenisation, super critical fluid crystallisation, ultrasonic crystallisation or combinations of these methods thereof, or other suitable particle formation methods known in the art that are used to produce fine particles with an aerodynamic particle size of 0.5-10 μm. The resultant particle size distribution may be measured using laser diffraction (e.g. with a Malvern Mastersizer 2000S instrument). The particles may either comprise the compound alone or in combination with suitable other excipients that may aid the processing. The resultant fine particles may form the final formulation for delivery to humans or may optionally be further formulated with other suitable excipients to facilitate delivery in an acceptable dosage form.

The compound of the invention may also be administered rectally, for example in the form of suppositories or enemas, which include aqueous or oily solutions as well as suspensions and emulsions and foams. Such compositions are prepared following standard procedures, well known by those skilled in the art. For example, suppositories can be prepared by mixing the active ingredient with a conventional suppository base such as cocoa butter or other glycerides. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the compound of general formula (I) will be about 0.0001 to less than 4.0% (w/w).

Preferably, for topical ocular administration, the compositions administered according to general formula (I) will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

An alternative for administration to the eye is intravitreal injection of a solution or suspension of the compound of general formula (I). In addition, the compound of general formula (I) may also be introduced by means of ocular implants or inserts.

The compositions administered according to general formula (I) may also include various other ingredients, including, but not limited to, tonicity agents, buffers, surfactants, stabilizing polymer, preservatives, co-solvents and viscosity building agents. Suitable pharmaceutical compositions of general formula (I) include a compound of the invention formulated with a tonicity agent and a buffer. The pharmaceutical compositions of general formula (I) may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g. sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of compound of general formula (I). The surfactants function to solubilise the compound and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, Triton, and sorbitan monolaurate. Preferred surfactants to be employed in the invention have a hydrophile/lipophile/ balance "HLB" in the range of 12.4 to 13.2 and are acceptable for ophthalmic use, such as TritonX114 and tyloxapol.

Additional agents that may be added to the ophthalmic compositions of compounds of general formula (I) are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers and Pemulen®, specifically Carbomer 974p (polyacrylic acid), at 0.1-0.5% w/w.

Other compounds may also be added to the ophthalmic compositions of the compound of general formula (I) to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of general formula (I) will be sterile, but typically unpreserved. Such compositions, therefore, generally will not contain preservatives.

The medical practitioner, or other skilled person, will be able to determine a suitable dosage for the compound of general formula (I), and hence the amount of the compound of the invention that should be included in any particular pharmaceutical formulation (whether in unit dosage form or otherwise).

Compounds of general formula (I) may be used in combination with one or more other active agents which are useful in the treatment or prophylaxis of respiratory diseases and conditions.

An additional active agent of this type may be included in the pharmaceutical composition described above but alternatively it may be administered separately, either at the same time as the compound of general formula (I) or at an earlier or later time.

Therefore, in a further aspect of the present invention there is provided a product comprising a compound of general formula (I) and an additional agent useful in the treatment or prevention of respiratory conditions as a combined preparation for simultaneous, sequential or separate use in the treatment of a disease or condition mediated by ENaC and especially a respiratory disease or condition, for example one of the diseases and conditions mentioned above.

There is also provided a compound of general formula (I) in combination with an additional agent useful in the treatment or prevention of respiratory conditions as a combined preparation for simultaneous, sequential or separate use in the treatment of a disease or condition mediated by ENaC and especially a respiratory disease or condition, for example one of the diseases and conditions mentioned above.

Suitable additional active agents which may be included in a pharmaceutical composition or a combined preparation with the compounds of general formula (I) include:

β2 adrenoreceptor agonists such as metaproterenol, isoproterenol, isoprenaline, albuterol, salbutamol, formoterol, salmeterol, indacaterol, terbutaline, orciprenaline, bitolterol mesylate and pirbuterol;

antihistamines, for example histamine $H_1$ receptor antagonists such as loratadine, cetirizine, desloratadine, levocetirizine, fexofenadine, astemizole, azelastine and chlorpheniramine or $H_4$ receptor antagonists;

dornase alpha;

corticosteroids such as prednisone, prednisolone, flunisolide, triamcinolone acetonide, beclomethasone dipropionate, budesonide, fluticasone propionate mometasone furoate and fluticasone furoate;

Leukotriene antagonists such as montelukast and zafirlukast;

CFTR repair therapies e.g. CFTR potentiators such as Ivacaftor and CFTR correctors such as Lumacaftor and Tezacaftor;

TMEM16A modulators, particularly TMEM16A potentiators;

Antibiotics.

The invention will now be further described with reference to the following examples.

EXAMPLES

All reactions involving moisture-sensitive reagents were carried out under a nitrogen atmosphere using standard vacuum line techniques and oven-dried glassware. Commercial anhydrous solvents were used in reactions and HPLC grade solvents were employed for work-up and chromatography. Water was purified using an Elix UV-5 system. All other reagents were used as supplied without prior purification. Reported yields are corrected for LC/MS purity (determined by UV (215 nm) or ELS detection) unless otherwise stated. Sealed tube reactions were carried out in heavy wall Ace pressure tubes. Microwave experiments were carried out using a Biotage Initiator+. Flash column chromatography was carried out using a Biotage Isolera 4 using Biotage SNAP columns. NMR spectra were recorded on a Bruker Avance III HD 500 MHz or a Bruker Avance III HD 250 MHz using the solvent as internal deuterium lock. Spectra were recorded at room temperature unless otherwise stated.

Analytical LC/MS were carried out on the following systems:

System A: stationary phase: Kinetex Core-Shell C18 2.1×50 mm, 5 μm, 40° C.; detection UV 215 nm-ELS-MS; mobile phase: A, water+0.1% formic acid; B, MeCN⁺0.1% formic acid; gradient (A:B ratio, time): 95:5-0:100, 1.20 min; 100:0, 0.10 min; 100:0-5:95, 0.01 min; flowrate: 1.2 ml/min;

System B: stationary phase: Phenomenex Gemini-NX C18 2.0×100 mm, 3 μm, 40° C.; detection UV 215 nm-ELS-MS; mobile phase: A, 2 mM ammonium bicarbonate pH 10; B, MeCN; gradient (A:B ratio, time): 95:5-0:100, 5.5 min; 0:100, 0.4 min; 0:100-95:5, 0.02 min; flowrate: 0.6 ml/min;

System C: stationary phase: Phenomenex Kinetex-XB C18 2.1×100 mm, 1.7 μm, 40° C.; detection UV 215 nm-ELS-MS; mobile phase: A, water+0.1% formic acid; B, MeCN⁺0.1% formic acid; gradient (A:B ratio, time): 95:5-0:100, 5.30 min; 100:0, 0.50 min; 100:0-5:95, 0.02 min; 5:95, 1.18 min; flowrate: 0.6 ml/min;

System D: stationary phase: Waters CSH C18 2.1×100 mm, 1.7 μm, 40° C.; detection UV 215 nm-ELS-MS; mobile phase: A, 5 mM ammonium acetate pH 7; B, MeCN; gradient (A:B ratio, time): 95:5-0:100, 5.30 min; 100:0, 0.50 min; 100:0-5:95, 0.02 min; 5:95, 1.18 min; flowrate: 0.6 ml/min;

System E: stationary phase: Waters CSH C18 2.1×100 mm, 1.7 μm, 40° C.; detection UV 215 nm-ELS-MS; mobile phase: A, water+0.1% formic acid; B, MeCN⁺0.1% formic acid; gradient; gradient (A:B ratio, time): 95:5-0:100, 1.10 min; 100:0, 0.25 min; 100:0-5:95, 0.05 min; 5:95, 0.1 min; flowrate: 0.9 ml/min;

System F: stationary phase: Phenomenex Gemini-NX C18 2×50 mm 3 μm, 40° C.; detection UV 215 nm-ELS-MS; mobile phase: A, 2 mM ammonium bicarbonate pH 10; B, MeCN; gradient (A:B ratio, time): 99:1-0:100, 1.80 min; 100:0, 0.20 min; 0:100-99:1, 0.01 min; flowrate 1 mL/min The following abbreviations and terms have the indicated meanings throughout:

AcOH glacial acetic acid
CDI 1,1'-carbonyldiimidazole
CV column volumes
dd doublet of doublets
DIPEA N,N-diisopropylethylamine
DMAP 4-dimethylaminopyridine
DMF N,N-dimethylformamide
DMSO dimethyl sulfoxide
ELS evaporative light scattering
ESI electrospray ionisation
EtOH ethanol
EtOAc ethyl acetate
HATU 1-[bis(dimethylamino)methylene]-1H-1,2,3-triazolo[4,5-b]pyridinium 3-oxide hexafluorophosphate
HPLC high-performance liquid chromatography
LC/MS liquid chromatographymass spectrometry
m multiplet
mCPBA meta-chloroperoxybenzoic acid
MeCN acetonitrile
MeOH methanol
NMR nuclear magnetic resonance
q quartet
RT room temperature
$R_t$ retention time
s singlet
t triplet
tBME methyl tert-butyl ether
TFA trifluoroacetic acid
THF tetrahydrofuran A. Synthesis of Intermediates Intermediate 1 Synthesis of 2-amino-5-bromo-3-(methoxycarbonyl)pyrazin-1-ium-1-olate

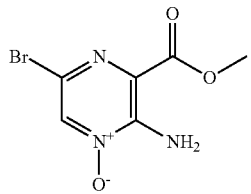

mCPBA (70%, 15.9 g, 64.7 mmol) was added to a mixture of methyl 3-amino-6-bromopyrazine-2-carboxylate (10.0 g, 43.1 mmol) in $CHCl_3$ (100 ml). The reaction mixture was heated at 60° C. for 2 h then allowed to cool to RT. The resultant mixture was cooled (0° C.) then filtered. The collected solid was washed with cold (0° C.) CHCl$_3$ (50 ml) then recrystallized from EtOH and dried in vacuo to afford the product as an orange solid (2.19 g, 20%).

$^1$H NMR (500 MHz, DMSO-d$_6$) δ 8.85 (s, 1H), 7.79 (s, 2H), 3.89 (s, 3H).

LC/MS (System A): m/z (ESI$^+$)=248 [M($^{79}$Br)H$^+$], 250 [M($^{81}$Br)H$^+$], R$_t$=0.64 min, UV purity=99%.

Intermediate 2 Synthesis of methyl 3-amino-6-bromo-5-chloropyrazine-2-carboxylate

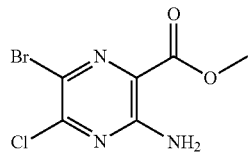

Phosphorus oxychloride (1.61 ml, 17.3 mmol) was added dropwise over 5 min to a cooled (0° C.) mixture of 2-amino-5-bromo-3-(methoxycarbonyl)pyrazin-1-ium-1-olate, Intermediate 1 (2.15 g, 8.66 mmol) in DMF (20 ml). The resultant mixture was allowed to warm to RT then stirred at RT for 1 h. Additional phosphorus oxychloride (0.80 ml, 8.6 mmol) was added then the reaction was left to stir at RT for 20 min. The resultant mixture was added dropwise to water (150 ml) over 10 min. The resultant mixture was left to stand at RT for 16 h then cooled (0° C.) and filtered. The collected solid was washed with cool (5° C.) water then dried in vacuo to afford the product as a pale orange solid (1.99 g, 86%).

$^1$H NMR (500 MHz, DMSO-d$_6$) δ 7.84 (s, 2H), 3.85 (s, 3H).

LC/MS (System A): m/z (ESI$^+$)=266 [M($^{35}$Cl$^{79}$Br)H$_1$], 268 [M($^{35}$Cl$^{81}$Br/$^{37}$Cl$^{79}$Br)H$_1$], 270 [M($^{37}$Cl$^{81}$Br)H$_1$], R$_t$=1.03 min, UV purity=100%.

Intermediate 3 Synthesis of methyl 3-{bis[(tert-butoxy)carbonyl]amino}-6-bromo-5-chloropyrazine-2-carboxylate

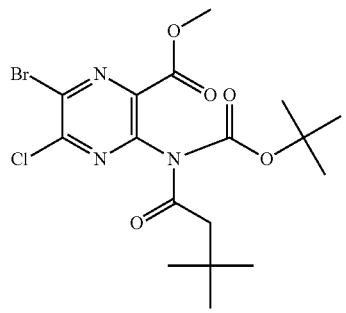 [SMILES: COC(=O)c1nc(Br)c(Cl)nc1N(C(=O)CC(C)(C)C)C(=O)OC(C)(C)C]

Di-tert-butyl dicarbonate (1.74 g, 7.99 mmol) was added portionwise over 3 min to a solution of methyl 3-amino-6-bromo-5-chloropyrazine-2-carboxylate, Intermediate 2 (968 mg, 3.63 mmol) and DMAP (22 mg, 0.18 mmol) in CH$_2$Cl$_2$ (10 ml). The reaction mixture was stirred at RT for 1 h. Additional di-tert-butyl dicarbonate (500 mg, 2.29 mmol) and DMAP (6 mg, 0.05 mmol) were added then the reaction was left to stir at RT for 45 min. The reaction mixture was concentrated in vacuo then the crude material was purified by flash column chromatography on a silica column (100 g). The column was eluted with EtOAc:heptane, increasing the gradient linearly from 0:100 to 34:76 over 8.5 CV. The desired fractions were combined then evaporated to afford the product as a pale yellow solid (1.55 g, 89%).

$^1$H NMR (500 MHz, DMSO-d$_6$) δ 3.90 (s, 3H), 1.37 (s, 18H).

LC/MS (System F): m/z (ESI$^+$)=466 [M($^{35}$Cl$^{79}$Br)H$_1$], 468 [M($^{35}$Cl$^{81}$Br/$^{37}$Cl$^{79}$Br)H$_1$], 470 [M($^{37}$Cl$^{81}$Br)H$_1$], R$_t$=2.06 min, UV purity=98%.

Intermediate 4 Synthesis of methyl 6-acetyl-3-amino-5-chloropyrazine-2-carboxylate

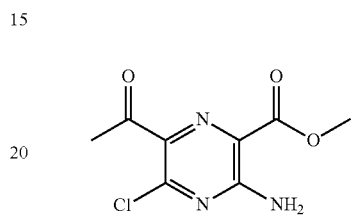

Degassed MeCN (20 ml) was added to a flask containing methyl 3-{bis[(tert-butoxy)carbonyl]amino}-6-bromo-5-chloropyrazine-2-carboxylate, Intermediate 3 (98%, 1.55 g, 3.25 mmol), PdCl$_2$(PPh$_3$)$_2$ (228 mg, 0.325 mmol) and CuI (124 mg, 0.649 mmol). Tributyl(1-ethoxyvinyl)stannane (2.19 ml, 6.49 mmol) was added then the resulting mixture was stirred at 40° C. for 50 min. Aqueous HCl solution (4.0 M, 20 ml, 80 mmol) was added then the reaction mixture was stirred at 60° C. for 1.5 h. The reaction mixture was allowed to cool to RT then added dropwise over 5 min to saturated aqueous NaHCO$_3$ solution (120 ml). The resultant mixture was extracted with EtOAc (150 ml). The phases were separated then aqueous KF solution (1 M, 100 ml, 100 mmol) was added to the organic layer. The mixture was stirred vigorously for 0.5 h then filtered through a Celite® pad (filter material).

The pad was rinsed with EtOAc (30 ml) then the combined filtrates were transferred to a separating funnel. The phases were separated then the organic phase was washed with water (2×120 ml) and brine (120 ml) then dried over Na$_2$SO$_4$ and concentrated in vacuo. The crude material was purified by flash column chromatography on a silica column (100 g). The column was eluted with EtOAc:heptane, increasing the gradient linearly from 0:100 to 54:46 over 9 CV. The desired fractions were combined then evaporated to afford the product as a pale orange solid (265 mg, 36%).

$^1$H NMR (500 MHz, DMSO-d$_6$) δ 8.62 (s, 1H), 7.96 (s, 1H), 3.89 (s, 3H), 2.51 (s, 3H+solvent).

LC/MS (System A): m/z (ESI$^+$)=230 [M($^{35}$Cl)H$_1$], 232 [M($^{37}$Cl)H$_1$], R$_t$=0.94 min, UV purity=100%.

Intermediate 5 Synthesis of methyl 6-amino-3-methyl-1H-pyrazolo[3,4-b]pyrazine-5-carboxylate

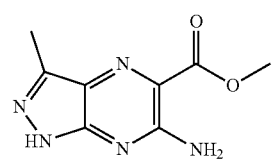

Hydrazine hydrate (161 μL, 3.31 mmol) was added to a mixture of methyl 6-acetyl-3-amino-5-chloropyrazine-2-carboxylate, Intermediate 4 (380 mg, 1.65 mmol) in EtOH (20 ml). The resulting mixture was heated to 50° C. for 1 h. Additional hydrazine hydrate (50 μL, 1.0 mmol) was added then the reaction was left to stir at 50° C. for a further 16 h. The reaction was allowed to cool to RT then concentrated in vacuo. The residue was suspended in refluxing EtOAc (25 ml). The mixture was allowed to cool to RT then filtered. The collected solid was washed with EtOAc (5 ml) then dried in vacuo to afford the product as a grey solid (366 mg, 85%).

$^1$H NMR (500 MHz, DMSO-$d_6$) δ 12.90 (s, 1H), 7.54 (s, 2H), 3.89 (s, 3H), 2.42 (s, 3H). NMR estimated purity=80%.

LC/MS (System A): m/z (ESI$^+$)=208 [MH$^+$], $R_t$=0.75 min, UV purity=95%.

Intermediate 6 Synthesis of 1,5-bis(1H-imidazole-1-carbonyl)-3-methyl-1H-pyrazolo[3,4-b]pyrazin-6-amine

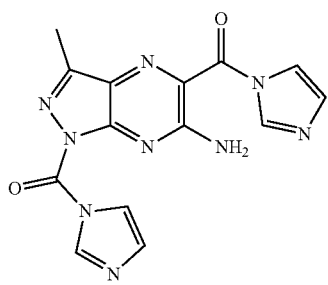 [SMILES: Cc1nn(C(=O)n2ccnc2)c2nc(N)c(C(=O)n3ccnc3)nc12]

Aqueous LiOH solution (1.0 M, 360 μl, 0.36 mmol) was added to a mixture of methyl 6-amino-3-methyl-1H-pyrazolo[3,4-b]pyrazine-5-carboxylate, Intermediate 5 (80%, 56 mg, 0.22 mmol) in MeOH (1 ml). The resulting mixture was stirred at 50° C. for 6 h then stirred at RT for 16 h. Additional LiOH solution (1.0 M, 30 μl, 0.030 mmol) was added then the reaction was heated at 50° C. for 4 h. Additional LiOH solution (1.0 M, 50 μl, 0.050 mmol) was added then the reaction was heated at 50° C. for 2 h. The reaction mixture was concentrated in vacuo to afford an orange solid (56 mg). The solid thus obtained was suspended in DMF (1 ml) then CDI (91 mg, 0.56 mmol) and imidazole hydrochloride (35 mg, 0.34 mmol) were added. The resultant mixture was stirred at RT for 0.5 h. Additional CDI (65 mg, 0.40) was added then the reaction was stirred at RT for 45 min.

Additional imidazole hydrochloride (50 mg, 0.48 mmol) and CDI (70 mg, 0.43 mmol) were added then the reaction was left to stir at RT for 15 min. The reaction mixture was cooled (0° C.) then cold (5° C.) water (2 ml) was added. The resultant mixture was stirred at RT for 5 min then left to stand at RT for 10 min. The mixture was filtered then the collected solid was washed with water and dried in vacuo to afford the product as an orange solid (21 mg, 26%).

$^1$H NMR (250 MHz, DMSO-$d_6$) δ 8.66-8.55 (m, 2H), 8.24 (s, 2H), 7.94-7.88 (m, 2H), 7.18-7.13 (m, 2H), 2.53 (s, 3H). Residual DMF (4.0 wt %) and imidazole (4.4 wt %). Overall NMR purity=92%.

LC/MS (System A): $R_t$=0.72 min, UV purity=100%.

Intermediate 7 Synthesis of 6-amino-3-methyl-1H-pyrazolo[3,4-b]pyrazine-5-carboxylic acid; trifluoroacetic acid

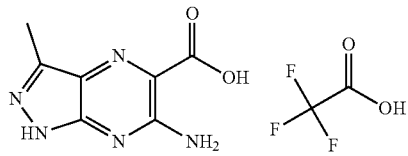

Aqueous LiOH solution (1.0 M, 2.7 ml, 2.7 mmol) was added to a mixture of methyl 6-amino-3-methyl-1H-pyrazolo[3,4-b]pyrazine-5-carboxylate, Intermediate 5 (80%, 310 mg, 1.20 mmol) in MeOH (2.5 ml). The resultant mixture was stirred at 50° C. for 1.5 h then concentrated in vacuo to afford a brown/orange solid (335 mg). A sample (165 mg) of the residue thus obtained was treated with $CH_2Cl_2$ (4 ml) and TFA (0.5 ml). The resultant mixture was stirred at RT for 20 min then concentrated in vacuo. The residue thus obtained was suspended in water (4 ml) with sonication. The solid was collected by filtration and washed with water. The solid was then treated with $CH_2Cl_2$ (4 ml) and TFA (0.5 ml). The resultant mixture was stirred at RT for 10 min then concentrated in vacuo to afford the product as a brown solid (149 mg, 37%).

$^1$H NMR (250 MHz, DMSO-$d_6$) δ 12.96 (s, 1H), 7.57 (s, 2H), 2.42 (s, 3H). LC/MS (System A): m/z (ESI$^+$)=194 [MH$^+$], $R_t$=0.60 min, UV purity (254 nm)=91%.

Intermediate 8—Synthesis of 5-(1H-imidazole-1-carbonyl)-3-methyl-1H-pyrazolo[3,4-b]pyrazin-6-amine

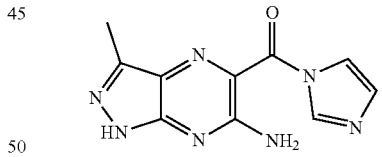

CDI (95 mg, 0.58 mmol) was added to a solution of 6-amino-3-methyl-1H-pyrazolo[3,4-b]pyrazine-5-carboxylic acid; trifluoroacetic acid, Intermediate 7 (91%, 149 mg, 0.441 mmol) in DMF (2 ml). The resulting mixture was stirred at RT for 0.5 h. $CH_2Cl_2$ (4 ml) was added then the reaction was left to stand for 20 min. The solid was collected by filtration, rinsed with $CH_2Cl_2$, then dried in vacuo to afford the product as a yellow solid (74 mg, 63%).

$^1$H NMR (500 MHz, DMSO-$d_6$) δ 13.05 (s, 1H), 8.68-8.64 (m, 1H), 7.94-7.90 (m, 1H), 7.68 (s, 2H), 7.14-7.10 (m, 1H), 2.44 (s, 3H). 5 wt % residual DMF.

Overall purity estimate=91% LC/MS (System A): m/z (ESI$^+$)=244 [MH$^+$], $R_t$=0.72 min, UV purity=96%.

Intermediate 9—Synthesis of 1-[(4-methoxyphenyl)methyl]-4-nitroso-1H-pyrazol-5-amine hydrochloride

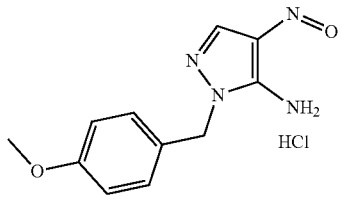 [SMILES: COc1ccc(Cn2ncc(N=O)c2N)cc1 ; Cl]

HCl solution in dioxane (4.0 M, 20 ml, 80 mmol) was added dropwise over 5 min to a cooled (0° C.) solution of 1-[(4-methoxyphenyl)methyl]-1H-pyrazol-5-amine (4.00 g, 19.7 mmol) in EtOH (40 ml). Amyl nitrite (2.64 ml, 19.7 mmol) was added dropwise over 1 min then the resultant solution was left to stir at 0° C. for 3 h. The resultant suspension was filtered, then the collected solid was rinsed with cold (0° C.) EtOH then dried in vacuo to afford the product as a pale peach solid (2.05 g, 38%).

$^1$H NMR (500 MHz, DMSO-d$_6$) δ 9.20-7.47 (m, 3H), 7.32-7.16 (m, 2H), 6.96-6.84 (m, 2H), 5.18-5.01 (m, 2H), 3.75-3.70 (m, 3H).

LC/MS (System A): m/z (ESI$^+$)=233 [MH$^+$], R$_t$=0.88 min, UV purity=99%.

Intermediate 10—Synthesis of 6-amino-1-[(4-methoxyphenyl)methyl]-1H-pyrazolo[3,4-b]pyrazine-5-carboxylic acid

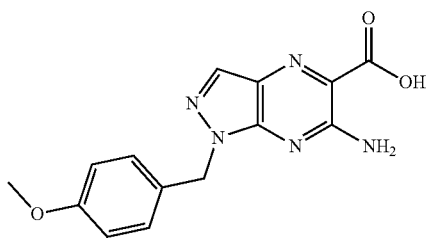 [SMILES: COc1ccc(Cn2ncc3nc(C(=O)O)c(N)nc32)cc1]

Potassium tert-butoxide (3.93 g, 35.0 mmol) was added portionwise over 5 min to a cooled (0° C.) suspension of 1-[(4-methoxyphenyl)methyl]-4-nitroso-1H-pyrazol-5-amine hydrochloride, Intermediate 9 (0.950 g, 3.50 mmol) and 2-cyanoacetic acid (1.19 g, 14.0 mmol) in EtOH (19 ml). The reaction was allowed to warm to RT then heated under microwave irradiation at 140° C. for 1 h 30 min. The resultant suspension was filtered then the collected solid was rinsed with EtOH and dried in vacuo. The solid thus obtained was suspended in water (15 ml) then the resultant suspension was acidified to pH=3 by drop-wise addition of aqueous HCl solution (2 M). The resultant suspension was filtered then the collected solid was rinsed with water (3 ml) and dried in vacuo to afford the product as a brown solid (214 mg, 20%).

$^1$H NMR (500 MHz, DMSO-d$_6$) δ 13.26 (s, 1H), 8.22 (s, 1H), 7.81 (s, 2H), 7.21-7.15 (m, 2H), 6.91-6.84 (m, 2H), 5.37 (s, 2H), 3.71 (s, 3H).

LC/MS (System A): m/z (ESI$^+$)=300 [MH$^+$], R$_t$=0.96 min, UV purity=100%.

Intermediate 11—Synthesis of 6-amino-1H-pyrazolo[3,4-b]pyrazine-5-carboxylic acid; trifluoroacetic acid

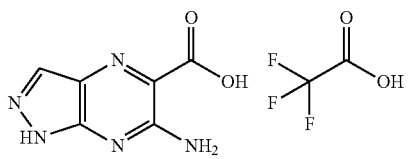

A solution of 6-amino-1-[(4-methoxyphenyl)methyl]-1H-pyrazolo[3,4-b]pyrazine-5-carboxylic acid, Intermediate 10 (190 mg, 0.635 mmol) and anisole (1.0 ml) in TFA (4 ml) was heated under microwave irradiation for 15 min at 100° C. The reaction mixture was concentrated in vacuo then the residue was suspended in toluene (5 ml). The mixture was sonicated then the solid was collected by filtration, rinsed with toluene, then dried under suction to afford the product as a dark brown solid (131 mg, 70%).

$^1$H NMR (500 MHz, DMSO-d$_6$) δ 13.70-12.47 (m, 2H), 8.19 (s, 1H), 7.64 (s, 2H).

LC/MS (System A): m/z (ESI$^+$)=180 [MH$^+$], R$_t$=0.15 min, ELS purity=100%.

Intermediate 12—Synthesis of 5-(1H-imidazole-1-carbonyl)-1H-pyrazolo[3,4-b]pyrazin-6-amine

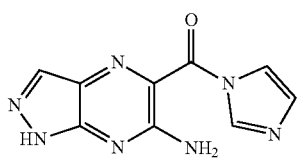 [SMILES: Nc1nc2[nH]ncc2nc1C(=O)n1ccnc1]

CDI (104 mg, 0.640 mmol) was added to a solution of 6-amino-1H-pyrazolo[3,4-b]pyrazine-5-carboxylic acid; trifluoroacetic acid, Intermediate 11 (125 mg, 0.426 mmol) in DMF (2 ml). The reaction mixture was left to stir at RT for 3 h. Additional CDI (69 mg, 0.43 mmol) was added then the reaction was stirred at RT for a further 1 h. The reaction mixture was concentrated to ~1 ml under a stream of nitrogen then diluted with CH$_2$Cl$_2$ (2 ml). The resultant suspension was filtered then the collected solid was rinsed with CH$_2$Cl$_2$ (2×1 ml) and dried under suction to afford the product as a dark yellow/green solid (70 mg, 72%).

$^1$H NMR (500 MHz, DMSO-d$_6$) δ 13.43 (s, 1H), 8.63-8.59 (m, 1H), 8.30 (s, 1H), 7.91-7.87 (m, 1H), 7.66 (s, 2H), 7.11 (dd, J=1.6, 0.8 Hz, 1H).

LC/MS (System E): m/z (ESI$^+$)=230 [MH$^+$], R$_t$=0.32 min, UV purity=100%.

Intermediate 13—Synthesis of 2-[(1-ethyl-6-methoxy-1H-1,3-benzodiazol-2-yl)methyl]-2,3-dihydro-1H-isoindole-1,3-dione

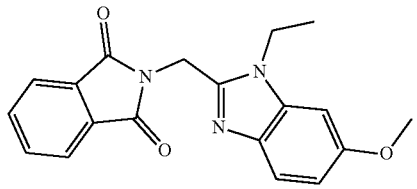 [SMILES: CCn1c(CN2C(=O)c3ccccc3C2=O)nc2ccc(OC)cc21]

Intermediate 13 was synthesised according to literature procedures (US 2015/0018314 A1).

Intermediate 14—Synthesis of 2-[(1,3-dioxo-2,3-dihydro-1H-isoindol-2-yl)methyl]-1,3-diethyl-6-methoxy-1H-1,3-benzodiazol-3-ium iodide

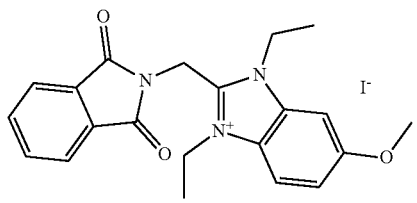 [SMILES: CCn1c(CN2C(=O)c3ccccc3C2=O)[n+](CC)c2ccc(OC)cc21 ; [I-]]

Iodoethane (715 µl, 8.95 mmol) was added to a suspension of 2-[(1-ethyl-6-methoxy-1H-1,3-benzodiazol-2-yl)methyl]-2,3-dihydro-1H-isoindole-1,3-dione, Intermediate 13 (3.00 g, 8.95 mmol) in MeCN (20 ml). The mixture was heated at 80° C. for 4 h. Iodoethane (715 µl, 8.95 mmol) was added and mixture was stirred at 80° C. for 16 h. Iodoethane (715 µl, 8.95 mmol) was added and mixture was stirred at 80° C. for a further 24 h the allowed to cool to RT. The mixture was concentrated in vacuo to approximately one third of the original volume. The precipitate was collected by filtration then washed with MeCN to afford a grey solid (2.6 g). The filtrate was concentrated to afford a dark grey solid. The two batches of solid thus obtained were combined and suspended in MeCN (20 ml). Iodoethane (715 µl, 8.95 mmol) was added then the reaction mixture was stirred at 80° C. for 18 h then at 100° C. for 4 h. The reaction mixture was split into two equal portions in pressure tubes. Iodoethane (300 µl, 3.75 mmol) was added to both reaction mixtures then the pressure tubes were sealed and left to heat at 100° C. for 16 h. The reaction mixtures were allowed to cool to RT then combined. The resultant mixture was concentrated in vacuo to ~5 ml then filtered. The collected solid was washed with the minimum of MeCN (0.5 ml) to yield the product as a grey solid (2.37 g). The filtrate was concentrated under reduced pressure to afford a dark brown solid, which was triturated with EtOAc (~10 ml) and filtered. The filtrate was left to stand for 16 h then it was filtered again. The solids obtained from the EtOAc filtrations were combined and dried to yield an additional batch of the product as a grey solid (1.24 g). The two batches of product obtained were combined as an EtOAc suspension then evaporated and dried under vacuum to afford the product as a grey solid (3.61 g, 81%).

$^1$H NMR (250 MHz, DMSO-$d_6$) δ 8.02 (d, J=9.2 Hz, 1H), 7.98-7.86 (m, 4H), 7.63 (d, J=2.2 Hz, 1H), 7.31 (dd, J=9.1, 2.3 Hz, 1H), 5.40 (s, 2H), 4.74-4.60 (m, 4H), 3.92 (s, 3H), 1.49-1.33 (m, 6H).

LC/MS (System A): m/z (ESI$^+$)=364 [M$^+$], $R_t$=0.93 min, UV purity=99%.

Intermediate 15—Synthesis of 2-(aminomethyl)-1,3-diethyl-6-methoxy-1H-1,3-benzodiazol-3-ium iodide

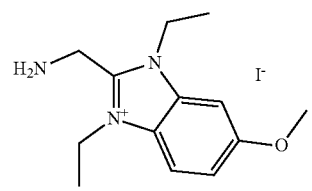 [SMILES: CCn1c(CN)[n+](CC)c2ccc(OC)cc21 ; [I-]]

Hydrazine hydrate (1.18 ml, 24.1 mmol) was added to a suspension of 2-[(1,3-dioxo-2,3-dihydro-1H-isoindol-2-yl)methyl]-1,3-diethyl-6-methoxy-1H-1,3-benzodiazol-3-ium iodide, Intermediate 14 (2.37 g, 4.82 mmol) in MeOH (25 ml). The mixture was then heated at 75° C. for 2.5 h then left to cool to RT over 16 h. The reaction mixture was concentrated in vacuo and the resulting solid was suspended in CH$_2$Cl$_2$:MeOH (10:1) then filtered. The collected solid was washed with CH$_2$Cl$_2$. The filtrate was concentrated in vacuo to afford the product as a grey solid (1.89 g, >99%).

$^1$H NMR (250 MHz, DMSO-$d_6$) δ 7.95 (d, J=9.1 Hz, 1H), 7.58 (d, J=2.3 Hz, 1H), 7.25 (dd, J=9.1, 2.3 Hz, 1H), 4.65-4.50 (m, 4H), 4.25 (s, 2H), 3.91 (s, 3H), 1.43 (m, 1.50-1.39 6H).

LC/MS (System A): m/z (ESI$^+$)=234 [M$^+$], $R_t$=0.16 min, ELS purity=92%.

Intermediate 16 Synthesis of methyl 2-({[tert-butoxy)carbonyl]amino}methyl)-1-ethyl-1H-1,3-benzodiazole-6-carboxylate

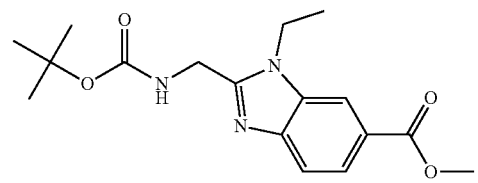 [SMILES: CCn1c(CNC(=O)OC(C)(C)C)nc2ccc(C(=O)OC)cc21]

A mixture of 2-{[(tert-butoxy)carbonyl]amino}acetic acid (8.57 g, 48.9 mmol), HATU (20.5 g, 53.8 mmol) and DIPEA (17.0 ml, 97.8 mmol) in DMF (200 ml) was stirred at RT for 1 h. Methyl 4-amino-3-(ethylamino)benzoate (9.59 g, 48.9 mmol) was added portionwise then rinsed into the reaction with THF (20 ml). The reaction mixture was stirred at RT for 18 h. A solution of 2-{[(tert-butoxy)carbonyl]amino}acetic acid (0.857 g, 4.89 mmol), HATU (1.86 g, 4.89 mmol) and DIPEA (1.70 ml, 9.78 mmol) in DMF (3 ml) was stirred at RT for 15 min then added to the main reaction. The resulting solution was stirred at RT for 3 h. A solution of 2-{[(tert-butoxy)carbonyl]amino}acetic acid (0.857 g, 4.89 mmol), HATU (1.86 g, 4.89 mmol) and DIPEA (1.70 ml, 9.78 mmol) in DMF (3 ml) was stirred at RT for 15 min then added to the main reaction. The resulting solution was stirred at RT for 64 h. The reaction mixture was added to saturated aqueous NaHCO$_3$ solution (200 ml). EtOAc (150 ml) and water (100 ml) were added then the phases were separated. The aqueous phase was extracted with EtOAc (2×150 ml), then the combined organic phases were washed with water (4×100 ml) and brine (50 ml) then dried over Na$_2$SO$_4$, filtered and evaporated to afford the crude intermediate as a black oil (18 g). The oil thus obtained was dissolved in acetic acid (80 ml) and stirred at 70° C. for 1 h. The reaction was allowed to cool to RT then evaporated to afford a brown solid. The solid was suspended in EtOAc (200 ml) then filtered and was washed with EtOAc, then dried under vacuum to afford a pale pink solid (6.5 g). The solid thus obtained was suspended in EtOAc (200 ml). The resulting suspension was heated at 50° C. for 15 min then allowed to cool to RT. The solid was collected by filtration to afford the product as a white solid (2.43 g). The filtrate was again filtered and the solid was collected by filtration, washed with EtOAc:heptane then dried under vacuum to afford a second batch of the product as a white solid (1.34 g). The filtrate was transferred to a separating funnel then extracted with saturated aqueous NaHCO$_3$ solution (3×100 ml), water (100 ml) and brine (50 ml) then dried over Na$_2$SO$_4$, filtered and evaporated to a yellow solid which was suspended in the minimum volume of EtOAc:heptane (1:4) and filtered then dried under vacuum to afford a third batch of the product as a white solid (1.77 g). The filtrate from the first filtration was transferred to a separating funnel then extracted with saturated aqueous NaHCO$_3$ solution (3×100 ml), water (100 ml) and brine (50 ml) then dried over Na$_2$SO$_4$, filtered and evaporated to a dark brown solid. The solid was suspended in EtOAc (50 ml) then filtered. The solid was dried under vacuum to afford a fourth batch of the product as a white solid (3.4 g). The filtrate was evaporated to afford a dark solid (8 g). The solid thus obtained was dissolved in CH$_2$Cl$_2$ then evaporated onto silica (16 g). The crude material was purified by flash column chromatography on a silica column (100 g). The column was eluted with EtOAc:heptane, increasing the gradient linearly from 0:100 to 100:0 over 10 CV. The desired fractions were combined and evaporated to afford a brown solid. The solid thus obtained was suspended in EtOAc:heptane (1:4, 20 ml) then filtered. The solid was washed with EtOAc:heptane then dried under vacuum to afford a fifth batch of the product as a white solid (1.45 g). The filtrate was concentrated in vacuo then the residue was suspended in EtOAc, filtered and dried under vacuum to afford a sixth batch of the product as an off-white solid (0.32 g).

The 6 batches of solid were combined as an EtOAc suspension then evaporated and dried under vacuum to yield the product as an off-white solid (10.7 g, 66%).

$^1$H NMR (500 MHz, DMSO-d$_6$) δ 8.16 (d, J=1.1 Hz, 1H), 7.82 (dd, J=8.4, 1.6 Hz, 1H), 7.66 (d, J=8.4 Hz, 1H), 7.52 (t, J=4.9 Hz, 1H), 4.47 (d, J=5.8 Hz, 2H), 4.35 (q, J=7.2 Hz, 2H), 3.88 (s, 3H), 1.46-1.22 (m, 12H).

LC/MS (System A): m/z (ESI$^+$)=334 [MH$^+$], R$_t$=0.98 min, UV purity=100%.

Intermediate 17—2-({[(tert-butoxy)carbonyl]amino}methyl)-1-ethyl-1H-1,3-benzodiazole-6-carboxylic acid

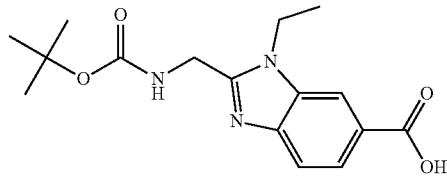 [SMILES: CCn1c(CNC(=O)OC(C)(C)C)nc2ccc(C(=O)O)cc21]

Aqueous LiOH solution (2.0 M, 16 ml, 32 mmol) was added to a suspension of methyl 2-({[(tert-butoxy)carbonyl]amino}methyl)-1-ethyl-1H-1,3-benzodiazole-6-carboxylate, Intermediate 16 (6.91 g, 20.7 mmol) in THF (100 ml). The reaction mixture was stirred at 50° C. for 16 h then allowed to cool to RT. The reaction mixture was concentrated in vacuo then the resulting solid was suspended in water (50 ml). Aqueous HCl solution (2 M) was added dropwise until pH 4 was reached. The resultant suspension was filtered then the solid was washed with the minimum of water and MeCN then dried under vacuum to afford the product as a white solid (6.05 g, 90%).

$^1$H NMR (500 MHz, DMSO-d$_6$) δ 12.77 (s, 1H), 8.18-8.07 (m, 1H), 7.80 (dd, J=8.4, 1.5 Hz, 1H), 7.63 (d, J=8.4 Hz, 1H), 7.52 (t, J=5.4 Hz, 1H), 4.47 (d, J=5.8 Hz, 2H), 4.34 (q, J=7.2 Hz, 2H), 1.46-1.21 (m, 12H).

LC/MS (System A): m/z (ESI$^+$)=320 [MH$^+$], R$_t$=0.84 min, UV purity=99%.

Intermediate 18—Synthesis of 2-(aminomethyl)-1-ethyl-1H-1,3-benzodiazole-6-carboxylic acid dihydrochloride

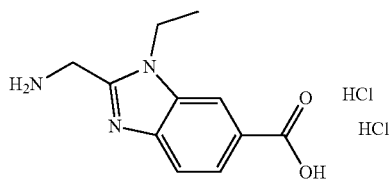 [SMILES: CCn1c(CN)nc2ccc(C(=O)O)cc21 ; Cl ; Cl]

HCl solution in dioxane (4.0 M, 14 ml, 56 mmol) was added to a suspension of 2-({[tert-butoxy)carbonyl]amino}methyl)-1-ethyl-1H-1,3-benzodiazole-6-carboxylic acid, Intermediate 17 (3.55 g, 11.1 mmol) in MeCN (60 ml). The reaction mixture was stirred at RT for 4 h then filtered. The solid was dried under vacuum to afford the product as a white solid (3.39 g, 98%).

$^1$H NMR (500 MHz, DMSO-d$_6$) δ 8.78 (s, 3H), 8.25 (s, 1H), 7.88 (dd, J=8.5, 1.2 Hz, 1H), 7.74 (d, J=8.4 Hz, 1H), 4.54-4.47 (m, 2H), 4.38 (q, J=7.2 Hz, 2H), 1.34 (t, J=7.2 Hz, 3H).

LC/MS (System A): m/z (ESI$^+$)=220 [MH$^+$], R$_t$=0.16 min, ELS purity=94%.

Intermediate 19—Synthesis of 2-({[(benzyloxy)carbonyl]amino}methyl)-1-ethyl-1H-1,3-benzodiazole-6-carboxylic acid

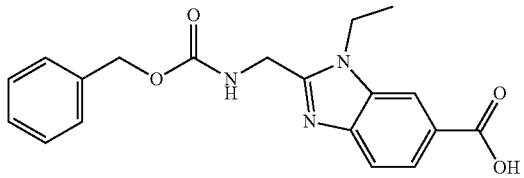 [SMILES: CCn1c(CNC(=O)OCc2ccccc2)nc2ccc(C(=O)O)cc21]

NaHCO₃ (4.83 g, 57.5 mmol) was added portionwise to a cooled (0° C.) suspension of 2-(aminomethyl)-1-ethyl-1H-1,3-benzodiazole-6-carboxylic acid dihydrochloride, Intermediate 18 (4.20 g, 14.4 mmol) in water (40 ml). The reaction mixture was allowed to warm to RT then a solution of benzyl 2,5-dioxopyrrolidin-1-yl carbonate (3.94 g, 15.8 mmol) in THF (40 ml) was added dropwise over 15 min. The reaction mixture was left to stir at RT for 16 h. The resultant mixture was extracted with EtOAc (50 ml). The phases were separated then the organic phase was washed with water (3×10 ml). The combined aqueous phases were acidified to pH 5 by addition of aqueous HCl solution (2 M), resulting in precipitation of a solid. The resultant suspension was filtered then the solid was dried under vacuum to afford the product as a white solid (3.5 g, 69%).

¹H NMR (500 MHz, DMSO-d₆) δ 8.12 (s, 1H), 7.97 (t, J=5.8 Hz, 1H), 7.80 (dd, J=8.4, 1.4 Hz, 1H), 7.62 (d, J=8.4 Hz, 1H), 7.42-7.09 (m, 5H), 5.06 (s, 2H), 4.54 (d, J=5.9 Hz, 2H), 4.33 (q, J=7.0 Hz, 2H), 1.28 (t, J=7.1 Hz, 3H).

LC/MS (System A): m/z (ESI⁺)=354 [MH⁺], R$_t$=0.89 min, UV purity=100%.

Intermediate 20—tert-butyl 2-({[(benzyloxy)carbonyl]amino}methyl)-1-ethyl-1H-1,3-benzodiazole-6-carboxylate

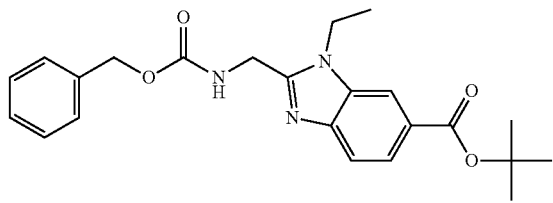 [SMILES: CCn1c(CNC(=O)OCc2ccccc2)nc2ccc(C(=O)OC(C)(C)C)cc21]

1,1-Di-tert-butoxy-N,N-dimethylmethanamine (6.77 ml, 28.3 mmol) was added to a suspension of 2-({[(benzyloxy)carbonyl]amino}methyl)-1-ethyl-1H-1,3-benzodiazole-6-carboxylic acid, Intermediate 19 (2.50 g, 7.08 mmol) in α,α,α-trifluorotoluene (50 ml). The reaction mixture was heated at 100° C. for 1 h. The reaction mixture was allowed to cool to RT then 1,1-di-tert-butoxy-N,N-dimethylmethanamine (6.77 ml, 28.3 mmol) was added dropwise over 15 min. The resultant mixture was heated at 100° C. for 45 min. The reaction mixture was cooled to 50° C. then 1,1-di-tert-butoxy-N,N-dimethylmethanamine (3.38 ml, 14.2 mmol) was added dropwise over 5 min. The resultant mixture was heated at 100° C. for 0.5 h then allowed to cool to RT. The reaction mixture was partitioned between EtOAc (50 ml) and water (50 ml). The phases were separated then the organic phase was washed with water (2×30 ml), saturated aqueous NaHCO₃ solution (20 ml) and brine (10 ml) then dried over Na₂SO₄, filtered and concentrated in vacuo to afford a beige solid (2.5 g). The solid thus obtained was suspended in MeCN (10 ml). The solid was collected by filtration then dried under vacuum to afford the product as an off-white solid (2.30 g, 79%).

¹H NMR (500 MHz, DMSO-d₆) δ 8.07 (s, 1H), 7.97 (m, 1H), 7.76 (dd, J=8.4, 1.5 Hz, 1H), 7.64 (d, J=8.4 Hz, 1H), 7.34 (m, 5H), 5.07 (s, 2H), 4.55 (d, J=6.0 Hz, 2H), 4.38-4.25 (m, 2H), 1.57 (s, 9H), 1.29 (m, 3H).

LC/MS (System A): m/z (ESI⁺)=410 [MH⁺], R$_t$=1.17 min, UV purity=99%.

Intermediate 21—Synthesis of 2-({[(benzyloxy)carbonyl]amino}methyl)-6-[(tert-butoxy)carbonyl]-1,3-diethyl-1H-1,3-benzodiazol-3-ium iodide

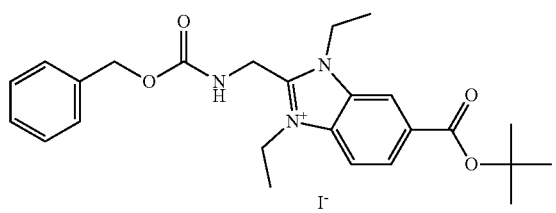 [SMILES: CCn1c(CNC(=O)OCc2ccccc2)[n+](CC)c2ccc(C(=O)OC(C)(C)C)cc21 ; [I-]]

Three reactions were run independently as follows then combined for work-up. Reaction 1: a suspension of tert-butyl 2-({[(benzyloxy)carbonyl]amino}methyl)-1-ethyl-1H-1,3-benzodiazole-6-carboxylate, Intermediate 20 (800 mg, 1.95 mmol) and iodoethane (629 μl, 7.82 mmol) in MeCN (10 ml) was heated under microwave irradiation for 2 h at 120° C. The reaction was retreated with iodoethane (629 μl, 7.82 mmol) then the reaction mixture was heated under microwave irradiation for a further 2 h at 120° C. Reaction 2: a suspension of tert-butyl 2-({[(benzyloxy)carbonyl]amino}methyl)-1-ethyl-1H-1,3-benzodiazole-6-carboxylate, Intermediate 20 (800 mg, 1.95 mmol) and iodoethane (629 μl, 7.82 mmol) in MeCN (10 ml) was heated under microwave irradiation for 1 h 45 min at 120° C. The reaction was retreated with iodoethane (629 μl, 7.82 mmol) then the reaction mixture was heated under microwave irradiation for a further 1.5 h at 120° C. Reaction 3: a suspension of tert-butyl 2-({[(benzyloxy)carbonyl]amino}methyl)-1-ethyl-1H-1,3-benzodiazole-6-carboxylate, Intermediate 20 (700 mg, 1.71 mmol) and iodoethane (591 μl, 6.84 mmol) in MeCN (10 ml) was heated under microwave irradiation for 1.5 h at 120° C. The reaction was retreated with iodoethane (629 μl, 7.82 mmol) then the reaction mixture was heated under microwave irradiation for a further 1.5 h at 120° C. The three reactions were combined and concentrated in vacuo. The crude material was purified by flash column chromatography on C18 (60 g). The column was eluted with MeCN:water+0.1% formic acid using the following gradient (% MeCN, column volumes): 5%, 2 CV; 5-31%, 5 CV; 31%, 4 CV; 31-59%, 6 CV; 59-100%, 3 CV; 100% 1 CV. The desired fractions were combined and concentrated in vacuo to afford the product as a white foam (2.13 g, 67%).

¹H NMR (500 MHz, DMSO-d₆) δ 8.54 (s, 1H), 8.43 (t, J=5.1 Hz, 1H), 8.22-8.12 (m, 2H), 7.42-7.27 (m, 5H), 5.06 (s, 2H), 4.90 (d, J=5.3 Hz, 2H), 4.79-4.59 (m, 4H), 1.61 (s, 9H), 1.47-1.36 (m, 6H).

LC/MS (System A): m/z (ESI⁺)=438 [M⁺], $R_t$=1.07 min, UV purity=100%.

Intermediate 22—Synthesis of 2-(aminomethyl)-6-carboxy-1,3-diethyl-1H-1,3-benzodiazol-3-ium hydrobromide bromide

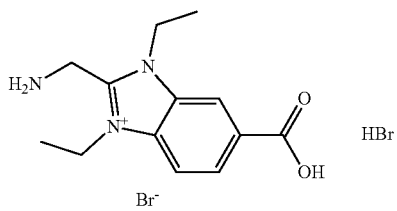 [SMILES: CCn1c(CN)[n+](CC)c2ccc(C(=O)O)cc21 ; Br ; [Br-]]

HBr solution in AcOH (33 wt %, 4.28 ml, 18.8 mmol) was added to a solution of 2-({[(benzyloxy)carbonyl]amino}methyl)-6-[(tert-butoxy)carbonyl]-1,3-diethyl-1H-1,3-benzodiazol-3-ium iodide, Intermediate 21 (2.13 g, 3.77 mmol) in AcOH (10 ml). The reaction mixture was stirred at RT for 0.5 h. The resultant suspension was concentrated in vacuo then azeotroped with MeCN. The solid thus obtained was suspended in the minimum volume of MeCN then filtered and dried under vacuum to afford the product as a white solid (1.52 g, 99%).

¹H NMR (500 MHz, DMSO-d₆) δ 8.69 (s, 1H), 8.31-8.20 (m, 2H), 4.85-4.63 (m, 6H), 1.53-1.40 (m, 6H).

LC/MS (System A): m/z (ESI⁺)=248 [M⁺], $R_t$=0.15 min, ELS purity=100%. Intermediate 23 Synthesis of (9H-fluoren-9-yl)methyl 4-{bis[(2S,3R)-2,3-dihydroxy-3-[(4R,5R)-5-hydroxy-2-phenyl-1,3-dioxan-4-yl]propyl]amino}piperidine-1-carboxylate; formic acid A mixture of 9H-fluoren-9-ylmethyl 4-aminopiperidine-1-carboxylate hydrochloride (commercially available)(7.80 g, 21.7 mmol) and 4,6-O-benzylidene-D-glucopyranose (23.3 g, 86.9 mmol) in MeOH (110 ml) was stirred at RT for 0.5 h. NaCNBH₃ (5.46 g, 86.9 mmol) was added then the reaction was heated at 60° C. The reaction was stirred at 60° C. for 18 h. The reaction was recharged with 4,6-O-benzylidene-D-glucopyranose (23.3 g, 86.9 mmol) then left to stir at 60° C. for a further 6 h. The reaction was allowed to cool to RT then added to saturated aqueous NaHCO₃ solution (200 ml) and EtOAc (200 ml). The resultant mixture was filtered through a Celite® pad then the filtrate was transferred to a separating funnel. The phases were separated then the organic phase was washed with brine:water (1:1, 2×200 ml), brine (100 ml), dried over Na₂SO₄, filtered and concentrated in vacuo. The residue was suspended in MeCN (200 ml) and tBME (250 ml) the filtered. The solid obtained was suspended in MeOH then filtered. The combined filtrates were concentrated in vacuo. The crude material thus obtained was purified by flash column chromatography on C18 (400 g). The column was eluted with MeCN:water+0.1% formic acid using the following gradient (% MeCN, column volumes): 20%, 1 CV; 20-50%, 10 CV; 50-100%, 2 CV; 100%, 2 CV. The desired fractions were combined and concentrated in vacuo to remove most of the MeCN and some of the water then the residual aqueous solution was lyophilised to afford the product as an off-white solid (12.6 g, 66%).

¹H NMR (500 MHz, DMSO-d6) δ 8.16 (s, 1H), 7.90 (d, J=7.4 Hz, 2H), 7.64-7.54 (m, 2H), 7.45-7.27 (m, 14H), 5.46 (s, 2H), 5.23-5.07 (m, 2H), 4.88-4.21 (m, 6H), 4.13 (dd, J=10.5, 5.3 Hz, 2H), 4.02-3.67 (m, 9H), 3.61 (d, J=9.2 Hz, 2H), 3.50 (t, J=10.5 Hz, 2H), 2.64-2.56 (m, 3H), 2.42-2.31 (m, 2H), 1.69-1.51 (m, 2H), 1.31-0.90 (m, 2H). LC/MS (System A): m/z (ESI⁺)=827 [MH⁺], $R_t$=1.08 min, UV purity=100%.

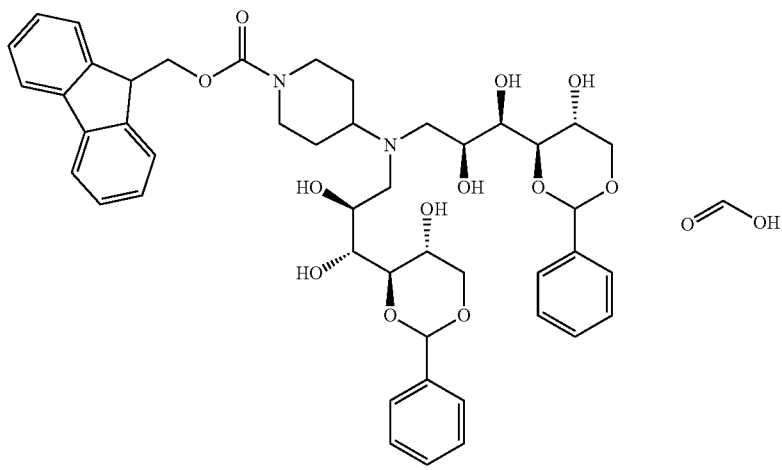

Intermediate 24 Synthesis of (1R,2S)-3-{[(2S,3R)-2,3-dihydroxy-3-[(4R,5R)-5-hydroxy-2-phenyl-1,3-dioxan-4-yl]propyl](piperidin-4-yl)amino}-1-[(4R,5R)-5-hydroxy-2-phenyl-1,3-dioxan-4-yl]propane-1,2-diol

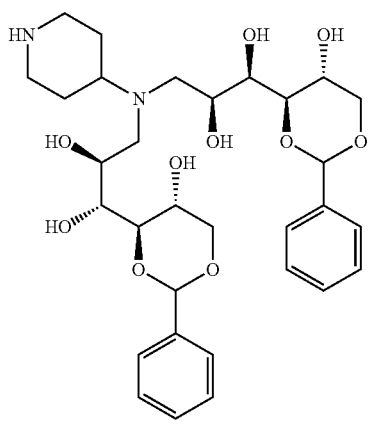

Piperidine (9.01 ml, 91.2 mmol) was added to a solution of (9H-fluoren-9-yl)methyl 4-{bis[(2S,3R)-2,3-dihydroxy-3-[(4R,5R)-5-hydroxy-2-phenyl-1,3-dioxan-4-yl]propyl]amino}piperidine-1-carboxylate; formic acid, Intermediate 23 (12.6 g, 14.4 mmol) in THF (150 ml). The reaction was left to stir at RT for 16 h then concentrated in vacuo. The crude solid material was suspended in MeOH (100 ml) then heated to dissolve. The solution was allowed to cool then concentrated in vacuo until solid was observed. The resultant suspension was stirred at RT for 15 min then filtered. The filtrate was concentrated in vacuo until solid was observed. The resultant suspension was stirred at RT for 15 min then filtered. The filtrate was purified by flash column chromatography on C18 (400 g). The column was eluted with MeCN:H$_2$O+0.1% formic acid using the following gradient (% MeCN, column volumes): 10%, 1 CVs; 10-25%, 6 CVs; 25%, 2 CVs; 25-50%, 1 CV; 50-100%, 1 CVs; 100%, 2 CVs. The desired fractions were combined and concentrated in vacuo to remove the majority of the solvent. The residual solution thus obtained was lyophilised to afford a pale-yellow solid (6.35 g). The solid thus obtained was partitioned between EtOAc (100 ml) and saturated aqueous NaHCO$_3$ solution (100 ml). The phases were separated then the aqueous phase was extracted with CHCl$_3$:1 PA (2:1, 100 ml) and n-BuOH (2×100 ml). The combined organic phases were dried over Na$_2$SO$_4$ then concentrated in vacuo. The residue was dissolved in 1:2 MeCN:water then lyophilised to afford the product as a white solid (5.81 g, 67%).

$^1$H NMR (500 MHz, CD$_3$OD) δ 7.48 (dd, J=7.5, 2.0 Hz, 4H), 7.38-7.28 (m, 6H), 5.50 (s, 2H), 4.23 (dd, J=10.6, 5.4 Hz, 2H), 4.00-3.88 (m, 4H), 3.85 (dd, J=5.5, 2.4 Hz, 2H), 3.70 (dd, J=9.3, 2.4 Hz, 2H), 3.60 (t, J=10.5 Hz, 2H), 3.09-3.02 (m, 1H), 3.00-2.91 (m, 1H), 2.78 (dd, J=13.4, 3.7 Hz, 2H), 2.75-2.65 (m, 1H), 2.59 (dd, J=13.4, 8.8 Hz, 2H), 2.54-2.47 (m, 1H), 2.37-2.28 (m, 1H), 1.81-1.70 (m, 2H), 1.55-1.49 (m, 1H), 1.42-1.35 (m, 1H).

LC/MS (System A): m/z (ESI$^+$)=605 [MH$^+$], R$_t$=0.77 min, UV purity=100%.

Intermediate 25 Synthesis of (2R,3R,4R,5S)-6-{[(2S,3R,4R,5R)-2,3,4,5,6-pentahydroxyhexyl](piperidin-4-yl)amino}hexane-1,2,3,4,5-pentol dihydrochloride

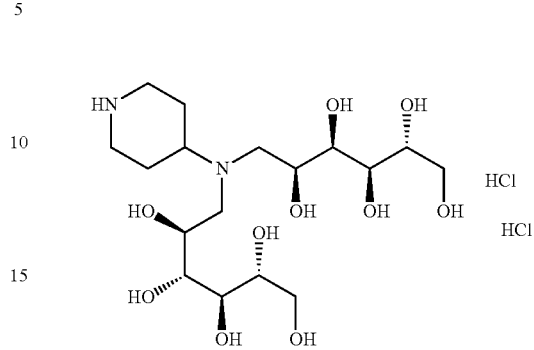

A mixture of (1R,2S)-3-{[(2S,3R)-2,3-dihydroxy-3-[(4R,5R)-5-hydroxy-2-phenyl-1,3-dioxan-4-yl]propyl](piperidin-4-yl)amino}-1-[(4R,5R)-5-hydroxy-2-phenyl-1,3-dioxan-4-yl]propane-1,2-diol, Intermediate 24 (5.81 g, 8.93 mmol) and aqueous HCl solution (2 M, 90 ml, 180 mmol) was stirred at RT for 18 h. The reaction mixture was concentrated in vacuo then re-dissolved in water and lyophilised to afford the product as a white solid (4.14 g, 92%).

$^1$H NMR (500 MHz, D$_2$O) δ 4.34-4.21 (m, 2H), 4.10-3.97 (m, 1H), 3.95-3.76 (m, 6H), 3.75-3.34 (m, 10H), 3.25-3.12 (m, 2H), 2.51-2.35 (m, 2H), 2.27-1.94 (m, 2H).

LC/MS (System A): m/z (ESI$^+$)=429 [MH$^+$], R$_t$=0.12 min, ELS purity=100%.

Intermediate 26 Synthesis of tert-butyl N-[(1-ethyl-6-fluoro-1H-1,3-benzodiazol-2-yl)methyl]carbamate

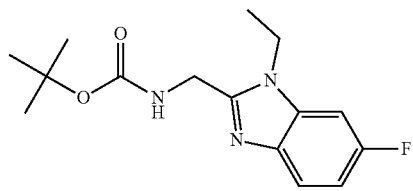 [SMILES: CCn1c(CNC(=O)OC(C)(C)C)nc2ccc(F)cc21]

A solution of 2-{[(tert-butoxy)carbonyl]amino}acetic acid (1.70 g, 9.73 mmol), HATU (4.07 g, 10.7 mmol) and DIPEA (3.39 ml, 19.5 mmol) in DMF (20 ml) was stirred at RT for 20 min. A solution of 1-N-ethyl-5-fluorobenzene-1,2-diamine (1.05 g, 9.73 mmol) in THF (10 ml) was added and the resulting mixture was stirred at RT for 16 h. The reaction mixture was poured onto saturated aqueous NaHCO$_3$ solution (80 ml). EtOAc (100 ml) and water (50 ml) were added then the phases were separated. The aqueous phase was extracted with EtOAc (2×50 ml) then the combined organic phases were washed with water (4×50 ml) and brine (50 ml), then dried over Na$_2$SO$_4$, filtered and evaporated to afford the intermediate as a black oil (4 g). The intermediate was dissolved in acetic acid (30 ml) then heated at 60° C. for 4 h. The reaction mixture was allowed to cool to RT then stirred at RT for 16 h. The resulting mixture was evaporated then the resulting residue was partitioned between EtOAc (150 ml) and water (100 ml). The aqueous phase was extracted with EtOAc (50 ml) then the combined organic phases were washed with water (4×50 ml) and brine (50 ml), then dried over Na$_2$SO$_4$, filtered and evaporated to a black solid (4 g). The solid was dissolved in the minimum of CH$_2$Cl$_2$/MeOH then evaporated onto silica (9 g).

The crude material was purified by flash column chromatography on a silica column (120 g). The column was eluted with CH$_2$Cl$_2$:MeOH, increasing the gradient linearly from 100:0 to 95:5 over 10 column volumes. The desired fractions were combined and evaporated to a black solid (2.9 g). The solid thus obtained was dissolved in EtOAc (100 ml) and extracted with saturated aqueous sodium bicarbonate solution (3×50 ml) and water (50 ml) then dried over Na$_2$SO$_4$, filtered and evaporated to a black solid (2.5 g). The solid was dissolved in the minimum of CH$_2$Cl$_2$/MeOH then evaporated onto silica (10 g). The material was further purified by flash column chromatography on a silica column (120 g). The column was eluted with EtOAc:heptane, increasing the gradient linearly from 0:100 to 100:0 over 10 column volumes. The desired fractions were combined and evaporated to afford the product as a pink solid (1.78 g, 62%).

$^1$H NMR (500 MHz, DMSO-d$_6$) δ 7.56 (dd, J=8.8, 4.9 Hz, 1H), 7.50-7.41 (m, 2H), 7.01 (ddd, J=9.9, 8.9, 2.5 Hz, 1H), 4.42 (d, J=5.9 Hz, 2H), 4.24 (q, J=7.2 Hz, 2H), 1.45-1.20 (m, 12H).

LC/MS (System A): m/z (ESI$^+$)=294 [MH$^+$], R$_t$=0.92 min, UV purity=100%.

Intermediate 27—Synthesis of 2-({[(tert-butoxy)carbonyl]amino}methyl)-1-ethyl-6-fluoro-3-methyl-1H-1,3-benzodiazol-3-ium iodide

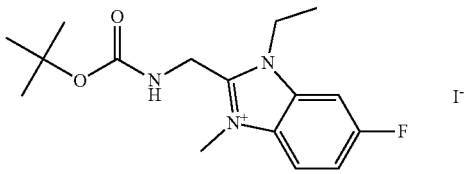 [SMILES: CCn1c(CNC(=O)OC(C)(C)C)[n+](C)c2ccc(F)cc21 ; [I-]]

Iodomethane (497 μl, 7.98 mmol) was added to a suspension of tert-butyl N-[(1-ethyl-6-fluoro-1H-1,3-benzodiazol-2-yl)methyl]carbamate, Intermediate 26 (780 mg, 2.66 mmol) in MeCN (12 ml) in a pressure tube. The tube was sealed then heated at 75° C. for 4 h. The reaction mixture was allowed to cool to RT then concentrated in vacuo to afford the product as a pale yellow solid (1.16 g, 99%).

$^1$H NMR (500 MHz, DMSO-d$_6$) δ 8.14-8.04 (m, 2H), 7.94 (t, J=5.2 Hz, 1H), 7.68-7.56 (m, 1H), 4.73 (d, J=5.4 Hz, 2H), 4.58 (q, J=7.2 Hz, 2H), 4.08 (s, 3H), 1.38 (d, J=11.2 Hz, 12H).

LC/MS (System A): m/z (ESI$^+$)=308 [M$^+$], R$_t$=0.87 min, UV purity=99%.

Intermediate 28—Synthesis of 2-(aminomethyl)-1-ethyl-6-fluoro-3-methyl-1H-1,3-benzodiazol-3-ium hydrochloride iodide

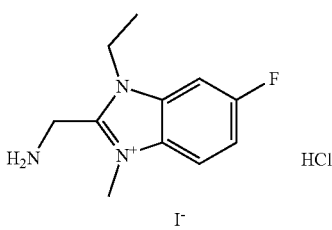

HCl solution in dioxane (4.0 M, 3.3 ml, 13.2 mmol) was added to a solution of 2-({[(tert-butoxy)carbonyl]amino}methyl)-1-ethyl-6-fluoro-3-methyl-1H-1,3-benzodiazol-3-ium iodide, Intermediate 27 (1.16 g, 2.66 mmol) in MeCN (5 ml). The reaction was stirred at RT for 0.5 h then concentrated in vacuo. The solid was azeotroped with MeCN (10 ml) then dried under vacuum to yield the product as a yellow/green solid (870 mg, 88%).

$^1$H NMR (500 MHz, DMSO-d$_6$) δ 9.21 (s, 3H), 8.25-8.14 (m, 2H), 7.69 (td, J=9.3, 2.4 Hz, 1H), 4.76 (s, 2H), 4.70 (q, J=7.2 Hz, 2H), 4.19 (s, 3H), 1.42 (t, J=7.2 Hz, 3H).

LC/MS (System A): m/z (ESI$^+$)=208 [M$^+$], R$_t$=0.14 min, ELS purity=100%.

Intermediate 29—Synthesis of 2-[(6-chloro-1-ethyl-1H-1,3-benzodiazol-2-yl)methyl]-2,3-dihydro-1H-isoindole-1,3-dione

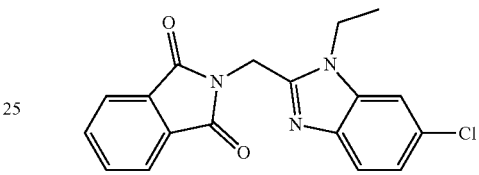

A mixture of N-phthaloylglycine (2.15 g, 10.5 mmol), TBTU (3.52 g, 11.0 mmol) and triethylamine (2.31 ml, 13.0 mmol) in DMF (30 ml) was stirred at RT for 45 min. A solution of 5-chloro-1-N-ethylbenzene-1,2-diamine (1.70 g, 9.96 mmol) in THF (20 ml) was added and the resulting mixture was stirred at RT for 18 h. The reaction mixture was added to saturated aqueous NaHCO3 solution (100 ml) which caused a pale brown solid to precipitate from solution. The solid was filtered, washed with water and dried under vacuum. The solid thus obtained was triturated in MeCN then filtered and dried under vacuum to afford the intermediate as a pale pink solid (5.4 g). The solid thus obtained was added portion-wise to acetic acid (30 ml). The resulting suspension was heated at 100° C. for 45 min then allowed to cool to RT over 16 h. The resulting suspension was filtered and washed with EtOAc then dried under vacuum to afford the product as a pale pink solid (585 mg). The solid was suspended in MeCN (5 ml) then MeCN:water (1:1, 1 ml) was added. The resulting suspension was filtered then the solid was dried under vacuum to afford the product as a pale pink solid (430 mg, 13%). The filtrate was again filtered, then the solid was washed with EtOAc and dried under vacuum to afford a second batch of product as a pale pink solid (2.00 g). The solid was suspended in MeCN (20 ml) then MeCN:water (1:1, 5 ml) was added. The resulting suspension was filtered then the solid was dried under vacuum to afford second batch of the product as a pale pink solid (1.33 g, 38%). The two batches of product were as a suspension in MeCN then concentrated in vacuo and dried under vacuum to afford the product as a pale pink solid (1.76 g, 51%).

$^1$H NMR (250 MHz, DMSO-d$_6$) δ 8.02-7.85 (m, 4H), 7.76 (d, J=1.9 Hz, 1H), 7.49 (d, J=8.6 Hz, 1H), 7.15 (dd, J=8.6, 2.0 Hz, 1H), 5.13 (s, 2H), 4.39 (q, J=7.1 Hz, 2H), 1.37 (t, J=7.2 Hz, 3H).

LC/MS (System A): m/z (ESI$^+$)=340 [M($^{35}$Cl)H$_1$], 342 [M($^{37}$Cl)H$_1$], R$_t$=1.12 min, UV purity=99%.

Intermediate 30 Synthesis of 6-chloro-2-[(1,3-di-oxo-2,3-dihydro-1H-isoindol-2-yl)methyl]-1-ethyl-3-methyl-1H-1,3-benzodiazol-3-ium iodide

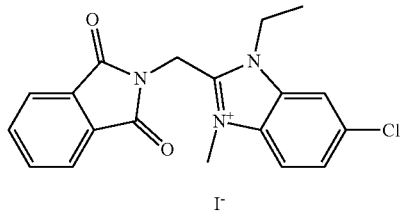 [SMILES: CCn1c(CN2C(=O)c3ccccc3C2=O)[n+](C)c2ccc(Cl)cc21 ; [I-]]

A mixture of 2-[(6-chloro-1-ethyl-1H-1,3-benzodiazol-2-yl)methyl]-2,3-dihydro-1H-isoindole-1,3-dione, Intermediate 29 (600 mg, 1.77 mmol) and iodomethane (330 µl, 5.30 mmol) in MeCN (6 ml) was heated at 75° C. in a sealed tube for 1.5 h then allowed to cool to RT. Iodomethane (165 µl, 2.65 mmol) was added then the reaction was heated at 80° C. for 5 h. The reaction was allowed to cool to RT then filtered to afford a solid which was washed with MeCN and dried under vacuum to afford the product as a yellow solid (644 mg, 73%).

$^1$H NMR (500 MHz, DMSO-$d_6$) δ 8.40 (d, J=1.8 Hz, 1H), 8.13 (d, J=8.9 Hz, 1H), 7.91 (ddt, J=18.3, 5.8, 3.1 Hz, 4H), 7.79 (dd, J=8.9, 1.9 Hz, 1H), 5.40 (s, 2H), 4.74 (q, J=7.2 Hz, 2H), 4.14 (s, 3H), 1.43 (t, J=7.2 Hz, 3H).

LC/MS (System A): m/z (ESI$^+$)=354 [M($^{35}$Cl)$^+$], 356 [M($^{37}$Cl)$^+$], R$_t$=0.90 min, UV purity=97%.

Intermediate 31 Synthesis of 2-(aminomethyl)-6-chloro-1-ethyl-3-methyl-1H-1,3-benzodiazol-3-ium iodide

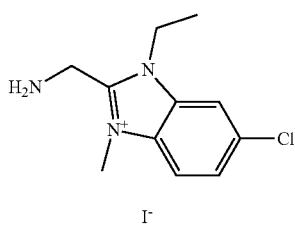

Hydrazine hydrate (446 µl, 9.17 mmol) was added to a suspension of 6-chloro-2-[(1,3-dioxo-2,3-dihydro-1H-isoindol-2-yl)methyl]-1-ethyl-3-methyl-1H-1,3-benzodiazol-3-ium iodide, Intermediate 30 (640 mg, 1.33 mmol) in MeOH (8 ml) in a pressure tube. The tube was sealed and heated at 75° C. for 3 h then allowed to cool to RT. The resulting suspension was filtered and the solid was washed with MeOH (10 ml). The filtrate was concentrated in vacuo to afford an orange solid, which was suspended in CH$_2$Cl$_2$ (10 ml) then filtered and washed through with CH$_2$Cl$_2$. The solid thus obtained was suspended in CH$_2$Cl$_2$ (10 ml). A few drops of MeOH were added and the suspension was sonicated. The resulting suspension was filtered then the solid was dried under vacuum to afford the product as an off-white solid (360 mg, 77%).

$^1$H NMR (500 MHz, DMSO-$d_6$) δ 8.31 (d, J=1.9 Hz, 1H), 8.06 (d, J=8.9 Hz, 1H), 7.73 (dd, J=8.8, 1.9 Hz, 1H), 4.60 (q, J=7.2 Hz, 2H), 4.25 (s, 2H), 4.06 (s, 3H), 2.52-2.10 (s, 2H+DMSO), 1.41 (t, J=7.2 Hz, 3H).

LC/MS (System A): m/z (ESI$^+$)=224 [M($^{35}$Cl)$^+$], 226 [M($^{37}$Cl)$^+$], R$_t$=0.16 min, ELS purity=100%.

Intermediate 32—Synthesis of 2-[(1,3-dioxo-2,3-dihydro-1H-isoindol-2-yl)methyl]-1-ethyl-6-methoxy-3-methyl-1H-1,3-benzodiazol-3-ium iodide

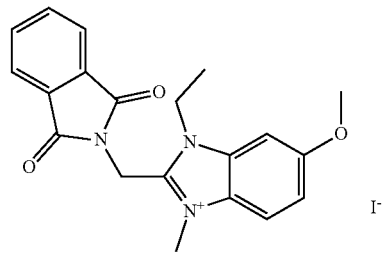 [SMILES: CCn1c(CN2C(=O)c3ccccc3C2=O)[n+](C)c2ccc(OC)cc21 ; [I-]]

Iodomethane (590 µl, 9.47 mmol) was added to a suspension of 2-[(1-ethyl-6-methoxy-1H-1,3-benzodiazol-2-yl)methyl]-2,3-dihydro-1H-isoindole-1,3-dione, Intermediate 13 (1.59 g, 4.74 mmol) in MeCN (13 ml) in a pressure tube. The mixture was heated at 80° C. for 4 h then allowed to cool to RT. The resulting suspension was reduced to approximately half of the original volume under a stream of nitrogen. The solid was collected by filtration then washed with further MeCN (3 ml) to yield the product as a white solid (1.99 g, 87%).

$^1$H NMR (500 MHz, DMSO-$d_6$) δ 8.01-7.84 (m, 5H), 7.62 (d, J=2.2 Hz, 1H), 7.32 (dd, J=9.2, 2.3 Hz, 1H), 5.37 (s, 2H), 4.71 (q, J=7.1 Hz, 2H), 4.11 (s, 3H), 3.92 (s, 3H), 1.42 (t, J=7.2 Hz, 3H).

LC/MS (System A): m/z (ESI$^+$)=350 [M$^+$], R$_t$=0.87 min, UV purity=99%.

Intermediate 33—Synthesis of 2-(aminomethyl)-1-ethyl-6-methoxy-3-methyl-1H-1,3-benzodiazol-3-ium iodide

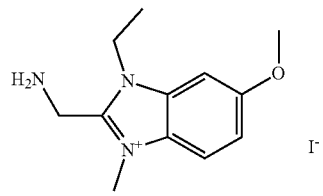 [SMILES: CCn1c(CN)[n+](C)c2ccc(OC)cc21 ; [I-]]

Hydrazine hydrate (1.17 ml, 24.0 mmol) was added to a suspension of 2-[(1,3-dioxo-2,3-dihydro-1H-isoindol-2-yl)methyl]-1-ethyl-6-methoxy-3-methyl-1H-1,3-benzodiazol-3-ium iodide, Intermediate 32 (2.29 g, 4.80 mmol) in MeOH (25 ml). The mixture was heated at 75° C. for 1 h. The reaction was concentrated in vacuo and the resulting solid was suspended in CH$_2$Cl$_2$:MeOH (10:1). The solid was collected by filtration and washed with CH$_2$Cl$_2$. The filtrate was concentrated in vacuo to afford the product as a pale brown solid (1.60 g, 96%).

$^1$H NMR (500 MHz, DMSO-$d_6$) δ 7.91 (d, J=9.1 Hz, 1H), 7.57 (d, J=2.3 Hz, 1H), 7.26 (dd, J=9.1, 2.3 Hz, 1H), 4.58 (q, J=7.2 Hz, 2H), 4.23 (s, 2H), 4.03 (s, 3H), 3.91 (s, 3H), 1.42 (t, J=7.2 Hz, 3H).

LC/MS (System A): m/z (ESI⁺)=220 [M⁺], $R_t$=0.14 min, ELS purity=100%.

Intermediate 34—Synthesis of tert-butyl N-{[1-ethyl-6-(trifluoromethyl)-1H-1,3-benzodiazol-2-yl]methyl}carbamate

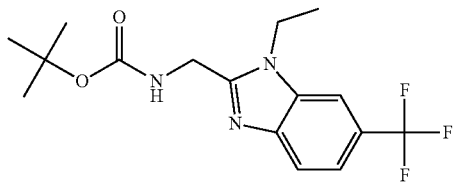 [SMILES: CCn1c(CNC(=O)OC(C)(C)C)nc2ccc(C(F)(F)F)cc21]

Intermediate 34 was synthesised according to literature procedures (WO 2009019506 A1).

Intermediate 35—Synthesis of 2-({[(tert-butoxy)carbonyl]amino}methyl)-1-ethyl-3-methyl-6-(trifluoromethyl)-1H-1,3-benzodiazol-3-ium iodide

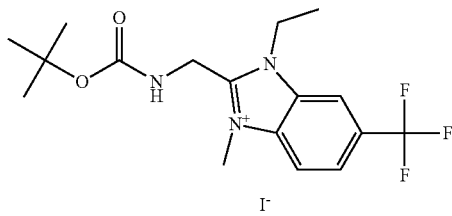 [SMILES: CCn1c(CNC(=O)OC(C)(C)C)[n+](C)c2ccc(C(F)(F)F)cc21 ; [I-]]

Iodomethane (381 µl, 6.12 mmol) was added to a suspension of tert-butyl N-{[1-ethyl-6-(trifluoromethyl)-1H-1,3-benzodiazol-2-yl]methyl}carbamate, Intermediate 34 (700 mg, 2.04 mmol) in MeCN (10 ml) in a pressure tube. The tube was sealed and heated at 75° C. for 8 h then allowed to cool to RT. The reaction mixture was concentrated in vacuo to afford the product as a pale yellow solid (1.01 g, >99%).

¹H NMR (500 MHz, DMSO-d₆) δ 8.64 (s, 1H), 8.29 (d, J=8.7 Hz, 1H), 8.08 (d, J=8.7 Hz, 1H), 7.98 (t, J=5.2 Hz, 1H), 4.80 (d, J=5.6 Hz, 2H), 4.73 (q, J=7.2 Hz, 2H), 4.14 (s, 3H), 1.40 (m, 12H).

LC/MS (System A): m/z (ESI⁺)=358 [M⁺], $R_t$=0.91 min, UV purity=98%.

Intermediate 36—Synthesis of 2-(aminomethyl)-1-ethyl-3-methyl-6-(trifluoromethyl)-1H-1,3-benzodiazol-3-ium hydrochloride iodide

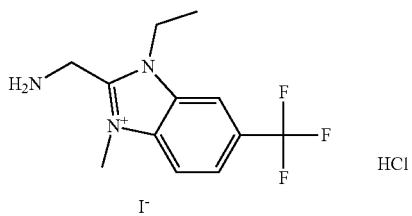 [SMILES: CCn1c(CN)[n+](C)c2ccc(C(F)(F)F)cc21 ; Cl ; [I-]]

HCl solution in dioxane (4.0 M, 2.8 ml, 11 mmol) was added to a solution of 2-({[(tert-butoxy)carbonyl]amino}methyl)-1-ethyl-3-methyl-6-(trifluoromethyl)-1H-1,3-benzodiazol-3-ium iodide, Intermediate 35 (1.07 g, 2.21 mmol) in MeCN (5 ml). The reaction was stirred at RT for 16 h then concentrated in vacuo to yield the product as an off-white solid (875 mg, 94%).

¹H NMR (500 MHz, DMSO-d₆) δ 9.14 (s, 3H), 8.74 (s, 1H), 8.38 (d, J=8.8 Hz, 1H), 8.14 (dd, J=8.8, 1.3 Hz, 1H), 4.84 (d, J=5.5 Hz, 4H), 4.24 (s, 3H), 1.45 (t, J=7.2 Hz, 3H).

LC/MS (System A): m/z (ESI⁺)=258 [M⁺], $R_t$=0.17 min, ELS purity=100%.

Intermediate 37—Synthesis of N-ethyl-2-nitro-5-(trifluoromethoxy)aniline

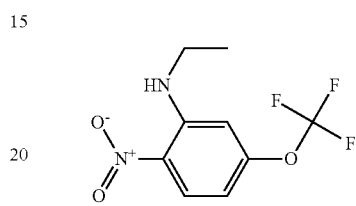

Two identical reactions were carried out in parallel as follows then combined for work-up. Ethylamine solution in THF (2.0 M, 4.1 ml, 8.2 mmol) was added to a suspension of 2-chloro-1-nitro-4-(trifluoromethoxy)benzene (1.00 g, 4.14 mmol) and K₂CO₃ (1.71 g, 6.21 mmol) in THF (12 ml) in a pressure tube. The tube was sealed then heated at 50° C. for 16 h then allowed to cool to RT. Additional ethylamine solution in THF (2.0 M, 2.1 ml, 4.2 mmol) was added then the reaction was heated at 50° C. for 24 h. The combined reactions were filtered then the solid thus obtained was rinsed with EtOAc (100 ml). The combined filtrates were extracted with saturated aqueous NaHCO₃ solution (2×100 ml), water (50 ml) and brine (50 ml) then dried over Na₂SO₄, then filtered and evaporated to an orange oil. The crude material was purified by flash column chromatography on C18 (120 g). The column was eluted with MeCN:water using the following gradient (% MeCN, column volumes): 10%, 2 CV; 10-100%, 20 CVs; 100%, 2 CV. The desired fractions were combined and concentrated in vacuo to remove most of the MeCN. The residual aqueous mixture was extracted with EtOAc (100 ml). The organic phase was separated, then dried over Na₂SO₄ and evaporated to afford the product as a bright orange oil (1.42 g, 69%).

¹H NMR (500 MHz, CDCl₃) δ 8.23 (d, J=9.4 Hz, 1H), 8.04 (s, 1H), 6.61 (d, J=2.0 Hz, 1H), 6.48 (ddd, J=9.4, 2.4, 1.2 Hz, 1H), 3.33 (qd, J=7.2, 5.1 Hz, 2H), 1.39 (t, J=7.2 Hz, 3H).

LC/MS (System A): m/z (ESI⁺)=251 [MH⁺], $R_t$=1.32 min, UV purity=100%.

Intermediate 38 Synthesis of tert-butyl N-([1-ethyl-6-(trifluoromethoxy)-1H-1,3-benzodiazol-2-yl]methyl) carbamate

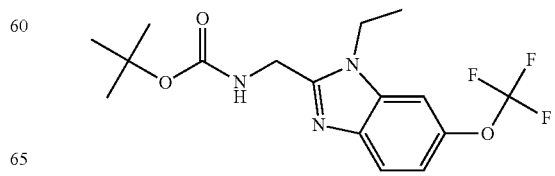

A suspension of palladium on carbon (10 wt %, 0.3 g) and N-ethyl-2-nitro-5-(trifluoromethoxy)aniline, Intermediate 37 (1.42 g, 5.68 mmol) solution in EtOH (40 ml) was stirred under a hydrogen atmosphere at RT for 16 h. The reaction mixture was filtered through glass fibre filter paper and washed through with EtOAc. The filtrate was concentrated in vacuo and then diluted with THF (10 ml). The resulting solution was added to a pre-mixed solution of 2-{[(tert-butoxy)carbonyl]amino}acetic acid (994 mg, 5.68 mmol), HATU (2.37 g, 6.24 mmol) and DIPEA (1.98 ml, 11.4 mmol) in DMF (20 ml). The reaction mixture was stirred at RT for 68 h then poured onto saturated aqueous NaHCO$_3$ (80 ml). EtOAc (50 ml) and water (50 ml) were added and the phases were separated. The aqueous phase was extracted with EtOAc (2×50 ml) then the combined organic phases were washed with water (4×50 ml) and brine (50 ml) then dried over Na$_2$SO$_4$, filtered and evaporated to a black oil. The oil thus obtained was dissolved in acetic acid (10 ml) and the resulting solution was heated at 70° C. for 1.5 h. The reaction solution was concentrated in vacuo then the residue was partitioned between EtOAc (50 ml) and saturated aqueous NaHCO$_3$ solution (50 ml). The organic phase was washed with saturated aqueous NaHCO$_3$ solution (4×50 ml), water (50 ml) and brine (10 ml) then dried over Na$_2$SO$_4$, filtered and evaporated to a brown solid (1.95 g). The crude material was dissolved in CH$_2$Cl$_2$/MeOH then evaporated onto silica (10 g) and purified by flash column chromatography on a silica column (120 g). The column was eluted with EtOAc:heptane, increasing the gradient linearly from 0:100 to 100:0 over 10 column volumes. The desired fractions were combined and evaporated to yield the product as a pink solid (1.04 g, 47%).

$^1$H NMR (500 MHz, DMSO-d$_6$) δ 7.70-7.61 (m, 2H), 7.49 (d, J=5.1 Hz, 1H), 7.19-7.10 (m, 1H), 4.44 (d, J=5.9 Hz, 2H), 4.29 (q, J=7.1 Hz, 2H), 1.45-1.23 (m, 12H).

LC/MS (System A): m/z (ESI$^+$)=360 [MH$^+$], R$_t$=1.11 min, UV purity=92%.

Intermediate 39 Synthesis of 2-({[(tert-butoxy)carbonyl]amino}methyl)-1-ethyl-3-methyl-6-(trifluoromethoxy)-1H-1,3-benzodiazol-3-ium iodide

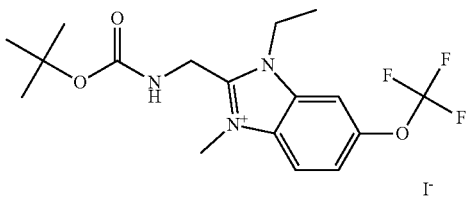 [SMILES: CCn1c(CNC(=O)OC(C)(C)C)[n+](C)c2ccc(OC(F)(F)F)cc21 ; [I-]]

Iodomethane (208 μl, 3.34 mmol) was added to a suspension of tert-butyl N-{[1-ethyl-6-(trifluoromethoxy)-1H-1,3-benzodiazol-2-yl]methyl} carbamate, Intermediate 38 (92%, 400 mg, 1.02 mmol) in MeCN (5 ml) in a pressure tube. The tube was sealed then heated at 75° C. for 5 h then allowed to cool to RT. The reaction mixture was concentrated in vacuo to yield the product as a dark green solid (552 mg, >99%).

$^1$H NMR (500 MHz, DMSO-d$_6$) δ 8.30 (s, 1H), 8.18 (d, J=9.1 Hz, 1H), 7.95 (t, J=5.2 Hz, 1H), 7.76 (d, J=9.1 Hz, 1H), 4.75 (d, J=5.4 Hz, 2H), 4.64 (q, J=7.1 Hz, 2H), 4.10 (s, 3H), 1.44-1.25 (m 12H).

LC/MS (System A): m/z (ESI$^+$)=374 [M$^+$], R$_t$=0.96 min, UV purity=93%.

Intermediate 40—Synthesis of 2-(aminomethyl)-1-ethyl-3-methyl-6-(trifluoromethoxy)-1H-1,3-benzodiazol-3-ium hydrochloride iodide

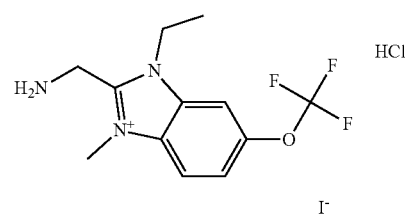 [SMILES: CCn1c(CN)[n+](C)c2ccc(OC(F)(F)F)cc21 ; Cl ; [I-]]

HCl solution in dioxane (4.0 M, 1.4 ml, 5.6 mmol) was added to a solution of 2-({[(tert-butoxy)carbonyl]amino}methyl)-1-ethyl-3-methyl-6-(trifluoromethoxy)-1H-1,3-benzodiazol-3-ium iodide, Intermediate 39 (93%, 550 mg, 1.02 mmol) in MeCN (5 ml). The reaction was left to stir at RT for 16 h then concentrated in vacuo. The solid was azeotroped with MeCN (10 ml) then dried under vacuum to yield the product as a brown solid (480 mg, 94%).

$^1$H NMR (500 MHz, DMSO-d$_6$) δ 9.11 (s, 3H), 8.40 (d, J=1.6 Hz, 1H), 8.28 (d, J=9.1 Hz, 1H), 7.83 (dd, J=9.1, 1.2 Hz, 1H), 4.80 (s, 2H), 4.75 (q, J=7.2 Hz, 2H), 4.21 (s, 3H), 1.42 (t, J=7.2 Hz, 3H).

LC/MS (System A): m/z (ESI$^+$)=274 [M$^+$], R$_t$=0.37 min, ELS purity=87%.

Intermediate 41—Synthesis of 6-chloro-2-[(1,3-dioxo-2,3-dihydro-1H-isoindol-2-yl)methyl]-1,3-diethyl-1H-1,3-benzodiazol-3-ium iodide

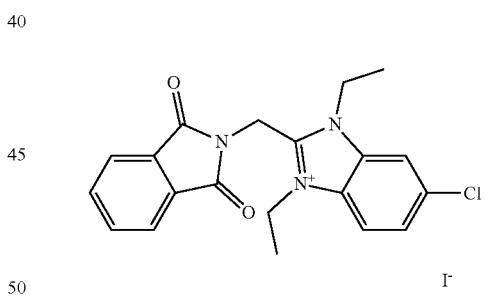

A mixture of 2-[(6-chloro-1-ethyl-1H-1,3-benzodiazol-2-yl)methyl]-2,3-dihydro-1H-isoindole-1,3-dione, Intermediate 29 (850 mg, 2.50 mmol) and iodomethane (2.0 ml, 25 mmol) in MeCN (12 ml) was heated under microwave irradiation for 3 h at 120° C. The resulting solution was left to stand at RT for 64 h, resulting in precipitation of a solid. The solid was collected by filtration then washed with MeCN and dried under vacuum to afford the product as a pale yellow solid (850 mg, 67%).

$^1$H NMR (500 MHz, DMSO-d$_6$) δ 8.41 (d, J=1.8 Hz, 1H), 8.18 (d, J=8.9 Hz, 1H), 7.98-7.94 (m, 2H), 7.93-7.89 (m, 2H), 7.79 (dd, J=8.9, 1.9 Hz, 1H), 5.43 (s, 2H), 4.74-4.66 (m, 4H), 1.46-1.38 (m, 6H).

LC/MS (System A): m/z (ESI$^+$)=368 [M($^{35}$Cl)$^+$], 370 [M($^{37}$Cl)$^+$], R$_t$=0.93 min, UV purity=98%.

Intermediate 42—Synthesis of 2-(aminomethyl)-6-chloro-1,3-diethyl-1H-1,3-benzodiazol-3-ium iodide

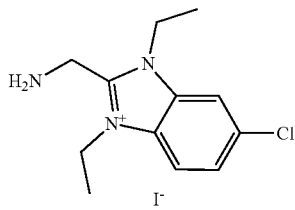 [SMILES: CCn1c(CN)[n+](CC)c2ccc(Cl)cc21 ; [I-]]

Hydrazine hydrate (787 µl, 16.2 mmol) was added to a suspension of 6-chloro-2-[(1,3-dioxo-2,3-dihydro-1H-isoindol-2-yl)methyl]-1,3-diethyl-1H-1,3-benzodiazol-3-ium iodide, Intermediate 41 (845 mg, 1.62 mmol) in MeOH (6 ml) in a pressure tube. The tube was sealed and heated at 80° C. for 4 h then allowed to cool to RT. The reaction mixture was concentrated in vacuo. The resultant residue was suspended in CH$_2$Cl$_2$:MeOH (9:1, 20 ml) then filtered. The filtrate was concentrated in vacuo to afford the product as a yellow solid (301 mg, 49%).

$^1$H NMR (500 MHz, DMSO-d$_6$) δ 8.32 (d, J=1.8 Hz, 1H), 8.11 (d, J=8.9 Hz, 1H), 7.73 (dd, J=8.8, 1.9 Hz, 1H), 4.65-4.56 (m, 4H), 4.29 (s, 2H), 1.46-1.40 (m, 6H).

LC/MS (System F): m/z (ESI$^+$)=238 [M($^{35}$Cl)$^+$], 240 [M($^{37}$Cl)$^+$], R$_t$=2.00 min, UV purity=97%.

Intermediate 43—Synthesis of 3-benzyl-2-[(1,3-dioxo-2,3-dihydro-1H-isoindol-2-yl)methyl]-1-ethyl-6-methoxy-1H-1,3-benzodiazol-3-ium bromide

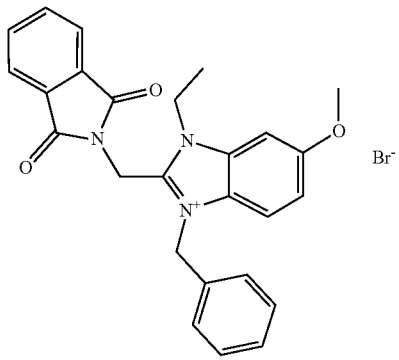 [SMILES: CCn1c(CN2C(=O)c3ccccc3C2=O)[n+](Cc2ccccc2)c2ccc(OC)cc21 ; [Br-]]

A mixture of 2-[(1-ethyl-6-methoxy-1H-1,3-benzodiazol-2-yl)methyl]-2,3-dihydro-1H-isoindole-1,3-dione, Intermediate 13 (500 mg, 1.49 mmol) and (bromomethyl)benzene (531 µl, 4.47 mmol) in MeCN (5 ml) was heated at 80° C. in a sealed tube for 16 h. The reaction mixture allowed to cool to RT then filtered. The solid was washed with MeCN then dried under vacuum to afford the product as a white solid (665 mg, 87%).

$^1$H NMR (500 MHz, DMSO-d$_6$) δ 7.84-7.79 (m, 3H), 7.78-7.74 (m, 2H), 7.71 (d, J=2.3 Hz, 1H), 7.29 (dd, J=9.2, 2.3 Hz, 1H), 7.09 (t, J=7.7 Hz, 2H), 7.00-6.94 (m, 3H), 5.85 (s, 2H), 5.50 (s, 2H), 4.79 (q, J=7.2 Hz, 2H), 3.94 (s, 3H), 1.51 (t, J=7.2 Hz, 3H).

LC/MS (System A): m/z (ESI$^+$)=426 [M$^+$], R$_t$=1.02 min, UV purity=99%.

Intermediate 44—Synthesis of 2-(aminomethyl)-3-benzyl-1-ethyl-6-methoxy-1H-1,3-benzodiazol-3-ium bromide

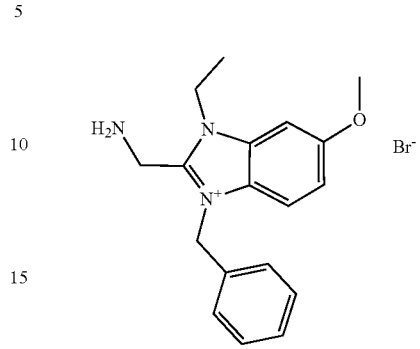

A mixture of 3-benzyl-2-[(1,3-dioxo-2,3-dihydro-1H-isoindol-2-yl)methyl]-1-ethyl-6-methoxy-1H-1,3-benzodiazol-3-ium bromide, Intermediate 43 (665 mg, 1.31 mmol) and hydrazine hydrate (638 µl, 13.1 mmol) in MeOH (5 ml) was stirred at 80° C. for 2 h in a sealed tube. The reaction mixture was allowed to cool then concentrated in vacuo to a yellow solid. The residue was suspended in CH$_2$Cl$_2$ (20 ml) with sonication. The resultant suspension was filtered then the solid was re-suspended in CH$_2$Cl$_2$:MeOH (1:1, 30 ml) with sonication. The resultant suspension was filtered then the combined filtrates were concentrated in vacuo to afford the product as a yellow solid (526 mg, 60%).

$^1$H NMR (500 MHz, DMSO-d$_6$) δ 7.71 (d, J=9.1 Hz, 1H), 7.62 (d, J=2.3 Hz, 1H), 7.41-7.31 (m, 5H), 7.20 (dd, J=9.1, 2.3 Hz, 1H), 5.86 (s, 2H), 4.63 (q, J=7.2 Hz, 2H), 4.34 (s, 2H), 3.90 (s, 3H), 1.48 (t, J=7.2 Hz, 3H).

LC/MS (System A): m/z (ESI$^+$)=296 [M$^+$], R$_t$=0.76 min, UV purity=56%.

Intermediate 45—Synthesis of tert-butyl N-[(1-ethyl-6-methoxy-1H-1,3-benzodiazol-2-yl)methyl]carbamate

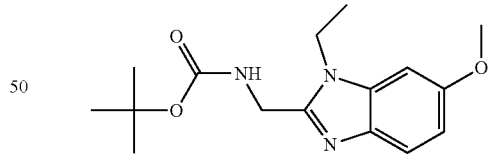

HATU (8.53 g, 22.3 mmol) and DIPEA (7.1 ml, 41 mmol) were added to a solution of N-(tert-butoxycarbonyl)glycine (3.93 g, 22.4 mmol) in DMF (40 ml). The resulting solution was stirred at RT for 0.5 h then a solution of 1-N-ethyl-5-methoxybenzene-1,2-diamine (3.39 g, 20.4 mmol) in THF (20 ml) was added. The reaction was left to stir at RT for 80 min then the reaction mixture was diluted with EtOAc (200 ml) and water (150 ml). The phases were separated then the organic phase was washed with water (3×150 ml) and brine (150 ml). The combined organic phases were dried over Na$_2$SO$_4$ then concentrated in vacuo to afford the crude intermediate as a dark red viscous oil. The intermediate was taken up in AcOH (40 ml) and the resulting solution was stirred at 60° C. for 18 h. The reaction mixture was allowed to cool then concentrated in vacuo. The residue was then dissolved in EtOAc (200 ml) then the pH was adjusted to 9 by the addition of saturated aqueous NaHCO$_3$ solution. The phases were separated and the organic phase was washed with water (2×150 ml) and brine (150 ml), then dried over Na$_2$SO$_4$ and concentrated in vacuo to afford the crude product as a dark red oil. The crude material was purified by flash column chromatography on a silica column (340 g). The column was eluted with CH$_2$Cl$_2$:MeOH, increasing the gradient linearly from 100:0 to 92:8 over 10 column volumes. The desired fractions were combined and evaporated to a viscous dark red oil which solidified on standing to yield the product as a dark red solid (5.02 g, 77%).

$^1$H NMR (500 MHz, DMSO-d$_6$) δ 7.47-7.39 (m, 2H), 7.06 (d, J=2.4 Hz, 1H), 6.78 (dd, J=8.7, 2.4 Hz, 1H), 4.39 (d, J=5.9 Hz, 2H), 4.22 (q, J=7.1 Hz, 2H), 3.81 (s, 3H), 1.39 (s, 9H), 1.28 (t, J=7.2 Hz, 3H).

LC/MS (System A): m/z (ESI$^+$)=306 [MH$^+$], R$_t$=0.88 min, UV purity=96%.

Intermediate 46 Synthesis of 2-({[(tert-butoxy)carbonyl]amino}methyl)-1-ethyl-6-methoxy-3-(2-methoxy-2-oxoethyl)-1H-1,3-benzodiazol-3-ium bromide

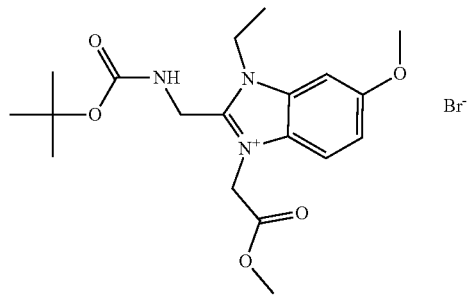 [SMILES: CCn1c(CNC(=O)OC(C)(C)C)[n+](CC(=O)OC)c2ccc(OC)cc21 ; [Br-]]

Methyl bromoacetate (395 μl, 4.18 mmol) was added to a suspension of tert-butyl N-[(1-ethyl-6-methoxy-1H-1,3-benzodiazol-2-yl)methyl]carbamate, Intermediate 45 (96%, 500 mg, 1.39 mmol) in MeCN (4 ml) in a pressure tube. The tube was sealed and the resulting mixture was stirred at 75° C. for 4 h then allowed to cool to RT. The resultant suspension was filtered then the solid was washed with cold MeCN and dried under vacuum to afford the product as a white solid (454 mg, 71%).

$^1$H NMR (500 MHz, DMSO-d$_6$) δ 7.90 (d, J=9.2 Hz, 1H), 7.86 (t, J=5.3 Hz, 1H), 7.62 (d, J=2.2 Hz, 1H), 7.29 (dd, J=9.1, 2.3 Hz, 1H), 5.58 (s, 2H), 4.75 (d, J=5.4 Hz, 2H), 4.65 (q, J=7.2 Hz, 2H), 3.92 (s, 3H), 3.75 (s, 3H), 1.43 (t, J=7.2 Hz, 3H), 1.35 (s, 9H).

LC/MS (System A): m/z (ESI$^+$)=378 [M$^+$], R$_t$=0.88 min, UV purity=100%.

Intermediate 47 Synthesis of 2-(aminomethyl)-1-ethyl-6-methoxy-3-(2-methoxy-2-oxoethyl)-1H-1,3-benzodiazol-3-ium hydrochloride bromide

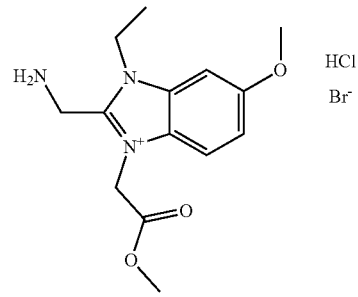 [SMILES: CCn1c(CN)[n+](CC(=O)OC)c2ccc(OC)cc21 ; Cl ; [Br-]]

A mixture of 2-({[(tert-butoxy)carbonyl]amino}methyl)-1-ethyl-6-methoxy-3-(2-methoxy-2-oxoethyl)-1H-1,3-benzodiazol-3-ium bromide, Intermediate 46 (454 mg, 0.990 mmol) and HCl solution in dioxane (4.0 M, 2.5 ml, 10 mmol) was stirred at RT for 0.5 h. The reaction mixture was concentrated in vacuo to afford the product as a pale orange foam (580 mg, 96% yield corrected for 35 wt % residual dioxane observed in NMR).

$^1$H NMR (500 MHz, DMSO-d$_6$) $^1$H NMR (500 MHz, DMSO-d$_6$) δ 8.86 (s, 3H), 7.97 (d, J=9.2 Hz, 1H), 7.68 (d, J=2.3 Hz, 1H), 7.35 (dd, J=9.2, 2.3 Hz, 1H), 5.77 (s, 2H), 4.79 (s, 2H), 4.72 (q, J=7.2 Hz, 2H), 3.94 (s, 3H), 3.77 (s, 3H), 1.47 (t, J=7.2 Hz, 3H).

LC/MS (System A): m/z (ESI$^+$)=278 [M$^+$], R$_t$=0.14 min, ELS purity=95%.

Intermediate 48 Synthesis of 2-({[(tert-butoxy)carbonyl]amino}methyl)-3-(carbamoylmethyl)-1-ethyl-6-methoxy-1H-1,3-benzodiazol-3-ium bromide

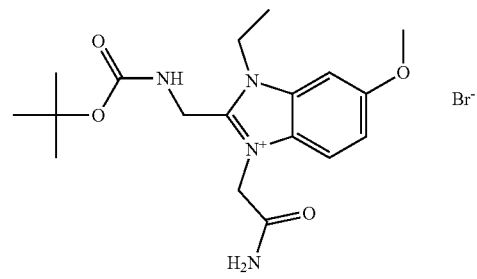 [SMILES: CCn1c(CNC(=O)OC(C)(C)C)[n+](CC(N)=O)c2ccc(OC)cc21 ; [Br-]]

2-Bromoacetamide (691 mg, 5.01 mmol) was added to a suspension of tert-butyl N-[(1-ethyl-6-methoxy-1H-1,3-benzodiazol-2-yl)methyl]carbamate, Intermediate 45 (85%, 600 mg, 1.67 mmol) in MeCN (6 ml) in a pressure tube. The tube was sealed then the reaction mixture was stirred at 80° C. for 5 h. The reaction was allowed to cool to RT then stirred at RT for 64 h. The reaction mixture was heated to 80° C. for a further 2 h then allowed to cool to RT. The resultant mixture was concentrated in vacuo to a viscous red oil. The crude material was purified by flash column chromatography on a silica column (50 g). The column was eluted with CH$_2$Cl$_2$:MeOH, using the following gradient (% MeOH, column volumes): 0%, 1 CV; 0-9%, 8 CV; 9%, 3 CV; 9-14%, 2 CV, 14%, 1 CV; 14-20%, 2 CV. The desired fractions were combined and evaporated to afford the product as a pale magenta foam (638 mg, 84%).

¹H NMR (500 MHz, DMSO-d₆) δ 7.90 (s, 1H), 7.86-7.77 (m, 2H), 7.63 (s, 1H), 7.60 (d, J=2.2 Hz, 1H), 7.29 (dd, J=9.1, 2.3 Hz, 1H), 5.30 (s, 2H), 4.70 (d, J=5.4 Hz, 2H), 4.62 (q, J=7.2 Hz, 2H), 3.92 (s, 3H), 1.42 (t, J=7.2 Hz, 3H), 1.36 (s, 9H).

LC/MS (System A): m/z (ESI⁺)=363 [M⁺], $R_t$=0.83 min, UV purity=98%.

Intermediate 49—Synthesis of 2-(aminomethyl)-3-(carbamoylmethyl)-1-ethyl-6-methoxy-1H-1,3-benzodiazol-3-ium hydrochloride bromide

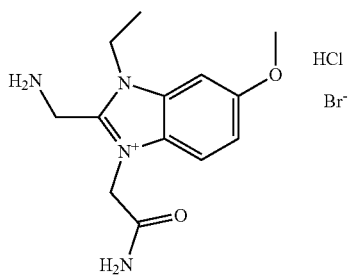 [SMILES: CCn1c(CN)[n+](CC(N)=O)c2ccc(OC)cc21 ; Cl ; [Br-]]

A mixture of 2-({[(tert-butoxy)carbonyl]amino}methyl)-3-(carbamoylmethyl)-1-ethyl-6-methoxy-1H-1,3-benzodiazol-3-ium bromide, Intermediate 48 (98%, 638 mg, 1.41 mmol) and HCl solution in dioxane (4.0 M, 3.5 ml, 14 mmol) was stirred at RT for 0.5 h. The reaction mixture was concentrated in vacuo to afford the product as a purple solid (719 mg, 97%-yield corrected for 28 wt % residual dioxane observed in NMR).

¹H NMR (500 MHz, DMSO-d₆) δ 8.91 (s, 3H), 8.35 (s, 1H), 7.98-7.89 (m, 2H), 7.68 (d, J=2.3 Hz, 1H), 7.38 (dd, J=9.2, 2.3 Hz, 1H), 5.45 (s, 2H), 4.77 (s, 2H), 4.71 (q, J=7.2 Hz, 2H), 3.94 (s, 3H), 1.46 (t, J=7.2 Hz, 3H).

LC/MS (System A): m/z (ESI⁺)=263 [M⁺], $R_t$=0.15 min, ELS purity=100%.

Intermediate 50—Synthesis of 2-[(1,3-dioxo-2,3-dihydro-1H-isoindol-2-yl)methyl]-1-ethyl-6-methoxy-3-[2-(methylsulfanyl)ethyl]-1H-1,3-benzodiazol-3-ium iodide

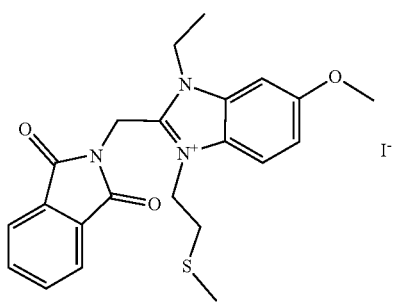 [SMILES: CCn1c(CN2C(=O)c3ccccc3C2=O)[n+](CCSC)c2ccc(OC)cc21 ; [I-]]

A mixture of 2-[(1-ethyl-6-methoxy-1H-1,3-benzodiazol-2-yl)methyl]-2,3-dihydro-1H-isoindole-1,3-dione, Intermediate 13 (500 mg, 1.49 mmol), 1-chloro-2-(methylsulfanyl) ethane (730 μl, 7.45 mmol) and NaI (1.12 g, 7.45 mmol) in MeCN (8 ml) was heated to 100° C. in a sealed tube for 5 h then allowed to cool to RT. The reaction mixture was concentrated in vacuo to a brown solid. The solid thus obtained was suspended in MeOH (8 ml) with sonication. The resultant suspension was filtered then the solid was washed with MeOH and dried under vacuum to afford the product as a brown solid (1.13 g, 50%) ¹H NMR (500 MHz, DMSO-d₆) δ 8.04 (d, J=9.2 Hz, 1H), 7.99-7.88 (m, 4H), 7.64 (t, J=2.6 Hz, 1H), 7.32 (dd, J=9.2, 2.3 Hz, 1H), 5.47-5.37 (m, 2H), 4.90-4.68 (m, 4H), 4.11 (s, 1H), 3.92 (d, J=1.4 Hz, 3H), 3.03 (t, J=7.1 Hz, 2H), 2.15 (s, 2H), 1.42 (q, J=6.9 Hz, 3H).

LC/MS (System A): m/z (ESI⁺)=410 [M⁺], $R_t$=0.99 min, UV purity=66%.

Intermediate 51—Synthesis of 2-(aminomethyl)-1-ethyl-6-methoxy-3-[2-(methylsulfanyl)ethyl]-1H-1,3-benzodiazol-3-ium iodide

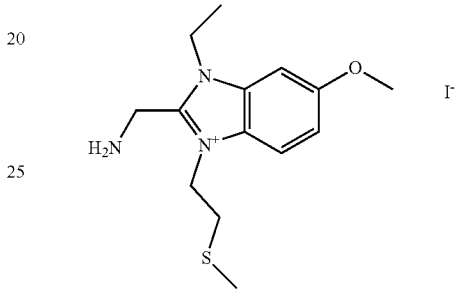

A mixture of 2-[(1,3-dioxo-2,3-dihydro-1H-isoindol-2-yl) methyl]-1-ethyl-6-methoxy-3-[2-(methylsulfanyl)ethyl]-1H-1,3-benzodiazol-3-ium iodide, Intermediate 50 (66%, 1.00 g, 1.62 mmol) and hydrazine hydrate (226 μl, 4.65 mmol) in MeOH (5 ml) was heated to 80° C. in a sealed tube for 80 min. The reaction mixture was concentrated in vacuo to an orange solid. The solid thus obtained was suspended in CH₂Cl₂ (50 ml) with sonication. The suspension was filtered then the filtrate was concentrated in vacuo to afford the product as a pale orange solid (395 mg, 48%).

¹H NMR (500 MHz, DMSO-d₆) δ 7.96 (d, J=9.1 Hz, 1H), 7.60-7.56 (m, 1H), 7.27 (dt, J=9.1, 2.1 Hz, 1H), 4.76 (t, J=6.9 Hz, 2H), 4.61 (q, J=6.1, 4.9 Hz, 2H), 4.30 (s, 2H), 3.92 (d, J=1.4 Hz, 3H), 3.01 (t, J=6.9 Hz, 2H), 2.41-2.30 (m, 2H), 2.13 (s, 3H), 1.45 (t, J=7.3 Hz, 3H).

LC/MS (System A): m/z (ESI⁺)=280 [M⁺], $R_t$=0.65 min, UV purity=80%.

Intermediate 52—Synthesis of 2-({[(tert-butoxy) carbonyl]amino}methyl)-1-ethyl-3-(2-hydroxyethyl)-6-methoxy-1H-1,3-benzodiazol-3-ium bromide

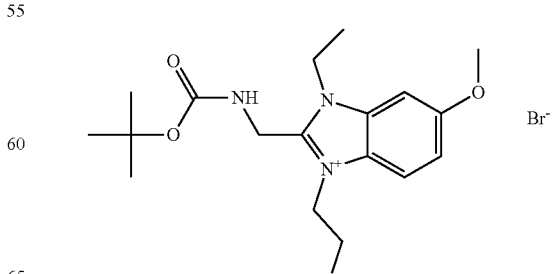

(2-Bromoethoxy)(tert-butyl)dimethylsilane (1.66 g, 6.96 mmol) was added to a suspension of tert-butyl N-[(1-ethyl-6-methoxy-1H-1,3-benzodiazol-2-yl)methyl]carbamate, Intermediate 45 (85%, 500 mg, 1.39 mmol) in MeCN (5 ml) in a pressure tube. The tube was sealed then the reaction mixture was stirred at 80° C. for 0.5 h then at 100° C. for 16 h. The reaction was allowed to cool to RT then additional (2-bromoethoxy)(tert-butyl)dimethylsilane (1.00 g, 4.18 mmol) was added. The tube was sealed then the reaction was left to stir at 100° C. for a further 24 h. The reaction mixture was allowed to cool then concentrated in vacuo to a red oil. The crude material was purified by flash column chromatography on a silica column (25 g). The column was eluted with $CH_2Cl_2$:MeOH, increasing the gradient linearly from 100:0 to 90:10 over 10 column volumes. The desired fractions were combined and evaporated to yield a viscous dark red oil (615 mg). The material was further purified by flash column chromatography on C18 (30 g). The column was eluted with MeCN:water+0.1% formic acid using the following gradient (% MeCN, column volumes): 10%, 2 CV; 10-36%; 36%, 2 CV; 36-50%, 4 CV; 50-100%, 3 CV; 100%, 3 CV. The desired fractions were combined and evaporated to yield the product as a viscous dark red oil (278 mg, 43%).

$^1$H NMR (500 MHz, DMSO-$d_6$) δ 8.28 (s, 1H), 7.99-7.84 (m, 2H), 7.57 (d, J=2.2 Hz, 1H), 7.28 (dd, J=9.1, 2.3 Hz, 1H), 4.76 (d, J=5.5 Hz, 2H), 4.71-4.65 (m, 2H), 4.59 (q, J=7.1 Hz, 2H), 3.92 (s, 3H), 3.77 (t, J=4.7 Hz, 2H), 1.41 (t, J=7.2 Hz, 3H), 1.38 (d, J=2.8 Hz, 9H).

LC/MS (System A): m/z (ESI$^+$)=350 [MH$^+$], $R_t$=0.88 min, UV purity=92%.

Intermediate 53 Synthesis of 2-(aminomethyl)-1-ethyl-3-(2-hydroxyethyl)-6-methoxy-1H-1,3-benzodiazol-3-ium hydrochloride bromide

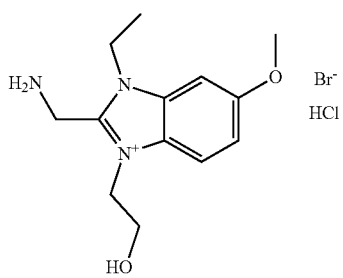 [SMILES: CCn1c(CN)[n+](CCO)c2ccc(OC)cc21 ; Cl ; [Br-]]

Hydrogen chloride solution in dioxane (4.0 M, 1.2 ml, 4.8 mmol) was added to a solution of 2-({[(tert-butoxy)carbonyl]amino}methyl)-1-ethyl-3-(2-hydroxyethyl)-6-methoxy-1H-1,3-benzodiazol-3-ium bromide, Intermediate 52 (92%, 227 mg, 0.49 mmol) in MeCN (3 ml). The resulting mixture was stirred at RT for 1 h. The reaction mixture was concentrated in vacuo to afford the product as a dark purple solid (174 mg, 97%).

$^1$H NMR (500 MHz, DMSO-$d_6$) δ 8.89 (s, 3H), 8.03 (d, J=9.2 Hz, 1H), 7.66 (d, J=2.3 Hz, 1H), 7.35 (dd, J=9.2, 2.3 Hz, 1H), 4.82-4.73 (m, 4H), 4.69 (q, J=7.2 Hz, 2H), 3.94 (s, 3H), 3.80 (t, J=4.6 Hz, 2H), 1.45 (t, J=7.2 Hz, 3H).

LC/MS (System F): m/z (ESI$^+$)=250 [MH$^+$], $R_t$=1.58 min, UV purity=99%.

Intermediate 54 Synthesis of 2-{[(2-carboxyphenyl)formamido]methyl}-1-ethyl-3-{2-[2-(2-hydroxyethoxy)ethoxy]ethyl}-6-methoxy-1H-1,3-benzodiazol-3-ium iodide

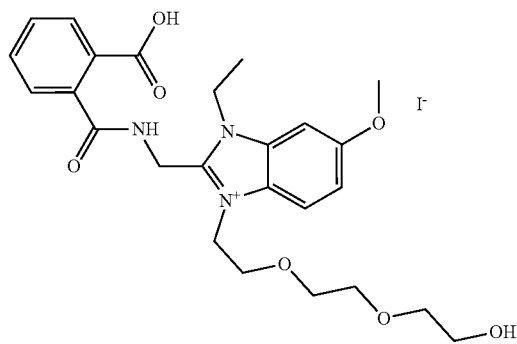 [SMILES: CCn1c(CNC(=O)c2ccccc2C(=O)O)[n+](CCOCCOCCO)c2ccc(OC)cc21 ; [I-]]

A mixture of 2-[(1-ethyl-6-methoxy-1H-1,3-benzodiazol-2-yl)methyl]-2,3-dihydro-1H-isoindole-1,3-dione, Intermediate 13 (2.00 g, 5.96 mmol) and 2-[2-(2-iodoethoxy)ethoxy]ethan-1-ol (90%, 8.62 g, 29.8 mmol) in MeCN (15 ml) was heated at 130° C. in a sealed tube for 16 h then allowed to cool to RT. The reaction mixture was concentrated in vacuo then the crude material was purified by flash column chromatography on C18 (12 g). The column was eluted with MeCN:water+0.1% formic acid using the following gradient (% MeCN, column volumes): 10%, 2 CV; 10-14%, 2 CV; 14-18%, 1 CV; 18-27%, 2 CV; 27-31%, 0.5 CV; 31-60%, 0.5 CV; 60-100%, 1 CV; 100%, 1 CV. The desired fractions were combined and evaporated to yield the product as a yellow amorphous solid (1.72 g, 47%).

$^1$H NMR (500 MHz, DMSO-$d_6$) δ 12.97-12.91 (m, 1H), 7.96 (d, J=9.2 Hz, 1H), 7.72 (dd, J=7.8, 1.2 Hz, 1H), 7.60 (dd, J=7.7, 1.3 Hz, 1H), 7.57 (d, J=2.3 Hz, 1H), 7.37 (td, J=7.5, 1.4 Hz, 1H), 7.30-7.24 (m, 2H), 5.04 (d, J=5.0 Hz, 2H), 4.91 (t, J=4.8 Hz, 2H), 4.77-4.62 (m, 3H), 3.91 (s, 3H), 3.83 (t, J=4.9 Hz, 2H), 3.51-3.46 (m, 2H), 3.43-3.39 (m, 4H), 3.36-3.28 (m, 2H+HDO), 1.41 (t, J=7.2 Hz, 3H).

LC/MS (System A): m/z (ESI$^+$)=486 [M$^+$], $R_t$=0.80 min, UV purity=100%.

Intermediate 55 Synthesis of 2-(aminomethyl)-1-ethyl-3-{2-[2-(2-hydroxyethoxy)ethoxy]ethyl}-6-methoxy-1H-1,3-benzodiazol-3-ium iodide

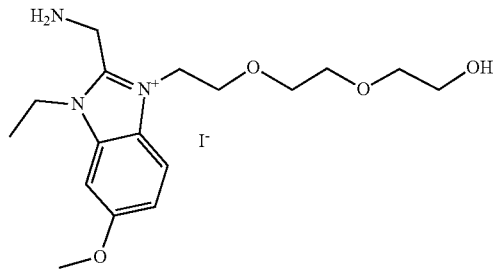 [SMILES: CCn1c(CN)[n+](CCOCCOCCO)c2ccc(OC)cc21 ; [I-]]

Hydrazine hydrate (639 μl, 13.2 mmol) was added to a solution of 2-{[(2-carboxyphenyl)formamido]methyl}-1-ethyl-3-{2-[2-(2-hydroxyethoxy)ethoxy]ethyl}-6-methoxy-1H-1,3-benzodiazol-3-ium iodide, Intermediate 54 (1.52 g, 2.48 mmol) in MeOH (12 ml) in a pressure tube. The tube was sealed and the reaction solution was heated at 75° C. for 3.5 h. The reaction was allowed to cool to RT then stirred at RT for 64 h. Additional hydrazine hydrate (639 μl, 13.2 mmol) was added and the reaction was heated at 75° C. for a further 18 h, then at 80° C. for a further 24 h. The reaction mixture was allowed to cool to RT then concentrated in vacuo to an orange solid. The solid thus obtained was suspended in CH$_2$Cl$_2$:MeOH (9:1, 30 ml) then filtered. The filtrate was concentrated in vacuo to afford the product as a viscous orange oil (1.21 g, 88%).

LC/MS (System F): m/z (ESI$^+$)=338 [M$^+$], Rt=1.41 min, UV purity=84%.

Intermediate 56—Synthesis of 3-benzyl-6-chloro-2-[(1,3-dioxo-2,3-dihydro-1H-isoindol-2-yl)methyl]-1-ethyl-1H-1,3-benzodiazol-3-ium bromide

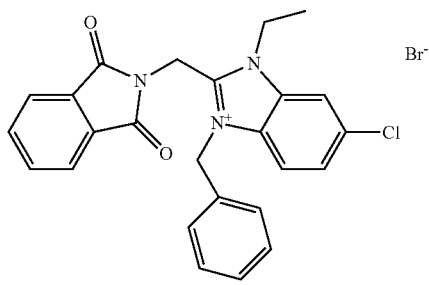 [SMILES: CCn1c(CN2C(=O)c3ccccc3C2=O)[n+](Cc2ccccc2)c2ccc(Cl)cc21 ; [Br-]]

Benzyl bromide (88 μl, 0.74 mmol) was added to a suspension of 2-[(6-chloro-1-ethyl-1H-1,3-benzodiazol-2-yl)methyl]-2,3-dihydro-1H-isoindole-1,3-dione, Intermediate 20 (0.25 g, 0.74 mmol) in MeCN (5 ml) in a pressure tube. The tube was sealed then the reaction was stirred at 80° C. for 16 h then allowed to cool to RT. Benzyl bromide (88 μl, 0.74 mmol) was added then the reaction was stirred at 80° C. for a further 6 h. The reaction was allowed to cool to RT then left to stand at RT for 64 h. Benzyl bromide (88 μl, 0.74 mmol) was added then the reaction was stirred at 80° C. for a further 24 h. The reaction was allowed to cool to RT then filtered. The solid was washed with MeCN then dried under vacuum to afford the product as a white solid (370 mg, 97%).

$^1$H NMR (500 MHz, DMSO-d$_6$) δ 8.50 (d, J=1.8 Hz, 1H), 7.98 (d, J=8.9 Hz, 1H), 7.85-7.68 (m, 5H), 7.14-7.05 (m, 2H), 6.99 (t, J=6.5 Hz, 3H), 5.89 (s, 2H), 5.52 (s, 2H), 4.82 (q, J=7.2 Hz, 2H), 1.51 (t, J=7.2 Hz, 3H).

LC/MS (System A): m/z (ESI$^+$)=430 [M$^+$], Rt=0.98 min, UV purity=99%.

Intermediate 57—Synthesis of 2-(aminomethyl)-3-benzyl-6-chloro-1-ethyl-1H-1,3-benzodiazol-3-ium bromide

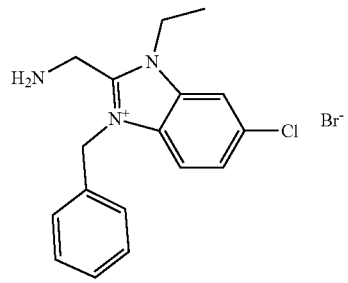 [SMILES: CCn1c(CN)[n+](Cc2ccccc2)c2ccc(Cl)cc21 ; [Br-]]

Hydrazine hydrate (0.18 ml, 3.62 mmol) was added to a suspension of 3-benzyl-6-chloro-2-[(1,3-dioxo-2,3-dihydro-1H-isoindol-2-yl)methyl]-1-ethyl-1H-1,3-benzodiazol-3-ium bromide, Intermediate 56 (370 mg, 0.724 mmol) in MeOH (4 ml) in a pressure tube. The tube was sealed then the reaction was stirred at 75° C. for 3 h. The reaction mixture was allowed to cool to RT then filtered. The filtrate was concentrated in vacuo to afford an orange solid. The solid thus obtained was suspended in CH$_2$Cl$_2$:MeOH (9:1, 10 ml) then filtered. The solid was dried under vacuum then suspended in MeOH. The suspension was filtered then the filtrate was concentrated in vacuo. The resultant residue was suspended in CH$_2$Cl$_2$:MeOH (9:1, 10 ml) with sonication. The resultant suspension was filtered then the filtrate was concentrated in vacuo to afford the product as a pale yellow solid (107 mg, 33%).

$^1$H NMR (500 MHz, DMSO-d$_6$) δ 8.36 (d, J=1.8 Hz, 1H), 7.83 (d, J=8.9 Hz, 1H), 7.66 (dd, J=8.9, 1.9 Hz, 1H), 7.43-7.30 (m, 5H), 5.89 (s, 2H), 4.63 (q, J=7.2 Hz, 2H), 4.35 (s, 2H), 1.46 (t, J=7.2 Hz, 3H).

LC/MS (System A): m/z (ESI$^+$)=300 [M$^+$], Rt=0.81 min, UV purity=85%.

Intermediate 58—Synthesis of 3-benzyl-2-({[(tert-butoxy)carbonyl]amino}methyl)-1-ethyl-6-(trifluoromethyl)-1H-1,3-benzodiazol-3-ium bromide

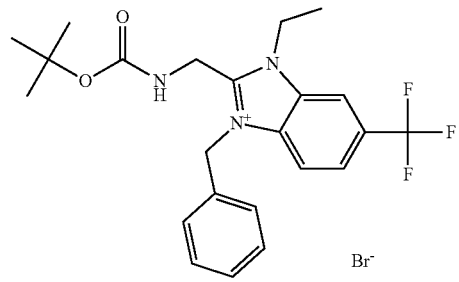 [SMILES: CCn1c(CNC(=O)OC(C)(C)C)[n+](Cc2ccccc2)c2ccc(C(F)(F)F)cc21 ; [Br-]]

Benzyl bromide (173 μl, 1.46 mmol) was added to a suspension of tert-butyl N-{[1-ethyl-6-(trifluoromethyl)-1H-1,3-benzodiazol-2-yl]methyl}carbamate, Intermediate 34 (250 mg, 0.73 mmol) in MeCN (3 ml) in a pressure tube. The tube was sealed and heated at 80° C. for 16 h then the reaction mixture was concentrated in vacuo to afford an orange oil which solidified on standing. The resulting solid was suspended in MeCN (2 ml). The solid was collected by filtration then dried under vacuum to afford the product as a white solid (160 mg). The filtrate was concentrated in vacuo. The residue was suspended in the minimum volume of MeCN then filtered. The solid thus obtained was dried under vacuum to yield a second batch of product as an off-white solid (90 mg). The 2 batches of product were combined in MeCN then evaporated to afford the product as an off-white solid (250 mg, 64%).

$^1$H NMR (500 MHz, DMSO-d$_6$) δ 8.69 (s, 1H), 8.03-7.87 (m, 3H), 7.43-7.36 (m, 3H), 7.31-7.23 (m, 2H), 5.92 (s, 2H), 4.97-4.85 (m, 2H), 4.78 (q, J=7.1 Hz, 2H), 1.49 (t, J=7.1 Hz, 3H), 1.30 (s, 9H).

LC/MS (System A): m/z (ESI$^+$)=435 [M$^+$], R$_t$=1.05 min, UV purity=96%.

Intermediate 59—Synthesis of 2-(aminomethyl)-3-benzyl-1-ethyl-6-(trifluoromethyl)-1H-1,3-benzodiazol-3-ium hydrochloride bromide

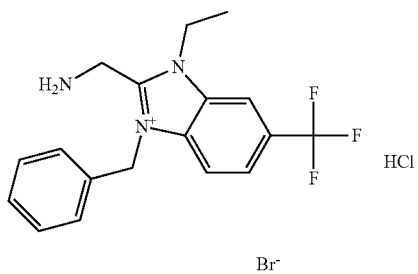 [SMILES: CCn1c(CN)[n+](Cc2ccccc2)c2ccc(C(F)(F)F)cc21 ; Cl ; [Br-]]

HCl solution in dioxane (4.0 M, 0.61 ml, 2.4 mmol) was added to a solution of 3-benzyl-2-({[(tert-butoxy)carbonyl]amino}methyl)-1-ethyl-6-(trifluoromethyl)-1H-1,3-benzodiazol-3-ium bromide, Intermediate 58 (250 mg, 0.49 mmol) in MeCN (2.5 ml). The reaction was stirred at RT for 18 h then concentrated in vacuo. The residue was azeotroped with MeCN then dried under vacuum to afford the product as a pale yellow solid (209 mg, 95%).

$^1$H NMR (500 MHz, DMSO-d$_6$) δ 9.18 (s, 3H), 8.77 (s, 1H), 8.10-7.99 (m, 2H), 7.51-7.46 (m, 2H), 7.44-7.34 (m, 3H), 6.05 (s, 2H), 4.94-4.79 (m, 4H), 1.53 (t, J=7.2 Hz, 3H).

LC/MS (System A): m/z (ESI$^+$)=334 [M$^+$], R$_t$=0.86 min, UV purity=100%.

Intermediate 60—Synthesis of tert-butyl N-[(1-benzyl-1H-1,3-benzodiazol-2-yl)methyl]carbamate

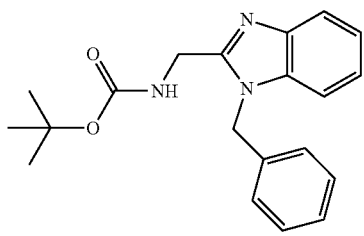 [SMILES: CC(C)(C)OC(=O)NCc1nc2ccccc2n1Cc1ccccc1]

Benzyl bromide (1.29 ml, 10.8 mmol) was added to a mixture of tert-butyl N-(1H-1,3-benzodiazol-2-ylmethyl) carbamate (85%, 3.15 g, 10.8 mmol) and K$_2$CO$_3$ (2.25 g, 16.3 mmol) in DMF (25 ml). The resulting mixture was stirred at RT for 16 h. The reaction mixture was partitioned between water (150 ml) and EtOAc (150 ml). The phases were separated then the aqueous phase was extracted with EtOAc (5×150 ml). The combined organics were dried over Na$_2$SO$_4$ then concentrated in vacuo to approximately 50 ml. The resultant slurry was recrystallized from the minimum volume of refluxing EtOAc to afford the product as white solid (2.22 g, 61%).

$^1$H NMR (500 MHz, DMSO-d$_6$) δ 7.64-7.58 (m, 1H), 7.51-7.45 (m, 1H), 7.40-7.34 (m, 1H), 7.34-7.24 (m, 3H), 7.20-7.11 (m, 4H), 5.51 (s, 2H), 4.44 (d, J=5.8 Hz, 2H), 1.32 (s, 9H).

LC/MS (System A): m/z (ESI$^+$)=338 [MH$^+$], R$_t$=1.02 min, UV purity=100%.

Intermediate 61—Synthesis of 1-benzyl-2-({[(tert-butoxy)carbonyl]amino}methyl)-3-(2-methoxy-2-oxoethyl)-1H-1,3-benzodiazol-3-ium bromide

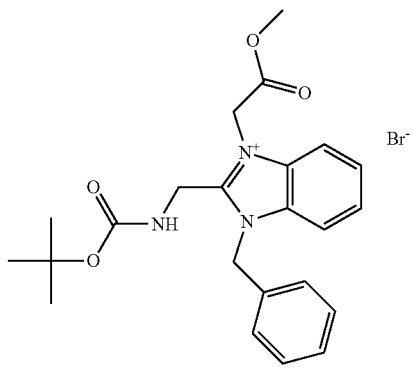 [SMILES: COC(=O)C[n+]1c(CNC(=O)OC(C)(C)C)n(Cc2ccccc2)c2ccccc21 ; [Br-]]

A mixture of tert-butyl N-[(1-benzyl-1H-1,3-benzodiazol-2-yl)methyl]carbamate, Intermediate 60 (500 mg, 1.48 mmol) and methyl bromoacetate (421 μl, 4.45 mmol) in MeCN (5 ml) was stirred at 70° C. in a sealed tube for 16 h. The reaction mixture was allowed to cool then concentrated in vacuo to afford the product as a white solid (717 mg, 96%).

$^1$H NMR (500 MHz, DMSO-d$_6$) δ 8.06 (d, J=8.3 Hz, 1H), 7.89 (t, J=5.4 Hz, 1H), 7.81 (d, J=8.2 Hz, 1H), 7.73-7.60 (m, 2H), 7.42-7.32 (m, 3H), 7.28 (d, J=6.8 Hz, 2H), 5.97 (s, 2H), 5.69 (s, 2H), 4.89 (d, J=5.4 Hz, 2H), 3.77 (s, 3H), 1.32 (s, 9H).

LC/MS (System A): m/z (ESI$^+$)=410 [M$^+$], R$_t$=0.94 min, UV purity=97%.

Intermediate 62—Synthesis of 1-benzyl-2-({[(tert-butoxy)carbonyl]amino}methyl)-3-[2-oxo-2-(piperidin-1-yl)ethyl]-1H-1,3-benzodiazol-3-ium bromide

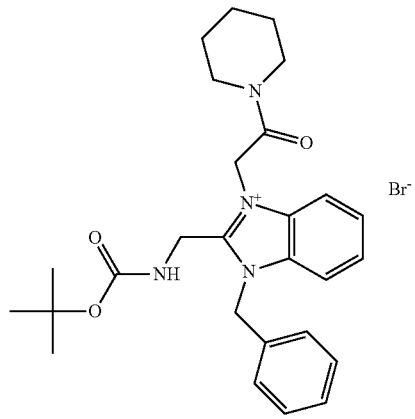 [SMILES: CC(C)(C)OC(=O)NCc1n(Cc2ccccc2)c2ccccc2[n+]1CC(=O)N1CCCCC1 ; [Br-]]

A mixture of 1-benzyl-2-({[(tert-butoxy)carbonyl]amino}methyl)-3-(2-methoxy-2-oxoethyl)-1H-1,3-benzodiazol-3-ium bromide, Intermediate 61 (350 mg, 0.71 mmol) in aqueous LiOH solution (1.0 M, 1.4 ml, 1.4 mmol) and MeOH (1.5 ml) was stirred at RT for 16 h. The reaction mixture was acidified to pH 3 by dropwise addition of aqueous HCl solution (1 M) then concentrated in vacuo to afford the crude intermediate as a beige solid (469 mg). The crude intermediate thus obtained was dissolved in DMF (4 ml) then HATU (340 mg, 0.89 mmol) and DIPEA (206 μl, 1.18 mmol) were added. Piperidine (88 μl, 0.89 mmol) was added to the reaction solution then the resulting mixture was stirred at RT for 45 min. Additional piperidine (150 μl, 1.52 mmol) and HATU (300 mg, 0.89 mmol) were added and the reaction was left to stir at RT for an additional 64 h. The reaction mixture was concentrated in vacuo then the crude material was purified by flash column chromatography on C18 (30 g). The column was eluted with MeCN:water+0.1% formic acid using the following gradient (% MeCN, column volumes): 10-45%, 12 CV; 45%, 2 CV; 45-53%, 3 CV; 53-100%, 3 CV; 100%, 1 CV. The desired fractions were combined and evaporated to afford the product as a pale orange foam (209 mg, 53%).

¹H NMR (500 MHz, DMSO-d₆) δ 7.98 (d, J=8.3 Hz, 1H), 7.83-7.76 (m, 2H), 7.70-7.58 (m, 2H), 7.43-7.32 (m, 3H), 7.25 (d, J=6.8 Hz, 2H), 5.97 (s, 2H), 5.76 (s, 2H), 4.78 (d, J=5.4 Hz, 2H), 3.58-3.51 (m, 2H), 3.47-3.42 (m, 2H), 1.76-1.62 (m, 4H), 1.51 (s (br), 2H), 1.32 (s, 9H).

LC/MS (System A): m/z (ESI⁺)=463 [M⁺], R$_t$=1.00 min, UV purity=99%.

Intermediate 63 Synthesis of 2-(aminomethyl)-1-benzyl-3-[2-oxo-2-(piperidin-1-yl)ethyl]-1H-1,3-benzodiazol-3-ium hydrochloride bromide

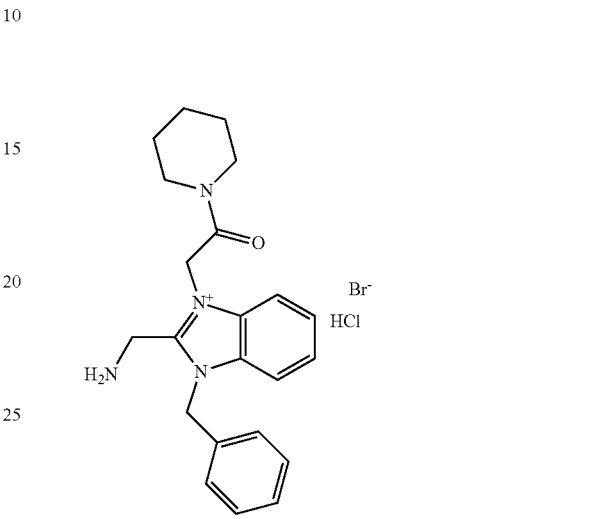

A mixture of 1-benzyl-2-({[(tert-butoxy)carbonyl]amino}methyl)-3-[2-oxo-2-(piperidin-1-yl)ethyl]-1H-1,3-benzodiazol-3-ium bromide, Intermediate 62 (205 mg, 0.377 mmol) and HCl solution in dioxane (4.0 M, 1.1 ml, 4.4 mmol) was stirred at RT for 0.5 h. The reaction mixture was concentrated in vacuo to afford the product as a viscous orange oil (219 mg, 92% yield corrected for 24 wt % residual dioxane observed in NMR).

¹H NMR (500 MHz, DMSO-d₆) δ 8.15-8.09 (m, 1H), 7.91 (d, J=8.3 Hz, 1H), 7.74 (t, J=7.7 Hz, 1H), 7.68 (t, J=7.8 Hz, 1H), 7.44-7.33 (m, 3H), 7.32 (d, J=7.0 Hz, 2H), 6.05 (s, 2H), 5.97 (s, 2H), 4.74 (s, 2H), 3.63-3.58 (m, 2H), 3.48-3.45 (m, 2H), 1.79-1.71 (m, 2H), 1.71-1.63 (m, 2H), 1.57-1.46 (m, 2H).

LC/MS (System A): m/z (ESI⁺)=363 [M⁺], R$_t$=0.82 min, UV purity=93%.

Intermediate 64 Synthesis of 6-(2-{[(tert-butoxy)carbonyl]amino}ethoxy)-1,3-diethyl-2-({[(9H-fluoren-9-ylmethoxy)carbonyl]amino}methyl)-1H-1,3-benzodiazol-3-ium iodide

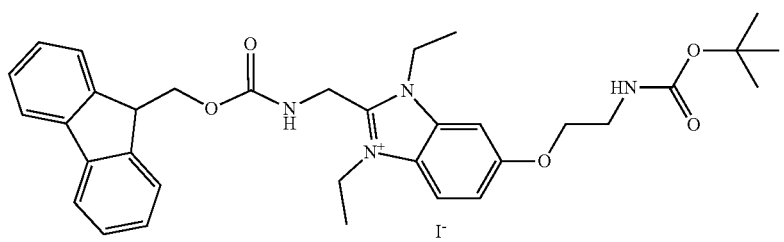 [SMILES: CCn1c(CNC(=O)OCC2c3ccccc3-c3ccccc32)[n+](CC)c2ccc(OCCNC(=O)OC(C)(C)C)cc21 ; [I-]]

Intermediate 64 was synthesised by according to literature procedures (US 2015/0018313 A1).

Intermediate 65—Synthesis of 2-(aminomethyl)-6-(2-{[(tert-butoxy)carbonyl]amino}ethoxy)-1,3-diethyl-1H-1,3-benzodiazol-3-ium iodide

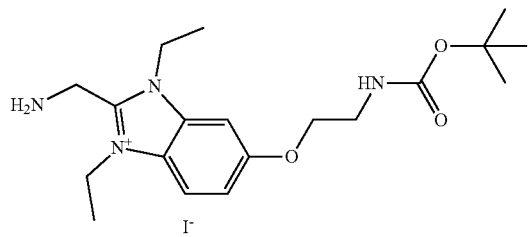 [SMILES: CCn1c(CN)[n+](CC)c2ccc(OCCNC(=O)OC(C)(C)C)cc21 ; [I-]]

Morpholine (3.46 ml, 40.0 mmol) was added to a solution of 6-(2-{[(tert-butoxy)carbonyl]amino}ethoxy)-1,3-diethyl-2-({[(9H-fluoren-9-ylmethoxy)carbonyl]amino}methyl)-1H-1,3-benzodiazol-3-ium iodide, Intermediate 64 (95%, 3.00 g, 4.00 mmol) in THF (50 ml). The reaction mixture was stirred at RT for 25 min then diluted with diethyl ether (150 ml). The resulting mixture was agitated then the supernatant was decanted off. The residual gum was washed further with ether (2×60 ml) then dried under vacuum. The residue was dissolved in THF then concentrated in vacuo afford the product as a pale orange solid (1.99 g, 83%).

$^1$H NMR (500 MHz, DMSO-$d_6$) δ 7.95 (d, J=9.1 Hz, 1H), 7.65-7.61 (m, 1H), 7.25 (dd, J=9.1, 2.3 Hz, 1H), 7.11-7.05 (m, 1H), 4.61-4.53 (m, 4H), 4.25 (s, 2H), 4.11 (t, J=5.9 Hz, 2H), 3.36 (q, J=5.9 Hz, 2H), 1.45-1.41 (m, 6H), 1.39 (s, 9H).

LC/MS (System A): m/z (ESI$^+$)=363 [M$^+$], R$_t$=0.76 min, UV purity=82%.

Intermediate 66—Synthesis tert-butyl N-[3-(3-fluoro-4-nitrophenoxy)propyl]carbamate

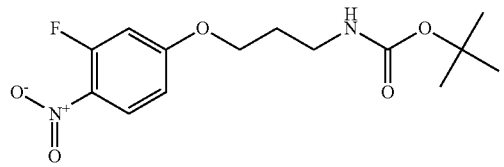 [SMILES: CC(C)(C)OC(=O)NCCCOc1ccc([N+](=O)[O-])c(F)c1]

A suspension of 3-fluoro-4-nitrophenol (2.50 g, 15.9 mmol), tert-butyl (3-bromopropyl)carbamate (3.98 g, 16.7 mmol) and K$_2$CO$_3$ (2.64 g, 19.1 mmol) in acetone (15 ml) was stirred at 60° C. for 18 h. The reaction mixture was concentrated in vacuo then the residue was partitioned between EtOAc (50 ml) and water (50 ml). The phases were separated then the organic phase was extracted with water (2×50 ml) and brine (50 ml) then dried over Na$_2$SO$_4$ and concentrated in vacuo to afford the product as a viscous orange oil (4.65 g, 84%).

$^1$H NMR (500 MHz, Acetone-d6) δ 8.14 (t, J=9.2 Hz, 1H), 7.16 (dd, J=13.7, 2.5 Hz, 1H), 6.96 (dd, J=9.3, 2.6 Hz, 1H), 6.92 (t, J=5.5 Hz, 1H), 4.13 (t, J=6.2 Hz, 2H), 3.07 (q, J=6.6 Hz, 2H), 1.84 (p, J=6.5 Hz, 2H), 1.37 (s, 9H).

LC/MS (System A): R$_t$=1.22 min, UV purity=90%.

Intermediate 67—Synthesis of tert-butyl N-{3-[3-(ethylamino)-4-nitrophenoxy]propyl}carbamate

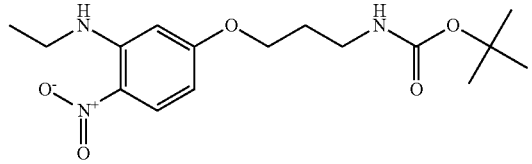 [SMILES: CCNc1cc(OCCCNC(=O)OC(C)(C)C)ccc1[N+](=O)[O-]]

Ethylamine solution in THF (2.0 M, 10 ml, 20 mmol) was added to a mixture of tert-butyl N-[3-(3-fluoro-4-nitrophenoxy)propyl]carbamate, Intermediate 66 (90%, 4.65 g, 13.3 mmol) and K$_2$CO$_3$ (2.20 g, 16.0 mmol) in THF (30 ml). The reaction mixture was stirred at RT for 16 h then additional ethylamine solution in THF (2.0 M, 3.0 ml, 6.0 mmol) was added. The reaction mixture was left to stir at RT for a further 70 h then filtered. The filter pad was rinsed with EtOAc then the combined filtrate was extracted with water (2×150 ml) and brine (150 ml) then dried over Na$_2$SO$_4$ and concentrated in vacuo to afford the product as a viscous yellow/orange oil (4.69 g, 93%).

$^1$H NMR (500 MHz, DMSO-$d_6$) δ 8.26 (t, J=5.0 Hz, 1H), 8.02 (d, J=10.0 Hz, 1H), 6.92-6.86 (m, 1H), 6.30-6.27 (m, 2H), 4.09 (t, J=6.3 Hz, 2H), 3.40-3.35 (m, 2H), 3.08 (q, J=6.7 Hz, 2H), 1.84 (p, J=6.5 Hz, 2H), 1.37 (s, 9H), 1.24 (t, J=7.1 Hz, 3H).

LC/MS (System A): m/z (ESI$^+$)=340 [MH$^+$], R$_t$=1.30 min, UV purity=90%.

Intermediate 68—Synthesis of (9H-fluoren-9-yl)methyl N-{[6-(3-{[(tert-butoxy)carbonyl]amino}propoxy)-1-ethyl-1H-1,3-benzodiazol-2-yl]methyl}carbamate

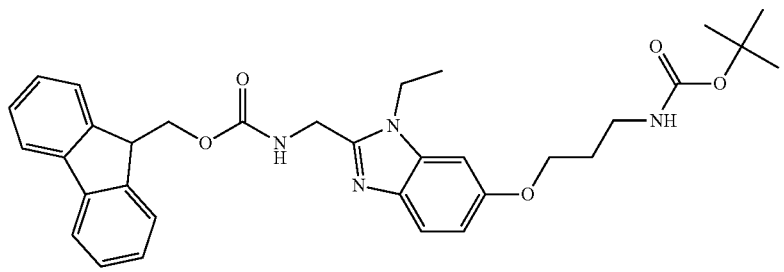 [SMILES: CCn1c(CNC(=O)OCC2c3ccccc3-c3ccccc32)nc2ccc(OCCCNC(=O)OC(C)(C)C)cc21]

Palladium on carbon (10 wt %, 662 mg) was added to a solution of tert-butyl N-{3-[3-(ethylamino)-4-nitrophenoxy]propyl}carbamate, Intermediate 67 (90%, 4.69 g, 12.4 mmol) in EtOH (60 ml). The resulting mixture was stirred under a hydrogen atmosphere for 20 h. The reaction mixture was filtered through a Celite pad then the filtrate was concentrated in vacuo. The residue was dissolved in DMF (10 ml) to give a solution of the phenylenediamine intermediate. A solution of FMOC-glycine (3.88 g, 13.1 mmol), HATU (5.20 g, 13.7 mmol) and DIPEA (4.3 ml, 25 mmol) in DMF (20 ml) was stirred at RT for 0.5 h. The phenylenediamine DMF solution was then added and the resulting solution was stirred at RT for 1 h. Additional FMOC-glycine (2.00 g, 6.73 mmol and HATU (2.50 g, 6.57 mmol) were added then the reaction was left to stir at RT for a further 45 min. The reaction mixture was partitioned between EtOAc (100 ml) and water (100 ml). The phases were separated then the organic phase was washed with water (2×100 ml) and brine (100 ml) then dried over $Na_2SO_4$ and concentrated in vacuo to afford a red solid. The solid thus obtained was dissolved in AcOH (20 ml) then heated at 60° C. for 16 h. The reaction was allowed to cool to RT then concentrated in vacuo. The residue thus obtained was treated with saturated aqueous $NaHCO_3$ solution until pH 9 then partitioned between EtOAc (250 ml) and water (250 ml). The phases were separated then the organic phase was dried over $Na_2SO_4$ and concentrated in vacuo.

The crude material was purified by flash column chromatography on a silica column (340 g). The column was eluted with $CH_2Cl_2$:MeOH, using the following gradient (% MeOH, column volumes): 0%, 1 CV; 0-3.3%, 7 CV; 3.3%, 1 CV; 3.3-4.5%, 2 CV. The desired fractions were combined and evaporated to afford the product as a pale orange solid (4.73 g, 53%).

LC/MS (System A): m/z (ESI$^+$)=571 [MH$^+$], $R_f$=1.18 min, UV purity=80%.

Intermediate 69—Synthesis of 6-(3-{[(tert-butoxy)carbonyl]amino}propoxy)-1,3-diethyl-2-[({[(9H-fluoren-9-yl)methoxy]carbonyl}amino)methyl]-1H-1,3-benzodiazol-3-ium iodide

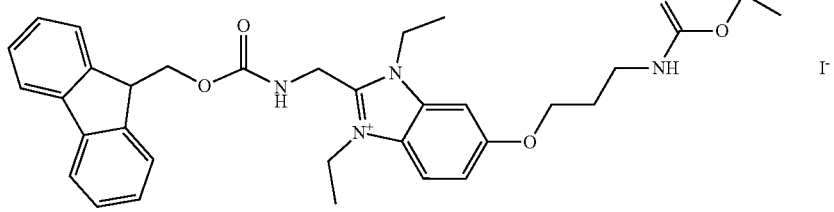

A mixture of 9H-fluoren-9-ylmethyl N-{[6-(3-{[(tert-butoxy)carbonyl]amino}propoxy)-1-ethyl-1H-1,3-benzodiazol-2-yl]methyl}carbamate, Intermediate 68 (80%, 1.50 g, 2.10 mmol) and iodoethane (1.69 ml, 21.0 mmol) in THF (15 ml) was heated under microwave irradiation for 1.5 h at 120° C. The reaction mixture was concentrated in vacuo then the crude material was purified by flash column chromatography on a silica column (100 g).

The column was eluted with $CH_2Cl_2$:MeOH, using the following gradient (% MeOH, column volumes): 0%, 1 CV; 0-3.4%, 7 CV; 3.4-4.3%, 2 CV, 4.3-6.0%, 2 CV. The desired fractions were combined and evaporated to afford the product as a pale orange foam (1.03 g, 61%).

$^1$H NMR (500 MHz, DMSO-d$_6$) δ 8.24 (t, J=5.1 Hz, 1H), 7.95 (d, J=9.1 Hz, 1H), 7.86 (d, J=7.5 Hz, 2H), 7.62 (d, J=7.5 Hz, 2H), 7.56 (s, 1H), 7.36 (t, J=7.4 Hz, 2H), 7.30-7.22 (m, 3H), 6.93-6.88 (m, 1H), 4.74 (d, J=5.1 Hz, 2H), 4.55-4.47 (m, 6H), 4.22 (t, J=5.8 Hz, 1H), 4.13 (t, J=6.0 Hz, 2H), 3.12 (q, J=6.4 Hz, 2H), 1.94-1.85 (m, 2H), 1.37-1.31 (m, 15H).

LC/MS (System A): m/z (ESI$^+$)=599 [M$^+$], $R_f$=1.15 min, UV purity=90%.

Intermediate 70—Synthesis of 2-(aminomethyl)-6-(3-{[(tert-butoxy)carbonyl]amino}propoxy)-1,3-diethyl-1H-1,3-benzodiazol-3-ium iodide

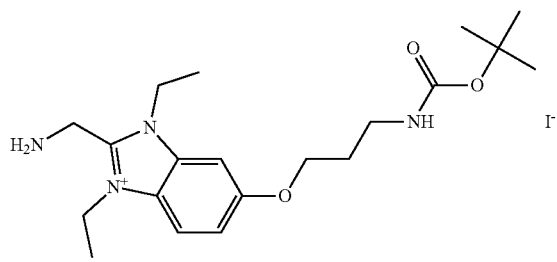 [SMILES: CCn1c(CN)[n+](CC)c2ccc(OCCCNC(=O)OC(C)(C)C)cc21 ; [I-]]

Morpholine (1.10 ml, 12.7 mmol) was added to a solution of 6-(3-{[(tert-butoxy)carbonyl]amino}propoxy)-1,3-diethyl-2-({[(9H-fluoren-9-ylmethoxy)carbonyl]amino}methyl)-1H-1,3-benzodiazol-3-ium iodide, Intermediate 69 (90%, 1.03 g, 1.27 mmol) in THF (10 ml). The reaction mixture was stirred at RT for 2 h then diluted with diethyl ether (40 ml). The mixture was agitated then the supernatant was decanted off. The procedure was repeated with further diethyl ether washes (2×20 ml). The residue thus obtained was dried under vacuum to afford the product as a pale orange foam (700 mg, 99%).

$^1$H NMR (500 MHz, DMSO-d$_6$) δ 7.94 (d, J=9.1 Hz, 1H), 7.56 (d, J=2.1 Hz, 1H), 7.25 (dd, J=9.1, 2.2 Hz, 1H), 6.99-6.83 (m, 1H), 4.56 (q, J=7.2 Hz, 4H), 4.24 (s, 2H), 4.12 (t, J=6.2 Hz, 2H), 3.12 (q, J=6.6 Hz, 2H), 1.94-1.84 (m, 2H), 1.42 (t, J=7.2 Hz, 6H), 1.37 (s, 9H).

LC/MS (System A): m/z (ESI$^+$)=377 [M$^+$], $R_f$=0.82 min, UV purity=91%.

Intermediate 71—Synthesis of 2-[(6-bromo-1-ethyl-1H-1,3-benzodiazol-2-yl)methyl]-2,3-dihydro-1H-isoindole-1,3-dione

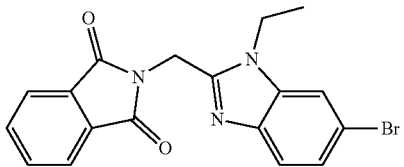 [SMILES: CCn1c(CN2C(=O)c3ccccc3C2=O)nc2ccc(Br)cc21]

A mixture of N-phthaloylglycine (13.1 g, 63.8 mmol), TBTU (21.5 g, 67.0 mmol) and triethylamine (14.1 ml, 79.1 mmol) in DMF (150 ml) was stirred at RT for 45 min. A solution of 5-bromo-1-N-ethylbenzene-1,2-diamine (13.1 g, 60.9 mmol) in THF (50 ml) was added and the resulting mixture was stirred at RT for 18 h. The reaction mixture was added onto saturated aqueous NaHCO3 solution (400 ml). The resulting precipitate was collected by filtration then washed with water and dried under vacuum to afford the intermediate as a light grey solid. The solid thus obtained was added portionwise to acetic acid (150 ml). The resulting suspension was heated at 100° C. for 2.5 h then allowed to cool to RT. The reaction mixture was concentrated in vacuo then the residue was partitioned between EtOAc (300 ml) and water (300 ml). The resulting precipitate was collected by filtration and washed with EtOAc (200 ml) and water (200 ml) then dried under vacuum to afford the product as a pink solid (17.9 g, 76%).

$^1$H NMR (500 MHz, DMSO-$d_6$) δ 7.96 (dd, J=5.6, 3.0 Hz, 2H), 7.93-7.88 (m, 3H), 7.44 (d, J=8.5 Hz, 1H), 7.27 (dd, J=8.5, 1.9 Hz, 1H), 5.12 (s, 2H), 4.39 (q, J=7.2 Hz, 2H), 1.37 (t, J=7.2 Hz, 3H).

LC/MS (System A): m/z (ESI$^+$)=384 [M($^{79}$Br)H$_1$], 386 [M($^{81}$Br)H$_1$], R$_t$=1.12 min, UV purity=100%.

Intermediate 72—Synthesis of tert-butyl N-(3-{2-[(1,3-dioxo-2,3-dihydro-1H-isoindol-2-yl)methyl]-1-ethyl-1H-1,3-benzodiazol-6-yl}prop-2-yn-1-yl)carbamate

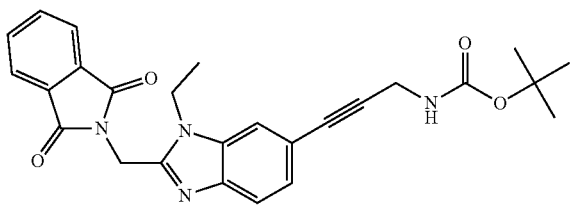 [SMILES: CCn1c(CN2C(=O)c3ccccc3C2=O)nc2ccc(C#CCNC(=O)OC(C)(C)C)cc21]

CuI (0.25 g, 1.29 mmol) was added to a solution of 2-[(6-bromo-1-ethyl-1H-1,3-benzodiazol-2-yl)methyl]-2,3-dihydro-1H-isoindole-1,3-dione, Intermediate 71 (5.00 g, 13.0 mmol) and tert-butyl N-(prop-2-yn-1-yl)carbamate (2.40 g, 15.5 mmol) in DMF (60 ml). Nitrogen was bubbled through the reaction mixture for 5 min then Pd(PPh$_3$)$_4$ (0.74 g, 0.64 mmol) was added, followed by triethylamine (2.92 ml, 19.3 mmol). The reaction mixture was heated at 65° C. for 24 h then concentrated in vacuo. The crude material was purified by flash column chromatography on a silica column (100 g). The column was eluted with EtOAc:heptane, increasing the gradient linearly from 0:100 to 50:50 over 10 column volumes. The desired fractions were combined and evaporated to afford the product as a yellow foam (2.45 g, 39%).

$^1$H NMR (250 MHz, DMSO-$d_6$) δ 7.99-7.88 (m, 4H), 7.71 (s, 1H), 7.46 (d, J=8.3 Hz, 1H), 7.35 (s, 1H), 7.16 (dd, J=8.3, 1.3 Hz, 1H), 5.13 (s, 2H), 4.40 (q, J=7.1 Hz, 2H), 4.02-3.97 (m, 2H), 1.41 (s, 9H), 1.36 (t, J=7.1 Hz, 3H).

LC/MS (System A): m/z (ESI$^+$)=459 [MH$^+$], R$_t$=1.17 min, UV purity=95%.

Intermediate 73—Synthesis of tert-butyl N-(3-{2-[(1,3-dioxo-2,3-dihydro-1H-isoindol-2-yl)methyl]-1-ethyl-1H-1,3-benzodiazol-6-yl}propyl)carbamate

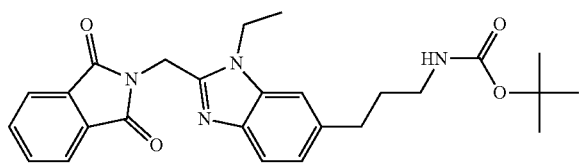 [SMILES: CCn1c(CN2C(=O)c3ccccc3C2=O)nc2ccc(CCCNC(=O)OC(C)(C)C)cc21]

Palladium on carbon (10 wt %, 557 mg) was added to a solution of tert-butyl N-(3-{2-[(1,3-dioxo-2,3-dihydro-1H-isoindol-2-yl)methyl]-1-ethyl-1H-1,3-benzodiazol-6-yl}prop-2-yn-1-yl)carbamate, Intermediate 72 (2.4 g, 5.23 mmol) in EtOH (120 ml). The reaction mixture was stirred at RT under a hydrogen atmosphere for 48 h. The reaction was recharged with palladium on carbon (10 wt %, 278 mg) and stirred at RT under a hydrogen atmosphere for a further 24 h. The reaction was re-charged with palladium on carbon (10 wt %, 278 mg) and stirred at RT under a hydrogen atmosphere for a further 24 h. The reaction mixture was filtered through a Celite pad. The Celite pad was rinsed with EtOH (100 ml), MeOH (100 ml), EtOAc (100 ml), and DMF (5 ml). The combined filtrate was concentrated in vacuo then the crude material was purified by flash column chromatography on a silica column (25 g). The column was eluted with EtOAc:heptane, increasing the gradient linearly from 0:100 to 75:25 over 10 column volumes. The desired fractions were combined and evaporated to afford the product as a light yellow solid (1.20 g, 43%).

$^1$H NMR (500 MHz, DMSO-$d_6$) δ 7.98-7.93 (m, 2H), 7.92-7.88 (m, 2H), 7.37-7.34 (m, 2H), 6.97 (dd, J=8.2, 1.5 Hz, 1H), 6.84 (t, J=5.3 Hz, 1H), 5.09 (s, 2H), 4.35 (q, J=7.2 Hz, 2H), 2.96-2.90 (m, 2H), 2.69-2.63 (m, 2H), 1.71 (p, J=7.3 Hz, 2H), 1.40-1.35 (m, 12H).

LC/MS (System A): m/z (ESI$^+$)=463 [MH$^+$], R$_t$=1.07 min, UV purity=86%.

Intermediate 74 Synthesis of 6-(3-{[(tert-butoxy)carbonyl]amino}propyl)-2-[(1,3-dioxo-2,3-dihydro-1H-isoindol-2-yl)methyl]-1,3-diethyl-1H-1,3-benzodiazol-3-ium iodide

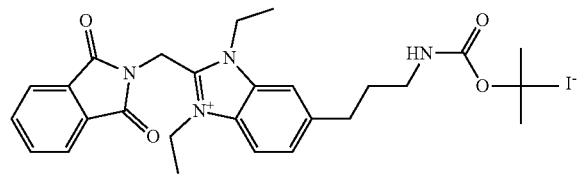 [SMILES: CCn1c(CN2C(=O)c3ccccc3C2=O)[n+](CC)c2ccc(CCCNC(=O)OC(C)(C)C)cc21 ; [I-]]

Iodoethane (1.04 ml, 13.0 mmol) was added to a solution of tert-butyl N-(3-{2-[(1,3-dioxo-2,3-dihydro-1H-isoindol-2-yl)methyl]-1-ethyl-1H-1,3-benzodiazol-6-yl}propyl)carbamate, Intermediate 73 (86%, 1.20 g, 2.23 mmol) in MeCN (18 ml) in a pressure tube. The tube was sealed and heated at 110° C. for 4 h. The reaction was allowed to cool to RT then iodoethane (1.04 ml, 13.0 mmol) was added then the reaction was heated at 110° C. for a further 4 h. The reaction mixture was allowed to cool to RT then concentrated in vacuo to afford the product as a brown solid (1.52 g, >99%).

$^1$H NMR (500 MHz, DMSO-d$_6$) δ 8.02 (d, J=8.6 Hz, 1H), 7.97-7.93 (m, 3H), 7.92-7.88 (m, 2H), 7.58 (d, J=8.6 Hz, 1H), 6.89 (s, 1H), 5.42 (s, 2H), 4.70-4.66 (m, 4H), 2.93 (q, J=6.2 Hz, 2H), 2.79 (t, J=7.4 Hz, 2H), 1.81-1.72 (m, 2H), 1.44-1.40 (m, 6H), 1.37 (s, 9H).

LC/MS (System A): m/z (ESI$^+$)=491 [M$^+$], R$_t$=1.08 min, UV purity=91%.

Intermediate 75 Synthesis of 2-(aminomethyl)-6-(3-{[(tert-butoxy)carbonyl]amino}propyl)-1,3-diethyl-1H-1,3-benzodiazol-3-ium iodide

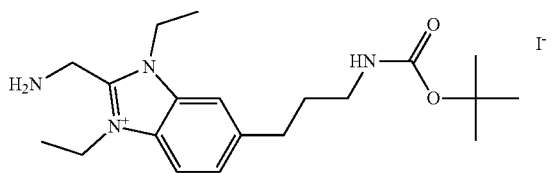 [SMILES: CCn1c(CN)[n+](CC)c2ccc(CCCNC(=O)OC(C)(C)C)cc21 ; [I-]]

Hydrazine hydrate (609 μl, 12.5 mmol) was added to a solution of 6-(3-{[(tert-butoxy)carbonyl]amino}propyl)-2-[(1,3-dioxo-2,3-dihydro-1H-isoindol-2-yl)methyl]-1,3-diethyl-1H-1,3-benzodiazol-3-ium iodide, Intermediate 74 (91%, 1.52 g, 2.23 mmol) in MeOH (20 ml) in a pressure tube. The tube was sealed then heated at 75° C. for 3 h. The reaction mixture was allowed to cool to RT then concentrated in vacuo. The residue was suspended in CH$_2$Cl$_2$:MeOH (9:1, 20 ml) then filtered. The filtrate was concentrated in vacuo to afford the product as a yellow foam (1.21 g, 89%).

$^1$H NMR (500 MHz, DMSO-d$_6$) δ 7.95 (d, J=8.5 Hz, 1H), 7.88 (s, 1H), 7.51 (dd, J=8.5, 1.3 Hz, 1H), 6.91 (t, J=5.5 Hz, 1H), 4.60-4.52 (m, 4H), 4.26 (s, 2H), 2.93 (app. q, J=6.6 Hz, 2H), 2.78 (t, J=7.5 Hz, 2H), 1.80-1.70 (m, 2H), 1.46-1.40 (m, 6H), 1.37 (s, 9H).

LC/MS (System A): m/z (ESI$^+$)=361 [M$^+$], R$_t$=0.81 min, UV purity=80%.

Intermediate 76 Synthesis of tert-butyl 4-{2-[(1,3-dioxo-2,3-dihydro-1H-isoindol-2-yl)methyl]-1-ethyl-1H-1,3-benzodiazol-6-yl}-1,2,3,6-tetrahydropyridine-1-carboxylate

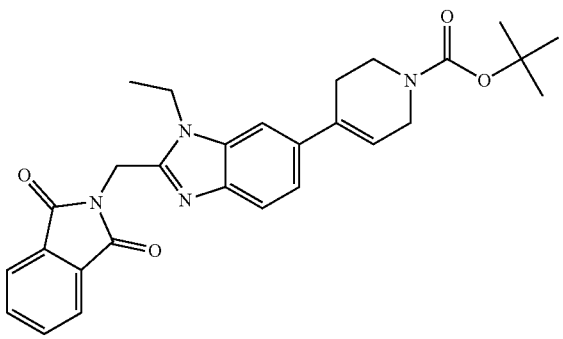 [SMILES: CCn1c(CN2C(=O)c3ccccc3C2=O)nc2ccc(C3=CCN(C(=O)OC(C)(C)C)CC3)cc21]

tert-Butyl 4-(4,4,5,5-tetramethyl-1,3,2-dioxaborolan-2-yl)-3,6-dihydropyridine-1(2H)-carboxylate (966 mg, 3.12 mmol) was added to a solution of 2-[(6-bromo-1-ethyl-1H-1,3-benzodiazol-2-yl)methyl]-2,3-dihydro-1H-isoindole-1,3-dione, Intermediate 71 (1.00 g, 2.60 mmol) in dioxane (10 ml) and water (2 ml). K$_2$CO$_3$ (1.08 g, 7.81 mmol) was added then nitrogen was bubbled through the resulting suspension for 10 min. Pd(dppf)$_2$Cl$_2$ (190 mg, 0.26 mmol) was added then the reaction mixture was heated under microwave irradiation for 2 h at 85° C. The reaction mixture was partitioned between EtOAc (100 ml) and water (50 ml). The phases were separated then the organic phase was washed with brine (50 ml) then dried over Na$_2$SO$_4$, filtered and concentrated in vacuo. The crude material was purified by flash column chromatography on a silica column (50 g). The column was eluted with EtOAc:heptane, using the following gradient (% EtOAc, column volumes): 0%, 1 CV; 0-50%, 7 CV; 50-79%, 3 CV; 79%, 2 CV; 79-92%, 2 CV, 100%, 2 CV. The desired fractions were combined and concentrated in vacuo to afford the product as a white solid (670 mg, 50%).

$^1$H NMR (250 MHz, DMSO-d$_6$) δ 7.99-7.87 (m, 4H), 7.60 (s, 1H), 7.42 (d, J=8.5 Hz, 1H), 7.25 (dd, J=8.5, 1.5 Hz, 1H), 6.16 (s, 1H), 5.11 (s, 2H), 4.49-4.31 (m, 2H), 4.05-3.97 (m, 2H), 3.56 (t, J=5.6 Hz, 2H), 2.54 (s, 2H), 1.43 (s, 9H), 1.37 (t, J=7.1 Hz, 3H).

LC/MS (System A): m/z (ESI$^+$)=487 [MH$^+$], R$_t$=1.18 min, UV purity=95%.

Intermediate 77 Synthesis of tert-butyl 4-{2-[(1,3-dioxo-2,3-dihydro-1H-isoindol-2-yl)methyl]-1-ethyl-1H-1,3-benzodiazol-6-yl}piperidine-1-carboxylate

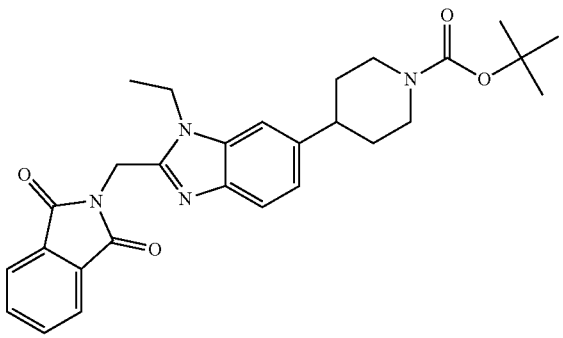 [SMILES: CCn1c(CN2C(=O)c3ccccc3C2=O)nc2ccc(C3CCN(C(=O)OC(C)(C)C)CC3)cc21]

Palladium on carbon (10 wt %, 142 mg) was added to a solution of tert-butyl 4-{2-[(1,3-dioxo-2,3-dihydro-1H-isoindol-2-yl)methyl]-1-ethyl-1H-1,3-benzodiazol-6-yl}-1,2,3,6-tetrahydropyridine-1-carboxylate, Intermediate 76 (95%, 660 mg, 1.29 mmol) in EtOH (40 ml). The reaction mixture was stirred at RT under a hydrogen atmosphere for 16 h. The reaction was recharged with palladium on carbon (10 wt %, 140 mg) and stirred at RT under a hydrogen atmosphere for a further 48 h. The reaction mixture was filtered through Celite pad then concentrated in vacuo to afford the product as a colourless oil (635 mg, 94%).

$^1$H NMR (500 MHz, DMSO-$d_6$) δ 7.96 (dd, J=5.6, 2.9 Hz, 2H), 7.91 (dd, J=5.6, 3.0 Hz, 2H), 7.45 (s, 1H), 7.38 (d, J=8.3 Hz, 1H), 7.02 (dd, J=8.4, 1.4 Hz, 1H), 5.09 (s, 2H), 4.37 (q, J=7.2 Hz, 2H), 4.33 (t, J=5.1 Hz, 1H), 4.10 (d, J=10.4 Hz, 2H), 2.84-2.75 (m, 2H), 1.78 (d, J=12.8 Hz, 2H), 1.58 (qd, J=12.7, 4.3 Hz, 2H), 1.42 (s, 9H), 1.37 (t, J=7.2 Hz, 3H).

LC/MS (System A): m/z (ESI$^+$)=489 [MH$^+$], $R_t$=1.13 min, UV purity=93%.

Intermediate 78 Synthesis of 6-{1-[(tert-butoxy)carbonyl]piperidin-4-yl}-2-[(1,3-dioxo-2,3-dihydro-1H-isoindol-2-yl)methyl]-1,3-diethyl-1H-1,3-benzodiazol-3-ium iodide

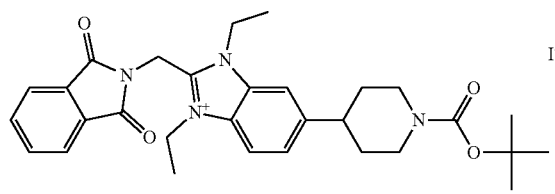 [SMILES: CCn1c(CN2C(=O)c3ccccc3C2=O)[n+](CC)c2ccc(C3CCN(C(=O)OC(C)(C)C)CC3)cc21 ; [I-]]

Iodoethane (486 µl, 6.04 mmol) was added to a solution of tert-butyl 4-{2-[(1,3-dioxo-2,3-dihydro-1H-isoindol-2-yl)methyl]-1-ethyl-1H-1,3-benzodiazol-6-yl}piperidine-1-carboxylate, Intermediate 77 (93%, 635 mg, 1.21 mmol) in MeCN (10 ml). The reaction mixture was heated under microwave irradiation for 3 h at 120° C. The reaction mixture was concentrated in vacuo to afford the product as a brown solid (765 mg, 84%).

$^1$H NMR (250 MHz, DMSO-$d_6$) δ 8.07-8.01 (m, 2H), 7.98-7.88 (m, 4H), 7.64 (d, J=9.3 Hz, 1H), 5.43 (s, 2H), 4.69 (q, J=7.0 Hz, 4H), 4.20-4.04 (m, 2H), 3.05-2.71 (m, 3H), 1.85-1.75 (m, 2H), 1.67 (td, J=12.3, 3.5 Hz, 2H), 1.46-1.37 (m, 15H).

LC/MS (System A): m/z (ESI$^+$)=517 [M$^+$], $R_t$=1.06 min, UV purity=86%.

Intermediate 79 Synthesis of 2-(aminomethyl)-6-{1-[(tert-butoxy)carbonyl]piperidin-4-yl}-1,3-diethyl-1H-1,3-benzodiazol-3-ium iodide

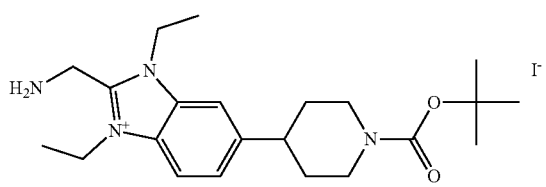 [SMILES: CCn1c(CN)[n+](CC)c2ccc(C3CCN(C(=O)OC(C)(C)C)CC3)cc21 ; [I-]]

Hydrazine hydrate (284 µl, 5.82 mmol) was added to a solution of 6-{1-[(tert-butoxy)carbonyl]piperidin-4-yl}-2-[(1,3-dioxo-2,3-dihydro-1H-isoindol-2-yl)methyl]-1,3-diethyl-1H-1,3-benzodiazol-3-ium iodide, Intermediate 78 (86%, 750 mg, 1.00 mmol) in MeOH (10 ml) in a pressure tube. The tube was sealed then the reaction mixture was heated at 75° C. for 5 h. The reaction mixture was allowed to cool to RT then concentrated in vacuo. The residue was suspended in CH$_2$Cl$_2$:MeOH (9:1, 20 ml) then filtered. The filtrate was concentrated in vacuo to afford the product as a yellow foam (605 mg, 85%).

$^1$H NMR (250 MHz, DMSO-$d_6$) δ 7.96 (d, J=8.7 Hz, 1H), 7.95 (s, 1H), 7.58 (d, J=8.7 Hz, 1H), 4.65-4.51 (m, 4H), 4.27 (s, 2H), 4.13 (d, J=13.3 Hz, 2H), 3.02-2.77 (m, 3H), 1.89-1.76 (m, 2H), 1.72-1.58 (m, 2H), 1.47-1.39 (m, 15H).

LC/MS (System A): m/z (ESI$^+$)=387 [M$^+$], $R_t$=0.89 min, UV purity=72%.

Intermediate 80 Synthesis of tert-butyl 4-(4-{2-[(1,3-dioxo-2,3-dihydro-1H-isoindol-2-yl)methyl]-1-ethyl-1H-1,3-benzodiazol-6-yl}-1H-pyrazol-1-yl)piperidine-1-carboxylate

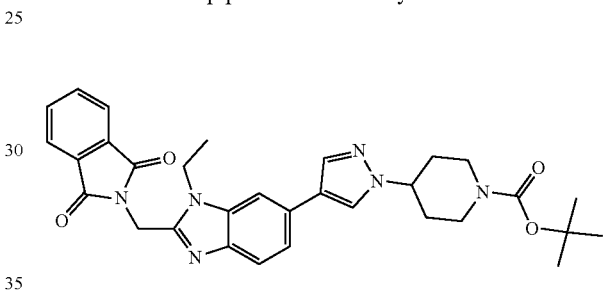

tert-Butyl 4-[4-(tetramethyl-1,3,2-dioxaborolan-2-yl)-1H-pyrazol-1-yl]piperidine-1-carboxylate (540 mg, 1.43 mmol) was added to a solution of 2-[(6-bromo-1-ethyl-1H-1,3-benzodiazol-2-yl)methyl]-2,3-dihydro-1H-isoindole-1,3-dione, Intermediate 71 (500 mg, 1.30 mmol) in dioxane (10 ml) and water (0.5 ml) in a pressure tube. Cs$_2$CO$_3$ (848 mg, 2.60 mmol) was added then the resulting suspension was de-gassed by bubbling a stream of nitrogen through the reaction mixture for 10 min. XPhos-Pd-G2 (61 mg, 0.078 mmol) was added then the nitrogen bubbling was continued for a further 5 min. The tube was sealed then heated at 100° C. for 16 h. The reaction mixture was concentrated in vacuo then partitioned between EtOAc (100 ml) and water (100 ml). The phases were separated then the organic phase was washed with water (50 ml) and brine (2×50 ml), then dried over MgSO$_4$, filtered and evaporated. The crude material was purified by flash column chromatography on a silica column (50 g). The column was eluted with EtOAc:heptane, increasing the gradient linearly from 0:100 to 100:0 over 10 column volumes. The desired fractions were combined and evaporated to yield the product as a light yellow foam (226 mg, 31%).

$^1$H NMR (500 MHz, DMSO-$d_6$) δ 8.28 (s, 1H), 7.98-7.94 (m, 2H), 7.94-7.89 (m, 3H), 7.81-7.76 (m, 1H), 7.43 (d, J=8.4 Hz, 1H), 7.38 (dd, J=8.4, 1.5 Hz, 1H), 5.11 (s, 2H), 4.43-4.34 (m, 3H), 4.04 (dd, J=15.8, 8.8 Hz, 2H), 2.93 (s, 2H), 2.09-2.02 (m, 2H), 1.81 (qd, J=12.4, 4.3 Hz, 2H), 1.43 (s, 9H), 1.42-1.39 (m, 3H).

LC/MS (System A): m/z (ESI$^+$)=555 [MH$^+$], $R_t$=1.13 min, UV purity=100%.

Intermediate 81—Synthesis of 6-(1-{1-[(tert-butoxy)carbonyl]piperidin-4-yl}-1H-pyrazol-4-yl)-2-[(1,3-dioxo-2,3-dihydro-1H-isoindol-2-yl)methyl]-1,3-diethyl-1H-1,3-benzodiazol-3-ium iodide

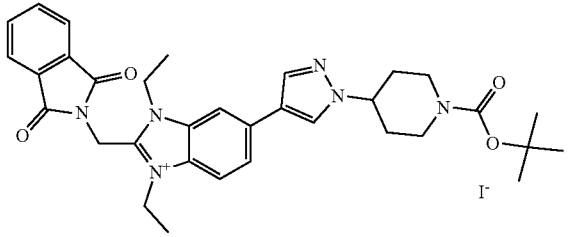

Iodoethane (159 µl, 1.98 mmol) was added to a solution of tert-butyl 4-(4-{2-[(1,3-dioxo-2,3-dihydro-1H-isoindol-2-yl)methyl]-1-ethyl-1H-1,3-benzodiazol-6-yl}-1H-pyrazol-1-yl)piperidine-1-carboxylate, Intermediate 80 (220 mg, 0.397 mmol) in MeCN (5 ml). The reaction mixture was heated under microwave irradiation for 2 h at 120° C. Iodoethane (130 µl, 1.62 mmol) was added then the reaction mixture was heated under microwave irradiation for 1 h at 120° C. The reaction mixture was concentrated in vacuo then azeotroped with diethyl ether. The residue was dried under vacuum to afford the product as a light yellow solid (280 mg, 80%).

$^1$H NMR (500 MHz, DMSO-$d_6$) δ 8.50 (s, 1H), 8.29 (s, 1H), 8.12 (s, 1H), 8.10 (d, J=8.8 Hz, 1H), 7.98-7.94 (m, 3H), 7.94-7.89 (m, 2H), 5.42 (s, 2H), 4.74-4.65 (m, 4H), 4.48-4.35 (m, 1H), 4.06 (d, 2H), 2.95 (br. s, 2H), 2.08 (d, J=6.7 Hz, 2H), 1.81 (qd, J=12.7, 4.7 Hz, 2H), 1.49-1.40 (m, 15H).

LC/MS (System A): m/z (ESI$^+$)=583 [M$^+$], R$_t$=1.13 min, UV purity=81%.

Intermediate 82—Synthesis of 2-(aminomethyl)-6-(1-{1-[(tert-butoxy)carbonyl]piperidin-4-yl}-1H-pyrazol-4-yl)-1,3-diethyl-1H-1,3-benzodiazol-3-ium iodide

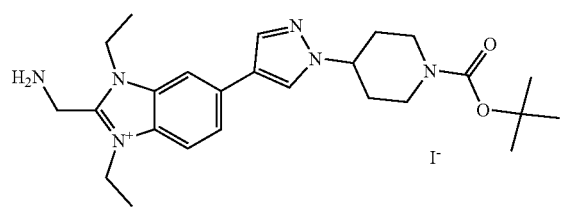

Hydrazine hydrate (96 µl, 2.0 mmol) was added to a solution of 6-(1-{1-[(tert-butoxy)carbonyl]piperidin-4-yl}-1H-pyrazol-4-yl)-2-[(1,3-dioxo-2,3-dihydro-1H-isoindol-2-yl)methyl]-1,3-diethyl-1H-1,3-benzodiazol-3-ium iodide, Intermediate 81 (81%, 280 mg, 0.32 mmol) in MeOH (5 ml) in a pressure tube. The tube was sealed then heated at 75° C. for 1 h. The reaction mixture was allowed to cool to RT then concentrated in vacuo. The residue was suspended in CH$_2$Cl$_2$ (9:1, 20 ml) then filtered. The solid thus obtained was washed further CH$_2$Cl$_2$ (20 ml). The filtrates were combined and evaporated to dryness to afford the product as a light yellow solid (224 mg, >99%).

$^1$H NMR (500 MHz, DMSO-$d_6$) δ 8.48 (s, 1H), 8.23 (s, 1H), 8.10 (s, 1H), 8.03 (d, J=8.7 Hz, 1H), 7.90 (dd, J=8.7, 1.3 Hz, 1H), 4.62-4.56 (m, 4H), 4.44-4.36 (m, 1H), 4.28 (s, 2H), 4.07 (d, J=10.4 Hz, 2H), 2.94 (br. s, 2H), 2.08 (d, J=10.4 Hz, 2H), 1.82 (tt, J=12.2, 6.2 Hz, 2H), 1.46-1.40 (m, 15H).

LC/MS (System A): m/z (ESI$^+$)=453 [M$^+$], R$_t$=0.91 min, UV purity=83%.

Intermediate 83—Synthesis of 5-(2-aminoethoxy)-1,3-diethyl-2-[({[(9H-fluoren-9-yl)methoxy]carbonyl}amino)methyl]-1H-1,3-benzodiazol-3-ium hydrochloride chloride

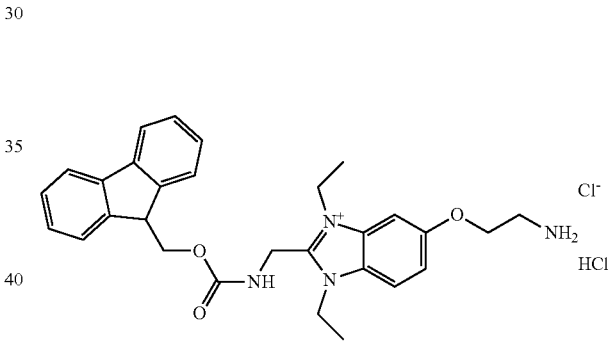

HCl solution in dioxane (4.0 M, 14 ml, 56 mmol) was added to a mixture of 6-(2-{[(tert-butoxy)carbonyl]amino}ethoxy)-1,3-diethyl-2-({[(9H-fluoren-9-ylmethoxy)carbonyl]amino}methyl)-1H-1,3-benzodiazol-3-ium iodide, Intermediate 64 (4.28 g, 6.01 mmol) in MeCN (50 ml). The resulting mixture was stirred at RT for 20 min then concentrated in vacuo to afford the product as a brown/orange foam (3.87 g, 98%).

$^1$H NMR (500 MHz, DMSO-$d_6$) δ 8.30 (t, J=5.3 Hz, 1H), 8.15 (s (br), 3H), 7.99 (d, J=9.1 Hz, 1H), 7.86 (d, J=7.5 Hz, 2H), 7.69-7.60 (m, 3H), 7.38-7.30 (m, 3H), 7.25 (t, J=7.3 Hz, 2H), 4.75 (d, J=5.2 Hz, 2H), 4.58-4.45 (m, 6H), 4.34 (t, J=4.9 Hz, 2H), 4.22 (t, J=6.0 Hz, 1H), 1.37-1.30 (m, 6H).

LC/MS (System A): m/z (ESI$^+$)=485 [M$^+$], R$_t$=0.84 min, UV purity=85%.

Intermediate 84 Synthesis of 5-(2-{bis[(2S,3R)-2,3-dihydroxy-3-[(4R,5R)-5-hydroxy-2-phenyl-1,3-dioxan-4-yl]propyl]amino}ethoxy)-1,3-diethyl-2-[({[(9H-fluoren-9-yl)methoxy]carbonyl}amino)methyl]-1H-1,3-benzodiazol-3-ium chloride

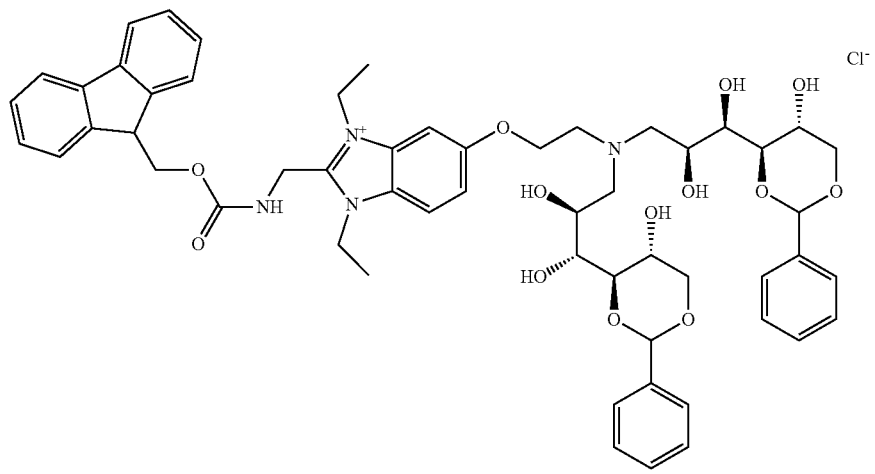

A mixture of 4,6-O-benzylidene-D-glucopyranose (95%, 6.67 g, 23.6 mmol), 5-(2-aminoethoxy)-1,3-diethyl-2-[({[(9H-fluoren-9-yl)methoxy]carbonyl}amino)methyl]-1H-1,3-benzodiazol-3-ium hydrochloride chloride, Intermediate 83 (85%, 3.87 g, 5.91 mmol) and AcOH (1.35 ml, 23.6 mmol) in MeOH (100 ml) was stirred at RT for 0.5 h. NaCNBH$_3$ (1.48 g, 23.6 mmol) was added then the resulting mixture was stirred at RT for 20 h. More MeOH (40 ml) was added then the reaction was left to stir at RT for a further 24 h. More MeOH (80 ml) was added, then the reaction was retreated with 4,6-O-benzylidene-D-glucopyranose (95%, 1.60 g, 5.67 mmol), AcOH (0.34 ml, 5.94 mmol) and NaCNBH$_3$ (0.38 g, 6.05 mmol). The reaction was left to stir at RT for a further 92 h then added to saturated aqueous NaHCO$_3$ solution (250 ml). The resultant suspension was stirred at RT for 20 min. The solid was collected by filtration then washed with water and dried under vacuum to afford the product as a pale pink solid (6.43 g, 89%).

LC/MS (System A): m/z (ESI$^+$)=990 [M$^+$], 496 [(M$^+$)+H$^+$], R$_t$=0.93 min, UV purity=84%.

Intermediate 85—2-(aminomethyl)-5-(2-{bis[(2S,3R)-2,3-dihydroxy-3-[(4R,5R)-5-hydroxy-2-phenyl-1,3-dioxan-4-yl]propyl]amino}ethoxy)-1,3-diethyl-1H-1,3-benzodiazol-3-ium chloride

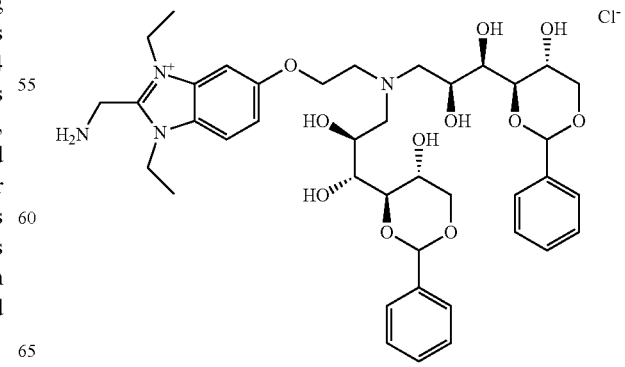

Morpholine (4.77 ml, 55.1 mmol) was added to a stirred mixture of 5-(2-{bis[(2S,3R)-2,3-dihydroxy-3-[(4R,5R)-5-hydroxy-2-phenyl-1,3-dioxan-4-yl]propyl]amino}ethoxy)-1,3-diethyl-2-[({[(9H-fluoren-9-yl)methoxy]carbonyl}amino)methyl]-1H-1,3-benzodiazol-3-ium chloride, Intermediate 84 (84% 6.42 g, 5.26 mmol) in THF (60 ml). The resulting mixture was stirred at RT for 4 h. The reaction mixture was diluted with diethyl ether (150 ml). The resulting suspension was agitated then the suspension was decanted off, leaving behind a viscous oil. More diethyl ether (80 ml) was added to the oil residue then the mixture was sonicated. The resulting suspension was again decanted off to leave behind a viscous oil. The process was repeated once more with diethyl ether (80 ml) then the resulting viscous oil was dried under vacuum to afford the product as a pale purple foam (4.39 g, 85%).

LC/MS (System A): m/z (ESI$^+$)=767 [M$^+$], 384 [(M$^+$)+H$^+$], R$_t$=0.75 min, UV purity=82%.

Intermediate 86 Synthesis of 2-(aminomethyl)-5-(2-{bis[(2S,3R,4R,5R)-2,3,4,5,6-pentahydroxyhexyl]amino}ethoxy)-1,3-diethyl-1H-1,3-benzodiazol-3-ium dihydrochloride chloride

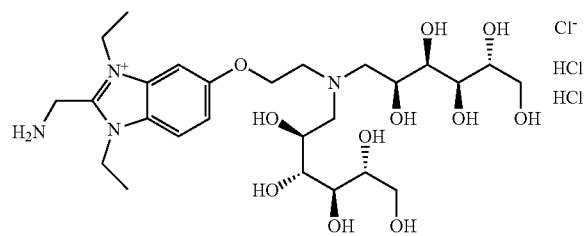 [SMILES: CCn1c(CN)[n+](CC)c2cc(OCCN(C[C@H](O)[C@@H](O)[C@H](O)[C@H](O)CO)C[C@H](O)[C@@H](O)[C@H](O)[C@H](O)CO)ccc21 ; Cl ; Cl ; [Cl-]]

A mixture of 2-(aminomethyl)-5-(2-{bis[(2S,3R)-2,3-dihydroxy-3-[(4R,5R)-5-hydroxy-2-phenyl-1,3-dioxan-4-yl]propyl]amino}ethoxy)-1,3-diethyl-1H-1,3-benzodiazol-3-ium chloride, Intermediate 85 (82%, 1.50 g, 1.53 mmol) and aqueous HCl solution (2.0 M, 25 ml, 50 mmol) was stirred at RT for 1 h. The reaction mixture was concentrated in vacuo then the residue was dissolved in water (10 ml) and lyophilised to afford the product as a pale purple foam (1.53 g, >99%).

LC/MS (System A): m/z (ESI$^+$)=591 [M$^+$], 296 [(M$^+$)+H$^+$], R$_t$=0.13 min, UV purity=70%.

Intermediate 87 Synthesis of 5-(3-aminopropoxy)-1,3-diethyl-2-[({[(9H-fluoren-9-yl)methoxy]carbonyl}amino)methyl]-1H-1,3-benzodiazol-3-ium hydrochloride chloride

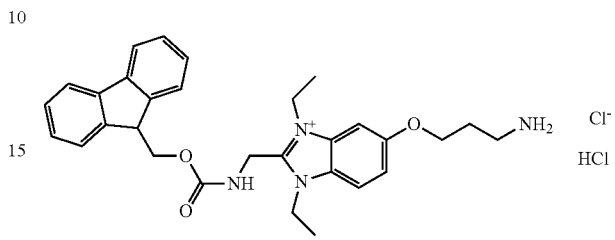

HCl solution in dioxane (4.0 M, 3.3 ml, 13 mmol) was added to a mixture of 6-(3-{[(tert-butoxy)carbonyl]amino}propoxy)-1,3-diethyl-2-({[(9H-fluoren-9-ylmethoxy)carbonyl]amino}methyl)-1H-1,3-benzodiazol-3-ium iodide, Intermediate 69 (95%, 1.00 g, 1.31 mmol) in MeCN (15 ml). The reaction mixture was stirred at RT for 0.5 h then concentrated in vacuo to afford the product as a viscous yellow oil (875 mg, >99%—yield corrected for 15 wt % residual dioxane observed in NMR).

$^1$H NMR (500 MHz, DMSO-d$_6$) δ 8.30 (t, J=5.3 Hz, 1H), 8.00-7.85 (m, 6H), 7.65-7.59 (m, 3H), 7.37 (t, J=7.4 Hz, 2H), 7.31 (dd, J=9.1, 2.1 Hz, 1H), 7.27 (t, J=7.4 Hz, 2H), 4.76 (d, J=5.4 Hz, 2H), 4.58-4.46 (m, 6H), 4.27-4.19 (m, 3H), 3.05-2.95 (m, 2H), 2.12-2.06 (m, 2H), 1.34 (t, J=7.1 Hz, 6H).

LC/MS (System A): m/z (ESI$^+$)=499 [M$^+$], R$_t$=0.89 min, UV purity=98%.

Intermediate 88 Synthesis of 5-(3-{bis[(2S,3R)-2,3-dihydroxy-3-[(4R,5R)-5-hydroxy-2-phenyl-1,3-dioxan-4-yl]propyl]amino}propoxy)-1,3-diethyl-2-[({[(9H-fluoren-9-yl)methoxy]carbonyl}amino)methyl]-1H-1,3-benzodiazol-3-ium hydrochloride chloride

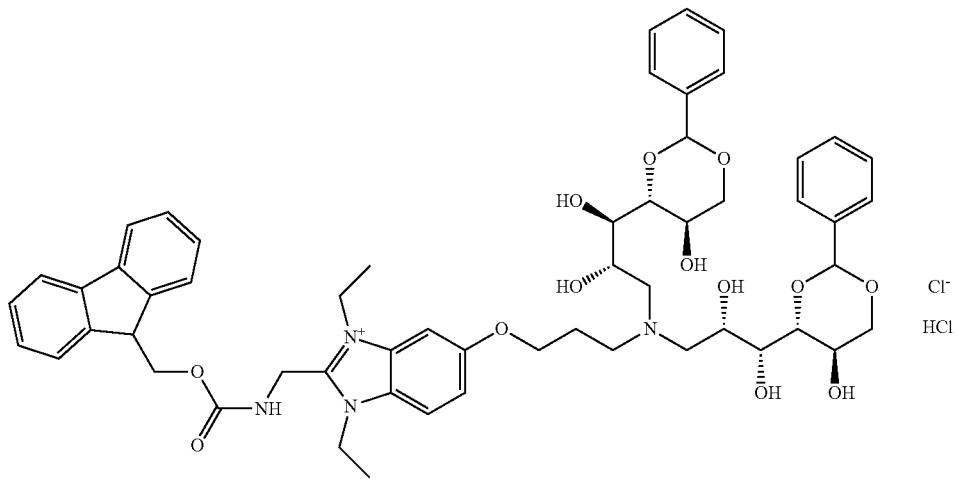

A mixture of 4,6-O-benzylidene-D-glucopyranose (1.43 g, 5.32 mmol), 5-(3-aminopropoxy)-1,3-diethyl-2-[({[(9H-fluoren-9-yl)methoxy]carbonyl}amino)methyl]-1H-1,3-benzodiazol-3-ium hydrochloride chloride, Intermediate 87 (85%, 875 mg, 1.30 mmol) and AcOH (305 μl, 5.32 mmol) in MeOH (25 ml) was stirred at RT for 0.5 h. NaCNBH$_3$ (334 mg, 5.32 mmol) was added then the resulting mixture was stirred at RT for 64 h. Additional 4,6-O-benzylidene-D-glucopyranose (500 mg, 1.86 mmol) and AcOH (110 μl, 1.92 mmol) was added. The mixture was stirred for 0.5 h then NaCNBH$_3$ (115 mg, 1.83 mmol) was added. The resulting mixture was stirred at RT for a further 16 h. Saturated aqueous NaHCO$_3$ solution (40 ml) was added over 5 min whereupon a white precipitate formed. The resultant suspension was filtered and the collected solid was washed with water then dried under vacuum to afford the product as a white solid (1.39 g, 60%).

LC/MS (System A): m/z (ESI$^+$)=503 [(M$^+$)+H$^+$], R$_t$=1.00 min, UV purity=60%. Intermediate 89 Synthesis of 2-(aminomethyl)-5-(3-{bis[(2S,3R)-2,3-dihydroxy-3-[(4R,5R)-5-hydroxy-2-phenyl-1,3-dioxan-4-yl]propyl]amino}propoxy)-1,3-diethyl-1H-1,3-benzodiazol-3-ium hydrochloride chloride

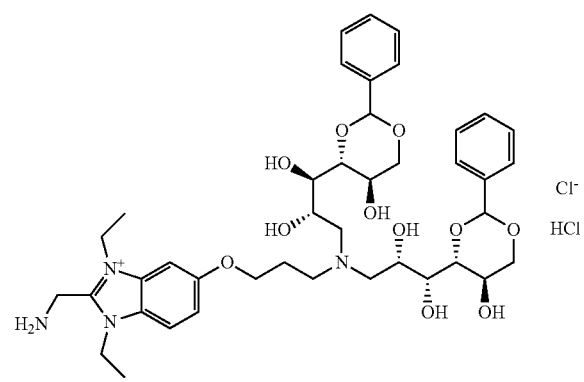

Morpholine (659 μl, 7.62 mmol) was added to a mixture of 5-(3-{bis[(2S,3R)-2,3-dihydroxy-3-[(4R,5R)-5-hydroxy-2-phenyl-1,3-dioxan-4-yl]propyl]amino}propoxy)-1,3-diethyl-2-({[(9H-fluoren-9-ylmethoxy)carbonyl]amino}methyl)-1H-1,3-benzodiazol-3-ium chloride hydrochloride, Intermediate 88 (60%, 1.32 g, 0.762 mmol) in THF (10 ml). The mixture was stirred at RT for 2.5 h. The reaction mixture was diluted with diethyl ether (20 ml). The resulting suspension was sonicated then the suspension was decanted off, leaving behind a viscous oil. More diethyl ether (20 ml) was added to the oil residue then the mixture was sonicated. The resulting suspension was again decanted off to leave behind a viscous oil. The process was repeated once more with diethyl ether (20 ml) then the resulting viscous oil was dried under vacuum to afford the product as a pale orange solid (639 mg, 79%).

LC/MS (System A): m/z (ESI$^+$)=781 [M$^+$], 391 [(M$^+$)+H$^+$], R$_t$=0.78 min, UV purity=80%.

Intermediate 90 Synthesis of 2-(aminomethyl)-5-(3-{bis[(2S,3R,4R,5R)-2,3,4,5,6-pentahydroxyhexyl]amino}propoxy)-1,3-diethyl-1H-1,3-benzodiazol-3-ium hydrochloride chloride

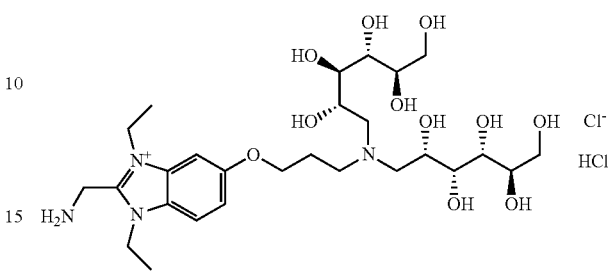

A mixture of 2-(aminomethyl)-5-(3-{bis[(2S,3R)-2,3-dihydroxy-3-[(4R,5R)-5-hydroxy-2-phenyl-1,3-dioxan-4-yl]propyl]amino}propoxy)-1,3-diethyl-1H-1,3-benzodiazol-3-ium hydrochloride chloride, Intermediate 89 (80%, 375 mg, 0.367 mmol) and aqueous HCl solution (2.0 M, 8.0 ml, 16 mmol) was stirred at RT for 40 min. The reaction mixture was concentrated in vacuo then diluted with water and lyophilised to afford the product as a pale orange solid (305 mg, 98%).

LC/MS (System A): m/z (ESI$^+$)=605 [M$^+$], 303 [(M$^+$)+H$^+$], R$_t$=0.13 min, UV purity=80%.

Intermediate 91—Synthesis of tert-butyl 4-{1-ethyl-2-[({[(9H-fluoren-9-yl)methoxy]carbonyl}amino)methyl]-1H-1,3-benzodiazol-6-yl}piperidine-1-carboxylate

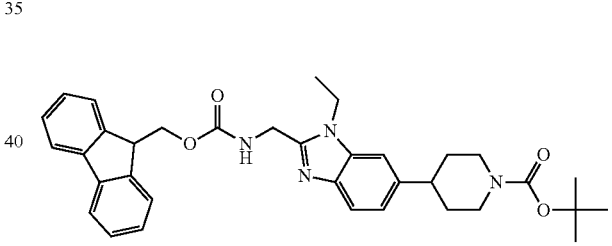

Step 1: A suspension of hydrazine hydrate (1.27 ml, 1.31 mmol) and tert-butyl 4-{2-[(1,3-dioxo-2,3-dihydro-1H-isoindol-2-yl)methyl]-1-ethyl-1H-1,3-benzodiazol-6-yl}piperidine-1-carboxylate Intermediate 77 (2.56 g, 5.24 mmol) in MeOH (30 ml) was heated under reflux for 2.5 h then allowed to cool to RT. The resultant suspension was left to stand at RT for 16 h then filtered. The collected solid was washed solid with CH$_2$Cl$_2$ then the filtrate was concentrated in vacuo and azeotroped with MeCN to afford the intermediate as a white solid (1.24 g). Step 2: A solution of (2,5-dioxopyrrolidin-1-yl) 9H-fluoren-9-ylmethyl carbonate (1.16 g, 3.43 mmol) in MeCN (20 ml) was added dropwise over 10 min to a mixture of the intermediate from Step 1 and NaHCO$_3$ (576 mg, 6.86 mmol) in MeCN (40 ml) and water (30 ml). The reaction mixture was stirred at RT for 21 h then partitioned between EtOAc (100 ml) and water (100 ml). The phases were separated then the organic phase was washed with water (2×50 ml), brine (50 ml), then dried over Na$_2$SO$_4$, filtered and concentrated in vacuo. The solid thus obtained was suspended in MeCN (150 ml) under reflux, with sonication at various intervals. The resultant suspension was allowed to cool to RT then filtered. The collected solid was dried under vacuum to afford the product as a white solid (1.52 g, 50% over 2 steps).

¹H NMR (500 MHz, DMSO-d₆) δ 7.99 (s, 1H), 7.88 (d, J=7.5 Hz, 2H), 7.72 (d, J=7.4 Hz, 2H), 7.48 (d, J=8.2 Hz, 1H), 7.44-7.37 (m, 3H), 7.31 (t, J=7.4 Hz, 2H), 7.07 (d, J=8.3 Hz, 1H), 4.48 (d, J=5.7 Hz, 2H), 4.32 (d, J=7.1 Hz, 2H), 4.23 (t, J=6.9 Hz, 3H), 4.15-4.05 (m, 2H), 2.95-2.75 (m, 3H), 1.80 (d, J=12.0 Hz, 2H), 1.65-1.52 (m, 2H), 1.42 (s, 9H), 1.26 (t, J=7.1 Hz, 3H).

LC/MS (System A): m/z (ESI⁺)=581 [MH⁺], $R_t$=1.12 min, UV purity=100%.

Intermediate 92—Synthesis of 6-{1-[(tert-butoxy)carbonyl]piperidin-4-yl}-1,3-diethyl-2-[({[(9H-fluoren-9-yl)methoxy]carbonyl}amino)methyl]-1H-1,3-benzodiazol-3-ium iodide

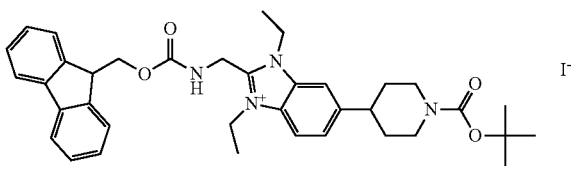 [SMILES: CCn1c(CNC(=O)OCC2c3ccccc3-c3ccccc32)[n+](CC)c2ccc(C3CCN(C(=O)OC(C)(C)C)CC3)cc21 ; [I-]]

A suspension of tert-butyl 4-{1-ethyl-2-[({[(9H-fluoren-9-yl)methoxy]carbonyl}amino)methyl]-1H-1,3-benzodiazol-6-yl}piperidine-1-carboxylate, Intermediate 91 (1.55 g, 2.67 mmol) and iodoethane (1.07 ml, 13.4 mmol) in MeCN (20 ml) was heated under microwave irradiation for 2.5 h at 120° C. The reaction mixture was concentrated in vacuo then the crude material was purified by flash column chromatography on a silica column (25 g). The column was eluted with CH₂Cl₂:MeOH, using the following gradient (% MeOH, column volumes): 0%, 1 CV; 0-2.3%, 5 CV; 2.3%, 2 CV; 2.3-10%, 7 CV, 10%, 7 CV. The desired fractions were combined and evaporated to afford the product as a light pink foam (1.60 g, 75%).

¹H NMR (500 MHz, DMSO-d₆) δ 8.26 (t, J=5.2 Hz, 1H), 7.98 (d, J=9.1 Hz, 2H), 7.86 (d, J=7.5 Hz, 2H), 7.62 (d, J=7.7 Hz, 3H), 7.35 (t, J=7.4 Hz, 2H), 7.25 (t, J=7.3 Hz, 2H), 4.76 (d, J=5.2 Hz, 2H), 4.59-4.44 (m, 6H), 4.22 (t, J=5.6 Hz, 1H), 4.16-4.10 (m, 2H), 3.00-2.80 (m, 3H), 1.83 (d, J=12.1 Hz, 2H), 1.66 (qd, J=12.5, 4.0 Hz, 2H), 1.44 (s, 9H), 1.34 (t, J=7.0 Hz, 6H).

LC/MS (System A): m/z (ESI⁺)=609 [M⁺], $R_t$=1.11 min, UV purity=92%.

Intermediate 93—Synthesis of 1,3-diethyl-2-[({[(9H-fluoren-9-yl)methoxy]carbonyl}amino)methyl]-6-(piperidin-4-yl)-1H-1,3-benzodiazol-3-ium hydrochloride iodide

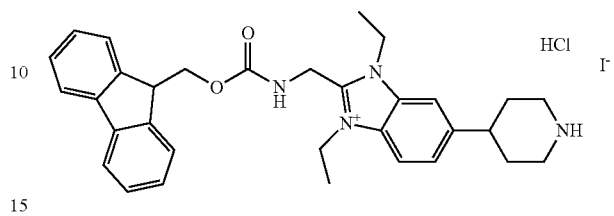

HCl solution in dioxane (4.0 M, 2.0 ml, 8.0 mmol) was added to a solution of 6-{1-[(tert-butoxy)carbonyl]piperidin-4-yl}-1,3-diethyl-2-[({[(9H-fluoren-9-yl)methoxy]carbonyl}amino)methyl]-1H-1,3-benzodiazol-3-ium iodide, Intermediate 92 (1.59 g, 1.99 mmol) in MeCN (50 ml). The reaction mixture was stirred at RT for 2 h then concentrated in vacuo and azeotroped with MeCN (3×25 ml) to afford the product as a yellow solid (1.34 g, >99%).

¹H NMR (500 MHz, DMSO-d₆) δ 9.00 (br.s, 1H), 8.87 (br.s, 1H), 8.35 (t, J=5.1 Hz, 1H), 8.04 (d, J=8.6 Hz, 1H), 7.88 (s, 1H), 7.85 (d, J=7.6 Hz, 2H), 7.62 (d, J=7.5 Hz, 2H), 7.58 (d, J=8.5 Hz, 1H), 7.34 (t, J=7.4 Hz, 2H), 7.24 (t, J=7.4 Hz, 2H), 4.77 (d, J=5.1 Hz, 2H), 4.61-4.50 (m, 4H), 4.48 (d, J=5.9 Hz, 2H), 4.21 (t, J=5.8 Hz, 1H), 3.42 (d, 1H), 3.15-2.96 (m, 4H), 2.04-1.91 (m, 4H), 1.34 (t, J=7.1 Hz, 6H).

LC/MS (System A): m/z (ESI⁺)=509 [M⁺], $R_t$=0.85 min, UV purity=100%.

Intermediate 94—Synthesis of 6-{1-[(2S,3R)-2,3-dihydroxy-3-[(4R,5R)-5-hydroxy-2-phenyl-1,3-dioxan-4-yl]propyl]piperidin-4-yl}-1,3-diethyl-2-[({[(9H-fluoren-9-yl)methoxy]carbonyl}amino)methyl]-1H-1,3-benzodiazol-3-ium iodide

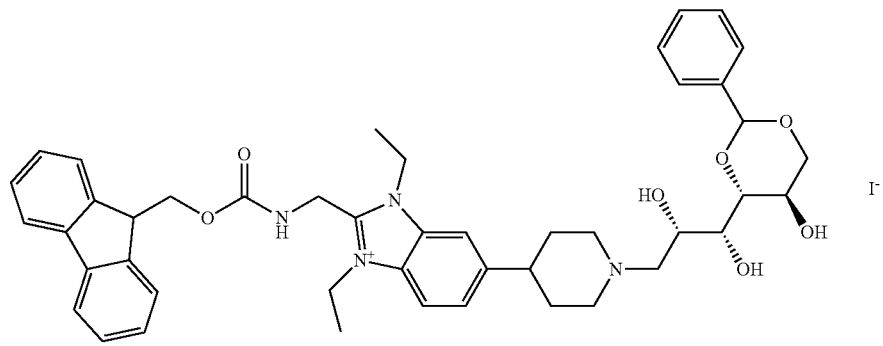

A solution of 1,3-diethyl-2-[({[(9H-fluoren-9-yl)methoxy]carbonyl}amino)methyl]-6-(piperidin-4-yl)-1H-1,3-benzodiazol-3-ium hydrochloride iodide, Intermediate 93 (1.33 g, 1.98 mmol), 4,6-O-benzylidene-D-glucopyranose (1.06 g, 3.95 mmol) and AcOH (226 μl, 3.95 mmol) in MeOH (50 ml) was stirred at RT for 0.5 h. NaCNBH₃ (248 mg, 3.95 mmol) was added then the resultant solution was stirred at RT for 24 h. The reaction mixture was recharged with 4,6-O-benzylidene-D-glucopyranose (1.06 g, 3.95 mmol) and AcOH (226 μl, 3.95 mmol) then left to stir at RT for 0.5 h. NaCNBH$_3$ (150 mg, 2.37 mmol) was added then the resultant solution was stirred at RT for a further 16 h. Saturated aqueous NaHCO$_3$ solution (50 ml) was added over 5 min then the resultant suspension was allowed to stand at RT for 0.5 h then filtered. The collected solid was washed with water (100 ml) then dried under vacuum for afford the product as a beige solid (1.24 g, 57%).

LC/MS (System A): m/z (ESI$^+$)=381 [(M$^+$)+H$^+$], R$_t$=0.94 min, UV purity=81%.

Intermediate 95 Synthesis of 2-(aminomethyl)-6-{1-[(2S,3R)-2,3-dihydroxy-3-[(4R,5R)-5-hydroxy-2-phenyl-1,3-dioxan-4-yl]propyl]piperidin-4-yl}-1,3-diethyl-1H-1,3-benzodiazol-3-ium iodide

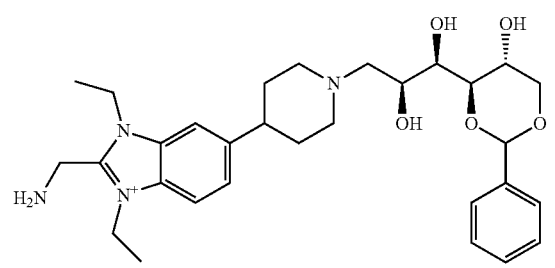

Morpholine (370 μl, 11.3 mmol) was added to a suspension of 6-{1-[(2S,3R)-2,3-dihydroxy-3-[(4R,5R)-5-hydroxy-2-phenyl-1,3-dioxan-4-yl]propyl]piperidin-4-yl}-1,3-diethyl-2-[({[(9H-fluoren-9-yl)methodoxy]carbonyl}amino)methyl]-1H-1,3-benzodiazol-3-ium iodide, Intermediate 94 (81% 1.00 g, 0.90 mmol) in THF (10 ml). The resulting suspension was sonicated for 10 min then left to stir at RT for 2.5 h. The reaction mixture was diluted with diethyl ether (25 ml). The resulting white precipitate was filtered and washed with diethyl ether (25 ml) then dried under vacuum to afford the product as a white solid (615 mg, 92%).

LC/MS (System A): m/z (ESI$^+$)=539 [M$^+$], R$_t$=0.73 min, UV purity=90%.

Intermediate 96 Synthesis of tert-butyl N-[3-({[(9H-fluoren-9-yl)methoxy]carbonyl}amino)propyl]carbamate

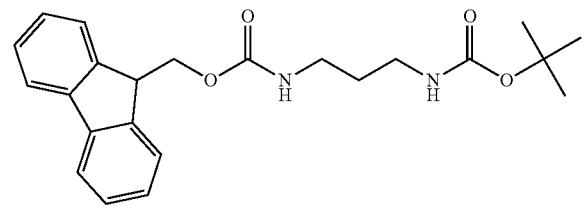 [SMILES: CC(C)(C)OC(=O)NCCCNC(=O)OCC1c2ccccc2-c2ccccc21]

A solution of 2,5-dioxopyrrolidin-1-yl 9H-fluoren-9-ylmethyl carbonate (3.87 g, 11.5 mmol) in MeCN (30 ml) was added dropwise over 20 min to a mixture of NaHCO$_3$ (1.93 g, 23.0 mmol) and tert-butyl N-(3-aminopropyl)carbamate (2.00 g, 11.5 mmol) in MeCN (40 ml) and water (40 ml). The resultant mixture was stirred at RT for 1 h then filtered. The collected solid was washed with water (2×20 ml) then MeCN (2×20 ml), then dried under vacuum to afford a white solid (1.28 g). The solid thus obtained was suspended in EtOAc (10 ml) then filtered. The solid collected was dried under vacuum to afford a first batch of the product as a white solid (1.24 g). The MeCN/water filtrate was concentrated in vacuo then the resulting residue was partitioned between EtOAc (100 ml) and water (50 ml). The phases were separated then the organic phase was washed with water (2×50 ml), brine (20 ml), then dried over Na$_2$SO$_4$, filtered and concentrated in vacuo to afford a white solid (2.30 g). The solid thus obtained was combined with the filtrate from the EtOAc trituration then the combined material was purified by flash column chromatography on a silica column (25 g). The column was eluted with heptane:EtOAc:MeOH using the following gradient: 100:0:0, 3 CV; 100:0:0-81:19:0, 3 CV; 81:19:0%, 2 CV; 81:19:0-61:39:0, 3 CV; 61:39:0, 5 CV; 61:39:0-12:88:0, 8 CV; 12:88:0-0:100:0, 2 CV; 0:100:0, 1 CV; 0:100:0-0:93:7, 4 CV; 0:93:7, 3 CV; 0:93:7-0:91:9, 1 CV. The desired fractions were combined and evaporated to afford a second batch of the product as a white solid (2.60 g), which was analytically identical to the first batch. Overall yield=3.84 g (84%).

$^1$H NMR (500 MHz, DMSO-d$_6$) δ 7.89 (d, J=7.5 Hz, 2H), 7.73-7.59 (m, 2H), 7.41 (t, J=7.4 Hz, 2H), 7.36-7.29 (m, 2H), 7.22 (t, J=5.6 Hz, 1H), 6.74 (s, 1H), 4.29 (d, J=6.9 Hz, 2H), 4.21 (t, J=6.8 Hz, 1H), 3.04-2.78 (m, 4H), 1.56-1.43 (m, 2H), 1.37 (s, 9H).

LC/MS (System A): m/z (ESI$^+$)=419 [(M$^+$Na)$^+$], R$_t$=1.25 min, UV purity=99%.

Intermediate 97 Synthesis of (9H-fluoren-9-yl)methyl N-(3-aminopropyl)carbamate hydrochloride

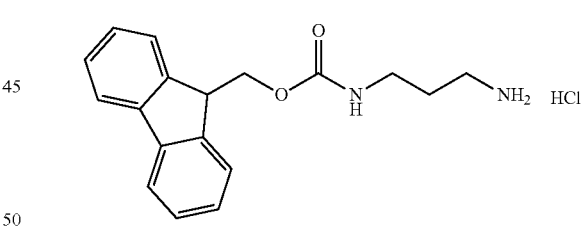

HCl solution in dioxane (4.0 M, 8.0 ml, 32 mmol) was added to a suspension of tert-butyl N-(3-{[(9H-fluoren-9-ylmethoxy)carbonyl]amino}propyl)carbamate, Intermediate 96 (2.60 g, 6.56 mmol) in MeCN (40 ml). The reaction mixture was stirred at RT for 1 h then filtered.

The collected solid was rinsed with MeCN then dried under vacuum to afford the product as a white solid (1.89 g, 87%).

$^1$H NMR (500 MHz, DMSO-d$_6$) δ 7.95-7.77 (m, 5H), 7.68 (d, J=7.4 Hz, 2H), 7.48-7.38 (m, 3H), 7.37-7.29 (m, 2H), 4.33 (d, J=6.8 Hz, 2H), 4.26-4.17 (m, 1H), 3.10-2.99 (m, 2H), 2.81-2.71 (m, 2H), 1.76-1.64 (m, 2H).

LC/MS (System A): m/z (ESI$^+$)=297 [MH$^+$], R$_t$=0.91 min, UV purity=100%.

Intermediate 98 Synthesis of (9H-fluoren-9-yl) methyl N-(3-{bis[(2S,3R)-2,3-dihydroxy-3-[(4R, 5R)-5-hydroxy-2-phenyl-1,3-dioxan-4-yl]propyl] amino}propyl)carbamate; formic acid

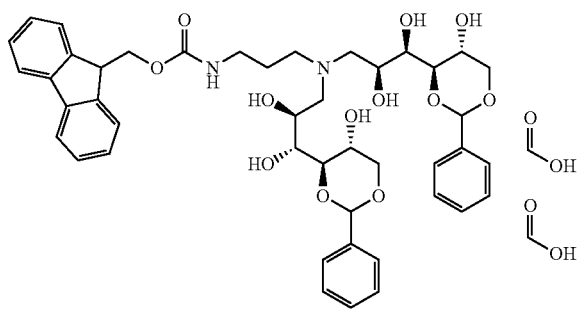

A mixture of 9H-fluoren-9-ylmethyl N-(3-aminopropyl) carbamate hydrochloride, Intermediate 97 (900 mg, 2.70 mmol) and 4,6-O-benzylidene-D-glucopyranose (1.45 g, 5.41 mmol) in MeOH (40 ml) was stirred at RT for 1.5 h. AcOH (0.31 ml, 5.4 mmol) and NaCNBH₃ (340 mg, 5.41 mmol) were added then the reaction was stirred at RT for 18 h. The reaction was recharged with 4,6-O-benzylidene-D-glucopyranose (1.45 g, 5.41 mmol) then the reaction was stirred at RT for 1 h. NaCNBH₃ (340 mg, 5.41 mmol) was added then the reaction was left to stir at RT for a further 114 h. Saturated aqueous NaHCO₃ solution (50 ml) was added dropwise over 10 min then the resultant mixture was partitioned between EtOAc (50 ml) and water (50 ml). The phases were separated then the organic phase was washed with saturated aqueous NaHCO₃ solution (2×50 ml), water (50 ml) and brine (20 ml), then dried using Na₂SO₄, filtered and concentrated in vacuo to afford a white solid (2.25 g). The crude material thus obtained was purified by flash column chromatography on C18 (120 g). The column was eluted with MeCN:water+0.1% formic acid using the following gradient (% MeCN, column volumes): 10%, 2 CV; 10-29%, 4 CV; 29-39%, 2 CV; 39%, 2 CV; 39-47%, 1 CV; 47-73%, 1 CV; 73-100%, 1 CV; 100% 1 CV. The desired fractions were combined and concentrated in vacuo to afford the product as a white solid (1.12 g, 49%).

$^1$H NMR (500 MHz, DMSO-d$_6$) δ 8.16 (m, 1H), 7.88 (d, J=7.5 Hz, 2H), 7.67 (d, J=7.4 Hz, 2H), 7.45-7.37 (m, 6H), 7.36-7.25 (m, 8H), 7.24-7.16 (m, 1H), 5.49-5.39 (m, 2H), 5.27-5.01 (m, 2H), 4.32-4.25 (m, 2H), 4.23-4.16 (m, 1H), 4.16-4.09 (m, 2H), 3.84-3.74 (m, 4H), 3.73-3.66 (m, 2H), 3.64-3.56 (partially obscured m, 2H), 3.53-3.45 (obscured m, 2H), 2.99-2.89 (obscured m, 2H), 2.68-2.54 (obscured m, 6H), 1.60-1.48 (m, 2H).

LC/MS (System A): m/z (ESI⁺)=801 [MH⁺], R$_t$=1.01 min, UV purity=100%.

Intermediate 99 Synthesis of (1R,2S)-3-[(3-aminopropyl)[(2S,3R)-2,3-dihydroxy-3-[(4R,5R)-5-hydroxy-2-phenyl-1,3-dioxan-4-yl]propyl]amino]-1-[(4R,5R)-5-hydroxy-2-phenyl-1,3-dioxan-4-yl] propane-1,2-diol; bis(formic acid

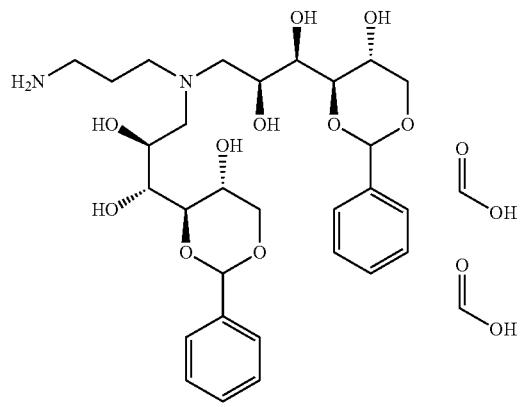

Diethylamine (1.44 ml, 14.0 mmol) was added to a solution of 9H-fluoren-9-ylmethyl N-(3-{bis[(2S,3R)-2,3-dihydroxy-3-[(4R,5R)-5-hydroxy-2-phenyl-1,3-dioxan-4-yl]propyl]amino}propyl)carbamate; formic acid, Intermediate 98 (1.32 g, 1.40 mmol) in THF (20 ml). The reaction mixture was stirred at RT for 16 h then concentrated in vacuo. The crude material thus obtained was purified by flash column chromatography on C18 (60 g). The column was eluted with MeCN:water+0.1% formic acid using the following gradient (% MeCN, column volumes): 5%, 2 CV; 5-18%, 3 CV; 18%, 2 CV; 18-26%, 2 CV; 26-100%, 2 CV; 100% 1 CV. The desired fractions were combined and concentrated in vacuo to afford the product as a white solid (710 mg, 80%).

$^1$H NMR (500 MHz, DMSO-d$_6$) δ 8.36-8.24 (m, 2H), 7.44-7.38 (m, 4H), 7.38-7.29 (m, 6H), 5.44 (s, 2H), 4.18-4.08 (obscured m, 2H), 3.87-3.75 (obscured m, 4H), 3.73-3.65 (obscured m, 2H), 3.63-3.56 (obscured m, 2H), 3.53-3.44 (obscured m, 2H), 2.90-2.78 (m, 2H), 2.75-2.55 (obscured m, 6H), 1.78-1.65 (m, 1H), 1.55 (m, 1H).

LC/MS (System A): m/z (ESI⁺)=579 [MH⁺], R$_t$=0.74 min, UV purity=100%.

Intermediate 100 Synthesis of (2R,3R,4R,5S)-6-[(3-aminopropyl)[(2S,3R,4R,5R)-2,3,4,5,6-pentahydroxyhexyl]amino]hexane-1,2,3,4,5-pentol dihydrochloride

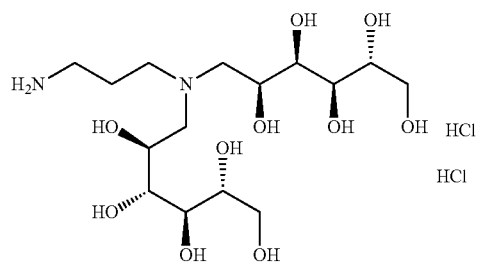 [SMILES: NCCCN(C[C@H](O)[C@@H](O)[C@H](O)[C@H](O)CO)C[C@H](O)[C@@H](O)[C@H](O)[C@H](O)CO ; Cl ; Cl]

A mixture of (1R,2S)-3-[(3-aminopropyl)[(2S,3R)-2,3-dihydroxy-3-[(4R,5R)-5-hydroxy-2-phenyl-1,3-dioxan-4-yl]propyl]amino]-1-[(4R,5R)-5-hydroxy-2-phenyl-1,3-dioxan-4-yl]propane-1,2-diol; bis(formic acid), Intermediate 99 (335 mg, 0.50 mmol) and aqueous HCl solution (2 M, 5 ml, 10 mmol) was stirred at RT for 3 h. The reaction mixture was concentrated in vacuo then the residue was azeotroped with MeCN (3×10 ml) to afford the product as a colourless viscous oil (235 mg, 99%).

$^1$H NMR (500 MHz, CD$_3$OD) δ 4.25-4.18 (m, 2H), 3.91-3.83 (m, 2H), 3.81-3.76 (m, 2H), 3.74-3.64 (m, 6H), 3.62-3.51 (m, 2H), 3.50-3.39 (m, 4H), 3.10-3.03 (m, 2H), 2.22-2.13 (m, 2H).

LC/MS (System A): m/z (ESI$^+$)=403 [MH$^+$], R$_t$=0.12 min, ELS purity=100%.

Intermediate 101—Synthesis of tert-butyl 4-({[(9H-fluoren-9-yl)methoxy]carbonyl}amino)piperidine-1-carboxylate

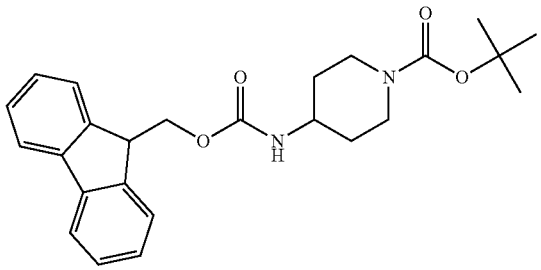 [SMILES: CC(C)(C)OC(=O)N1CCC(NC(=O)OCC2c3ccccc3-c3ccccc32)CC1]

A solution of 2,5-dioxopyrrolidin-1-yl 9H-fluoren-9-ylmethyl carbonate (5.05 g, 15.0 mmol) in MeCN (50 ml) was added dropwise over 20 min to a mixture of tert-butyl 4-aminopiperidine-1-carboxylate (3.00 g, 15.0 mmol) and NaHCO$_3$ (2.52 g, 30.0 mmol) in MeCN (50 ml) and water (50 ml). The resulting mixture was left to stir at RT for 16 h then partitioned between EtOAc (100 ml) and water (100 ml). The phases were separated then the organic phase was washed with water (100 ml) and brine (100 ml) then dried over Na$_2$SO$_4$ and concentrated in vacuo to afford the product as a white foam (6.20 g, 95%).

$^1$H NMR (500 MHz, DMSO-d$_6$) δ 7.89 (d, J=7.5 Hz, 2H), 7.69 (d, J=7.4 Hz, 2H), 7.41 (t, J=7.4 Hz, 2H), 7.33 (td, J=7.4, 0.9 Hz, 2H), 7.27 (d, J=7.7 Hz, 1H), 4.31 (d, J=6.7 Hz, 2H), 4.21 (t, J=6.6 Hz, 1H), 3.84 (br. d, J=11.7 Hz, 2H), 3.52-3.40 (m, 1H), 2.80 (br. s, 2H), 1.70 (d, J=10.8 Hz, 2H), 1.39 (s, 9H), 1.20-1.29 (m, 2H).

LC/MS (System A): m/z (ESI$^+$)=445 [(M$^+$Na)$^+$], R$_t$=1.38 min, UV purity=97%.

Intermediate 102—Synthesis of (9H-fluoren-9-yl)methyl N-(piperidin-4-yl)carbamate hydrochloride

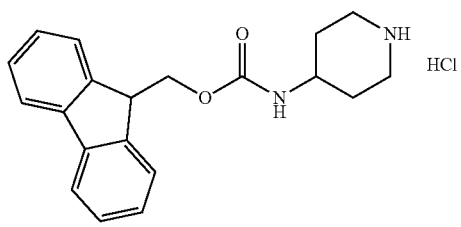 [SMILES: O=C(NC1CCNCC1)OCC1c2ccccc2-c2ccccc21 ; Cl]

HCl solution in dioxane (4.0 M, 11 ml, 44 mmol) was added to a solution of tert-butyl 4-({[(9H-fluoren-9-yl)methoxy]carbonyl}amino)piperidine-1-carboxylate, Intermediate 101 (6.20 g, 14.7 mmol) in MeCN (100 ml). The resulting solution was stirred at RT for 2 h. The reaction was re-dosed with HCl solution in dioxane (4.0 M, 2.0 ml, 8.0 mmol) then the reaction mixture was left to stir at RT for a further 1 h. The reaction mixture was filtered then the collected solid was washed with MeCN then dried under vacuum to afford the product as a white solid (4.60 g, 87%).

$^1$H NMR (500 MHz, DMSO-d$_6$) δ 8.85 (s, 1H), 8.69 (s, 1H), 7.89 (d, J=7.5 Hz, 2H), 7.69 (d, J=7.4 Hz, 2H), 7.50 (d, J=7.2 Hz, 1H), 7.42 (t, J=7.4 Hz, 2H), 7.36-7.31 (m, 2H), 4.33 (d, J=6.6 Hz, 2H), 4.22 (t, J=6.4 Hz, 1H), 3.62-3.54 (m, 1H), 3.21 (d, J=12.0 Hz, 2H), 2.96-2.88 (m, 2H), 1.88 (d, J=12.1 Hz, 2H), 1.67-1.50 (m, 2H).

LC/MS (System A): m/z (ESI$^+$)=323 [MH$^+$], R$_t$=0.89 min, UV purity=100%.

Intermediate 103—Synthesis of (9H-fluoren-9-yl)methyl N-{1-[(2S,3R)-2,3-dihydroxy-3-[(4R,5R)-5-hydroxy-2-phenyl-1,3-dioxan-4-yl]propyl]piperidin-4-yl}carbamate

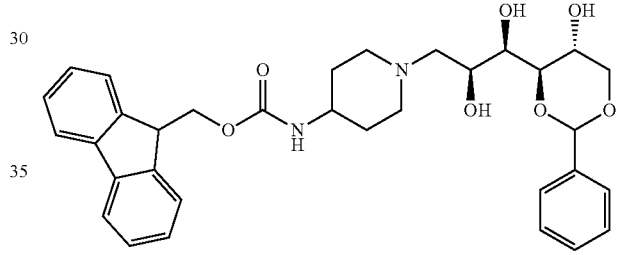

4,6-O-benzylidene-D-glucopyranose (2.99 g, 11.2 mmol) was added to a solution of (9H-fluoren-9-yl)methyl N-(piperidin-4-yl)carbamate hydrochloride, Intermediate 102 (2.00 g, 5.57 mmol) in MeOH (75 ml). The reaction mixture was stirred at RT for 20 min then AcOH (670 µl, 11.7 mmol) and NaCNBH$_3$ (700 mg, 11.2 mmol) were added. The reaction mixture was stirred at RT for 22 h. Saturated aqueous NaHCO$_3$ solution (50 ml) was added dropwise over 10 min. The resulting mixture was partitioned between EtOAc (200 ml) and water (100 ml). The phases were separated then the organic phase was washed with saturated aqueous NaHCO$_3$ solution (100 ml), water (2×100 ml) and brine (2×100 ml). The combined organic phases were dried over Na$_2$SO$_4$ and concentrated in vacuo to afford the product as a white solid (3.13 g, 92%).

$^1$H NMR (500 MHz, CD$_3$OD) δ 7.78 (d, J=7.4 Hz, 2H), 7.63 (d, J=7.1 Hz, 2H), 7.52-7.45 (m, 2H), 7.39-7.27 (m, 7H), 5.55 (s, 1H), 4.34 (d, J=6.4 Hz, 2H), 4.25 (dd, J=10.7, 5.4 Hz, 1H), 4.21-4.17 (m, 1H), 4.07-4.00 (m, 1H), 3.97-3.92 (m, 1H), 3.90-3.87 (d, J=6.4 Hz, 1H), 3.82 (d, J=9.3 Hz, 1H), 3.61 (t, J=10.5 Hz, 1H), 3.39-3.32 (m, 1H), 2.97-2.94 (m, 1H), 2.77-2.64 (m, 2H), 2.47 (dd, J=11.8, 6.7 Hz, 1H), 2.14 (t, J=10.5 Hz, 1H), 2.06-2.02 (m, 1H), 1.75 (dd, J=59.2, 11.6 Hz, 2H), 1.53-1.36 (m, 2H).

LC/MS (System A): m/z (ESI$^+$)=575 [MH$^+$], R$_t$=0.96 min, UV purity=94%.

Intermediate 104—Synthesis of (1R,2S)-3-(4-aminopiperidin-1-yl)-1-[(4R,5R)-5-hydroxy-2-phenyl-1,3-dioxan-4-yl]propane-1,2-diol

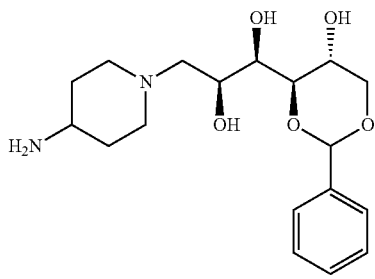

Diethylamine (2.64 ml, 25.6 mmol) was added to a solution of (9H-fluoren-9-yl)methyl N-{1-[(2S,3R)-2,3-dihydroxy-3-[(4R,5R)-5-hydroxy-2-phenyl-1,3-dioxan-4-yl]propyl]piperidin-4-yl}carbamate, Intermediate 103 (94%, 3.13 g, 5.12 mmol) in THF (40 ml). The reaction mixture was left to stir at RT for 1 h. The reaction mixture was re-dosed with diethylamine (2.64 ml, 25.6 mmol) then the reaction was left to stir at RT for a further 20 h. The reaction mixture was concentrated in vacuo then the resultant residue was suspended in EtOAc (10 ml) and water (10 ml). Diethyl ether (50 ml) was added then the mixture was sonicated. The resulting suspension was filtered then the collected solid was rinsed with diethyl ether (20 ml) then dried under vacuum to afford the product as a white solid (1.98 g, >99%).

$^1$H NMR (500 MHz, DMSO-d$_6$) δ 7.41 (dd, J=6.5, 3.1 Hz, 2H), 7.38-7.31 (m, 3H), 5.49 (s, 1H), 4.11 (dd, J=10.5, 4.9 Hz, 1H), 3.81 (q, J=6.2 Hz, 1H), 3.79-3.69 (m, 3H), 3.52-3.48 (m, 1H), 2.83 (d, J=11.3 Hz, 1H), 2.58-2.52 (m, 1H), 2.45-2.45 (m, 2H+DMSO), 2.24 (dd, J=12.4, 6.1 Hz, 1H), 1.93-1.73 (m, 2H), 1.61 (d, J=12.5 Hz, 1H), 1.49 (d, J=12.1 Hz, 1H), 1.17-1.14 (m, 2H).

LC/MS (System A): m/z (ESI$^+$)=353 [MH$^+$], R$_t$=0.13 min, ELS purity=100%.

Intermediate 105—Synthesis of (2R,3R,4R,5S)-6-(4-aminopiperidin-1-yl)hexane-1,2,3,4,5-pentol dihydrochloride

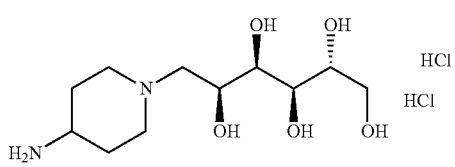 [SMILES: NC1CCN(C[C@H](O)[C@@H](O)[C@H](O)[C@H](O)CO)CC1 ; Cl ; Cl]

Aqueous HCl solution (2.0 M, 11 ml, 22 mmol) was added to a suspension of (1R,2S)-3-(4-aminopiperidin-1-yl)-1-[(4R,5R)-5-hydroxy-2-phenyl-1,3-dioxan-4-yl]propane-1,2-diol, Intermediate 104 (400 mg, 1.13 mmol) in water (5 ml). The reaction mixture was left to stir at RT for 2 h then concentrated in vacuo. The resulting residue was dissolved in water (20 ml) then extracted with EtOAc (20 ml). The aqueous phase was concentrated in vacuo to afford the product as an off-white foam (279 mg, 73%).

$^1$H NMR (500 MHz, CD$_3$OD) δ 4.26-4.18 (m, 1H), 3.87-3.74 (m, 4H), 3.74-3.62 (m, 4H), 3.61-3.42 (m, 2H), 3.29-3.12 (m, 2H), 2.28 (t, J=13.2 Hz, 2H), 2.15-1.92 (m, 2H).

LC/MS (System A): m/z (ESI$^+$)=265 [MH$^+$], R$_t$=0.13 min, ELS purity=100%.

Intermediate 107 Synthesis of benzyl N-[1-(2-{[(tert-butoxy)carbonyl]amino}ethyl)piperidin-4-yl]carbamate

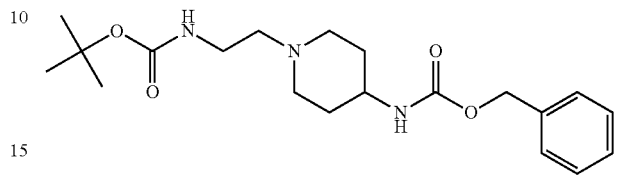

Triethylamine (515 μl, 3.69 mmol) was added to a solution of benzyl N-(4-piperidyl)carbamate hydrochloride (500 mg, 1.85 mmol) and tert-butyl N-(2-bromoethyl)carbamate (500 mg, 2.22 mmol) in MeCN (4 ml) in a pressure tube. The tube was sealed then the reaction mixture was heated at 85° C. for 16 h. Additional tert-butyl N-(2-bromoethyl)carbamate (150 mg, 0.67 mmol) was added then the reaction was left to heat at 85° C. for a further 1 h. The reaction mixture was concentrated in vacuo then the solid thus obtained was dissolved in the minimum of refluxing MeCN then allowed to cool to RT. The resultant suspension was filtered then the filtrate was concentrated in vacuo. The crude material was purified by flash column chromatography on a silica column (25 g). The column was eluted with CH$_2$Cl$_2$:MeOH, increasing the gradient linearly from 0-15% MeOH over 10 column volumes. The desired fractions were combined and evaporated to afford a viscous red oil (254 mg). The material thus obtained was partitioned between EtOAc (15 ml) and saturated aqueous NaHCO$_3$ solution (15 ml). The phases were separated then the organic phase was washed with water (2×15 ml) and brine (15 ml) then dried over Na$_2$SO$_4$ and concentrated in vacuo to afford the product as a pale red solid (140 mg, 20%).

$^1$H NMR (500 MHz, DMSO-d$_6$) δ 7.39-7.28 (m, 5H), 7.21 (d, J=7.6 Hz, 1H), 6.59 (t, J=5.3 Hz, 1H), 5.00 (s, 2H), 3.29-3.22 (m, 1H), 3.00 (q, J=6.4 Hz, 2H), 2.76 (d, J=11.5 Hz, 2H), 2.28 (t, J=6.9 Hz, 2H), 1.95 (t, J=11.0 Hz, 2H), 1.69 (d, J=10.5 Hz, 2H), 1.43-1.32 (m, 11H).

LC/MS (System A): m/z (ESI$^+$)=378 [MH$^+$], R$_t$=0.85 min, UV purity=100%.

Intermediate 108 Synthesis of tert-butyl N-[2-(4-aminopiperidin-1-yl)ethyl]carbamate

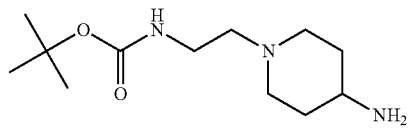 [SMILES: CC(C)(C)OC(=O)NCCN1CCC(N)CC1]

A mixture of benzyl N-[1-(2-{[(tert-butoxy)carbonyl]amino}ethyl)piperidin-4-yl]carbamate, Intermediate 107 (140 mg, 0.370 mmol) and palladium on carbon (10 wt %, 20 mg) in EtOH (5 ml) was stirred under a hydrogen atmosphere at RT for 2 h. The reaction mixture was filtered through a Celite pad then the filtrate was concentrated in vacuo to afford the product as a colourless oil (124 mg, 96% yield corrected for 70% purity determined by NMR).

$^1$H NMR (500 MHz, DMSO-$d_6$) δ 6.61-6.53 (m, 1H), 4.37 (s, 2H), 3.00 (q, J=6.5 Hz, 2H), 2.76-2.71 (m, 2H), 2.49-2.45 (m, 1H), 2.27 (t, J=7.0 Hz, 2H), 1.91 (t, J=10.6 Hz, 2H), 1.67-1.60 (m, 2H), 1.37 (s, 9H), 1.22-1.15 (m, 2H).

LC/MS (System A): m/z (ESI$^+$)=244 [MH$^+$], $R_t$=0.14 min, ELS purity=100%.

Intermediate 109—Synthesis of bis(formic acid); tert-butyl N-[2-(4-{bis[(2S,3R)-2,3-dihydroxy-3-[(4R,5R)-5-hydroxy-2-phenyl-1,3-dioxan-4-yl]propyl]amino}piperidin-1-yl)ethyl]carbamate

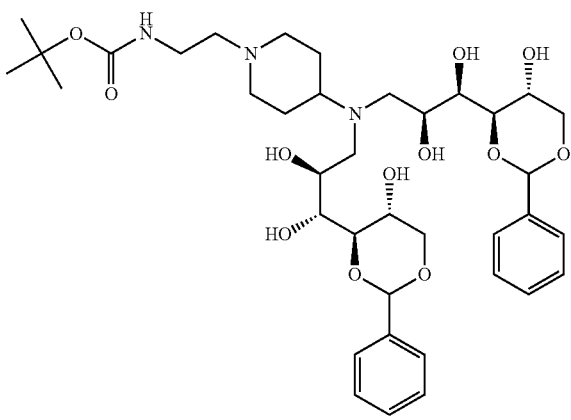

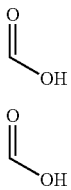

A mixture of tert-butyl N-[2-(4-aminopiperidin-1-yl)ethyl]carbamate, Intermediate 108 (70%, 725 mg, 2.08 mmol), 4,6-O-benzylidene-D-glucopyranose (3.57 g, 12.7 mmol) and AcOH (725 uL, 12.7 mmol) in MeOH (20 ml) was stirred at RT for 0.5 h. NaCNBH$_3$ (795 mg, 12.7 mmol) was added then the resulting mixture was stirred at RT for 5 days. The reaction was retreated with 4,6-O-benzylidene-D-glucopyranose (1.80 g, 6.29 mmol) and AcOH (362 uL, 6.32 mmol) then the reaction was left to stir at RT for 0.5 h. NaCNBH$_3$ (396 mg, 6.30 mmol) was added then the reaction was left to stir at RT for a further 18 h. The reaction was retreated with 4,6-O-benzylidene-D-glucopyranose (1.80 g, 6.29 mmol) and AcOH (362 uL, 6.32 mmol) then the reaction was left to stir at RT for 0.5 h. NaCNBH$_3$ (396 mg, 6.30 mmol) was added then the reaction was left to stir at RT for a further 18 h. The reaction mixture was concentrated under a stream of nitrogen then saturated aqueous NaHCO$_3$ solution was added dropwise until effervescence ceased. The resulting mixture was partitioned between saturated aqueous NaHCO$_3$ solution (150 ml) and EtOAc (150 ml). The phases were separated then the organic phase was washed with NaHCO$_3$ (150 ml), water (2×150 ml) and brine (150 ml), then dried over Na$_2$SO$_4$ and concentrated in vacuo to afford a pale yellow solid. The crude material was purified by flash column chromatography on C18 (120 g). The column was eluted with MeCN:water+0.1% formic acid using the following gradient (% MeCN, column volumes): 10%, 2 CV; 10-16%, 11 CV; 16%-100%, 4 CV; 100%, 1 CV. The desired fractions were combined and concentrated in vacuo to afford the product as a colourless oil (383 mg, 18%).

LC/MS (System A): m/z (ESI$^+$)=375 [(M$^+$)+H$^+$], 748 [MH$^+$], $R_t$=0.82 min, UV purity=83%.

Intermediate 110—Synthesis of (2R,3R,4R,5S)-6-{[1-(2-aminoethyl)piperidin-4-yl][(2S,3R,4R,5R)-2,3,4,5,6-pentahydroxyhexyl]amino}hexane-1,2,3,4,5-pentol trihydrochloride

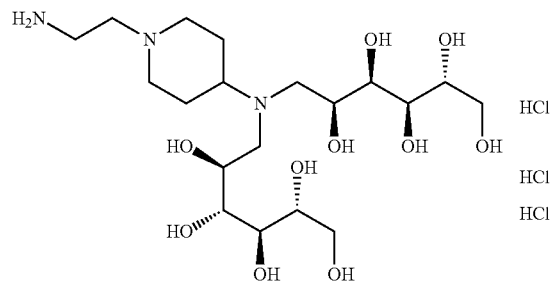 [SMILES: NCCN1CCC(N(C[C@H](O)[C@@H](O)[C@H](O)[C@H](O)CO)C[C@H](O)[C@@H](O)[C@H](O)[C@H](O)CO)CC1 ; Cl ; Cl ; Cl]

A mixture of tert-butyl N-[2-[4-[bis[(2S,3R)-2,3-dihydroxy-3-[(4R,5R)-5-hydroxy-2-phenyl-1,3-dioxan-4-yl]propyl]amino]-1-piperidyl]ethyl]carbamate, Intermediate 109 (83%, 360 mg, 0.356 mmol) and aqueous HCl solution (4.0 M, 3.6 ml, 14.4 mmol) was stirred at RT for 0.5 h then concentrated in vacuo. The residue was dissolved in water:MeCN (9:1, 12 ml) then lyophilised to afford the product as a white foam (220 mg, 94%).

$^1$H NMR (500 MHz, Deuterium Oxide) δ 4.34-4.26 (m, 2H), 4.16-4.05 (m, 1H), 3.95-3.88 (m, 4H), 3.87 (d, J=2.9 Hz, 1H), 3.84 (d, J=3.0 Hz, 1H), 3.83-3.78 (m, 2H), 3.73-3.67 (m, 4H), 3.64-3.46 (m, 8H), 3.40-3.31 (m, 2H), 2.58 (d, J=14.0 Hz, 1H), 2.51 (d, J=13.7 Hz, 1H), 2.35-2.24 (m, 1H), 2.23-2.12 (m, 1H).

LC/MS (System F): m/z (ESI$^+$)=472 [MH$^+$], $R_t$=0.29 min, ELS purity=88%.

Intermediate 111—Synthesis of (9H-fluoren-9-yl)methyl 4-({[(tert-butoxy)carbonyl]amino}methyl)piperidine-1-carboxylate

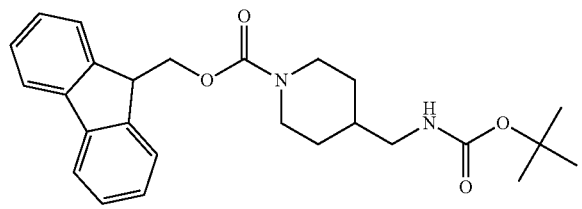 [SMILES: CC(C)(C)OC(=O)NCC1CCN(C(=O)OCC2c3ccccc3-c3ccccc32)CC1]

NaHCO$_3$ (2.35 g, 28.0 mmol) was added portionwise over 1 min to a stirred solution of tert-butyl N-(4-piperidylmethyl)carbamate (3.00 g, 14.0 mmol) in MeCN (50 ml) and water (50 ml). A solution of (2,5-dioxopyrrolidin-1-yl) 9H-fluoren-9-ylmethyl carbonate (4.72 g, 14.0 mmol) in MeCN (50 ml) was added dropwise over 1 h then the reaction was left to stir at RT for 18 h. The reaction mixture was partitioned between EtOAc (100 ml) and water (100 ml). Brine was added to aid separation of phases. The phases were separated then the aqueous phase was extracted with EtOAc (50 ml). The combined organic extracts were washed with brine (70 ml), dried over MgSO₄, filtered and concentrated in vacuo to afford the product as an off white solid (7.02 g, 96%).

¹H NMR (500 MHz, DMSO-d₆) δ 7.89 (d, J=7.5 Hz, 2H), 7.62 (d, J=7.4 Hz, 2H), 7.41 (t, J=7.3 Hz, 2H), 7.33 (td, J=7.4, 0.9 Hz, 2H), 6.85 (t, J=5.8 Hz, 1H), 4.53-4.29 (m, 2H), 4.26 (t, J=6.3 Hz, 1H), 3.97-3.67 (m, 2H), 2.78 (t, J=6.1 Hz, 2H), 2.75-2.61 (m, 2H), 1.60-1.44 (m, 3H), 1.38 (s, 9H), 0.93-0.73 (m, 2H). 5 wt % residual solvent.

LC/MS (System A): m/z (ESI⁺)=459 [M⁺Na⁺], R_f=1.40 min, UV purity=89%. Overall purity estimate=84%.

Intermediate 112—Synthesis of (9H-fluoren-9-yl)methyl 4-(aminomethyl)piperidine-1-carboxylate hydrochloride

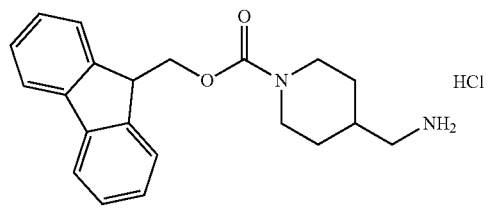 [SMILES: NCC1CCN(C(=O)OCC2c3ccccc3-c3ccccc32)CC1 ; Cl]

HCl solution in dioxane (4.0 M, 12 ml, 48 mmol) was added drop-wise over 8 min to a stirred solution of (9H-fluoren-9-yl)methyl 4-({[(tert-butoxy)carbonyl]amino}methyl)piperidine-1-carboxylate, Intermediate 111 (7.00 g, 16.0 mmol) in MeCN (100 ml). The resulting solution was stirred at RT for 17 h then concentrated in vacuo to afford the product as a white solid (5.56 g, 82%).

¹H NMR (500 MHz, DMSO-d₆) δ 8.04-7.82 (m, 5H), 7.62 (d, J=7.4 Hz, 2H), 7.42 (t, J=7.4 Hz, 2H), 7.34 (td, J=7.4, 0.9 Hz, 2H), 4.42-4.32 (m, 2H), 4.27 (t, J=6.3 Hz, 1H), 4.04-3.71 (m, 2H), 2.84-2.69 (m, 2H), 2.67 (d, J=6.8 Hz, 2H), 1.80-1.70 (m, 1H), 1.70-1.58 (m, 2H), 1.04-0.87 (m, 2H). 7 wt % residual dioxane.

LC/MS (System A): m/z (ESI⁺)=337 [MH⁺], R_f=0.86 min, UV purity=95%. Overall purity estimate=88%.

Intermediate 113—Synthesis of (9H-fluoren-9-yl)methyl 4-({bis[(2S,3R)-2,3-dihydroxy-3-[(4R,5R)-5-hydroxy-2-phenyl-1,3-dioxan-4-yl]propyl]amino}methyl)piperidine-1-carboxylate

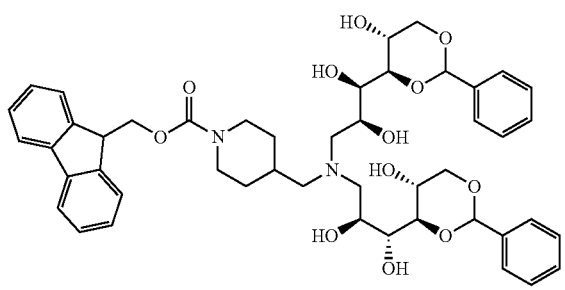

AcOH (3.11 ml, 54.3 mmol) was added to a solution of (9H-fluoren-9-yl)methyl 4-(aminomethyl)piperidine-1-carboxylate hydrochloride, Intermediate 112 (5.56 g, 14.9 mmol) and 4,6-O-benzylidene-D-glucopyranose (14.6 g, 54.3 mmol) in MeOH (100 ml).

The reaction was stirred at RT for 40 min then NaCNBH₃ (3.41 g, 54.3 mmol) was added in portions over 50 min. The resulting solution was stirred at RT for 17 h. The reaction mixture was re-treated with 4,6-O-benzylidene-D-glucopyranose (7.29 g, 27.2 mmol) and AcOH (1.56 ml, 27.2 mmol) then stirred at RT for 30 min. NaCNBH₃ (1.71 g, 27.2 mmol) was added in portions over 1 h. The resulting solution was stirred at RT for a further 70 h then added onto saturated aqueous NaHCO₃ solution (200 ml) in portions over 30 min. The resultant suspension was stirred at RT for 1 h then filtered. The solid was washed with water (100 ml) then dried in vacuo to afford a white solid (13.8 g). A portion (5.55 g) of the crude material thus obtained was purified by flash column chromatography on C18 (400 g). The column was eluted with MeCN:H₂O+0.1% NH₄OH using the following gradient (% MeCN, column volumes): 10%, 2 CV; 10-57%, 16 CV; 57%, 9 CV; 59-63%, 2 CV; 100%, 3 CV. The desired fractions were combined and concentrated in vacuo to afford the product as a beige solid (2.99 g, 23%).

¹H NMR (500 MHz, CD₃OD-d4) δ 7.86-7.75 (m, 2H), 7.65-7.55 (m, 2H), 7.53-7.44 (m, 4H), 7.43-7.37 (m, 2H), 7.36-7.27 (m, 8H), 5.51 (m, 2H), 4.64-4.36 (m, 5H), 4.27-4.20 (m, 3H), 4.04-3.92 (m, 4H), 3.86 (m, 2H), 3.71 (m, 2H), 3.64-3.57 (m, 2H), 2.73-2.58 (m, 3H), 2.54-2.44 (m, 2H), 2.36-2.23 (m, 2H), 1.81-1.42 (m, 3H), 0.89-0.58 (m, 2H).

LC/MS (System B): m/z (ESI⁺)=841 [MH⁺], R_t=4.78 min, UV purity=95%.

Intermediate 114 Synthesis of (1R,2S)-3-{[(2S,3R)-2,3-dihydroxy-3-[(4R,5R)-5-hydroxy-2-phenyl-1,3-dioxan-4-yl]propyl][(piperidin-4-yl)methyl]amino}-1-[(4R,5R)-5-hydroxy-2-phenyl-1,3-dioxan-4-yl]propane-1,2-diol; bis(formic acid

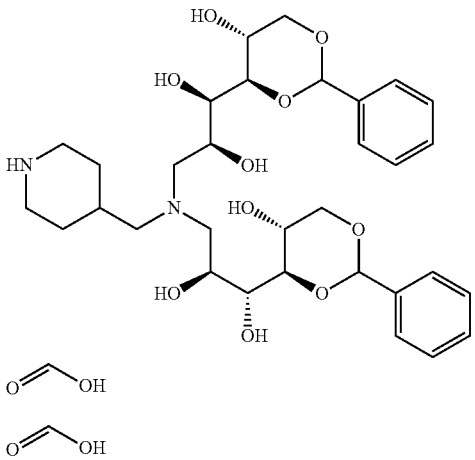

Piperidine (3.30 ml, 33.4 mmol) was added to a stirred solution of (9H-fluoren-9-yl)methyl 4-({bis[(2S,3R)-2,3-dihydroxy-3-[(4R,5R)-5-hydroxy-2-phenyl-1,3-dioxan-4-yl]propyl]amino}methyl)piperidine-1-carboxylate, Intermediate 113 (2.81 g, 3.34 mmol) in THF (40 ml). The reaction mixture was stirred at RT for 18 h then concentrated in vacuo. The residue was suspended in Et₂O (30 ml) with sonication then the resultant suspension was filtered. The solid collected was rinsed with Et₂O (20 ml) then dried under vacuum to afford a white solid (3.07 g). A sample (1.78 g) of the crude solid was purified by flash column chromatography on C18 (120 g). The column was eluted with MeCN:water+0.1% formic acid using the following gradient (% MeCN, column volumes): 10%, 2 CV; 10-16%, 1.5 CV; 16%, 2.5 CV; 16-39%, 6 CV; 39-100%, 1.5 CV; 100% 2 CV. The remaining crude solid material was purified by flash column chromatography on C18 (120 g). The column was eluted with MeCN:water+0.1% formic acid using the following gradient (% MeCN, column volumes): 10%, 2 CV; 10-14%, 2 CV; 14%, 2 CV; 14-17%, 1 CV; 17-55%, 7 CV; 55-100%, 1 CV; 100% 4 CV. The desired fractions from both columns were combined and concentrated in vacuo to afford the product as an off-white solid (1.58 g, 67%).

$^1$H NMR (500 MHz, CD$_3$OD) δ 8.33 (s, 2H), 7.53-7.45 (m, 4H), 7.41-7.31 (m, 6H), 5.53 (m, 2H), 4.25 (m, 2H), 4.02 (m, 2H), 3.96 (m, 2H), 3.89 (m, 2H), 3.74 (m, 2H), 3.62 (m, 2H), 3.30-3.20 (m, 2H), 2.96-2.80 (m, 4H), 2.78-2.68 (m, 2H), 2.65-2.58 (m, 2H), 2.09-2.00 (m, 1H), 1.92-1.68 (m, 2H), 1.33-1.18 (m, 2H).

LC/MS (System A): m/z (ESI$^+$)=619 [MH$^+$], R$_f$=0.73 min, UV purity=100%.

Intermediate 115 Synthesis of (2R,3R,4R,5S)-6-{[(2S,3R,4R,5R)-2,3,4,5,6-pentahydroxyhexyl][(piperidin-4-yl)methyl]amino}hexane-1,2,3,4,5-pentol dihydrochloride

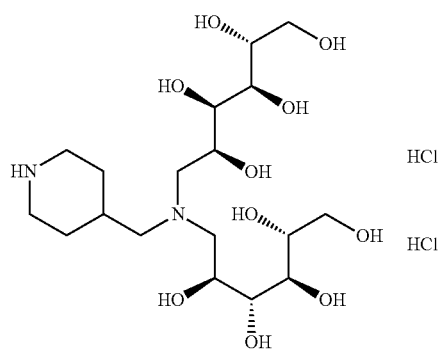 [SMILES: OC[C@@H](O)[C@@H](O)[C@H](O)[C@@H](O)CN(CC1CCNCC1)C[C@H](O)[C@@H](O)[C@H](O)[C@H](O)CO ; Cl ; Cl]

A solution of (1R,2S)-3-{[(2S,3R)-2,3-dihydroxy-3-[(4R,5R)-5-hydroxy-2-phenyl-1,3-dioxan-4-yl]propyl][(piperidin-4-yl)methyl]amino}-1-[(4R,5R)-5-hydroxy-2-phenyl-1,3-dioxan-4-yl]propane-1,2-diol; bis(formic acid), Intermediate 114 (1.52 g, 2.14 mmol) in aqueous HCl solution (2 M, 23 ml, 46 mmol) was stirred at RT for 4.5 h. The reaction was concentrated in vacuo to afford a viscous yellow gum (1.18 g, quantitative based on 93% estimated purity).

$^1$H NMR (500 MHz, D$_2$O) δ 4.32-4.21 (m, 2H), 3.89-3.81 (m, 4H), 3.81-3.75 (m, 2H), 3.72-3.59 (m, 4H), 3.56-3.48 (m, 6H), 3.39 (m, 2H), 3.09 (m, 2H), 2.40-2.27 (m, 1H), 2.21-2.13 (m, 1H), 2.06-1.99 (m, 1H), 1.66-1.53 (m, 2H).

LC/MS (System C): m/z (ESI$^+$)=443 [MH$^+$], R$_f$=0.32 min, ELS purity=100%.

Intermediate 116 Synthesis of formic acid; tert-butyl (3R)-3-{bis[(2S,3R)-2,3-dihydroxy-3-[(4R,5R)-5-hydroxy-2-phenyl-1,3-dioxan-4-yl]propyl]amino}pyrrolidine-1-carboxylate

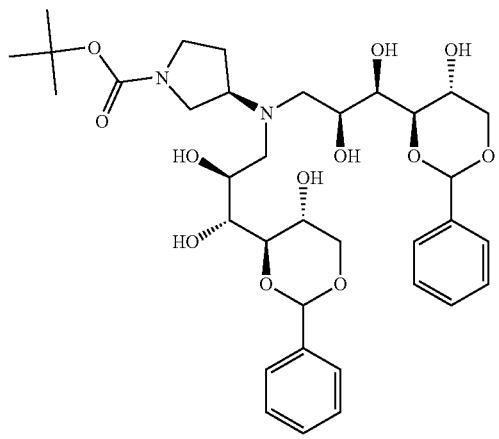

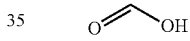

2-Picoline borane complex (0.86 g, 8.05 mmol) was added to a suspension of tert-butyl (3R)-3-aminopyrrolidine-1-carboxylate (500 mg, 2.68 mmol) and 4,6-O-benzylidene-D-glucopyranose (2.88 g, 10.7 mmol) in MeOH (5 ml). The mixture was heated at 60° C. for 17 h. The reaction mixture was allowed to cool to RT then concentrated in vacuo. The residue was partitioned between EtOAc (15 ml) and water (15 ml). The phases were separated then the organic phase was washed with water (15 ml) and brine (15 ml) then dried over Na$_2$SO$_4$ and concentrated in vacuo. The crude material was purified by flash column chromatography on C18 (60 g, Ultra). The column was eluted with MeCN:H$_2$O+0.1% formic acid using the following gradient (% MeCN, column volumes): 10%, 2 CV; 10-40%, 10 CV; 40-100%, 2 CV; 100%, 2 CV. The desired fractions were combined and concentrated in vacuo then the residual aqueous solution was lyophilised to afford the product as a white solid (1.39 g, 70%).

$^1$H NMR (500 MHz, CD$_3$OD-d4) δ 8.27 (s, 1H), 7.47 (dd, J=7.2, 2.3 Hz, 4H), 7.34 (qd, J=4.7, 1.8 Hz, 6H), 5.51 (s, 2H), 4.24 (dd, J=10.6, 5.4 Hz, 2H), 4.04 (s, 2H), 3.95 (td, J=9.9, 5.4 Hz, 2H), 3.89 (dd, J=5.3, 2.2 Hz, 2H), 3.75 (dd, J=9.4, 2.2 Hz, 2H), 3.69 (d, J=6.2 Hz, 1H), 3.59 (q, J=11.4, 11.0 Hz, 3H), 3.34-3.29 (m, 1H+CD$_3$OD), 3.24-3.15 (m, 1H), 2.92 (d, J=48.5 Hz, 5H), 1.96 (d, J=31.5 Hz, 1H), 1.75 (s, 1H), 1.45 (s, 9H). LC/MS (System A): m/z (ESI$^+$)=691 [MH$^+$], R$_f$=0.93 min, UV purity=100%.

Intermediate 117 Synthesis of (2R,3R,4R,5S)-6-{[(2S,3R,4R,5R)-2,3,4,5,6-pentahydroxyhexyl][(3R)-pyrrolidin-3-yl]amino}hexane-1,2,3,4,5-pentol dihydrochloride

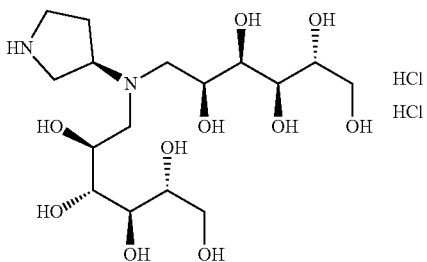 [SMILES: OC[C@@H](O)[C@@H](O)[C@H](O)[C@@H](O)CN(C[C@H](O)[C@@H](O)[C@H](O)[C@H](O)CO)[C@@H]1CCNC1 ; Cl ; Cl]

A suspension of formic acid; tert-butyl (3R)-3-{bis[(2S,3R)-2,3-dihydroxy-3-[(4R,5R)-5-hydroxy-2-phenyl-1,3-dioxan-4-yl]propyl]amino}pyrrolidine-1-carboxylate, Intermediate 116 (1.39 g, 1.89 mmol) in aqueous HCl solution (2 M, 30 ml, 60 mmol) was stirred at RT for 18 h. The reaction mixture was concentrated in vacuo then re-dissolved in water (20 ml) and lyophilised to afford the product as a cream foam (1.11 g, quantitative based on 83% estimated purity).

$^1$H NMR (500 MHz, D$_2$O) δ 4.67 (p, J=8.4 Hz, 1H), 4.33-4.28 (m, 2H), 3.99-3.92 (m, 1H), 3.88 (dd, J=5.0, 2.3 Hz, 2H), 3.83 (dd, J=11.8, 3.0 Hz, 2H), 3.81-3.76 (m, 2H), 3.75-3.64 (m, 6H), 3.63-3.58 (m, 2H), 3.52-3.46 (m, 2H), 3.47-3.39 (m, 1H), 2.75-2.67 (m, 1H), 2.37-2.28 (m, 1H). LC/MS (System A): m/z (ESI$^+$)=415 [MH$^+$], R$_t$=0.13 min, ELS purity=100%.

Intermediate 118 Synthesis of formic acid; tert-butyl (3S)-3-{bis[(2S,3R)-2,3-dihydroxy-3-[(4R,5R)-5-hydroxy-2-phenyl-1,3-dioxan-4-yl]propyl]amino}pyrrolidine-1-carboxylate

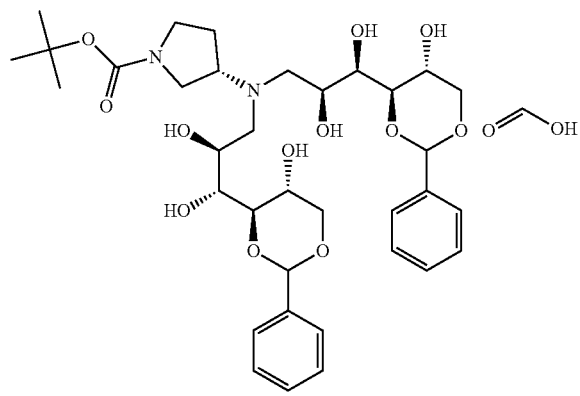

2-Picoline borane complex (861 mg, 8.05 mmol) was added to a suspension of tert-butyl (3S)-3-aminopyrrolidine-1-carboxylate (500 mg, 2.68 mmol) and 4,6-O-benzylidene-D-glucopyranose (2.88 g, 10.7 mmol) in MeOH (5 ml). The resultant mixture was heated at 60° C. for 16 h. The reaction mixture was allowed to cool to RT partitioned between EtOAc (20 ml) and water (20 ml). The phases were separated then the aqueous phase was extracted with EtOAc (20 ml). The combined organic phases were washed with water (20 ml) and 1:1 water:brine (20 ml) then dried over Na$_2$SO$_4$ and concentrated in vacuo. The crude material was purified by flash column chromatography on C18 (30 g). The column was eluted with MeCN:H$_2$O+0.1% formic acid using the following gradient (% MeCN, column volumes): 10%, 2 CV; 10-40%, 10 CV; 40-100%, 2 CV; 100%, 2 CV. The desired fractions were combined and concentrated in vacuo to afford the product as a pale yellow foam (1.73 g, 87%).

$^1$H NMR (500 MHz, CD$_3$OD) δ 8.25 (s, 1H), 7.54-7.46 (m, 4H), 7.41-7.30 (m, 6H), 5.54 (s, 2H), 4.30-4.22 (m, 2H), 4.14-4.07 (m, 2H), 4.01-3.92 (m, 2H), 3.91 (dd, J=5.3, 2.2 Hz, 2H), 3.82-3.72 (m, 3H), 3.68-3.53 (m, 3H), 3.41-3.33 (m, 1H), 3.25-3.04 (m, 4H), 3.04-2.89 (m, 2H), 2.17-2.07 (m, 1H), 1.99-1.83 (m, 1H), 1.56-1.36 (m, 9H).

LC/MS (System A): m/z (ESI$^+$)=691 [MH$^+$], R$_t$=0.93 min, ELS purity=100%. Intermediate 119 Synthesis of (2R,3R,4R,5S)-6-{[(2S,3R,4R,5R)-2,3,4,5,6-pentahydroxyhexyl][(3S)-pyrrolidin-3-yl]amino}hexane-1,2,3,4,5-pentol dihydrochloride

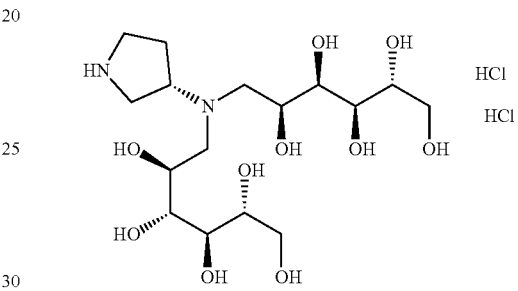

A suspension of formic acid; tert-butyl (3S)-3-{bis[(2S,3R)-2,3-dihydroxy-3-[(4R,5R)-5-hydroxy-2-phenyl-1,3-dioxan-4-yl]propyl]amino}pyrrolidine-1-carboxylate, Intermediate 118 (1.72 g, 2.33 mmol) in aqueous HCl solution (2 M, 30 ml, 60 mmol) and MeOH (1 ml) was stirred at RT for 4 h. The reaction mixture was concentrated in vacuo then re-dissolved in water and lyophilised to afford the product as a cream foam (1.05 g, 92%).

$^1$H NMR (500 MHz, CD$_3$OD) δ 4.72 (p, J=8.2 Hz, 1H), 4.30 (s, 2H), 3.98-3.36 (m, 18H), 2.76-2.66 (m, 1H), 2.48-2.36 (m, 1H).

LC/MS (System A): m/z (ESI$^+$)=415 [MH$^+$], R$_t$=0.13 min, ELS purity=100%.

Intermediate 120 Synthesis of formic acid; tert-butyl N-[(1r,4r)-4-{bis[(2S,3R)-2,3-dihydroxy-3-[(4R,5R)-5-hydroxy-2-phenyl-1,3-dioxan-4-yl]propyl]amino}cyclohexyl]carbamate

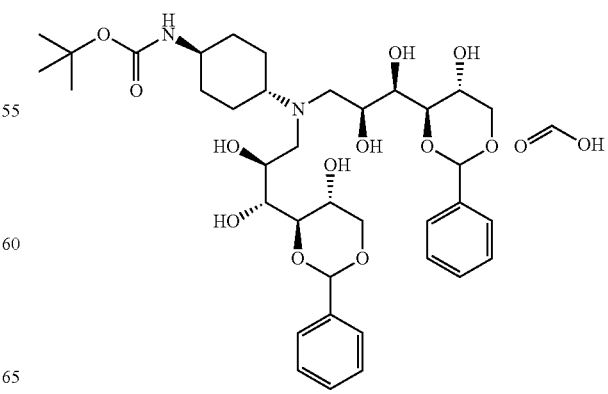

2-Picoline borane complex (939 mg, 8.78 mmol) was added to a suspension of tert-butyl N-(4-aminocyclohexyl)carbamate (627 mg, 2.93 mmol) and 4,6-O-benzylidene-D-glucopyranose (3.14 g, 11.7 mmol) in MeOH (6 ml). The mixture as heated at 60° C. for 16 h then concentrated in vacuo. The residue was partitioned between EtOAc (15 ml) and water (15 ml). The phases were separated then the organic phase was washed with water (10 ml) and brine (10 ml) then dried over $Na_2SO_4$ and concentrated in vacuo. The crude material was purified by flash column chromatography on C18 (30 g). The column was eluted with $MeCN:H_2O$+ 0.1% formic acid using the following gradient (% MeCN, column volumes): 10%, 2 CV; 10-40%, 10 CV; 40-100%, 2 CV; 100%, 2 CV. The desired fractions were combined and concentrated in vacuo then the residual aqueous solution was lyophilised to afford the product as a white solid (914 mg, 41% yield)).

$^1$H NMR (500 MHz, $CD_3OD$) δ 8.52 (s, 1H), 7.54-7.48 (m, 4H), 7.44-7.32 (m, 6H), 5.56 (s, 2H), 4.31-4.23 (m, 2H), 4.18-4.06 (m, 2H), 4.02-3.92 (m, 4H), 3.82-3.75 (m, 2H), 3.64 (t, J=10.5 Hz, 2H), 3.30-3.01 (m, 6H), 2.00-1.76 (m, 4H), 1.56-1.39 (m, 10H), 1.36-1.15 (m, 2H), 1.09-0.97 (m, 1H).

LC/MS (System C): m/z ($ESI^+$)=719 [$MH^+$], $R_t$=2.29 min, ELS purity=100%.

Intermediate 121—Synthesis of (2R,3R,4R,5S)-6-{[(2S,3R,4R,5R)-2,3,4,5,6-pentahydroxyhexyl][(1r,4r)-4-aminocyclohexyl]amino}hexane-1,2,3,4,5-pentol dihydrochloride

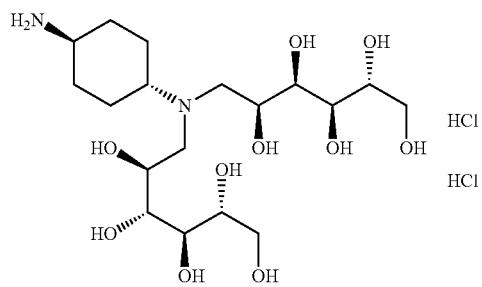 [SMILES: N[C@H]1CC[C@H](N(C[C@H](O)[C@@H](O)[C@H](O)[C@H](O)CO)C[C@H](O)[C@@H](O)[C@H](O)[C@H](O)CO)CC1 ; Cl ; Cl]

A suspension of formic acid; tert-butyl N-[(1r,4r)-4-{bis[(2S,3R)-2,3-dihydroxy-3-[(4R,5R)-5-hydroxy-2-phenyl-1,3-dioxan-4-yl]propyl]amino}cyclohexyl]carbamate, Intermediate 120 (910 mg, 1.19 mmol) in aqueous HCl solution (2 M, 20 ml, 40 mmol) was stirred at RT for 18 h.

The reaction mixture was concentrated in vacuo then the residue was dissolved in water (20 ml) and lyophilised to afford the product as a cream foam (718 mg, quantitative based on 85% estimated purity).

$^1$H NMR (500 MHz, $D_2O$) δ 4.19-4.09 (m, 2H), 3.81-3.66 (m, 6H), 3.63-3.51 (m, 6H), 3.39-3.14 (m, 4H), 2.24-2.13 (m, 3H), 2.11-2.04 (m, 1H), 1.87-1.76 (m, 1H), 1.69-1.45 (m, 3H).

LC/MS (System A): m/z ($ESI^+$)=443 [$MH^+$], $R_t$=0.13 min, ELS purity=100%.

Intermediate 122 Synthesis of (9H-fluoren-9-yl)methyl N-[(1s,4s)-4-{[(tert-butoxy)carbonyl]amino}cyclohexyl]carbamate

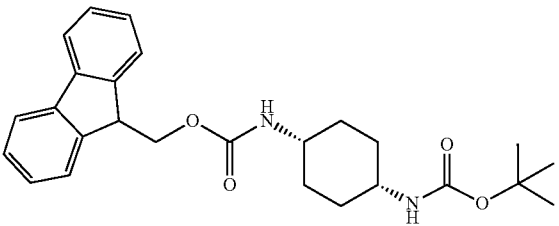 [SMILES: CC(C)(C)OC(=O)N[C@H]1CC[C@@H](NC(=O)OCC2c3ccccc3-c3ccccc32)CC1]

A solution of 9H-fluoren-9-ylmethyl carbonochloridate (4.04 g, 15.6 mmol) in THF (30 ml) was added dropwise over 5 min to a cooled (0° C.) mixture of tert-butyl N-[(1s,4s)-4-aminocyclohexyl]carbamate (3.35 g, 15.6 mmol) and aqueous sodium carbonate solution (1 M, 30 ml, 30 mmol) in THF (60 ml). The reaction was allowed to warm to RT then left to stir at RT for 16 h. The reaction mixture was diluted with water (100 ml) then extracted with EtOAc (100 ml). The organic phase was washed with water (100 ml) and brine (50 ml) then dried over $Na_2SO_4$ and concentrated in vacuo to afford the product as a pale beige foam (6.71 g, 91%).

$^1$H NMR (500 MHz, DMSO-$d_6$) δ 7.92-7.83 (m, 2H), 7.74-7.56 (m, 2H), 7.45-7.36 (m, 2H), 7.36-7.28 (m, 2H), 7.17 (d, J=5.4 Hz, 1H), 6.70-6.58 (m, 1H), 4.44-4.19 (m, 3H), 3.43-3.33 (m, 2H), 1.65-1.21 (m, 17H).

LC/MS (System A): m/z ($ESI^+$)=459 [$M^+Na^+$], $R_t$=1.35 min, UV purity=93%.

Intermediate 123—Synthesis of (9H-fluoren-9-yl)methyl N-[(1s,4s)-4-aminocyclohexyl]carbamate hydrochloride

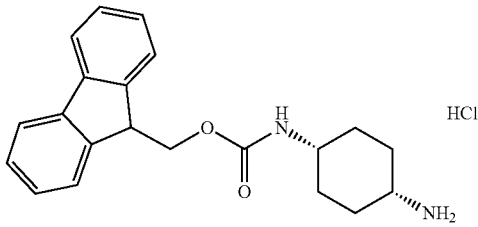 [SMILES: N[C@H]1CC[C@@H](NC(=O)OCC2c3ccccc3-c3ccccc32)CC1 ; Cl]

HCl solution in dioxane (4.0 M, 77 ml, 310 mmol) was added to a suspension of (9H-fluoren-9-yl)methyl N-[(1s,4s)-4-{[(tert-butoxy)carbonyl]amino}cyclohexyl]carbamate, Intermediate 122 (6.71 g, 15.4 mmol) in dioxane (80 ml). The reaction was left to stir at RT for 20 h.

The reaction mixture was concentrated in vacuo to afford the product as a white solid (6.04 g, 92%).

$^1$H NMR (500 MHz, DMSO-$d_6$) δ 7.95-7.81 (m, 5H), 7.78-7.62 (m, 2H), 7.46-7.40 (m, 2H), 7.36-7.32 (m, 2H), 7.28-7.20 (m, 1H), 4.36-4.16 (m, 3H), 3.54-3.44 (m, 1H), 3.12-2.99 (m, 1H), 1.86-1.41 (m, 8H). Residual solvent estimate: 6.8 wt % LC/MS (System A): m/z ($ESI^+$)=337 [$MH^+$], $R_t$=0.90 min, UV purity=94%.

Intermediate 124—Synthesis of (9H-fluoren-9-yl)methyl N-[(1s,4s)-4-{[(2S,3R)-2,3-dihydroxy-3-[(4R,5R)-5-hydroxy-2-phenyl-1,3-dioxan-4-yl]propyl][(2S,3R)-2,3-dihydroxy-3-[(5R)-5-hydroxy-2-phenyl-1,3-dioxan-4-yl]propyl]amino}cyclohexyl]carbamate

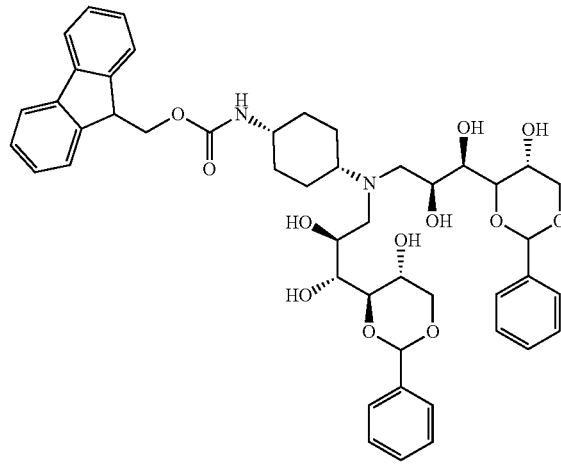

A solution of (9H-fluoren-9-yl)methyl N-[(1s,4s)-4-aminocyclohexyl]carbamate hydrochloride, Intermediate 123 (4.70 g, 12.6 mmol) and 4,6-O-benzylidene-D-glucopyranose (10.1 g, 37.8 mmol) in MeOH (100 ml) was stirred at RT for 0.5 h. NaCNBH3 (3.17 g, 50.4 mmol) was added then the reaction mixture was left to heat at 60° C. for 4.5 h. More 4,6-O-benzylidene-D-glucopyranose (10.1 g, 37.8 mmol) was added then the reaction was left to heat at 60° C. for 20 h. More 4,6-O-benzylidene-D-glucopyranose (10.1 g, 37.8 mmol) was added then the reaction was left to heat at 60° C. for 19 h. The reaction was allowed to cool to RT then added to saturated aqueous NaHCO$_3$ solution (100 ml) and EtOAc (100 ml). The resulting suspension was left to stir at RT for 2 h then filtered through a Celite pad. The pad was rinsed through with EtOAc (50 ml) then the filtrate was transferred to a separating funnel. Saturated aqueous NaHCO$_3$ solution (50 ml) was added then the phases were separated. Water (150 ml) was added to the organic phase then the resultant mixture was left to stir at RT for a further 1 h. The resultant mixture was transferred to a separating funnel then the phases were separated. The organic phase was washed with water (150 ml) and brine (100 ml) then dried over Na$_2$SO$_4$ and concentrated in vacuo to afford a golden viscous oil (19.1 g). The crude material was dissolved in refluxing isopropanol (200 ml). The mixture was stirred under reflux for 0.5 h then allowed to cool to RT. The solid was collected by filtration, then rinsed with IPA and dried under vacuum to afford the product as a cream solid (7.68 g). A sample of the solid thus obtained (3.0 g) was purified by flash column chromatography on C18 (120 g). The column was eluted with MeCN:H$_2$O+0.1% formic acid using the following gradient (% MeCN, column volumes): 20%, 2 CV; 20-50%, 10 CV; 50-100%, 2 CV; 100%, 2 CV. The desired fractions were combined and concentrated in vacuo to afford the product as a white solid (1.46 g, 13%)).

$^1$H NMR (500 MHz, CD$_3$OD) δ 8.35 (s, 1H), 7.85-7.77 (m, 2H), 7.67-7.58 (m, 2H), 7.53-7.43 (m, 4H), 7.41-7.26 (m, 10H), 5.52 (s, 2H), 4.58-4.35 (m, 2H), 4.31-4.23 (m, 2H), 4.23-4.13 (m, 3H), 4.00-3.89 (m, 4H), 3.75 (m, 2H), 3.71-3.65 (m, 1H), 3.62 (m, 2H), 3.44-3.32 (m, 4H), 1.89-1.26 (m, 8H).

LC/MS (System A): m/z (ESI$^+$)=841 [MH$^+$], R$_t$=1.09 min, UV purity=99%.

Intermediate 125 Synthesis of (1R,2S)-3-{[(2S,3R)-2,3-dihydroxy-3-[(4R,5R)-5-hydroxy-2-phenyl-1,3-dioxan-4-yl]propyl][(1s,4s)-4-aminocyclohexyl]amino}-1-[(4R,5R)-5-hydroxy-2-phenyl-1,3-dioxan-4-yl]propane-1,2-diol; bis(formic acid

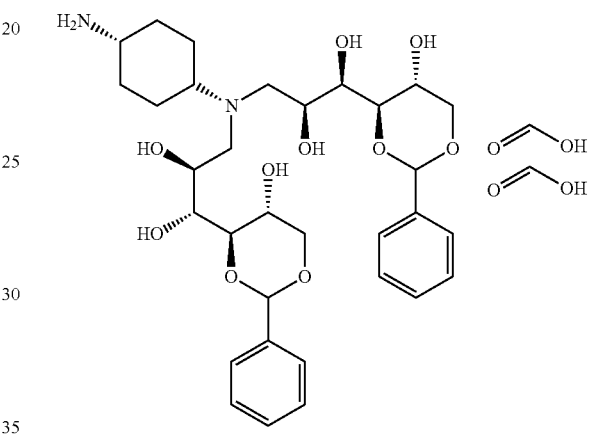

Piperidine (615 uL, 6.23 mmol) was added to a solution of (9H-fluoren-9-yl)methyl N-[(1s,4s)-4-{[(2S,3R)-2,3-dihydroxy-3-[(4R,5R)-5-hydroxy-2-phenyl-1,3-dioxan-4-yl]propyl][(2S,3R)-2,3-dihydroxy-3-[(5R)-5-hydroxy-2-phenyl-1,3-dioxan-4-yl]propyl]amino}cyclohexyl]carbamate, Intermediate 124 (1.46 g, 1.74 mmol) in THF (10 ml). The reaction was left to stir at RT for 21 h then concentrated in vacuo. The residue was suspended in MeOH (10 ml) then filtered. The filtrate was concentrated in vacuo then suspended in MeOH (5 ml) and filtered. The filtrate was purified by flash column chromatography on C18 (60 g). The column was eluted with MeCN:H$_2$O+0.1% formic acid using the following gradient (% MeCN, column volumes): 10%, 2 CV; 10-32%, 7 CV; 32-40%, 1 CV; 12 CV; 40-100%, 2 CV; 100%, 2 CV. The desired fractions were combined then concentrated in vacuo. The residual aqueous solution was lyophilised to afford the product as a white solid (388 mg, 31%).

$^1$H NMR (500 MHz, CD$_3$OD) δ 8.40 (s, 2H), 7.51-7.43 (m, 4H), 7.40-7.28 (m, 6H), 5.51 (s, 2H), 4.29-4.20 (m, 2H), 4.08-4.02 (m, 2H), 4.00-3.92 (m, 2H), 3.88 (dd, J=5.0, 2.5 Hz, 2H), 3.72 (dd, J=9.3, 2.5 Hz, 2H), 3.61 (t, J=10.5 Hz, 2H), 3.39-3.34 (m, 1H), 3.07-2.89 (m, 5H), 1.97-1.62 (m, 8H).

LC/MS (System A): m/z (ESI$^+$)=619 [MH$^+$], R$_t$=0.76 min, UV purity=100%.

Intermediate 126 Synthesis of (2R,3R,4R,5S)-6-{[(2S,3R,4R,5R)-2,3,4,5,6-pentahydroxyhexyl][(1s,4s)-4-aminocyclohexyl]amino}hexane-1,2,3,4,5-pentol

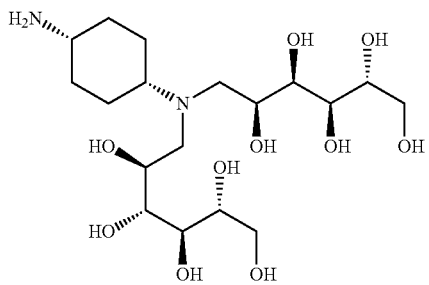 [SMILES: N[C@H]1CC[C@@H](N(C[C@H](O)[C@@H](O)[C@H](O)[C@H](O)CO)C[C@H](O)[C@@H](O)[C@H](O)[C@H](O)CO)CC1]

A solution of (1R,2S)-3-{[(2S,3R)-2,3-dihydroxy-3-[(4R,5R)-5-hydroxy-2-phenyl-1,3-dioxan-4-yl]propyl][(1s,4s)-4-aminocyclohexyl]amino}-1-[(4R,5R)-5-hydroxy-2-phenyl-1,3-dioxan-4-yl]propane-1,2-diol; bis(formic acid), Intermediate 125 (385 mg, 0.622 mmol) in aqueous HCl solution (2 M, 6 ml, 12 mmol) was stirred at RT for 4 h then concentrated in vacuo. The resulting oil was dissolved in water (10 ml) then lyophilised to afford a white foam (323 mg). The material thus obtained was dissolved in water/MeOH then loading on to a pre-wetted SCX cartridge (5 g). The cartridge was eluted with MeOH then the product was released by extensive elution with 7 M ammonia solution in MeOH. The ammonia eluent was concentrated in vacuo. The residue was dissolved in water/MeCN then lyophilised to afford the product as a white solid (212 mg, 77%).

$^1$H NMR (500 MHz, D$_2$O) δ 4.30-4.20 (m, 2H), 3.90-3.62 (m, 12H), 3.57-3.49 (m, 1H), 3.43-3.31 (m, 2H), 2.21-2.09 (m, 3H), 2.06-1.90 (m, 4H), 1.85-1.70 (m, 2H).

LC/MS (System A): m/z (ESI$^+$)=443 [MH$^+$], R$_t$=0.14 min, ELS purity=100%.

Intermediate 127—Synthesis of formic acid; tert-butyl N-(3-{bis[(2S,3R)-2,3-dihydroxy-3-[(4R,5R)-5-hydroxy-2-phenyl-1,3-dioxan-4-yl]propyl]amino}propyl)-N-methylcarbamate

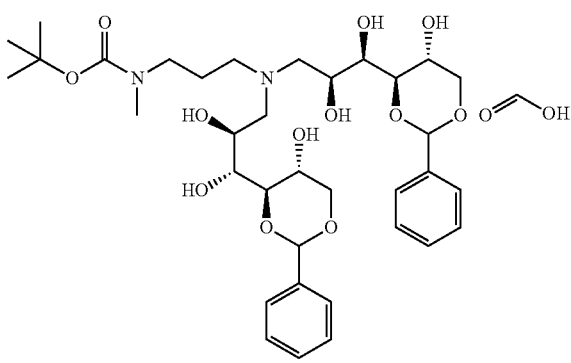

alpha-picoline borane (0.861 g, 8.05 mmol) was added to a suspension of tert-butyl N-(3-aminopropyl)-N-methylcarbamate (0.505 g, 2.68 mmol) and 4,6-O-benzylidene-D-glucopyranose (2.88 g, 10.7 mmol) in MeOH (5 ml). The mixture was heated at 60° C. for 16 h. The reaction mixture was allowed to cool to RT then partitioned between EtOAc (20 ml) and water (20 ml). The phases were separated then the aqueous phase was extracted with EtOAc (20 ml). The combined organic phases were washed with water (20 ml) and 1:1 water:brine (20 ml) then dried over Na$_2$SO$_4$ and concentrated in vacuo. The crude material was purified by flash column chromatography on C18 (60 g). The column was eluted with MeCN:H$_2$O+0.1% formic acid using the following gradient (% MeCN, column volumes): 10%, 2 CV; 10-40%, 10 CV; 40-100%, 2 CV; 100%, 2 CV. The desired fractions were combined and concentrated in vacuo to afford the product as a pale yellow foam (1.19 g, 60%).

$^1$H NMR (500 MHz, CD$_3$OD) δ 8.40 (s, 1H), 7.57-7.44 (m, 4H), 7.44-7.32 (m, 6H), 5.55 (s, 2H), 4.31-4.23 (m, 2H), 4.24-4.15 (m, 2H), 4.00-3.90 (m, 4H), 3.79 (dd, J=9.4, 2.2 Hz, 2H), 3.64 (t, J=10.5 Hz, 2H), 3.41-3.31 (m, 3H), 3.25-3.08 (m, 4H), 2.76-2.64 (m, 3H), 1.88-1.75 (m, 2H), 1.50-1.39 (m, 9H).

LC/MS (System A): m/z (ESI$^+$)=693 [MH$^+$], R$_t$=0.94 min, ELS purity=100%.

Intermediate 128 Synthesis of (2R,3R,4R,5S)-6-{[3-(methylamino)propyl][(2S,3R,4R,5R)-2,3,4,5,6-pentahydroxyhexyl]amino}hexane-1,2,3,4,5-pentol dihydrochloride

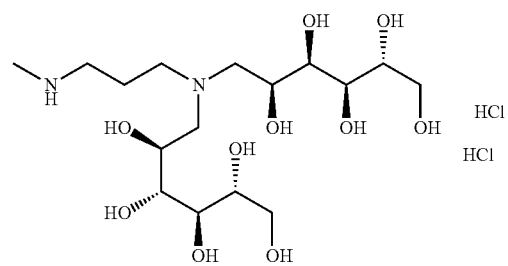 [SMILES: CNCCCN(C[C@H](O)[C@@H](O)[C@H](O)[C@H](O)CO)C[C@H](O)[C@@H](O)[C@H](O)[C@H](O)CO ; Cl ; Cl]

A suspension of formic acid; tert-butyl N-(3-{bis[(2S,3R)-2,3-dihydroxy-3-[(4R,5R)-5-hydroxy-2-phenyl-1,3-dioxan-4-yl]propyl]amino}propyl)-N-methylcarbamate, Intermediate 127 (1.18 g, 1.60 mmol) in aqueous HCl solution (2 M, 30 ml, 60 mmol) and MeOH (1 ml) was stirred at RT for 4 h then concentrated in vacuo. The residue was dissolved in water (30 ml) then lyophilised to afford the product as a cream foam (770 mg, 99%).

$^1$H NMR (500 MHz, CD$_3$OD) δ 4.29-4.20 (m, 2H), 3.96-3.86 (m, 2H), 3.83-3.77 (m, 2H), 3.77-3.65 (m, 6H), 3.63-3.39 (m, 6H), 3.18-3.10 (m, 2H), 2.77 (s, 3H), 2.28-2.18 (m, 2H).

LC/MS (System A): m/z (ESI$^+$)=417 [MH$^+$], R$_t$=0.13 min, ELS purity=100%.

Intermediate 129—Synthesis of formic acid; tert-butyl N-(2-{bis[(2S,3R)-2,3-dihydroxy-3-[(4R,5R)-5-hydroxy-2-phenyl-1,3-dioxan-4-yl]propyl]amino}ethyl)carbamate

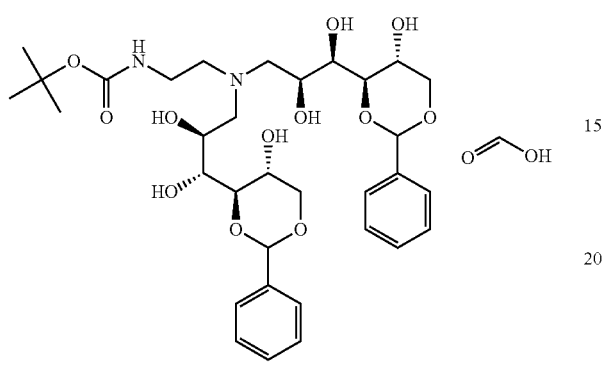

4,6-O-Benzylidene-D-glucopyranose (10.05 g, 37.45 mmol) was added to a solution of tert-butyl N-(2-aminoethyl)carbamate (1.50 g, 9.36 mmol) in MeOH (50 ml). The reaction was stirred at RT for 15 min before then AcOH (2.14 ml, 37.5 mmol) was added. The reaction was stirred at RT for a further 15 min then NaCNBH$_3$ (2.35 g, 37.5 mmol) was added portionwise over 5 min. The reaction was stirred at RT for 16 h then saturated aqueous NaHCO$_3$ solution (50 ml) was added dropwise over 15 min. Further saturated aqueous NaHCO$_3$ solution (50 ml) was added, followed by EtOAc (50 ml). The reaction was stirred at RT for 15 min then transferred to a separating funnel. More EtOAc (100 ml) was added then the phases were separated. The aqueous phase was extracted with EtOAc (150 ml), then the combined organic phases were washed with saturated aqueous NaHCO$_3$ solution (4×200 ml) and brine (50 ml), then dried over Na$_2$SO$_4$, filtered and concentrated in vacuo. The crude material was purified by flash column chromatography on C18 (400 g, Ultra). The column was eluted with MeCN:H$_2$O+0.1% formic acid using the following gradient (% MeCN, column volumes): 10%, 2 CV; 10-49%, 8 CV; 49-54%, 0.5 CV; 54-100%, 1 CV. The desired fractions were combined and concentrated in vacuo then the residual aqueous solution was lyophilised to afford the product as a white solid (2.77 g, 42%).

$^1$H NMR (500 MHz, CD$_3$OD) δ 8.34 (s, 1H), 7.53-7.43 (m, 4H), 7.40-7.26 (m, 6H), 5.52 (s, 2H), 4.25 (dd, J=10.7, 5.4 Hz, 2H), 4.14 (q, J=5.7 Hz, 2H), 3.94 (td, J=10.0, 5.4 Hz, 2H), 3.89 (dd, J=5.0, 2.3 Hz, 2H), 3.75 (dd, J=9.4, 2.2 Hz, 2H), 3.61 (t, J=10.5 Hz, 2H), 3.26-2.99 (m, 8H), 1.42 (s, 9H).

LC/MS (System A): m/z (ESI$^+$)=665 [MH$^+$], R$_t$=0.94 min, UV purity=100%.

Intermediate 130 Synthesis of (2R,3R,4R,5S)-6-[(2-aminoethyl)[(2S,3R,4R,5R)-2,3,4,5,6-pentahydroxyhexyl]amino]hexane-1,2,3,4,5-pentol dihydrochloride

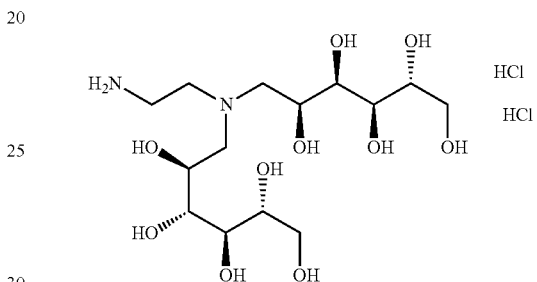

A suspension of formic acid; tert-butyl N-(2-{bis[(2S,3R)-2,3-dihydroxy-3-[(4R,5R)-5-hydroxy-2-phenyl-1,3-dioxan-4-yl]propyl]amino}ethyl)carbamate, Intermediate 129 (1.50 g, 2.11 mmol) in aqueous HCl (2 M, 21 ml, 42 mmol) was stirred at RT for 68 h. The reaction was concentrated in vacuo, then re-dissolved in MeCN/water and concentrated in vacuo. The residue was re-dissolved in MeCN/water then lyophilised to afford the product as a white solid (1.03 g, 99% based on 94% estimated purity).

$^1$H NMR (500 MHz, D$_2$O) δ 4.30 (dt, J=8.9, 4.7 Hz, 2H), 3.88 (dd, J=4.9, 2.2 Hz, 2H), 3.86-3.71 (m, 6H), 3.71-3.66 (m, 4H), 3.61-3.50 (m, 6H).

LC/MS (System A): m/z (ESI$^+$)=389 [MH$^+$], R$_t$=0.14 min, ELS purity=100%.

Intermediate 131 Synthesis of tert-butyl N-[2-(2-{2-[2-({[(9H-fluoren-9-yl)methoxy]carbonyl}amino)ethoxy]ethoxy}ethoxy)ethyl]carbamate

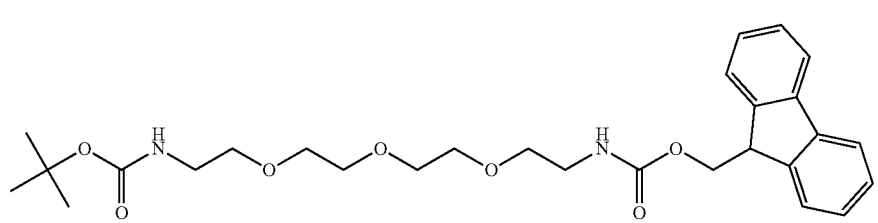 [SMILES: CC(C)(C)OC(=O)NCCOCCOCCOCCNC(=O)OCC1c2ccccc2-c2ccccc21]

NaHCO₃ (0.574 g, 6.84 mmol) was added portionwise over 2 min to a stirred solution of tert-butyl N-[2-[2-[2-(2-aminoethoxy)ethoxy]ethoxy]ethyl]carbamate (1.00 g, 3.42 mmol) in MeCN (15 ml) and water (15 ml) RT. A solution of (2,5-dioxopyrrolidin-1-yl) 9H-fluoren-9-ylmethyl carbonate (1.15 g, 3.42 mmol) in MeCN (15 ml) was added dropwise over 30 min.

The resulting solution was stirred at RT for 18 h. EtOAc (30 ml) and brine (10 ml) were added then the phases were separated. The aqueous phase was extracted with EtOAc (20 ml). The combined organic extracts were washed with brine (45 ml), dried over MgSO4, then concentrated in vacuo to afford the product as a yellow gum (1.61 g, 76% yield).

¹H NMR (500 MHz, DMSO-d₆) δ 7.89 (d, J=7.5 Hz, 2H), 7.72-7.61 (m, 2H), 7.41 (t, J=7.4 Hz, 2H), 7.37-7.27 (m, 3H), 6.74 (t, J=5.4 Hz, 1H), 4.29 (d, J=6.9 Hz, 2H), 4.21 (t, J=6.9 Hz, 1H), 3.55-3.44 (m, 8H), 3.40 (t, J=6.0 Hz, 2H), 3.36 (t, J=6.1 Hz, 2H), 3.13 (q, J=5.9 Hz, 2H), 3.05 (q, J=6.0 Hz, 2H), 1.36 (s, 9H).

LC/MS (System A): m/z (ESI⁺)=537 [M⁺Na⁺], R_t=1.28 min, UV purity=83%.

Intermediate 132—Synthesis of (9H-fluoren-9-yl) methyl N-(2-{2-[2-(2-aminoethoxy)ethoxy] ethoxy}ethyl)carbamate hydrochloride

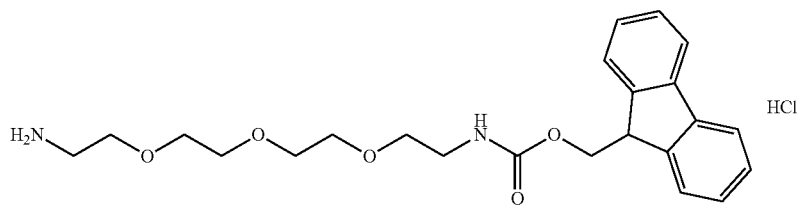 [SMILES: NCCOCCOCCOCCNC(=O)OCC1c2ccccc2-c2ccccc21 ; Cl]

HCl solution in dioxane (4 M, 2 ml, 8 mmol) was added to a stirred solution of tert-butyl N-[2-(2-{2-[2-({[(9H-fluoren-9-yl)methoxy]carbonyl}amino)ethoxy]ethoxy}ethoxy)ethyl]carbamate, Intermediate 131 (83%, 1.61 g, 2.61 mmol) in MeCN (16 ml). The resulting solution was left to stir at RT for 22 then concentrated in vacuo to afford the product as a yellow gum (1.57 g, quantitative based on 75% estimated purity).

¹H NMR (500 MHz, DMSO-d₆) δ 7.89 (d, J=7.5 Hz, 2H), 7.83 (s, 3H), 7.69 (d, J=7.4 Hz, 2H), 7.42 (t, J=7.4 Hz, 2H), 7.37-7.29 (m, 3H), 4.30 (d, J=6.9 Hz, 2H), 4.21 (t, J=6.8 Hz, 1H), 3.60-3.57 (m, 2H), 3.56-3.48 (m, 8H), 3.40 (t, J=6.0 Hz, 2H), 3.13 (q, J=5.9 Hz, 2H), 2.98-2.92 (m, 2H). 20 wt % residual solvent.

LC/MS (System A): m/z (ESI⁺)=415 [MH⁺], R_t=0.89 min, UV purity=92%.

Intermediate 133—Synthesis of (9H-fluoren-9-yl) methyl N-[(14S,15R)-12-[(2S,3R)-2,3-dihydroxy-3-[(4R,5R)-5-hydroxy-2-phenyl-1,3-dioxan-4-yl]propyl]-14,15-dihydroxy-15-[(4R,5R)-5-hydroxy-2-phenyl-1,3-dioxan-4-yl]-3,6,9-trioxa-12-azapentadecan-1-yl]carbamate; formic acid

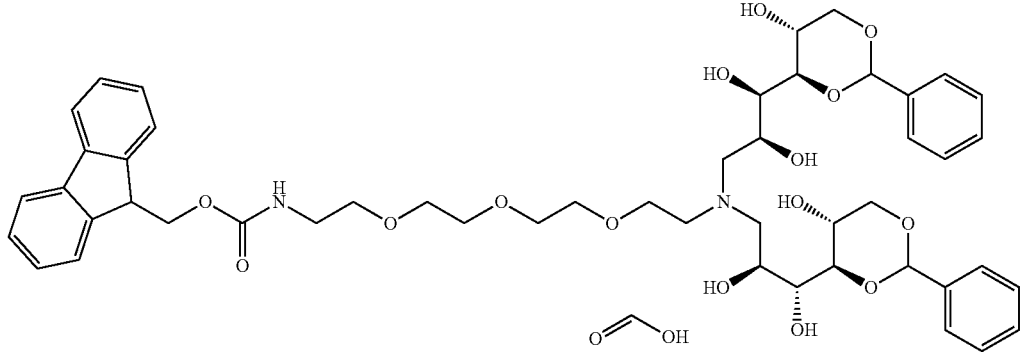

AcOH (737 μL, 12.9 mmol) was added to a solution of (9H-fluoren-9-yl)methyl N-(2-{2-[2-(2-aminoethoxy)ethoxy]ethoxy}ethyl)carbamate hydrochloride, Intermediate 132 (75%, 1.57 g, 3.22 mmol) and 4,6-O-benzylidene-D-glucopyranose (3.46 g, 12.9 mmol) in MeOH (30 ml). The reaction was stirred at RT for 45 min. NaCNBH$_3$ (809 mg, 12.9 mmol) was added portionwise over 50 min. The resultant solution was stirred at RT for 40 h. The reaction mixture was treated with 4,6-O-benzylidene-D-glucopyranose (1.73 g, 6.45 mmol), AcOH (368 μL, 6.43 mmol) and MeOH (10 ml). The reaction was stirred at RT for 1 h then NaCNBH$_3$ (403 mg, 6.41 mmol) was added portionwise over 20 min. MeOH (10 ml) was added then the reaction mixture was stirred at RT for 70 h. Saturated aqueous NaHCO$_3$ solution (100 ml) was added portionwise over 5 min then EtOAc (100 ml) was added. The phases were separated then the aqueous phase was extracted with EtOAc (3×30 ml). The combined organic phases were washed with saturated aqueous NaHCO$_3$ solution (2×50 ml), brine (50 ml), then dried over MgSO$_4$, filtered and concentrated in vacuo to afford a brown gum (3.86 g). A portion (2 g) of the crude material was purified by flash column chromatography on C18 (120 g, Ultra). The column was eluted with MeCN:H$_2$O+0.1% formic acid using the following gradient (% MeCN, column volumes): 10%, 2 CV; 10-31%, 8 CV; 31%, 4.5 CV; 31-35%, 1.5 CV; 35-47%, 1 CV; 47-61%, 1.5 CV; 100% 2 CV. The remaining crude material was purified by flash column chromatography on C18 (120 g, Ultra). The column was eluted with MeCN:H$_2$O+0.1% formic acid using the following gradient (% MeCN, column volumes): 10%, 2 CV; 10-27%, 4 CV; 27%, 0.5 CV; 27-68%, 9 CV; 68%, 0.5 CV; 68-78%, 2 CV; 78-100%, 1.5 CV; 100% 1 CV. The desired fractions from both columns were combined and concentrated in vacuo to afford the product as a light brown resin (1.30 g, 48%).

$^1$H NMR (500 MHz, CD$_3$OD) δ 8.44 (s, 1H), 7.81 (d, J=7.5 Hz, 2H), 7.68-7.59 (m, 2H), 7.52-7.44 (m, 4H), 7.44-7.37 (m, 2H), 7.37-7.30 (m, 8H), 5.52 (s, 2H), 4.36 (d, J=6.8 Hz, 2H), 4.28-4.15 (m, 5H), 3.98-3.88 (m, 4H), 3.75 (dd, J=9.4, 2.3 Hz, 2H), 3.67-3.44 (m, 14H), 3.40-3.33 (m, 4H), 3.31-3.21 (m, 4H). LC/MS (System A): m/z (ESI$^+$)= 919 [MH$^+$], R$_t$=1.02 min, UV purity=93%.

Intermediate 134 Synthesis of (14S,15R)-1-amino-12-[(2S,3R)-2,3-dihydroxy-3-[(4R,5R)-5-hydroxy-2-phenyl-1,3-dioxan-4-yl]propyl]-15-[(4R,5R)-5-hydroxy-2-phenyl-1,3-dioxan-4-yl]-3,6,9-trioxa-12-azapentadecane-14,15-diol: bis(formic acid Piperidine (1.34 ml, 13.6 mmol) was added to a stirred solution of (9H-fluoren-9-yl)methyl N-[(14S,15R)-12-[(2S,3R)-2,3-dihydroxy-3-[(4R,5R)-5-hydroxy-2-phenyl-1,3-dioxan-4-yl]propyl]-14,15-dihydroxy-15-[(4R,5R)-5-hydroxy-2-phenyl-1,3-dioxan-4-yl]-3,6,9-trioxa-12-azapentadecan-1-yl]carbamate; formic acid, Intermediate 133 (93%, 1.25 g, 1.20 mmol) in THF (15 ml). The resulting solution was stirred at RT for 6 h then concentrated in vacuo. The residue thus obtained was suspended in Et$_2$O (10 ml) with sonication. The supernatant was decanted off then the process was repeated with more Et$_2$O (10 ml). The residue thus obtained was purified by flash column chromatography on C18 (120 g, Ultra).

The column was eluted with MeCN:H$_2$O+0.1% formic acid using the following gradient (% MeCN, column volumes): 10%, 2 CV; 10-13%, 1.5 CV; 13%, 2.5 CV; 13-22%, 5.5 CV; 22-60%, 5.5 CV; 60-83%, 2 CV; 100% 2 CV. The desired fractions were combined and concentrated in vacuo to afford the product as a yellow solid (849 mg, 89%).

$^1$H NMR (500 MHz, CD$_3$OD) δ 8.40 (s, 2H), 7.54-7.43 (m, 4H), 7.41-7.28 (m, 6H), 5.53 (s, 2H), 4.26 (dd, J=10.7, 5.4 Hz, 2H), 4.20-4.12 (m, 2H), 3.97-3.87 (m, 4H), 3.74 (dd, J=9.4, 2.6 Hz, 2H), 3.70-3.54 (m, 14H), 3.29-3.19 (m, 3H), 3.16-3.08 (m, 2H), 3.07-2.99 (m, 1H), 2.98-2.86 (m, 2H).

LC/MS (System A): m/z (ESI$^+$)=697 [MH$^+$], R$_t$=0.74 min, UV purity=100%.

Intermediate 135 Synthesis of (14S,15R,16R,17R)-1-amino-12-[(2S,3R,4R,5R)-2,3,4,5,6-pentahydroxyhexyl]-3,6,9-trioxa-12-azaoctadecane-14,15,16,17,18-pentol dihydrochloride

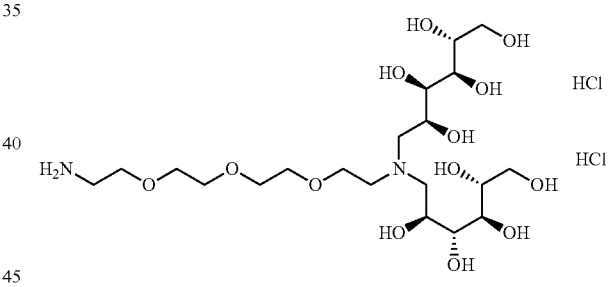

A solution of (14S,15R)-1-amino-12-[(2S,3R)-2,3-dihydroxy-3-[(4R,5R)-5-hydroxy-2-phenyl-1,3-dioxan-4-yl]propyl]-15-[(4R,5R)-5-hydroxy-2-phenyl-1,3-dioxan-4-yl]-

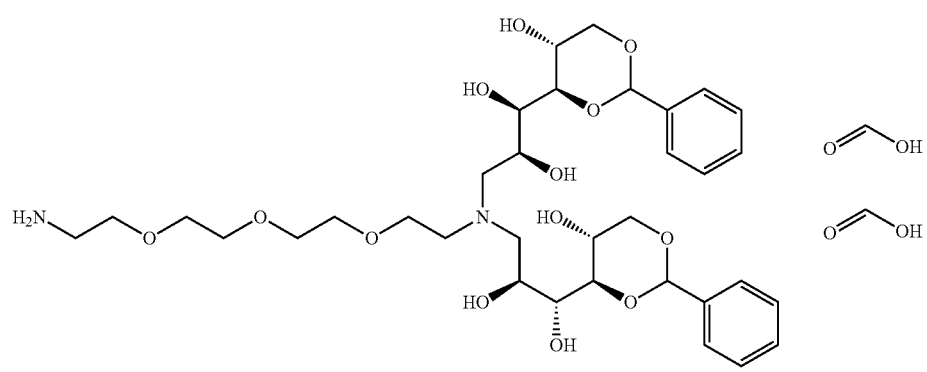

3,6,9-trioxa-12-azapentadecane-14,15-diol; bis(formic acid), Intermediate 134 (845 mg, 1.07 mmol) in aqueous HCl solution (2 M, 10 ml, 20 mmol) was stirred at RT for 5.5 h then concentrated in vacuo. The residue thus obtained was re-dissolved in water (15 ml) then lyophilised to afford a pale yellow gum (660 mg, quantitative based on 96% estimated purity).

$^1$H NMR (500 MHz, D$_2$O) δ 4.30-4.22 (m, 2H), 3.96-3.91 (m, 2H), 3.88-3.82 (m, 4H), 3.81-3.63 (m, 17H), 3.59-3.48 (m, 5H), 3.26-3.20 (m, 2H).

LC/MS (System C): m/z (ESI$^+$)=521 [MH$^+$], R$_t$=0.33 min, ELS purity=100%.

Intermediate 136 Synthesis of tert-butyl N-[2-(4-bromophenyl)ethyl]carbamate

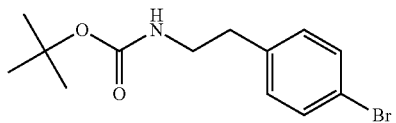 [SMILES: CC(C)(C)OC(=O)NCCc1ccc(Br)cc1]

Di-tert-butyl dicarbonate (3.93 g, 18.0 mmol) was added to a cooled (0° C.) stirred solution of 2-(4-bromophenyl)ethanamine (3.00 g, 15.0 mmol) in THF (20 ml). The resulting solution was allowed to warm to RT then stirred at RT for 18 h. The reaction mixture was partitioned between EtOAc (30 ml) and saturated aqueous NaHCO$_3$ solution (50 ml). The phases were separated then the aqueous phase was extracted with EtOAc (15 ml). The combined organic phases were washed with brine (50 ml), dried over MgSO$_4$, then concentrated in vacuo. The crude material was dissolved in the minimum volume of CH$_2$Cl$_2$, pre-adsorbed onto silica, then purified by flash column chromatography on a silica column (25 g). The column was eluted with EtOAc:heptane, using the following gradient (% EtOAc, column volumes): 0%, 1 CV; 0-8%, 2.5 CV; 8-12%, 1 CV; 12%, 3.5 CV; 12-27%, 5.5 CV; 27-30%, 0.5 CV; 30%, 2 CV; 30-90%, 4 CV; 100% 1 CV. The desired fractions were combined and concentrated in vacuo to afford the product as a white solid (3.99 g, 88%).

$^1$H NMR (500 MHz, DMSO-d$_6$) δ 7.50-7.42 (m, 2H), 7.19-7.11 (m, 2H), 6.86 (t, J=5.3 Hz, 1H), 3.12 (q, J=6.6 Hz, 2H), 2.70-2.63 (m, 2H), 1.41-1.26 (m, 9H).

LC/MS (System A): R$_t$=1.27 min, UV purity=99%.

Intermediate 137 Synthesis of tert-butyl N-{2-[4'-(cyanomethyl)-[1,1'-biphenyl]-4-yl]ethyl}carbamate

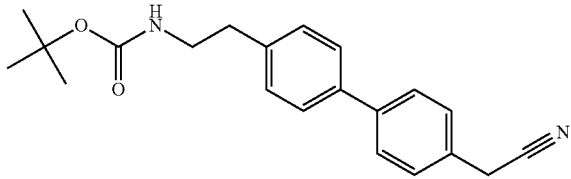 [SMILES: CC(C)(C)OC(=O)NCCc1ccc(-c2ccc(CC#N)cc2)cc1]

A mixture of tert-butyl N-[2-(4-bromophenyl)ethyl]carbamate, Intermediate 136 (4.09 g, 13.6 mmol), [4-cyanomethyl)phenyl]boronic acid (2.63 g, 16.4 mmol) and K$_2$CO$_3$ (5.65 g, 40.9 mmol) in 1,4-dioxane (105 ml) was degassed by bubbling a stream nitrogen through the mixture for 5 min. Pd(dppf)Cl$_2$·CH$_2$Cl$_2$ (445 mg, 0.545 mmol) was added and degassing was continued for a further 5 min. The reaction mixture was heated at 80° C. for 15 h then at 100° C. for 7 h. The reaction was allowed to cool to RT then retreated with K$_2$CO$_3$ (3.76 g, 27.2 mmol) and degassed for 5 min. Pd(dppf)Cl$_2$·CH$_2$Cl$_2$ (445 mg, 0.545 mmol) was added then the mixture was degassed for a further 5 min. The resultant mixture was heated at 100° C. for 24 h then allowed to cool to RT. The reaction was retreated with K$_2$CO$_3$ (1.88 g, 13.6 mmol) and [4-cyanomethyl)phenyl]boronic acid (0.88 g, 5.5 mmol) then degassed for 10 min. Pd(dppf)Cl$_2$·CH$_2$Cl$_2$ (445 mg, 0.545 mmol) was added then the mixture was degassed for a further 5 min. The reaction was heated at 100° C. for 18 h then allowed to cool to RT. The reaction mixture was filtered then the collected solids were washed with EtOAc (50 ml). The combined filtrate was concentrated in vacuo. The residue was re-dissolved in EtOAc:heptane (1:1) then filtered through a silica pad. The pad was rinsed with EtOAc:heptane (1:1, 200 ml). The filtrate was concentrated in vacuo to afford an off-white solid (3.94 g). The silica pad was rinsed through further with EtOAc (200 ml) to afford a brown solid (1.68 g). The brown solid from the EtOAc filtrate was pre-adsorbed onto silica, then purified by flash column chromatography on a silica column (50 g). The column was eluted with EtOAc:heptane, using the following gradient (% EtOAc, column volumes): 0%, 1 CV; 0-30%, 11 CV; 30%, 20 CV; 30-45%, 4.5 CV; 45%, 7.5 CV; 45-50%, 1 CV; 50%, 15 CV. The desired fractions were combined and concentrated in vacuo to afford an off-white solid (1.00 g, 21%).

$^1$H NMR (500 MHz, DMSO-d$_6$) δ 7.67 (d, J=8.2 Hz, 2H), 7.59 (d, J=8.2 Hz, 2H), 7.42 (d, J=8.2 Hz, 2H), 7.28 (d, J=8.1 Hz, 2H), 6.90 (t, J=5.5 Hz, 1H), 4.07 (s, 2H), 3.17 (q, J=6.5 Hz, 2H), 2.73 (t, J=7.4 Hz, 2H), 1.44-1.29 (m, 9H).

LC/MS (System A): R$_t$=1.27 min, UV purity=97%.

Intermediate 138—Synthesis of tert-butyl N-{2-[4'-(2-aminoethyl)-[1,1'-biphenyl]-4-yl]ethyl}carbamate

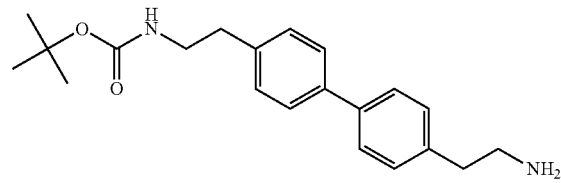 [SMILES: CC(C)(C)OC(=O)NCCc1ccc(-c2ccc(CCN)cc2)cc1]

A mixture of tert-butyl N-{2-[4'-(cyanomethyl)-[1,1'-biphenyl]-4-yl]ethyl}carbamate, Intermediate 137 (570 mg, 1.69 mmol), aqueous ammonia solution (35%, 0.5 ml) and aqueous Raney nickel slurry (50%, 2 ml) in EtOH (15 ml) and DMF (5 ml) was stirred under a hydrogen atmosphere for 18 h. The reaction mixture was filtered through a Celite pad. The pad was rinsed with EtOH (50 ml) and MeOH (100 ml) then the combined filtrate was concentrated in vacuo. The residue was azeotroped with heptane (3×100 ml) then dried in vacuo to afford the product as an off-white solid (515 mg, 84%).

$^1$H NMR (500 MHz, DMSO-d$_6$) δ 7.60-7.50 (m, 4H), 7.31-7.22 (m, 4H), 6.89 (t, J=5.3 Hz, 1H), 3.19-3.13 (m, 2H), 2.78 (t, J=7.2 Hz, 2H), 2.72 (t, J=7.4 Hz, 2H), 2.66 (t, J=7.2 Hz, 2H), 1.43-1.29 (m, 9H).

LC/MS (System A): m/z (ESI$^+$)=341 [MH$^+$], R$_t$=0.93 min, UV purity=94%.

Intermediate 139—Synthesis of tert-butyl N-{2-[4'-(2-{bis[(2S,3R)-2,3-dihydroxy-3-[(4R,5R)-5-hydroxy-2-phenyl-1,3-dioxan-4-yl]propyl]amino}ethyl)-[1,1'-biphenyl]-4-yl]ethyl}carbamate 0.1% NH$_4$OH using the following gradient (% MeCN, column volumes): 10%, 2 CV; 10-59%, 10 CV; 59%, 2 CV; 59-100%, 8 CV; 100%, 2 CV. The desired fractions were combined and concentrated in vacuo to afford the product as a white solid (932 mg, 78%).

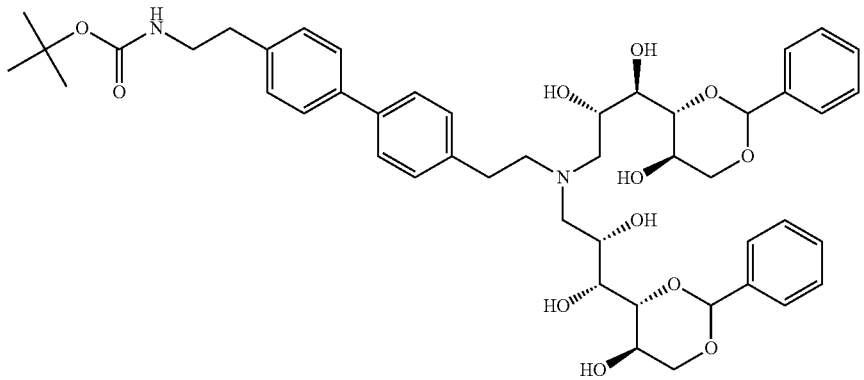

AcOH (0.33 ml, 5.8 mmol) was added to a solution of tert-butyl N-{2-[4'-(2-aminoethyl)-[1,1'-biphenyl]-4-yl]ethyl}carbamate, Intermediate 138 (94%, 515 mg, 1.42 mmol) and 4,6-O-benzylidene-D-glucopyranose (1.58 g, 5.89 mmol) in MeOH (50 ml). The reaction was left to stir at RT for 50 min then NaCNBH$_3$ (370 mg, 5.89 mmol) was added portionwise over 25 min. The resulting solution was stirred at RT for 24 h. Further 4,6-O-benzylidene-D-glucopyranose (790 mg, 2.94 mmol), AcOH (0.17 ml, 3.0 mmol) and MeOH (50 ml) were added then the reaction was left to stir at RT for 40 min. NaCNBH$_3$ (185 mg, 2.94 mmol) was added portionwise over 20 min then the reaction was left to stir at RT for 68 h. Further 4,6-O-benzylidene-D-glucopyranose (790 mg, 2.94 mmol), AcOH (0.17 ml, 3.0 mmol) and MeOH (50 ml) were added then the reaction was left to stir at RT for 30 min. NaCNBH$_3$ (185 mg, 2.94 mmol) was added portionwise over 20 min then the reaction was left to stir at RT for 18 h. Further 4,6-O-benzylidene-D-glucopyranose (790 mg, 2.94 mmol) and MeOH (25 ml) were added then the reaction heated at 40° C. for 18 h. The reaction mixture was allowed to cool to RT then saturated aqueous NaHCO$_3$ solution (40 ml) was added in portions over 15 min. The resultant mixture was stirred at RT for 30 min then the solid was collected by filtration, rinsed with water (10 ml), then dried in vacuo. The crude solid material thus obtained was purified by flash column chromatography on C18 (120 g). The column was eluted with MeCN:H$_2$O+

$^1$H NMR (500 MHz, DMSO-d$_6$) δ 7.57-7.49 (m, 2H), 7.46-7.37 (m, 6H), 7.34-7.29 (m, 6H), 7.28-7.23 (m, 2H), 7.09-7.01 (m, 2H), 6.90 (t, J=5.6 Hz, 1H), 5.48 (s, 2H), 5.14 (d, J=5.8 Hz, 2H), 4.50-4.40 (m, 4H), 4.12 (dd, J=10.5, 5.3 Hz, 2H), 3.87-3.75 (m, 4H), 3.75-3.69 (m, 2H), 3.67-3.60 (m, 2H), 3.50 (t, J=10.4 Hz, 2H), 3.21-3.10 (m, 2H), 2.82-2.65 (m, 8H), 2.57 (dd, J=12.9, 8.9 Hz, 2H), 1.43-1.29 (m, 9H).

LC/MS (System B): m/z (ESI$^+$)=845 [MH$^+$], R$_t$=4.80 min, UV purity=100%.

Intermediate 140—Synthesis of (2R,3R,4R,5S)-6-({2-[4'-(2-aminoethyl)-[1,1'-biphenyl]-4-yl]ethyl}[(2S,3R,4R,5R)-2,3,4,5,6-pentahydroxyhexyl]amino)hexane-1,2,3,4,5-pentol dihydrochloride

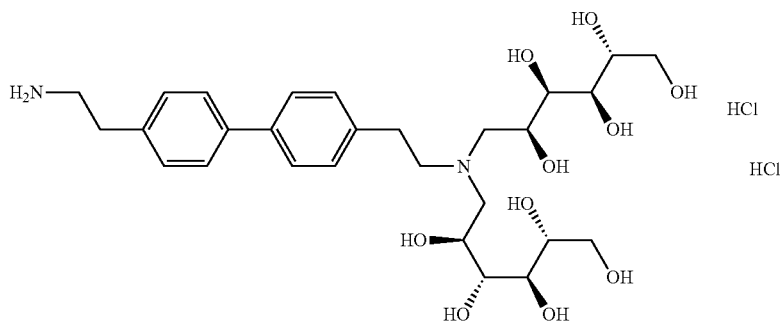 [SMILES: NCCc1ccc(-c2ccc(CCN(C[C@H](O)[C@@H](O)[C@H](O)[C@H](O)CO)C[C@H](O)[C@@H](O)[C@H](O)[C@H](O)CO)cc2)cc1 ; Cl ; Cl]

A suspension of tert-butyl N-{2-[4'-(2-{bis[(2S,3R)-2,3-dihydroxy-3-[(4R,5R)-5-hydroxy-2-phenyl-1,3-dioxan-4-yl]propyl]amino}ethyl)-[1,1'-biphenyl]-4-yl]ethyl}carbamate, Intermediate 139 (932 mg, 1.10 mmol) in aqueous HCl solution (2 M, 8.5 ml, 17 mmol) was stirred at RT for 24 h then further aqueous HCl solution (2 M, 8.5 ml, 17 mmol) was added. The reaction was left to stir at RT for a further 24 h. The reaction mixture was heated at 40° C. for 4 h then concentrated in vacuo. The residue thus obtained was dissolved in water (15 ml) then lyophilised to afford the product as a white resin (753 mg, quantitative based on 94% estimated purity).

¹H NMR (500 MHz, D₂O) δ 7.77-7.70 (m, 4H), 7.53-7.48 (m, 2H), 7.48-7.43 (m, 2H), 4.30-4.19 (m, 2H), 3.87-3.61 (m, 12H), 3.61-3.45 (m, 4H), 3.33 (t, J=7.4 Hz, 2H), 3.29-3.16 (m, 2H), 3.07 (t, J=7.4 Hz, 2H).

LC/MS (System A): m/z (ESI⁺)=569 [MH⁺], R_f=0.15 min, ELS purity=100%.

Intermediate 141—Synthesis of (2S)-2-{[(benzyloxy)carbonyl]amino}-4-{[(tert-butoxy)carbonyl]amino}butanoic acid

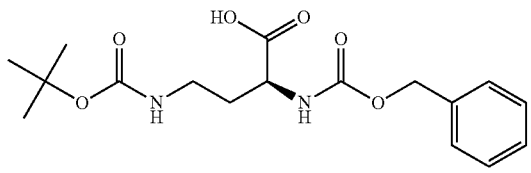

NaHCO₃ (3.13 g, 37.3 mmol) was added to a solution of (2S)-4-amino-2-{[(benzyloxy)carbonyl]amino}butanoic acid (4.70 g, 18.6 mmol) in THF (50 ml) and water (50 ml). The reaction was stirred at RT for 5 min then a solution of di-tert-butyl dicarbonate (4.88 g, 22.4 mmol) in THF (50 ml) was added dropwise over 10 min. The reaction was stirred at RT for 16 h then concentrated in vacuo to remove the majority of the THF. The residual aqueous solution was acidified to pH 2 by dropwise addition of 2 M aqueous HCl solution then extracted with EtOAc (100 ml then 50 ml). The combined organic phases were washed with water (50 ml) and brine (50 ml), then dried over Na₂SO₄, filtered and concentrated in vacuo to afford the product as a colourless oil (6.65 g, 98%).

¹H NMR (500 MHz, DMSO-d₆) δ 12.60 (s, 1H), 7.57 (d, J=8.0 Hz, 1H), 7.41-7.24 (m, 5H), 6.87-6.76 (m, 1H), 5.03 (s, 2H), 4.00-3.92 (m, 1H), 3.06-2.90 (m, 2H), 1.92-1.77 (m, 1H), 1.71-1.59 (m, 1H), 1.37 (s, 9H).

LC/MS (System A): m/z (ESI⁺)=375 [M⁺Na⁺], R_f=1.06 min, UV purity=97%.

Intermediate 142—Synthesis of tert-butyl N-[(3S)-3-{[(benzyloxy)carbonyl]amino}-3-carbamoylpropyl]carbamate

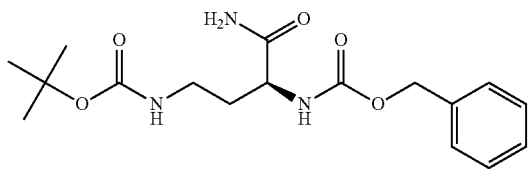 [SMILES: CC(C)(C)OC(=O)NCC[C@H](NC(=O)OCc1ccccc1)C(=O)O]

Isobutyl carbonochloridate (2.94 ml, 22.7 mmol) was added dropwise to a cooled (0°) solution of (2S)-2-{[(benzyloxy)carbonyl]amino}-4-{[(tert-butoxy)carbonyl]amino}butanoic acid, Intermediate 141 (6.15 g, 17.5 mmol) and N-methylmorpholine (2.88 ml, 26.2 mmol) in THF (100 ml). The reaction was allowed to warm to RT then stirred at RT for 17 h. The solution was cooled to 0° C. then ammonia solution in MeOH (7 M, 12 ml, 84 mmol) was added dropwise over 5 min. The reaction mixture was allowed to warm to RT then stirred at RT for 3 h. The resultant suspension was filtered then the filtrate was concentrated in vacuo. The residue was partitioned between EtOAc (200 ml) and saturated aqueous NaHCO₃ solution (100 ml). The phases were separated then the organic layer was washed with water (50 ml). The organic phase was concentrated in vacuo to afford an off white solid. The solid thus obtained was suspended in MeCN (50 ml) then filtered. The solid was dried in vacuo to afford the product as a white solid (2.56 g, 40%) ¹H NMR (500 MHz, DMSO-d₆) δ 7.42-7.24 (m, 7H), 7.08-6.97 (m, 1H), 6.80-6.68 (m, 1H), 5.09-4.92 (m, 2H), 3.98-3.86 (m, 1H), 3.03-2.88 (m, 2H), 1.82-1.68 (m, 1H), 1.67-1.54 (m, 1H), 1.44-1.30 (m, 9H).

LC/MS (System A): m/z (ESI⁺)=374 [M⁺Na⁺], R_f=1.52 min, UV purity=97%.

Intermediate 143—Synthesis of tert-butyl N-[(3S)-3-amino-3-carbamoyl propyl]carbamate

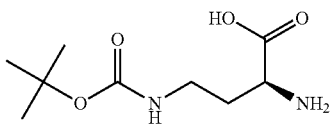

A mixture of tert-butyl N-[(3S)-3-{[(benzyloxy)carbonyl]amino}-3-carbamoylpropyl]carbamate, Intermediate 142 (2.06 g, 5.85 mmol) and 10% Pd/C (50% wet, 0.31 g) (50% wet) in THF (12 ml) and EtOH (12 ml) was stirred under an atmosphere of hydrogen for 18 h. The reaction was filtered through glass fibre filter paper, then concentrated in vacuo to afford the product as a white solid (1.27 g, quantitative).

¹H NMR (500 MHz, DMSO-d₆) δ 7.26 (s, 1H), 6.91 (s, 1H), 6.83-6.69 (m, 1H), 3.11-2.92 (m, 3H), 1.80-1.59 (m, 3H), 1.46-1.32 (m, 10H).

LC/MS (System A): m/z (ESI⁺)=218 [MH⁺].

Intermediate 144—Synthesis of tert-butyl N-[(3S)-3-[(3-{[(benzyloxy)carbonyl]amino}propyl)amino]-3-carbamoylpropyl]carbamate

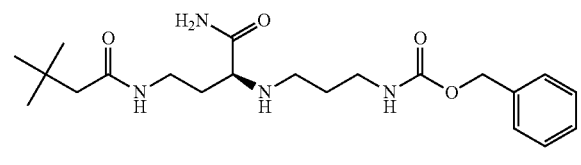 [SMILES: CC(C)(C)CC(=O)NCC[C@H](NCCCNC(=O)OCc1ccccc1)C(N)=O]

Sodium triacetoxyborohydride (2.37 g, 11.2 mmol) was added portionwise over 5 min to a solution of tert-butyl N-[(3S)-3-amino-3-carbamoylpropyl]carbamate, Intermediate 143 (1.62 g, 7.46 mmol) and benzyl N-(3-oxopropyl)carbamate (1.55 g, 7.46 mmol) in THF (40 ml). The reaction was stirred at RT for 16 h then water (50 ml) was added. The mixture was extracted with EtOAc (4×50 ml). The combined organic phases were washed with saturated aqueous NaHCO₃ solution (2×50 ml) and brine (10 ml), then dried over Na₂SO₄, filtered and concentrated in vacuo to afford the product as a colourless oil (2.89 g, 85%).

¹H NMR (500 MHz, CD₃OD) δ 7.39-7.22 (m, 5H), 5.06 (s, 2H), 3.25-3.06 (m, 5H), 2.69-2.45 (m, 2H), 1.85-1.61 (m, 4H), 1.42 (s, 9H).

LC/MS (System A): m/z (ESI⁺)=409 [MH⁺], R_f=0.87 min, UV purity=90%.

Intermediate 145—Synthesis of tert-butyl N-(3-{[(benzyloxy)carbonyl]amino}propyl)-N-[(1S)-3-{[(tert-butoxy)carbonyl]amino}-1-carbamoylpropyl]carbamate

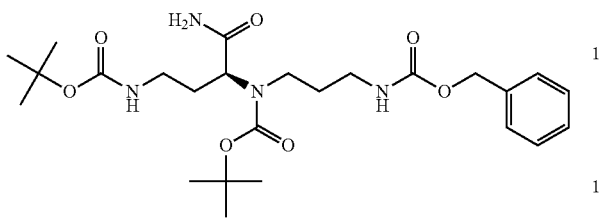

A solution of di-tert-butyl dicarbonate (1.85 g, 8.49 mmol) in THF (10 ml) was dropwise over 5 min to a solution of tert-butyl N-[(3S)-3-[(3-{[(benzyloxy)carbonyl]amino}propyl)amino]-3-carbamoylpropyl]carbamate, Intermediate 144 (2.89 g, 7.07 mmol)) and triethylamine (1.47 ml, 10.6 mmol) in THF (30 ml). The reaction mixture was left to stir at RT for 16 h then concentrated in vacuo. The resultant oil was partitioned between EtOAc (50 ml) and water (50 ml). The phases were separated then the organic phase was washed with saturated aqueous NaHCO₃ solution (50 ml) and brine (20 ml), then dried over Na₂SO₄, filtered and concentrated in vacuo. The crude material thus obtained was purified by flash column chromatography on a silica column (50 g). The column was eluted with CH₂Cl₂:MeOH, increasing the gradient linearly from 100:0 to 92:8 over 15 CV. The desired fractions were combined and concentrated in vacuo. The material thus obtained was further purified by flash column chromatography on C18 (120 g). The column was eluted with MeCN:H₂O+0.1% formic acid using the following gradient (% MeCN, column volumes): 5%, 2 CV; 5-100%, 20 CV; 100%, 2 CV. The desired fractions were combined and concentrated in vacuo to afford the product as an orange oil (0.42 g, 12%).

¹H NMR (500 MHz, DMSO-d₆) δ 7.42-7.28 (m, 5H), 7.27-6.96 (m, 3H), 6.92-6.61 (m, 1H), 5.08-4.93 (m, 2H), 4.43-3.93 (m, 1H), 3.21-2.78 (m, 6H), 2.03-1.52 (m, 4H), 1.46-1.30 (m, 18H).

LC/MS (System A): m/z (ESI⁺)=509 [MH⁺], R$_t$=1.16 min, UV purity=95%.

Intermediate 146 Synthesis of tert-butyl N-(3-aminopropyl)-N-[(1S)-3-{[(tert-butoxy)carbonyl]amino}-1-carbamoylpropyl]carbamate

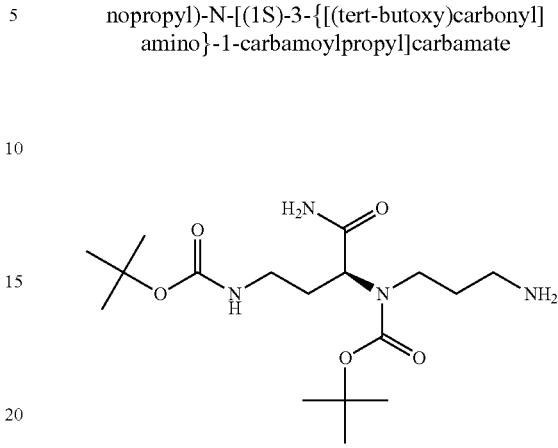

A mixture of tert-butyl N-(3-{[(benzyloxy)carbonyl]amino}propyl)-N-[(1 S)-3-{[(tert-butoxy)carbonyl]amino}-1-carbamoylpropyl]carbamate, Intermediate 145 (780 mg, 1.47 mmol) and 10% Pd/C (50% wet, 80 mg) in EtOH (20 ml) was stirred under an atmosphere of hydrogen for 40 h at RT. The reaction mixture was filtered through glass fibre filter paper then concentrated in vacuo to afford the product as a white foam (580 mg, quantitative based on 95% estimated purity).

¹H NMR (500 MHz, DMSO-d₆) δ 7.19 (s, 1H), 7.01 (s, 1H), 6.89-6.66 (m, 1H), 4.40-3.85 (m, 1H), 3.18-2.83 (m, 5H), 2.49-2.37 (m, 2H+solvent), 2.05-1.82 (m, 1H), 1.74-1.30 (m, 22H).

LC/MS (System A): m/z (ESI⁺)=375 [MH⁺], R$_t$=0.80 min, UV purity=100%.

Intermediate 147 Synthesis of formic acid; tert-butyl N-(3-{bis[(2S,3R)-2,3-dihydroxy-3-[(4R,5R)-5-hydroxy-2-phenyl-1,3-dioxan-4-yl]propyl]amino}propyl)-N-[(1S)-3-{[(tert-butoxy)carbonyl]amino}-1-carbamoylpropyl]carbamate

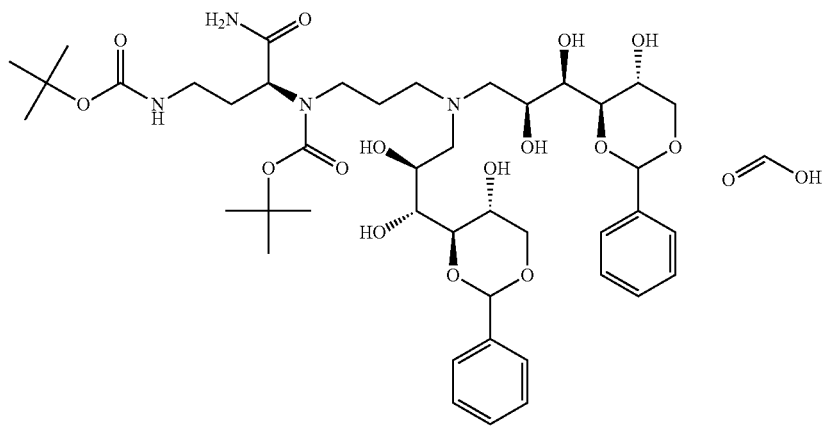

4,6-O-Benzylidene-D-glucopyranose (1.60 g, 5.96 mmol) was added to a solution of tert-butyl N-(3-aminopropyl)-N-[(1S)-3-{[(tert-butoxy)carbonyl]amino}-1-carbamoylpropyl]carbamate, Intermediate 146 (0.558 g, 1.49 mmol) in MeOH (25 ml). The reaction mixture was stirred at RT for 15 min then AcOH (0.341 ml, 5.96 mmol) was added. The reaction mixture was stirred at RT for a further 15 min then NaCNBH$_3$ (0.375 g, 5.96 mmol) was added portion-wise over 5 min. The reaction mixture was stirred at RT for 64 h. The reaction was re-treated with 4,6-O-benzylidene-D-glucopyranose (1.6 g, 5.96 mmol) and stirred for a further 24 h at RT. Saturated aqueous sodium bicarbonate solution (25 ml) was added dropwise over 5 min. EtOAc (20 ml) was added then the resultant mixture was left to stir at RT for 15 min. The phases were separated then the organic phase was washed with saturated aqueous sodium bicarbonate solution (4×50 ml) and brine (25 ml). The organic phase was dried over Na$_2$SO$_4$, filtered and concentrated in vacuo. The crude material was purified by flash column chromatography on C18 (120 g). The column was eluted with MeCN:H$_2$O+0.1% formic acid using the following gradient (% MeCN, column volumes): 10%, 2 CV; 10-46%, 8 CV; 46-52%, 1 CV; 52%, 2 CV; 52-97, 2 CV. The desired fractions were combined and concentrated in vacuo to afford the product as a white solid (690 mg, 50%).

$^1$H NMR (500 MHz, CD$_3$OD) δ 8.39 (s, 1H), 7.54-7.42 (m, 4H), 7.41-7.26 (m, 6H), 5.59-5.47 (m, 2H), 4.33-4.13 (m, 4H), 4.02-3.87 (m, 5H), 3.81-3.70 (m, 2H), 3.67-3.55 (m, 2H), 3.42-3.34 (m, 6H+solvent), 3.20-2.99 (m, 4H), 1.98-1.78 (m, 4H), 1.52-1.33 (m, 18H).

LC/MS (System A): m/z (ESI$^+$)=879 [MH$^+$], R$_t$=0.95 min, UV purity=100%.

Intermediate 148 Synthesis of (2S)-4-amino-2-[(3-{bis[(2S,3R,4R,5R)-2,3,4,5,6-pentahydroxyhexyl]amino}propyl)amino]butanamide trihydrochloride

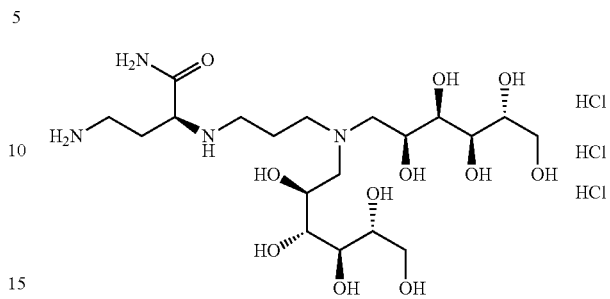

A suspension of formic acid; tert-butyl N-(3-{bis[(2S,3R)-2,3-dihydroxy-3-[(4R,5R)-5-hydroxy-2-phenyl-1,3-dioxan-4-yl]propyl]amino}propyl)-N-[(1S)-3-{[(tert-butoxy)carbonyl]amino}-1-carbamoylpropyl]carbamate, Intermediate 147 (690 mg, 0.746 mmol) in aqueous HCl solution (2.0 M, 7.5 ml, 15 mmol) was stirred at RT for 16 h. The reaction mixture was concentrated in vacuo. The residue was dissolved in MeCN/water then lyophilised to afford the product as a white solid (500 mg, quantitative based on 91% estimated purity).

$^1$H NMR (500 MHz, D$_2$O) δ 4.31-4.21 (m, 2H), 4.15-4.08 (m, 1H), 3.91-3.74 (m, 6H), 3.73-3.61 (m, 4H), 3.58-3.42 (m, 6H), 3.29-3.10 (m, 4H), 2.43-2.20 (m, 4H).

LC/MS (System A): m/z (ESI$^+$)=503 [MH$^+$], R$_t$=0.13 min, ELS purity=100%.

Intermediate 149 Synthesis of 4-[4-(4-aminobutyl)phenyl]-2-[(3-{bis[(2S,3R)-2,3-dihydroxy-3-[(4R,5R)-5-hydroxy-2-phenyl-1,3-dioxan-4-yl]propyl]amino}propyl)amino]butanamide; tetrakis(acetic acid

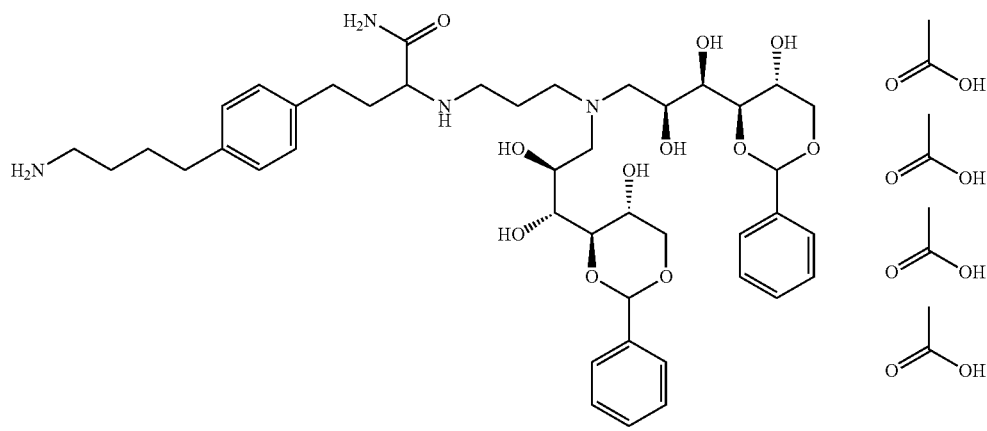

Intermediate 149 was synthesised according to literature procedures (WO2014/099673 A1).

Intermediate 150 Synthesis of 4-[4-(4-aminobutyl)phenyl]-2-[(3-{bis[(2S,3R,4R,5R)-2,3,4,5,6-pentahydroxyhexyl]amino}propyl)amino]butanamide trihydrochloride

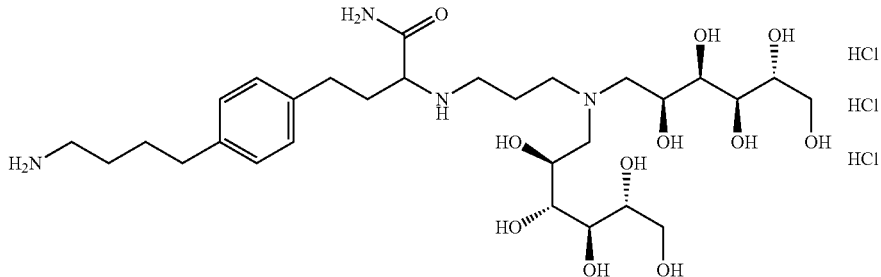 [SMILES: NCCCCc1ccc(CCC(NCCCN(C[C@H](O)[C@@H](O)[C@H](O)[C@H](O)CO)C[C@H](O)[C@@H](O)[C@H](O)[C@H](O)CO)C(N)=O)cc1 ; Cl ; Cl ; Cl]

A solution of 4-[4-(4-aminobutyl)phenyl]-2-[(3-{bis[(2S,3R)-2,3-dihydroxy-3-[(4R,5R)-5-hydroxy-2-phenyl-1,3-dioxan-4-yl]propyl]amino}propyl)amino]butanamide; tetrakis(acetic acid), Intermediate 149 (96%, 140 mg, 0.13 mmol) in aqueous HCl solution (2 M, 5 ml, 10 mmol) was stirred at RT for 2 h. The reaction mixture was concentrated in vacuo then lyophilised to afford the product as a beige solid (107 mg, quantitative based on 88% estimated purity).

$^1$H NMR (500 MHz, CD$_3$OD) δ 7.22-7.14 (m, 4H), 4.27-4.18 (m, 2H), 4.06-3.99 (m, 1H), 3.91-3.85 (m, 2H), 3.83-3.75 (m, 2H), 3.75-3.63 (m, 6H), 3.63-3.39 (m, 6H), 3.23-3.08 (m, 2H), 2.96-2.88 (m, 2H), 2.76-2.60 (m, 4H), 2.39-2.13 (m, 4H), 1.75-1.62 (m, 4H).

LC/MS (System A): m/z (ESI$^+$)=635 [MH$^+$], R$_t$=0.16 min, ELS purity=100%.

B. Synthesis of Example Compounds

Example 1 Synthesis of 2-[({6-amino-3-methyl-1H-pyrazolo[3,4-b]pyrazin-5-yl}formamido)methyl]-1,3-diethyl-6-methoxy-1H-1,3-benzodiazol-3-ium trifluoroacetate (Compound 1)

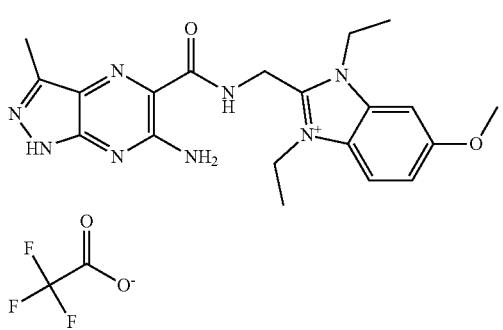

A mixture of 1,5-bis(1H-imidazole-1-carbonyl)-3-methyl-1H-pyrazolo[3,4-b]pyrazin-6-amine, Intermediate 6 (92%, 21 mg, 0.057 mmol) and 2-(aminomethyl)-1,3-diethyl-6-methoxy-1H-1,3-benzodiazol-3-ium iodide, Intermediate 15 (50 mg, 0.14 mmol) in DMF (1 ml) was stirred at RT for 16 h. The reaction mixture was concentrated in vacuo then the crude material was purified by flash column chromatography on C18 (12 g). The column was eluted with MeCN:H$_2$O+formic acid using the following gradient (% MeCN, column volumes): 5%, 2 CV; 5-31%, 14.5 CV; 31-98%, 4.5 CV. The desired fractions were combined then concentrated in vacuo. The material thus obtained was further purified by flash column chromatography on C18 (12 g). The column was eluted with MeCN:H$_2$O+TFA using the following gradient (% MeCN, column volumes): 2%, 2 CV; 2-33%, 16 CV; 33-100%, 5 CV. The desired fractions were combined then lyophilised to afford the product as a yellow solid (2.5 mg, 8.3%).

$^1$H NMR (500 MHz, DMSO-d$_6$) δ 12.90 (s, 1H), 9.65 (t, J=5.4 Hz, 1H), 7.97 (d, J=9.1 Hz, 1H), 7.88-7.49 (m, 3H), 7.28 (dd, J=9.1, 2.3 Hz, 1H), 5.08 (d, J=5.4 Hz, 2H), 4.70-4.61 (m, 4H), 3.91 (s, 3H), 2.46 (s, 3H), 1.43-1.39 (m, 6H).

LC/MS (System C): m/z (ESI$^+$)=409 [M$^+$], R$_t$=1.73 min, UV purity=99%.

Example 2 Synthesis of 2-[({6-amino-3-methyl-1H-pyrazolo[3,4-b]pyrazin-5-yl}formamido)methyl]-6-carboxy-1,3-diethyl-1H-1,3-benzodiazol-3-ium formate (Compound 2)

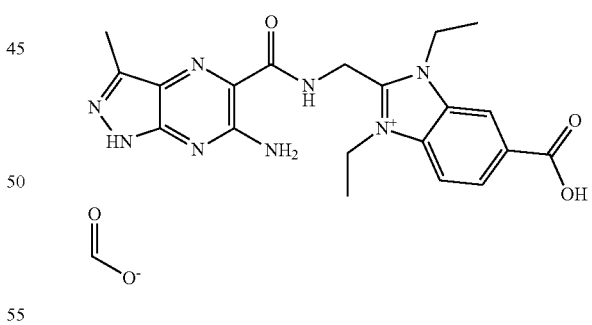

A mixture of 5-(1H-imidazole-1-carbonyl)-3-methyl-1H-pyrazolo[3,4-b]pyrazin-6-amine, Intermediate 8 (91%, 75 mg, 0.28 mmol) and 2-(aminomethyl)-6-carboxy-1,3-diethyl-1H-1,3-benzodiazol-3-ium hydrobromide bromide, Intermediate 22 (152 mg, 0.370 mmol) in DMF (1.5 ml) was stirred at RT for 16 h. The reaction mixture was concentrated in vacuo then the residue was suspended up in MeCN (4 ml) with sonication. The solid was collected by filtration and rinsed with MeCN. The solid thus obtained was dissolved in MeOH (50 ml) then concentrated in vacuo to afford a viscous magenta oil. The crude material was purified by flash column chromatography on C18 (30 g). The column was eluted with MeCN:H₂O+formic acid using the following gradient (% MeCN, column volumes): 5%, 2 CV; 5-32%, 13 CV; 32-100%, 2.5 CV. The desired fractions were combined then concentrated in vacuo to afford the product as an orange solid (54 mg, 41%).

¹H NMR (500 MHz, DMSO-d₆) δ 12.93 (s, 1H), 9.71 (t, J=5.4 Hz, 1H), 8.41 (s, 1H), 8.32 (5, 1H), 8.19 (dd, J=8.6, 1.0 Hz, 1H), 7.96 (d, J=8.6 Hz, 1H), 7.64 (s, 2H), 5.12 (d, J=5.4 Hz, 2H), 4.77-4.64 (m, 4H), 2.46 (s, 3H), 1.47-1.38 (m, 6H).

LC/MS (System C): m/z (ESI⁺)=423 [M⁺], R$_t$=1.23 min, UV purity=99%. Example 3 Synthesis of 2-[({6-amino-1H-pyrazolo[3,4-b]pyrazin-5-yl}formamido)methyl]-6-carboxy-1,3-diethyl-1H-1,3-benzodiazol-3-ium bromide (Compound 3)

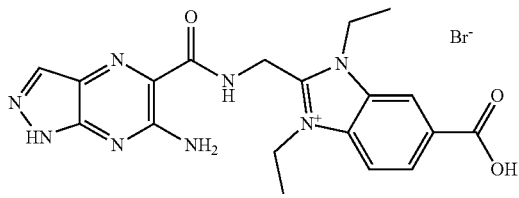 [SMILES: CCn1c(CNC(=O)c2nc3cn[nH]c3nc2N)[n+](CC)c2ccc(C(=O)O)cc21 ; [Br-]]

A suspension of 5-(1H-imidazole-1-carbonyl)-1H-pyrazolo[3,4-b]pyrazin-6-amine, Intermediate 12 (70 mg 0.29 mmol) and 2-(aminomethyl)-6-carboxy-1,3-diethyl-1H-1,3-benzodiazol-3-ium hydrobromide bromide, Intermediate 22 (120 mg, 0.293 mmol) in DMF (1.5 ml) was stirred at RT for 64 h. The reaction mixture was concentrated under a stream of nitrogen then the residue was suspended in MeCN (3 ml) with sonication. The solid was collected by filtration, rinsed with MeCN, then dried under suction to afford the product as a light brown solid (141 mg, 93%).

¹H NMR (500 MHz, DMSO-d₆) δ 13.33 (s, 1H), 9.94 (t, J=5.3 Hz, 1H), 8.62-8.60 (m, 1H), 8.23 (dd, J=8.7, 1.3 Hz, 1H), 8.21-8.16 (m, 2H), 7.77 (s, 2H), 5.11 (d, J=5.3 Hz, 2H), 4.79 (q, J=7.1 Hz, 2H), 4.72 (q, J=7.1 Hz, 2H), 1.45-1.39 (m, 6H).

LC/MS (System C): m/z (ESI⁺)=409 [M⁺], R$_t$=1.12 min, UV purity=99%.

Example 4 Synthesis of 2-[({6-amino-1H-pyrazolo[3,4-b]pyrazin-5-yl}formamido)methyl]-6-(4-{bis[(2S,3R,4R,5R)-2,3,4,5,6-pentahydroxyhexyl]amino}piperidine-1-carbonyl)-1,3-diethyl-1H-1,3-benzodiazol-3-ium trifluoroacetic acid trifluoroacetate (Compound 4)

A solution of 2-[({6-amino-1H-pyrazolo[3,4-b]pyrazin-5-yl}formamido)methyl]-6-carboxy-1,3-diethyl-1H-1,3-benzodiazol-3-ium bromide, Example 3 (135 mg, 0.276 mmol) and CDI (66 mg, 0.41 mmol) in DMF (1 ml) was stirred at RT for 3.5 h. The resultant solution was added to (2R,3R,4R,5S)-6-{[(2S,3R,4R,5R)-2,3,4,5,6-pentahydroxyhexyl](piperidin-4-yl)amino}hexane-1,2,3,4,5-pentol dihydrochloride, Intermediate 25 (164 mg, 0.328 mmol) and rinsed in with DMF (0.5 ml). The reaction mixture was stirred at RT for 16 h then concentrated under a stream of nitrogen. The crude material was purified by flash column chromatography on C18 (12 g). The column was eluted with MeCN:H₂O+TFA using the following gradient (% MeCN, column volumes): 2%, 2 CVs; 2-20%, 15 CVs; 20-100%, 2 CVs; 100%, 2 CVs.

The desired fractions were combined and concentrated in vacuo. The material thus obtained was further purified by flash column chromatography on C18 (12 g). The column was eluted with MeCN:H₂O+TFA using the following gradient (% MeCN, column volumes): 2%, 2 CVs; 2-20%, 15 CVs; 20-100%, 2 CVs; 100%, 2 CVs. The desired fractions were combined and concentrated in vacuo then lyophilised to afford the product as a yellow solid (80 mg, 28%).

¹H NMR (500 MHz, DMSO-d₆) δ 13.34 (s, 1H), 9.97 (t, J=5.1 Hz, 1H), 8.33-8.14 (m, 4H), 8.15-7.40 (m, 3H), 5.74-5.40 (m, 2H), 5.10 (d, J=5.0 Hz, 2H), 5.00-3.59 (m, 25H), 3.29-2.78 (m, 8H), 2.26-1.31 (m, 10H).

LC/MS (System D): m/z (ESI⁺)=819 [M⁺], R$_t$=1.16 min, UV purity=100%.

Example 5 Synthesis of Further Compounds of the Invention

Compounds of general formula (I) with cations of the formula:

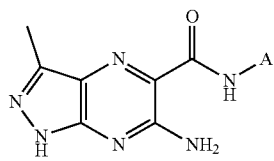

are prepared as shown in Table 1 below using methods similar to those set out in Examples 1-4 and the Examples of co-pending application PCT/GB2017/053499.

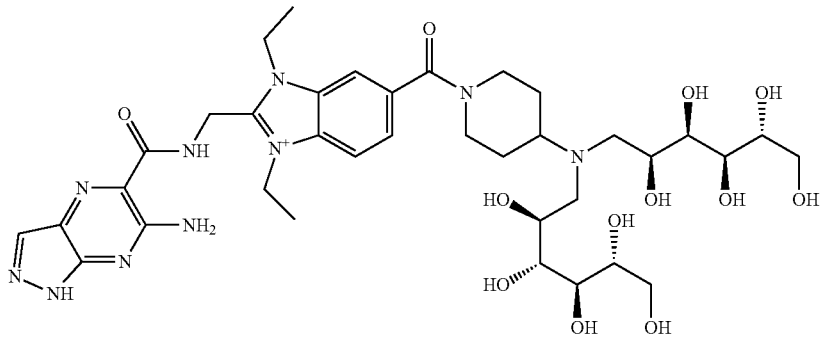
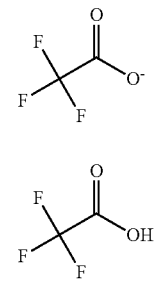

TABLE 1

| Compd No | A | Method |
|---|---|---|
| 5 | 1-ethyl-3-methyl-2-methylene-6-fluoro-benzimidazolium | Intermediate 6 + Intermediate 28 As Example 2 of PCT/GB2017/053499 |
| 6 | 1-ethyl-3-methyl-2-methylene-6-chloro-benzimidazolium | Intermediate 6 + Intermediate 31 As Example 3 of PCT/GB2017/053499 |
| 7 | 1-ethyl-3-methyl-2-methylene-6-methoxy-benzimidazolium | Intermediate 6 + Intermediate 33 As Example 4 of PCT/GB2017/053499 |
| 8 | 1-ethyl-3-methyl-2-methylene-6-trifluoromethyl-benzimidazolium | Intermediate 6 + Intermediate 36 As Example 5 of PCT/GB2017/053499 |
| 9 | 1-ethyl-3-methyl-2-methylene-6-trifluoromethoxy-benzimidazolium | Intermediate 6 + Intermediate 40 As Example 6 of PCT/GB2017/053499 |
| 10 | 1-ethyl-3-benzyl-2-methylene-6-methoxy-benzimidazolium | Intermediate 6 + Intermediate 44 As Example 8 of PCT/GB2017/053499 |

TABLE 1-continued

| Compd No | A | Method |
|---|---|---|
| 11 | (structure) | Intermediate 6 + Intermediate 47 As Example 9 of PCT/GB2017/053499 |
| 12 | (structure) | Base hydrolysis of Compound 11 using aqueous LiOH As Example 10 of PCT/GB2017/053499 |
| 13 | (structure) | Intermediate 6 + Intermediate 49 As Example 11 of PCT/GB2017/053499 |
| 14 | (structure) | Intermediate 6 + Intermediate 51 As Example 12 of PCT/GB2017/053499 |
| 15 | (structure) | Intermediate 6 + Intermediate 53 As Example 13 of PCT/GB2017/053499 |

TABLE 1-continued
| Compd No | A | Method |
|---|---|---|
| 16 | 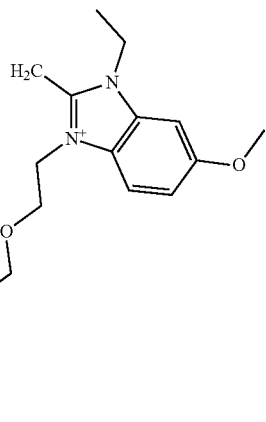 | Intermediate 6 + Intermediate 55 As Example 14 of PCT/GB2017/053499 |
| 17 | 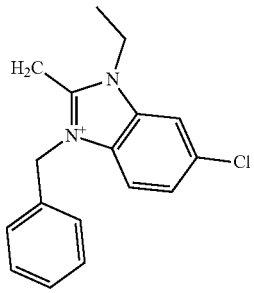 | Intermediate 6 + Intermediate 57 As Example 16 of PCT/GB2017/053499 |
| 18 | 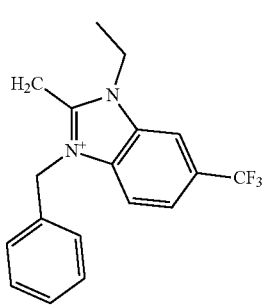 | Intermediate 6 + Intermediate 59 As Example 17 of PCT/GB2017/053499 |
| 19 | 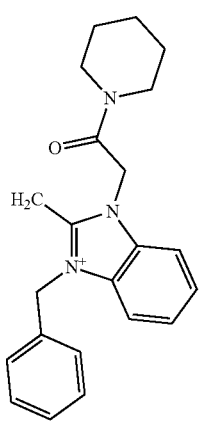 | Intermediate 6 + Intermediate 63 As Example 18 of PCT/GB2017/053499 |

TABLE 1-continued

| Compd No | A | Method |
|---|---|---|
| 20 | 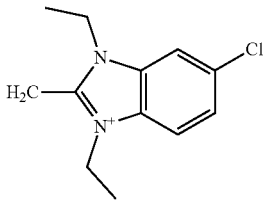 | Intermediate 6 + Intermediate 42 As Examples 20 and 21 of PCT/GB2017/053499 |
| 21 | 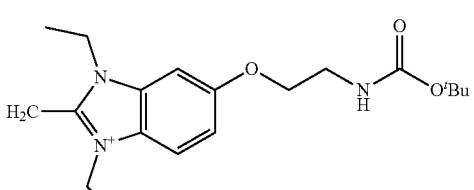 | Intermediate 6 + Intermediate 65 As Example 22 of PCT/GB2017/053499 |
| 22 | 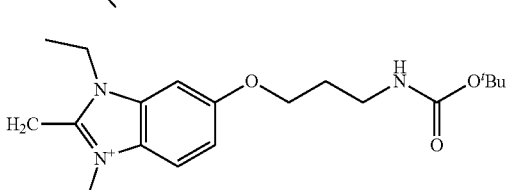 | Intermediate 6 + Intermediate 70 As Example 23 of PCT/GB2017/053499 |
| 23 | 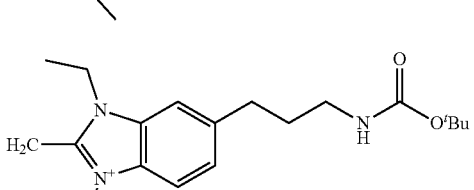 | Intermediate 6 + Intermediate 75 As Example 24 of PCT/GB2017/053499 |
| 24 | 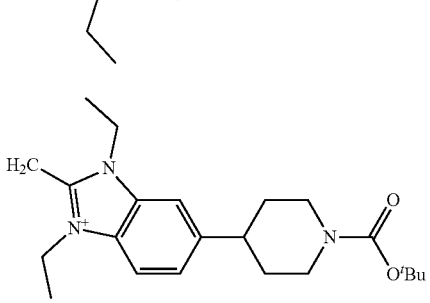 | Intermediate 6 + Intermediate 79 As Example 25 of PCT/GB2017/053499 |
| 25 | 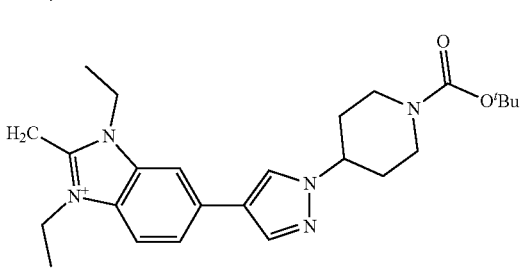 | Intermediate 6 + Intermediate 82 As Example 26 of PCT/GB2017/053499 |
| 26 | 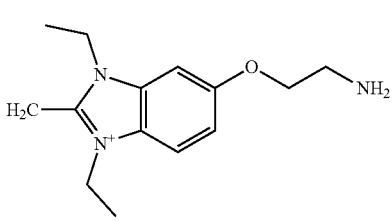 | Deprotection of Compound 21 using HCl solution in dioxane As Example 27 of PCT/GB2017/053499 |

TABLE 1-continued

| Compd No | A | Method |
|---|---|---|
| 27 | [structure: 1,3-diethyl-2-methyl-6-(3-aminopropoxy)benzimidazolium] | Deprotection of Compound 22 using HCl solution in dioxane As Example 28 of PCT/GB2017/053499 |
| 28 | [structure: 1,3-diethyl-2-methyl-6-(3-aminopropyl)benzimidazolium] | Deprotection of Compound 23 using HCl solution in dioxane As Example 29 of PCT/GB2017/053499 |
| 29 | [structure: 1,3-diethyl-2-methyl-6-(piperidin-4-yl)benzimidazolium] | Deprotection of Compound 24 using HCl solution in dioxane As Example 30 of PCT/GB2017/053499 |
| 30 | [structure: 1,3-diethyl-2-methyl-6-(1-(piperidin-4-yl)-1H-pyrazol-4-yl)benzimidazolium] | Deprotection of Compound 25 using HCl solution in dioxane As Example 31 of PCT/GB2017/053499 |
| 31 | [structure: 1,3-diethyl-2-methyl-6-(2-guanidinoethoxy)benzimidazolium] | Reaction of Compound 26 with 1H-1,2,4-triazole-1-carboximidamide hydrochloride As Example 32 of PCT/GB2017/053499 |
| 32 | [structure: 1,3-diethyl-2-methyl-6-(3-guanidinopropoxy)benzimidazolium] | Reaction of Compound 27 with 1H-1,2,4-triazole-1-carboximidamide hydrochloride |
| 33 | [structure: 1,3-diethyl-2-methyl-6-(3-guanidinopropyl)benzimidazolium] | Reaction of Compound 28 with 1H-1,2,4-triazole-1-carboximidamide hydrochloride As Example 33 of PCT/GB2017/053499 |

TABLE 1-continued

| Compd No | A | Method |
|---|---|---|
| 34 | [structure] | Reaction of Compound 2 with tert-Butyl N-(3-amino-propyl)carbamate As Example 35 of PCT/GB2017/053499 |
| 35 | [structure] | Reaction of Compound 2 with tert-Butyl 4-aminopiperidine-1-carboxylate As Example 36 of PCT/GB2017/053499 |
| 36 | [structure] | Reaction of Compound 2 with tert-Butyl N-(piperidin-4-yl)carbamate. As Example 37 of PCT/GB2017/053499 |
| 37 | [structure] | Reaction of Compound 2 with tert-butyl N-[1-(2-aminoethyl)-4-piperidyl]carbamate As Example 38 of PCT/GB2017/053499 |
| 38 | [structure] | Deprotection of Compound 34 using HCl in dioxane. As Example 39 of PCT/GB2017/053499 |
| 39 | [structure] | Deprotection of Compound 35 using HCl in dioxane As Example 40 of PCT/GB2017/053499 |

TABLE 1-continued

| Compd No | A | Method |
|---|---|---|
| 40 | [structure: 1,3-diethyl-2-methylbenzimidazolium with 6-carbonyl-(4-aminopiperidin-1-yl)] | Deprotection of Compound 36 using HCl in dioxane As Example 41 of PCT/GB2017/053499 |
| 41 | [structure: 1,3-diethyl-2-methylbenzimidazolium with 6-C(O)NH-CH2CH2-N(4-aminopiperidinyl)] | Deprotection of Compound 37 using HCl in dioxane As Example 42 of PCT/GB2017/053499 |
| 42 | [structure: 1,3-diethyl-2-methylbenzimidazolium with 6-O-CH2CH2-N(bis-polyhydroxyalkyl)] | Intermediate 6 + Intermediate 86 As Example 43 of PCT/GB2017/053499 |
| 43 | [structure: 1,3-diethyl-2-methylbenzimidazolium with 6-O-CH2CH2CH2-N(bis-polyhydroxyalkyl)] | Intermediate 6 + Intermediate 90 As Example 44 of PCT/GB2017/053499 |
| 44 | [structure: 1,3-diethyl-2-methylbenzimidazolium with 6-CH2CH2CH2-N(bis-polyhydroxyalkyl)] | Reaction of Compound 28 with 4,6-O-benzylidene-D-glucopyranose followed by deprotection with HCl. As Example 45 of PCT/GB2017/053499 |

TABLE 1-continued

| Compd No | A | Method |
|---|---|---|
| 45 | (structure) | Reaction of Compound 30 with 4,6-O-benzylidene-D-glucopyranose followed by deprotection with HCl. As Example 47 of PCT/GB2017/053499 |
| 46 | (structure) | Reaction of Compound 2 with Intermediate 100. As Example 48 of PCT/GB2017/053499 |
| 47 | (structure) | Reaction of Compound 2 with Intermediate 105. As Example 49 of PCT/GB2017/053499 |
| 48 | (structure) | Reaction of Compound 2 with Intermediate 25 using a method similar to that of Example 4 |
| 49 | (structure) | Reaction of Compound 2 with Intermediate 110. As Example 51 of PCT/GB2017/053499 |

TABLE 1-continued

| Compd No | A | Method |
|---|---|---|
| 50 | [structure] | Reaction of Compound 2 with Intermediate 115 As Example 52 of PCT/GB2017/053499 |
| 51 | [structure] | Reaction of Compound 2 with Intermediate 117 As Example 53 of PCT/GB2017/053499 |
| 52 | [structure] | Reaction of Compound 2 with Intermediate 119 As Example 54 of PCT/GB2017/053499 |
| 53 | [structure] | Reaction of Compound 2 with Intermediate 121 As Example 55 of PCT/GB2017/053499 |

TABLE 1-continued
| Compd No | A | Method |
|---|---|---|
| 54 | 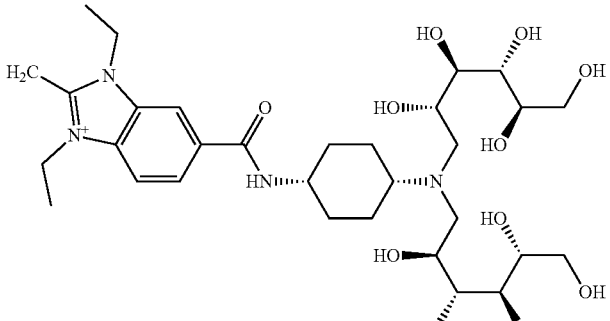 | Reaction of Compound 2 with Intermediate 126 As Example 56 of PCT/GB2017/053499 |
| 55 | 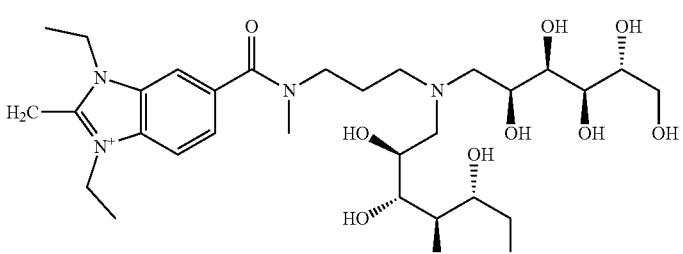 | Reaction of Compound 2 with Intermediate 128 As Example 57 of PCT/GB2017/053499 |
| 56 | 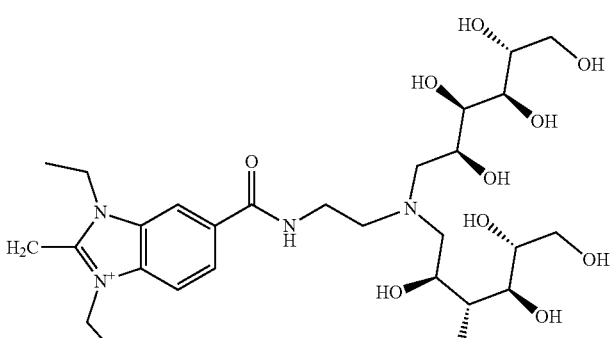 | Reaction of Compound 2 with Intermediate 130 As Example 58 of PCT/GB2017/053499 |
| 57 | 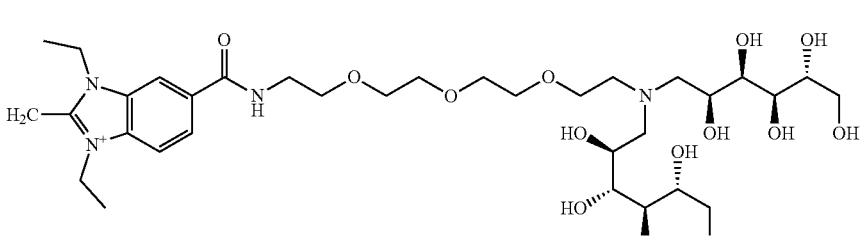 | Reaction of Compound 2 with Intermediate 135 As Example 59 of PCT/GB2017/053499 |

TABLE 1-continued
| Compd No | A | Method |
|---|---|---|
| 58 | 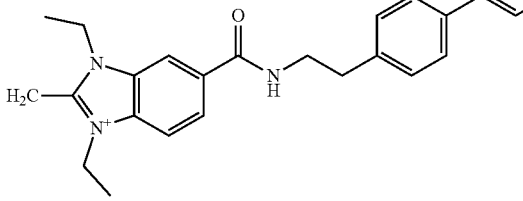 | Reaction of Compound 2 with Intermediate 140 As Example 60 of PCT/GB2017/053499 |
| 59 | 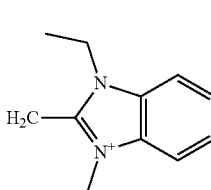 | Reaction of Compound 2 with Intermediate 148 As Example 61 of PCT/GB2017/053499 |
| 60 | 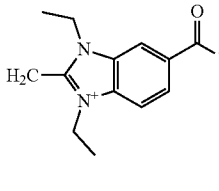 | Reaction of Compound 2 with Intermediate 150 As Example 62 of PCT/GB2017/053499 |
| 118 | 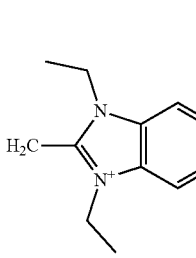 | Reaction of Compound 2 with Intermediate 95 followed by deprotection with aqueous HCl |

Compounds of the formula:

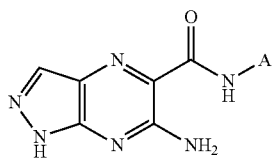

are prepared as shown in Table 2 below using methods similar to those set out in Examples 1-4 and the Examples of co-pending application PCT/GB2017/053499.

TABLE 2

| Compd No | A | Method |
|---|---|---|
| 61 | (1,3-diethyl-6-methoxy-2-methylidene-benzimidazol-3-ium-2-yl) | Intermediate 12 + Intermediate 15 Method as for Example 1 |
| 62 | (1-ethyl-6-fluoro-3-methyl-2-methylidene-benzimidazol-3-ium-2-yl) | Intermediate 12 + Intermediate 28 As Example 2 of PCT/GB2017/053499 |
| 63 | (6-chloro-1-ethyl-3-methyl-2-methylidene-benzimidazol-3-ium-2-yl) | Intermediate 12 + Intermediate 31 As Example 3 of PCT/GB2017/053499 |
| 64 | (1-ethyl-6-methoxy-3-methyl-2-methylidene-benzimidazol-3-ium-2-yl) | Intermediate 12 + Intermediate 33 As Example 4 of PCT/GB2017/053499 |
| 65 | (1-ethyl-3-methyl-2-methylidene-6-(trifluoromethyl)benzimidazol-3-ium-2-yl) | Intermediate 12 + Intermediate 36 As Example 5 of PCT/GB2017/053499 |
| 66 | (1-ethyl-3-methyl-2-methylidene-6-(trifluoromethoxy)benzimidazol-3-ium-2-yl) | Intermediate 12 + Intermediate 40 As Example 6 of PCT/GB2017/053499 |

TABLE 2-continued
| Compd No | A | Method |
|---|---|---|
| 67 | 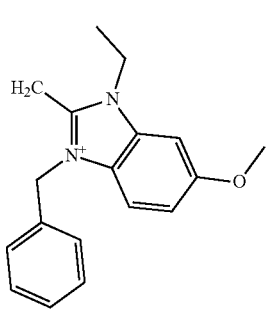 | Intermediate 12 + Intermediate 44 As Example 8 of PCT/GB2017/053499 |
| 68 | 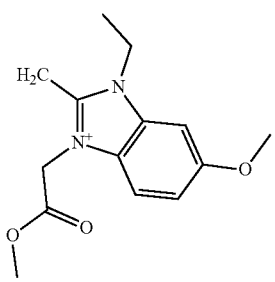 | Intermediate 12 + Intermediate 47 As Example 9 of PCT/GB2017/053499 |
| 69 | 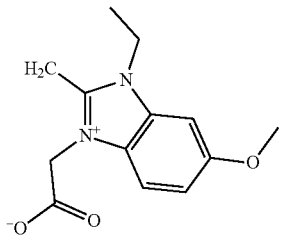 | Base hydrolysis of Compound 68 using aqueous LiOH As Example 10 of PCT/GB2017/053499 |
| 70 | 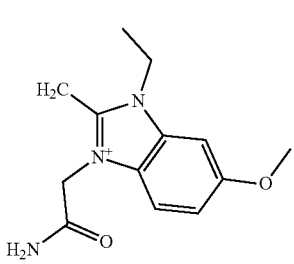 | Intermediate 12 + Intermediate 49 As Example 11 of PCT/GB2017/053499 |
| 71 | 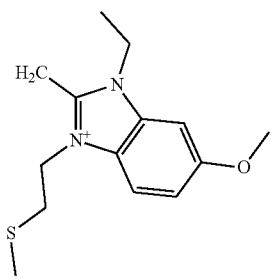 | Intermediate 12 + Intermediate 51 As Example 12 of PCT/GB2017/053499 |

TABLE 2-continued
| Compd No | A | Method |
|---|---|---|
| 72 | 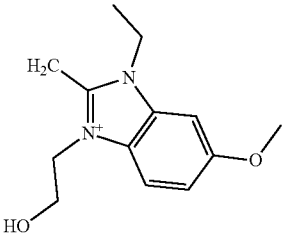 | Intermediate 12 + Intermediate 53 As Example 13 of PCT/GB2017/053499 |
| 73 | 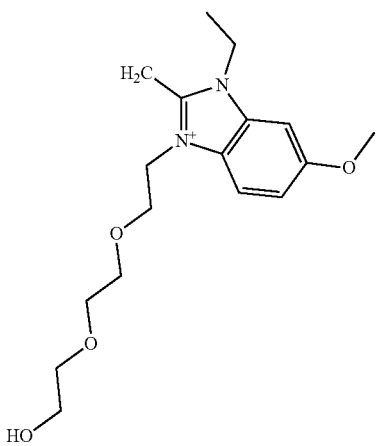 | Intermediate 12 + Intermediate 55 As Example 14 of PCT/GB2017/053499 |
| 74 | 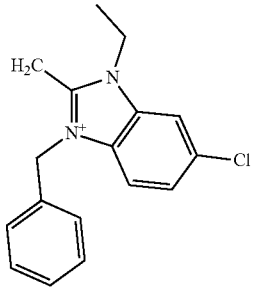 | Intermediate 12 + Intermediate 57 As Example 16 of PCT/GB2017/053499 |
| 75 | 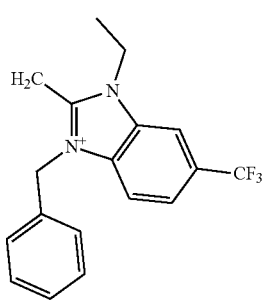 | Intermediate 12 + Intermediate 59 As Example 17 of PCT/GB2017/053499 |

TABLE 2-continued

| Compd No | A | Method |
|---|---|---|
| 76 | (structure) | Intermediate 12 + Intermediate 63 As Example 18 of PCT/GB2017/053499 |
| 77 | (structure) | Intermediate 12 + Intermediate 42 As Examples 20 and 21 of PCT/GB2017/053499 |
| 78 | (structure) | Intermediate 12 + Intermediate 65 As Example 22 of PCT/GB2017/053499 |
| 79 | (structure) | Intermediate 12 + Intermediate 70 As Example 23 of PCT/GB2017/053499 |
| 80 | (structure) | Intermediate 12 + Intermediate 75 As Example 24 of PCT/GB2017/053499 |
| 81 | (structure) | Intermediate 12 + Intermediate 79 As Example 25 of PCT/GB2017/053499 |

TABLE 2-continued

| Compd No | A | Method |
|---|---|---|
| 82 | [structure: 1,3-diethyl-2-methyl-benzimidazolium with pyrazole-piperidine-N-Boc substituent] | Intermediate 12 + Intermediate 82 As Example 26 of PCT/GB2017/053499 |
| 83 | [structure: 1,3-diethyl-2-methyl-benzimidazolium with O-CH2CH2-NH2 substituent] | Deprotection of Compound 78 As Example 27 of PCT/GB2017/053499 |
| 84 | [structure: 1,3-diethyl-2-methyl-benzimidazolium with O-(CH2)3-NH2 substituent] | Deprotection of Compound 79 using HCl solution in dioxane As Example 28 of PCT/GB2017/053499 |
| 85 | [structure: 1,3-diethyl-2-methyl-benzimidazolium with (CH2)3-NH2 substituent] | Deprotection of Compound 80 using HCl solution in dioxane As Example 29 of PCT/GB2017/053499 |
| 86 | [structure: 1,3-diethyl-2-methyl-benzimidazolium with piperidine substituent] | Deprotection of Compound 81 using HCl solution in dioxane As Example 30 of PCT/GB2017/053499 |
| 87 | [structure: 1,3-diethyl-2-methyl-benzimidazolium with pyrazole-piperidine substituent] | Deprotection of Compound 82 using HCl solution in dioxane As Example 31 of PCT/GB2017/053499 |
| 88 | [structure: 1,3-diethyl-2-methyl-benzimidazolium with O-CH2CH2-NH-C(=NH)NH2 guanidine substituent] | Reaction of Compound 83 with 1H-1,2,4-triazole-1-carboximidamide hydrochloride As Example 32 of PCT/GB2017/053499 |

TABLE 2-continued

| Compd No | A | Method |
|---|---|---|
| 89 | 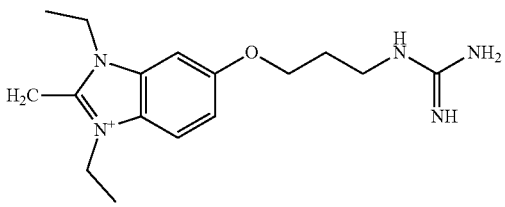 | Reaction of Compound 84 with 1H-1,2,4-triazole-1-carboximidamide hydrochloride |
| 90 | 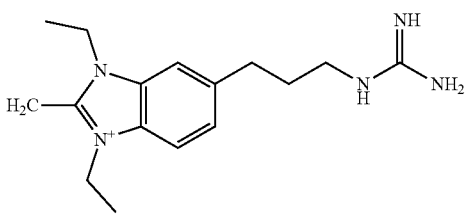 | Reaction of Compound 85 with 1H-1,2,4-triazole-1-carboximidamide hydrochloride As Example 33 of PCT/GB2017/053499 |
| 91 | 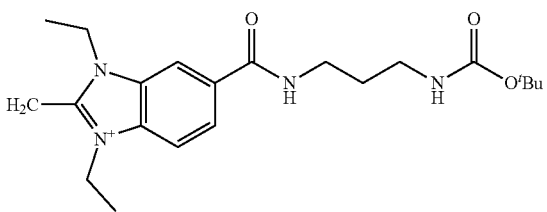 | Reaction of Example 3 with tert-Butyl N-(3-amino-propyl)carbamate As Example 35 of PCT/GB2017/053499 |
| 92 | 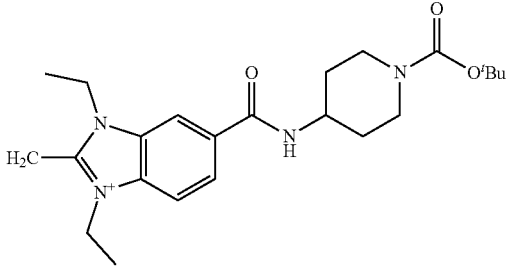 | Reaction of Compound 3 with tert-Butyl 4-aminopiperidine-1-carboxylate As Example 36 of PCT/GB2017/053499 |
| 93 | 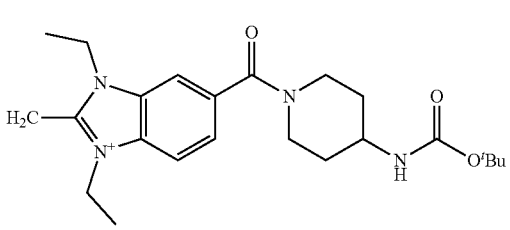 | Reaction of Compound 3 with tert-Butyl N-(piperidin-4-yl)carbamate. As Example 37 of PCT/GB2017/053499 |
| 94 | 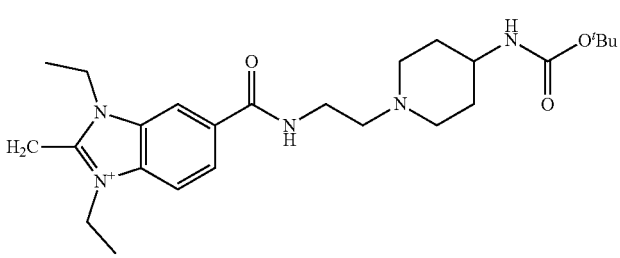 | Reaction of Compound 3 with tert-butyl N-[1-(2-aminoethyl)-4-piperidyl]carbamate As Example 38 of PCT/GB2017/053499 |

TABLE 2-continued

| Compd No | A | Method |
|---|---|---|
| 95 | [structure: 1,3-diethyl-2-methyl-benzimidazolium with 5-C(O)NH-CH₂CH₂CH₂-NH₂] | Deprotection of Compound 91 using HCl in dioxane. As Example 39 of PCT/GB2017/053499 |
| 96 | [structure: 1,3-diethyl-2-methyl-benzimidazolium with 5-C(O)NH-(piperidin-4-yl)] | Deprotection of Compound 92 using HCl in dioxane As Example 40 of PCT/GB2017/053499 |
| 97 | [structure: 1,3-diethyl-2-methyl-benzimidazolium with 5-C(O)-N(4-aminopiperidin-1-yl)] | Deprotection of Compound 93 using HCl in dioxane As Example 41 of PCT/GB2017/053499 |
| 98 | [structure: 1,3-diethyl-2-methyl-benzimidazolium with 5-C(O)NH-CH₂CH₂-N(4-aminopiperidin-1-yl)] | Deprotection of Compound 94 using HCl in dioxane As Example 42 of PCT/GB2017/053499 |
| 99 | [structure: 1,3-diethyl-2-methyl-benzimidazolium-5-O-CH₂CH₂-N(bis-glucamine)] | Intermediate 12 + Intermediate 86 As Example 43 of PCT/GB2017/053499 |
| 100 | [structure: 1,3-diethyl-2-methyl-benzimidazolium-5-O-CH₂CH₂CH₂-N(bis-glucamine)] | Intermediate 12 + Intermediate 90 As Example 44 of PCT/GB2017/053499 |

TABLE 2-continued

| Compd No | A | Method |
|---|---|---|
| 101 | 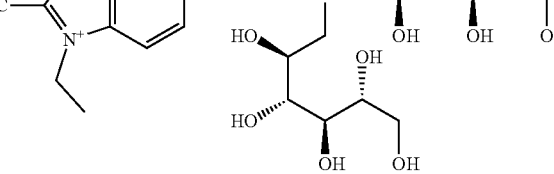 | Reaction of Compound 38 with 4,6-O-benzylidene-D-glucopyranose followed by deprotection with HCl. As Example 45 of PCT/GB2017/053499 |
| 102 | 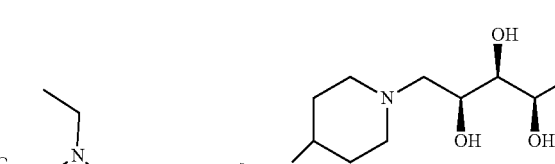 | Reaction of Compound 30 with 4,6-O-benzylidene-D-glucopyranose followed by deprotection with HCl. As Example 47 of PCT/GB2017/053499 |
| 103 | 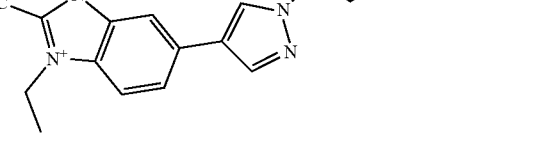 | Reaction of Compound 3 with Intermediate 100. As Example 48 of PCT/GB2017/053499 |
| 104 | 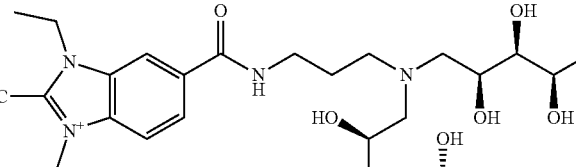 | Reaction of Compound 3 with Intermediate 105. As Example 49 of PCT/GB2017/053499 |
| 105 | 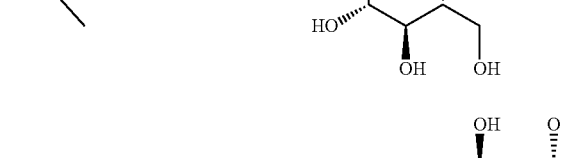 | Reaction of Compound 3 with Intermediate 110. As Example 51 of PCT/GB2017/053499 |

TABLE 2-continued

| Compd No | A | Method |
|---|---|---|
| 106 | | Reaction of Compound 3 with Intermediate 115 As Example 52 of PCT/GB2017/053499 |
| 107 | | Reaction of Compound 3 with Intermediate 117 As Example 53 of PCT/GB2017/053499 |
| 108 | | Reaction of Compound 3 with Intermediate 119 As Example 54 of PCT/GB2017/053499 |
| 109 | | Reaction of Compound 3 with Intermediate 121 As Example 55 of PCT/GB2017/053499 |

TABLE 2-continued

| Compd No | A | Method |
|---|---|---|
| 110 | | Reaction of Compound 3 with Intermediate 126 As Example 56 of PCT/GB2017/053499 |
| 111 | | Reaction of Compound 3 with Intermediate 128 As Example 57 of PCT/GB2017/053499 |
| 112 | | Reaction of Compound 3 with Intermediate 130 As Example 58 of PCT/GB2017/053499 |
| 113 | | Reaction of Compound 3 with Intermediate 135 As Example 59 of PCT/GB2017/053499 |

TABLE 2-continued

| Compd No | A | Method |
|---|---|---|
| 114 | | Reaction of Compound 3 with Intermediate 140 As Example 60 of PCT/GB2017/053499 |
| 115 | | Reaction of Compound 3 with Intermediate 148 As Example 61 of PCT/GB2017/053499 |
| 116 | | Reaction of Compound 3 with Intermediate 150 As Example 62 of PCT/GB2017/053499 |
| 117 | | Reaction of Compound 12 with Intermediate 95 followed by deprotection with aqueous HCl |

C. Biological Examples

Example 6 Short circuit current assay to determine ENaC blocker potency in human bronchial epithelial cells Cell culture Human bronchial epithelial cells (HBECs) (Lonza, UK) were cultured using a modification of the method described by Coote et al, (2008). Cells were seeded into plastic T-75 flasks and grown in Bronchial Epithelial Cell Growth Medium (BEGM) (Lonza, UK) supplemented with bovine pituitary extract (52 ng/mL), hydrocortisone (0.5 µg/mL), human recombinant Epidermal Growth Factor (0.5 ng/mL), epinephrine (0.5 ng/mL), transferrin (10 ng/mL), insulin (5 ng/mL), retinoic acid (0.1 ng/mL), triiodothyronine (6.5 ng/mL), gentamycin (50 µg/mL) and amphotericin-B (50 ng/mL). Medium was changed every 48 hours until cells were 90% confluent. Cells were then passaged and seeded ($8.25 \times 10^5$ cells/insert) onto polycarbonate Snapwell™ inserts (Costar, UK) in differentiation media containing 50% DMEM in BGEM with the same supplements as above but without triiodothyronine and a final retinoic acid concentration of 50 nM (all-trans retinoic acid; Sigma-Aldrich, UK). Cells were maintained submerged for the first 7 days in culture after which time they were exposed to an apical air interface for the remainder of the culture period. From the first day of establishment of an ALI, HBEC were fed with a DMEM:HAMS F-12 (1:1) media containing 2% Ultroser G (Pall BioSepra, France) with gentamycin (50 µg/mL) and amphotericin B (50 ng/mL). Cells were used for short-circuit current assay between days 14-21 after the establishment of the ALI. At all stages of culture, cells were maintained at 37° C. in 5% $CO_2$ in an air incubator.

Short-Circuit Current (ISC) Measurements

Snapwell inserts were mounted in Costar Vertical Diffusion Chambers (Costar, UK) and were bathed with continuously gassed Ringer solution (5% $CO_2$ in $O_2$; pH 7.4) maintained at 37° C. containing (in mM): 120 NaCl, 25 $NaHCO_3$, 3.3 $KH_2PO_4$, 0.8 $K_2HPO_4$, 1.2 $CaCl_2$, 1.2 $MgCl_2$ and 10 glucose. The solution osmolarity was always between 280-300 mOsm/kg $H_2O$ for all physiological salt solutions used. Cells were voltage clamped to 0 mV (model EVC4000, WPI). Transepithelial resistance (RT) was measured by applying a 2 mV pulse at 30 s intervals and calculating RT by Ohm's law. Data were recorded using a PowerLab workstation (ADInstruments, UK).

ENaC blocker compounds were added to the apical chamber from a 1000-fold stock solution (prepared in DMSO) to achieve a cumulative concentration response in terms of the inhibition of the basal ISC. At the completion of the concentration response, a supra-maximal concentration of amiloride (10 µM) was added. The concentration of test compound that induced a 50% inhibition of the total amiloride-sensitive ISC ($IC_{50}$) was calculated using GraphPad Prism v6.05. The results are presented in Table 3, from which it can be seen that the compounds of the present invention have ENaC inhibiting activity.

TABLE 3

| Example No. | Averages · ENaC $IC_{50}$ (nM) Avg |
|---|---|
| 1 | 2 |
| 2 | 91.5 |
| 3 | 106 |
| 4 | 47 |

REFERENCES

App E M, King M, Helfesrieder R, Köhler D and Matthys H. Acute and long-term amiloride inhalation in cystic fibrosis lung disease. A rational approach to cystic fibrosis therapy. Am Rev Respir Dis., 1990, 141(3):605-12.

Botero-Velez M, Curtis J J and Warnock D G. Brief report: Liddle's syndrome revisited—a disorder of sodium reabsorption in the distal tubule. N Engl J Med., 1994, 330(3):178-81.

Boucher R C. Evidence for airway surface dehydration as the initiating event in C F airway disease. J Intern Med., 2007, 261(1):5-16.

Bowler I M, Kelman B, Worthington D, Littlewood J M, Watson A, Conway S P, Smye S W, James S L and Sheldon T A. Nebulised amiloride in respiratory exacerbations of cystic fibrosis: a randomised controlled trial. Arch Dis Child., 1995, 73(5):427-30.

Chang S S, Grunder S, Hanukoglu A, Rösler A, Mathew P M, Hanukoglu I, Schild L, Lu Y, Shimkets R A, Nelson-Williams C, Rossier B C and Lifton R P. Mutations in subunits of the epithelial sodium channel cause salt wasting with hyperkalaemic acidosis, pseudohypoaldosteronism type 1. Nat Genet., 1996, 12(3):248-53.

Coote K, Atherton-Watson H C, Sugar R, Young A, MacKenzie-Beevor A, Gosling M, Bhalay G, Bloomfield G, Dunstan A, Bridges R J, Sabater J R, Abraham W M, Tully D, Pacoma R, Schumacher A, Harris J, Danahay H. Camostat attenuates airway epithelial sodium channel function in vivo through the inhibition of a channel-activating protease. J Pharmacol Exp Ther. 2009 May; 329(2):764-74.

Coote K J, Atherton H, Young A, Sugar R, Burrows R, Smith N J, Schlaeppi J M, Groot-Kormelink P J, Gosling M, Danahay H. The guinea-pig tracheal potential difference as an in vivo model for the study of epithelial sodium channel function in the airways. Br J Pharmacol. 2008 December; 155(7):1025-33.

Fajac I, Hubert D, Guillemot D, Honore I, Bienvenu T, Volter F, Dall'Ava-Santucci J and Dusser D J. Nasal airway ion transport is linked to the cystic fibrosis phenotype in adult patients. Thorax, 2004, 59(11):971-6.

Frateschi S, Charles R-P, Hummler E. The Epithelial Sodium Channel ENaC and its Regulators in the Epidermal Permeability Barrier Function. The Open Dermatology Journal, 2010, 4: 27-35.

Graham A, Hasani A, Alton E W, Martin G P, Marriott C, Hodson M E, Clarke S W and Geddes D M. No added benefit from nebulized amiloride in patients with cystic fibrosis. Eur Respir J., 1993, 6(9):1243-8.

Hirsh A J, Zhang J, Zamurs A, Fleegle J, Thelin W R, Caldwell R A, Sabater J R, Abraham W M, Donowitz M, Cha B, Johnson K B, St George J A, Johnson M R, Boucher R C. Pharmacological properties of N-(3,5-diamino-6-chloropyrazine-2-carbonyl)-N'-4-[4-(2,3-dihydroxypropoxy)phenyl]butyl-guanidine methanesulfonate (552-02), a novel epithelial sodium channel blocker with potential clinical efficacy for cystic fibrosis lung disease. J Pharmacol Exp Ther. 2008 April; 325(1): 77-88.

Kellenberger S and Schild L. Epithelial sodium channel/degenerin family of ion channels: a variety of functions for a shared structure. Physiol Rev., 2002 82(3):735-67.

Kerem E, Bistritzer T, Hanukoglu A, Hofmann T, Zhou Z, Bennett W, MacLaughlin E, Barker P, Nash M, Quittell L, Boucher R and Knowles M R. Pulmonary epithelial sodium-channel dysfunction and excess airway liquid in pseudohypoaldosteronism. N Engl J Med., 1999, 341(3): 156-62.

Knowles M R, Stutts M J, Spock A, Fischer N, Gatzy J T and Boucher R C. Abnormal ion permeation through cystic fibrosis respiratory epithelium. Science, 1983, 221(4615): 1067-70.

Knowles M R, Church N L, Waltner W E, Yankaskas J R, Gilligan P, King M, Edwards L J, Helms R W and Boucher R C. A pilot study of aerosolized amiloride for the treatment of lung disease in cystic fibrosis. N Engl J Med., 1990, 322(17):1189-94.

Leal T, Fajac I, Wallace H L, Lebecque P, Lebacq J, Hubert D, Dall'Ava J, Dusser D, Ganesan A P, Knoop C, Cumps J, Wallemacq P and Southern K W. Airway ion transport impacts on disease presentation and severity in cystic fibrosis. Clin Biochem., 2008, 41(10-11):764-72.

Matsui H, Grubb B R, Tarran R, Randell S H, Gatzy J T, Davis C W and Boucher R C. Evidence for periciliary liquid layer depletion, not abnormal ion composition, in the pathogenesis of cystic fibrosis airways disease. Cell, 1998, 95(7):1005-15.

Middleton P G, Geddes D M and Alton E W. Effect of amiloride and saline on nasal mucociliary clearance and potential difference in cystic fibrosis and normal subjects. Thorax, 1993, 48(8):812-6.

Noone P G, Regnis J A, Liu X, Brouwer K L, Robinson M, Edwards L and Knowles M R. Airway deposition and clearance and systemic pharmacokinetics of amiloride following aerosolization with an ultrasonic nebulizer to normal airways. Chest, 1997, 112(5):1283-90.

Perazella M A. Drug-induced hyperkalemia: old culprits and new offenders. Am J Med., 2000, 109(4):307-14.

Pons G, Marchand M C, d'Athis P, Sauvage E, Foucard C, Chaumet-Riffaud P, Sautegeau A, Navarro J and Lenoir G. French multicenter randomized double-blind placebo-controlled trial on nebulized amiloride in cystic fibrosis patients. The Amiloride-AFLM Collaborative Study Group. Pediatr Pulmonol., 2000, 30(1):25-31.

Thelin W R, Johnson M R, Hirsh A J, Kublin C L, Zoukhri D. Effect of Topically Applied Epithelial Sodium Channel Inhibitors on Tear Production in Normal Mice and in Mice with

The invention claimed is:

1. A compound of formula (I) or tautomeric form, enantiomer, isotopic variant, or salt thereof:

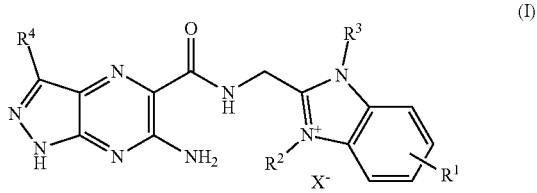

(I)

wherein
$X^-$ is an anion;
$R^1$ is:
i. H or halo; or
ii. $-L^1R^{10}$, wherein
$L^1$ is:
$-Z^1-$, $-Q^1-$, $-Z^1Q^1-$, $-Q^1Z^1-$, $-Z^1Q^1Z^2-$, $-Q^1Q^2-$, $-Q^1Q^2Z^1-$, $-Q^1Q^2Z^1Q^3Z^2-$, $-Z^1Q^1OQ^2OQ^3-$;
$OZ^1-$, $-OQ^1-$, $-OZ^1Q^1-$, $-OQ^1Z^1-$, $-OZ^1Q^1Z^2-$, $-OQ^1Q^2-$, $-OQ^1Q^2Z^1-$, $-OQ^1Q^2Z^1Q^3Z^2-$, $-OZ^1Q^1OQ^2OQ^3-$;
$-Z^1N(R^7)Z^2-$, $-Q^1Z^1N(R^7)Z^2-$, $-Z^1N(R^7)Z^2Q^1-$, $-Q^1Z^1N(R^7)Z^2Q^2Z^3-$;
$Z^1O(CH_2CH_2O)_nZ^2-$, $-Z^1O(CH_2CH_2O)_nQ^1-$, $-Z^1O(CH_2CH_2O)_nZ^2Q^1$, $-Z^1O(CH_2CH_2O)_nQ^1Z^2-$, $-Q^1Z^1O(CH_2CH_2O)_nZ^2-$, $-Q^1Z^1O(CH_2CH_2O)_nQ^1-$, $-Q^1Z^1O(CH_2CH_2O)_nZ^2Q^1$, $-Z^1O(CH_2CH_2O)_nZ^2Q^1Z^3-$;
$-C(O)Z^1-$, $-C(O)Q^1-$, $-C(O)Z^1Q^1-$, $-C(O)Z^1Q^1Z^2-$, $-C(O)Q^1Z^1-$, $-C(O)Q^1Q^2-$, $-C(O)Q^1Q^2Z^1-$, $-C(O)Q^1N(R^7)C(O)Z^1-$, $-C(O)Q^1N(R^7)C(O)Z^1Q^2-$, $-C(O)Q^1N(R^7)C(O)Z^1Q^2Q^3-$, $-C(O)Q^1N(R^7)C(O)Z^1Q^2Z^2-$, $-C(O)Z^1Q^1OQ^2OQ^3-$;
$-C(O)N(R^7)Z^1-$, $-C(O)N(R^7)Q^1-$, $-C(O)N(R^7)Z^1Q^1-$, $-C(O)N(R^7)Z^1Q^1Z^2-$, $-C(O)N(R^7)Q^1Z^1-$, $-C(O)N(R^7)Q^1Q^2-$, $-C(O)N(R^7)Q^1Q^2Z^1-$, $-C(O)N(R^7)Z^1Q^1Q^2Z^2-$, $-C(O)N(R^7)Z^1O(CH_2CH_2O)_nZ^2-$, $-C(O)N(R^7)Z^1O(CH_2O)_nZ^2-$, $-C(O)N(R^7)Z^1Q^1Z^2N(R^8)Z^3-$, $-C(O)N(R^7)Z^1N(R^8)Z^2-$, $-C(O)N(R^7)Q^1Z^1N(R^8)Z^2-$, $-C(O)N(R^7)Z^1Q^1OQ^2OQ^3-$, $-C(O)N(R^7)Z^1Q^1OQ^2OQ^3Z^2-$;
$Z^1C(O)N(R^7)Z^2-$, $-Z^1C(O)N(R^7)Q^1-$, $-Z^1C(O)N(R^7)Z^2Q^1-$, $-Z^1C(O)N(R^7)Q^1Z^2-$, $-Z^1C(O)N(R^7)Q^1Q^2-$, $-Z^1C(O)Q^1-$, $-Z^1C(O)Q^1Z^2-$, $-Z^1C(O)Q^1Q^2-$, $-Z^1C(O)N(R^7)Q^1Q^2Z^2-$;
$-C(O)OZ^1-$, $-C(O)OQ^1-$, $-C(O)OZ^1Q^1-$, $-C(O)OZ^1Q^1Z^2-$, $-C(O)OQ^1Z^1-$, $-C(O)OQ^1Q^2-$, $-C(O)OQ^1Q^2Z^1-$;
$Q^1C(O)Q^2-$, $Q^1C(O)Z^1-$, $-Q^1C(O)Q^2Z^1-$, $Q^1C(O)Q^2Q^3-$, $Q^1C(O)Z^1Q^2-$, $Q^1C(O)Q^2Q^3Z^1-$;
$-C(=NR^9)N(R^7)Z^1-$, $-C(=NR^9)N(R^7)Q^1-$, $-C(=NR^9)N(R^7)Z^1Q^1-$, $-C(=NR^9)N(R^7)Z^1Q^1Z^2-$, $-C(=NR^9)N(R^7)Q^1Z^1-$, $-C(=NR^9)N(R^7)Q^1Q^2-$ or $C(=NR^9)N(R^7)Q^1Q^2Z^1-$; wherein each of $Z^1$, $Z^2$ and $Z^3$ is independently $C_{1-12}$ alkylene, $C_{2-12}$ alkenylene, $C_{2-12}$ alkynylene any of which is optionally substituted by one or more substituents selected from halo, OH, $C(O)NR^{15}R^{16}$, $C(O)OR^{15}$ and $NR^{15}R^{16}$;

each $R^{15}$ and $R^{16}$ is independently H or $C_{1-6}$ alkyl or $R^{15}$ and $R^{16}$ together with the nitrogen atom to which they are attached may form a 5- or 6-membered heterocyclic ring optionally containing one or more further heteroatoms selected from N, O and S;

each of $Q^1$, $Q^2$ and $Q^3$ is independently carbocyclyl, heterocyclyl, aryl or heteroaryl any of which is optionally substituted with one or more substituents selected from halo, OH, $C_{1-4}$ alkyl, $C_{1-4}$ haloalkyl, $C(O)NR^{15}R^{16}$, $C(O)OR^{15}$ and $NR^{15}R^{16}$, and, for cycloalkyl and heterocyclyl groups, oxo, wherein $R^{15}$ and $R^{16}$ are as defined above;

n is 1 to 6;

each $R^7$ and $R^8$ is independently selected from H or $C_{1-12}$ alkyl optionally substituted with one or more halo or OH groups, or when an $R^7$ and an $R^8$ or two $R^8$ groups are attached to a nitrogen atom they may, together with the nitrogen atom combine to form a 5- or 6-membered heterocyclic ring optionally comprising one or more further heteroatoms selected from N, O and S;

$R^9$ is H or $C_{1-6}$ alkyl;

$R^{10}$ is H, $-N(R^7)R^8$, $-N(R^7)C(=NR^9)N(R^8)_2$, $-N(R^7)-C(O)OR^8$, $OR^7$ or $-C(O)OR^7$; or a cationic group selected from $-N(R^7)-C(O)-(C_{1-3}$ alkylene)-$N^+(R^8)_3$ and $-N^+(R^8)_3$, in which case, an additional anion $X^-$ will be required; and
$R^7$, $R^8$ and $R^9$ are as defined above; or iii. $-R^{12}$, $-OR^{12}$ $-SO_2R^{12}$, $-C(O)OR^{12}$, $-C(O)NR^{12}R^{13}$, $-C(=NR^9)NR^{12}R^{13}$, $-Q^1R^{12}-$, $-Q^1OR^{12}-$ $Q^1SO_2R^{12}$, $-Q^1C(O)OR^{12}$, $-Q^1C(O)NR^{12}R^{13}$, $-Q^1C(=NR^7)NR^{12}R^{13}$, $-Q^1Q^2OR^{12}$, $-Q^1SO_2R^{12}$, $-Q^1Q^2C(O)OR^{12}$, $-Q^1Q^2C(O)NR^{12}R^{13}$ or $-Q^1Q^2C(=NR^9)NR^{12}R^{13}$; wherein $Q^1$ and $Q^2$ are defined as above; and each $R^{12}$ and $R^{13}$ is independently H, $C_{1-6}$ alkyl, $C_{2-6}$ alkenyl, $C_{2-6}$ alkynyl, $C_{3-8}$ cycloalkyl or $C_{3-8}$ heterocyclyl, any of which is optionally substituted by one or more substituents selected from halo, $OR^7$, $C(O)OR^7$, $-N(R^7)R^8$ and $C(O)N(R^7)R^8$ and, in the case of cycloalkyl or heterocyclyl groups, oxo; wherein $R^7$, $R^8$ and $R^9$ are as defined above;

each of $R^2$ and $R^3$ is independently $C_{1-10}$ alkyl, wherein one or more $-CH_2-$ groups is optionally replaced by $-O-$, $-S-$ or $-NR_7-$ provided that adjacent $-CH_2-$ groups are not so replaced and which is optionally substituted with one or more substituents selected from halo, OH, SH, $N(R^7)R^8$, aryl, heteroaryl, cycloalkyl, heterocyclyl, —C(O)OR$^7$, —C(O)N(R$^7$)R$^8$, OR$^7$ and —N(R$^7$)R$^8$, wherein R$^7$ and R$^8$ are as defined above;

R$^4$ is H, halo, cyano, C$_{1-6}$ alkyl, C(O)OR$^{16}$ or C(O)N(R$^{16}$)R$^{17}$;

wherein alkyl groups are optionally substituted with one or more substituents selected from halo, —OR$^7$ and —N(R$^7$)R$^8$, wherein R$^7$ and R$^8$ are as defined above;

each R$^{16}$ and R$^{17}$ is independently H or C$_{1-6}$ alkyl or R$^{16}$ and R$^{17}$ together with the nitrogen atom to which they are attached may form a 5- or 6-membered heterocyclic ring optionally containing one or more further heteroatoms selected from O, N and S.

2. The compound according to claim 1, wherein the compound is of formula (IA):

(IA)

or the compound is of formula (IB):

(IB)

3. The compound according to claim 1, wherein R$^1$ is H, halo, —R$^{12}$, —C(O)OR$^{12}$, or —OR$^{12}$.

4. The compound according to claim 3, wherein R$^1$ is H, chloro, C(O)OH, methyl, trifluoromethyl, methoxy or trifluoromethoxy.

5. The compound according to claim 1, wherein R$^1$ is -L$^1$R$^{10}$.

6. The compound according to claim 5, wherein L$^1$ is:
—Z$^1$—, -Q$^1$-, —Z$^1$Q$^1$-, -Q$^1$Z$^1$—, —Z$^1$Q$^1$Z$^2$—, -Q$^1$Q$^2$-, -Q$^1$Q$^2$Z$^1$—, or -Q$^1$Q$^2$Z$^1$Q$^3$Z$^2$—;
—OZ$^1$—, —OZ$^1$Q$^1$-, or —OZ$^1$Q$^1$Z$^2$—;
—Z$^1$N(R$^7$)Z$^2$—, or -Q$^1$Z$^1$N(R$^7$)Z$^2$—;
—C(O)Q$^1$-, —C(O)Q$^1$Z$^1$—, —C(O)Q$^1$Q$^2$-, —C(O)Q$^1$Q$^2$Z$^1$—, —C(O)Q$^1$N(R$^7$)C(O)Z$^1$—, or —C(O)Q$^1$N(R$^7$)C(O)Z$^1$Q$^2$-;
—C(O)N(R$^7$)Z$^1$—, —C(O)N(R$^7$)Q$^1$-, —C(O)N(R$^7$)Z$^1$Q$^1$-, —C(O)N(R$^7$)Z$^1$Q$^1$Z$^2$—, —C(O)N(R$^7$)Q$^1$Z$^1$—, —C(O)N(R$^7$)Q$^1$Q$^2$-, —C(O)N(R$^7$)Q$^1$Q$^2$Z$^1$—, —C(O)N(R$^7$)Z$^1$Q$^1$Q$^2$Z$^2$—, —C(O)N(R$^7$)Z$^1$O(CH$_2$CH$_2$O)$_n$Z$^2$—, —C(O)N(R$^7$)Z$^1$O(CH$_2$O)$_n$Z$^2$—, —C(O)N(R$^7$)Z$^1$Q$^1$Z$^2$N(R$^8$)Z$^3$—, —C(O)N(R$^7$)Z$^1$N(R$^8$)Z$^2$—, —C(O)N(R$^7$)Q$^1$Z$^1$N(R$^8$)Z$^2$—, —C(O)N(R$^7$)Z$^1$Q$^1$OQ$^2$OQ$^3$Z$^2$—;
—C(O)OZ$^1$—, —C(O)OZ$^1$Q$^1$-, or C(O)OZ$^1$Q$^1$Z$^2$—;
-Q$^1$C(O)Q$^2$-, Q$^1$C(O)Z$^1$—, -Q$^1$C(O)Z$^1$Z$^2$—, Q$^1$C(O)Q$^2$Q$^3$-, Q$^1$C(O)Z$^1$Q$^2$- or Q$^1$C(O)Q$^2$Q$^3$Z$^1$—.

7. The compound according to claim 6, wherein L$^1$ is:
—Z$^1$—, -Q$^1$-, -Q$^1$Z$^1$—, -Q$^1$Q$^2$-, or -Q$^1$Q$^2$Z$^1$—;
—OZ$^1$—;
—C(O)Q$^1$-, or —C(O)Q$^1$Z$^1$—; or
—C(O)N(R$^7$)Z$^1$—, C(O)N(R$^7$)Q$^1$-, —C(O)N(R$^7$)Z$^1$Q$^1$-, —C(O)N(R$^7$)Q$^1$Z$^1$—, —C(O)N(R$^7$)Z$^1$Q$^1$Q$^2$Z$^2$—, —C(O)N(R$^7$)Z$^1$O(CH$_2$CH$_2$O)$_n$Z$^2$— or —C(O)N(R$^7$)Z$^1$Q$^1$Z$^2$N(R$^8$)Z$^3$—.

8. The compound according to claim 5, wherein R$^{10}$ is H, —N(R$^7$)R$^8$, —N(R$^7$)C(=NR$^9$)N(R$^8$)$_2$, —N(R$^7$)C(O)OR$^8$, —N(R$^7$)—C(O)—(C$_{1-3}$ alkylene)-N$^+$(R$^8$)$_3$, —N$^+$(R$^8$)$_3$, OR$^7$, or —C(O)OR$^7$.

9. The compound according to claim 8, wherein R$^{10}$ is H, —N(R$^7$)R$^8$, —N(R$^7$)C(=NR$^9$)N(R$^8$)$_2$, —N(R$^7$)C(O)OR$^8$, or —C(O)OR$^7$.

10. The compound according to claim 9, wherein R$^{10}$ is H and:
a) L$^1$ is —OZ$^1$, wherein Z$^1$ is C$_{1-4}$ alkylene; or
b) L$^1$ is -Q$^1$-, -Q$^1$Q$^2$- or —C(O)N(R$^7$)Q$^1$-, where the Q$^1$ group or, for -Q$^1$Q$^2$-, the Q$^2$ group, is a nitrogen-containing heterocyclyl group which is linked to the R$^{10}$ group via a ring nitrogen atom; or
c) L$^1$ is:
—Z$^1$—, Q$^1$, -Q$^1$Z$^1$—, -Q$^1$Q$^2$, or -Q$^1$Q$^2$Z$^1$—;
—OZ$^1$—, —OQ$^1$Z$^1$—, or —OQ$^1$Q$^2$Z$^1$—;
—C(O)Z$^1$—, —C(O)Q$^1$Z$^1$—, or —C(O)Q$^1$Q$^2$Z$^1$—;
—C(O)N(R$^7$)Z$^1$—, —C(O)N(R$^7$)Q$^1$Z$^1$—, or —C(O)N(R$^7$)Q$^1$Q$^2$Z$^1$—;
—C(O)OZ$^1$—, —C(O)OQ$^1$Z$^1$—, —C(O)OQ$^1$Q$^2$-, or C(O)OQ$^1$Q$^2$Z$^1$—; or
—C(=NR$^9$)N(R$^7$)Z$^1$—, —C(=NR$^9$)N(R$^7$)Q$^1$Z$^1$— or C(=NR$^9$)N(R$^7$)Q$^1$Q$^2$Z$^1$—; or
d) L$^1$ is:
Q$^1$Z$^1$—, —Z$^1$Q$^1$Z$^2$—, or -Q$^1$Q$^2$Z$^1$—;
—OQ$^1$Z$^1$—, —OZ$^1$Q$^1$Z$^2$—, or —OQ$^1$Q$^2$Z$^1$—;
—Z$^1$O(CH$_2$CH$_2$O)$_n$Q$^1$Z$^2$—, -Q$^1$Z$^1$O(CH$_2$CH$_2$O)$_n$Z$^2$—, or —Z$^1$O(CH$_2$CH$_2$O)$_n$Q$^1$Z$^3$—;
—C(O)Z$^1$Q$^1$Z$^2$—, —C(O)Q$^1$Z$^1$—, —C(O)Q$^1$Q$^2$Z$^1$—, —C(O)Q$^1$N(R$^7$)C(O)Z$^1$Q$^2$Z$^2$—, —C(O)N(R$^7$)Z$^1$Q$^1$Z$^2$—, or —C(O)N(R$^7$)Q$^1$Z$^1$—;
—C(O)N(R$^7$)Q$^1$Q$^2$Z$^1$—, —C(O)N(R$^7$)Z$^1$Q$^1$Q$^2$Z$^2$—, or —C(O)N(R$^7$)Z$^1$Q$^{10}$Q$^2$OQ$^3$Z$^2$—;
Z$^1$C(O)N(R$^7$)Q$^1$Z$^2$—, —Z$^1$C(O)Q$^1$Z$^2$—, or Z$^1$C(O)N(R$^7$)$_7$Q$^1$Q$^2$Z$^2$—;
—C(O)OZ$^1$Q$^1$Z$^2$—, —C(O)OQ$^1$Z$^1$—, or —C(O)OQ$^1$Q$^2$Z$^1$—;
Q$^1$C(O)Q$^2$Z$^1$—, or Q$^1$C(O)Q$^2$Q$^3$Z$^1$—; or
—C(=NR$^9$)N(R$^7$)Z$^1$Q$^1$Z$^2$—, —C(=NR$^9$)N(R$^7$)Q$^1$Z$^1$— or —C(=NR$^9$)N(R$^7$)Q$^1$Q$^2$Z$^1$—; and
the cyclic group Q$^1$, Q$^2$ or Q$^3$ is a nitrogen containing heterocyclyl group linked to Z$^1$ or Z$^2$ or Z$^3$ via a ring nitrogen atom; or
e) L$^1$ contains a moiety Z$^1$, Z$^2$ or Z$^3$ which is linked directly to R$^{10}$ and is a C$_{1-12}$ alkylene group substituted by 2 to 11 OH groups.

11. The compound according to claim 9, wherein R$^{10}$ is H and L$^1$ contains a moiety Z$^1$, Z$^2$, or Z$^3$; wherein Z$^1$, Z$^2$, or Z$^3$ is linked directly to R$^{10}$ and is —CH$_2$[CH(OH)]$_4$—CH(OH)— such that the group Z$^1$R$^{10}$, Z$^2$R$^{10}$, or Z$^3$R$^{10}$ is a moiety —CH$_2$[CH(OH)]$_4$—CH$_2$OH—.

12. The compound according to claim 8, wherein:
a) R$^{10}$ is —C(O)OR$^7$; and
L$^1$ is:
-Q$^1$- or -Q$^1$Q$^2$- where Q$^1$ or, for -Q$^1$Q$^2$-, Q$^2$ is a carbocyclyl or heterocyclyl group and is linked to R$^{10}$ via a ring carbon atom; or C(O)N(R⁷)Q¹, wherein Q¹ is a is a carbocyclyl or heterocyclyl group and is linked to R¹⁰ via a ring nitrogen atom; or b) R¹⁰ is —N(R⁷)R⁸, —N(R⁷)C(=NR⁹)N(R⁸)₂ or —N(R⁷)C(O)OR⁸—; and
L¹ is:
—Z¹—,
—OZ¹—;
—C(O)N(R⁷)Z¹—, —C(O)N(R⁷)Z¹Q¹Q²Z²—,
—C(O)N(R⁷)Z¹Q¹Z²N(R⁸)Z³, or —C(O)N(R⁷) Z¹O(CH₂CH₂O)ₙZ²; or
—C(O)N(R⁷)Q¹-, —C(O)N(R⁷)Z¹Q¹- or —C(O) Q¹-, wherein Q¹ is a carbocyclyl or heterocyclyl group and is linked to R¹⁰ via a ring carbon atom; or
C(O)Q¹Z¹—.

13. The compound according to claim 12, wherein R¹⁰ is —N(R⁷)R⁸; and
each of R⁷ and R⁸ is independently either H or C₁₋₈ alkyl optionally substituted with one or more OH groups.

14. The compound according to claim 13, wherein R⁷ and/or R⁸ is a moiety —CH₂[CH(OH)]₄—CH₂OH.

15. The compound according to claim 13, wherein R¹⁰ is —N{CH₂[CH(OH)]₄—CH₂OH}₂.

16. The compound according to claim 12, wherein R¹⁰ is —N(R⁷)C(=NR⁹)N(R⁸)₂; and
each of R⁷ and R⁹ is H or C₁₋₄ alkyl; and
one or both R⁸ groups are —CH₂[CH(OH)]₄—CH₂OH.

17. The compound according to claim 16, wherein each of R² and R³ is independently C₁₋₁₀ alkyl in which one or more —CH₂— groups is optionally replaced by —O— or —S— and which is optionally substituted.

18. The compound according to claim 17, wherein R² and R³ are the same or different and are both unsubstituted C₁₋₄ alkyl.

19. The compound according to claim 1, wherein R⁴ is H or methyl.

20. The compound according to claim 1, having a cation selected from:
2-[({6-amino-3-methyl-1H-pyrazolo[3,4-b]pyrazin-5-yl}formamido)methyl]-1,3-diethyl-6-methoxy-1H-1,3-benzodiazol-3-ium;
2-[({6-amino-3-methyl-1H-pyrazolo[3,4-b]pyrazin-5-yl}formamido)methyl]-6-carboxy-1,3-diethyl-1H-1,3-benzodiazol-3-ium;
2-[({6-amino-1H-pyrazolo[3,4-b]pyrazin-5-yl}formamido)methyl]-6-carboxy-1,3-diethyl-1H-1,3-benzodiazol-3-ium; or
2-[({6-amino-1H-pyrazolo[3,4-b]pyrazin-5-yl}formamido)methyl]-6-(4-{bis[(2S,3R,4R,5R)-2,3,4,5,6-pentahydroxyhexyl]amino}piperidine-1-carbonyl)-1,3-diethyl-1H-1,3-benzodiazol-3-ium trifluoroacetic acid;
and the anion X⁻.

21. A process for the preparation of a compound of formula (I) according to claim 1, comprising:
A. reacting a compound of formula (II):

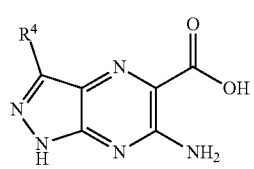

or a salt thereof or an activated derivative of formula (IVa) or (IVb):

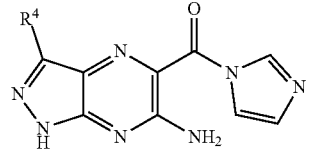

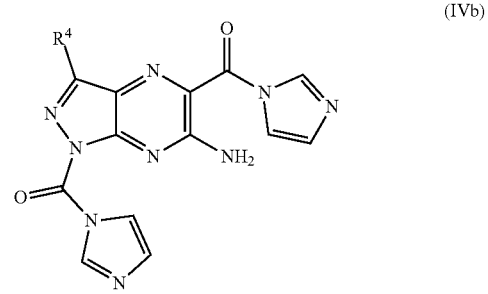

with a salt of formula (III):

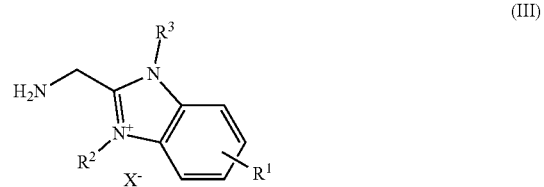

wherein X⁻ is the same or different from the X⁻ of the product of formula (I); or B. reacting a compound of formula (XVIII):

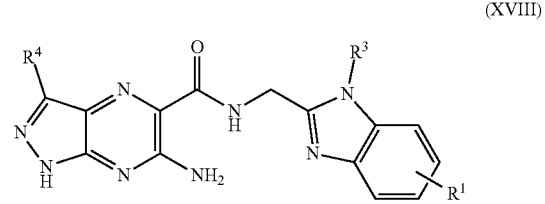

with a compound of formula (IX):

wherein R² is as defined for formula (I) and X¹ is a leaving group such as halo; or
with a compound of formula (IXa):

wherein X¹ is as defined above for formula (IX) and R²ᵃ is a protected R² group; or C. converting a compound of formula (I) in which R³ comprises a —C(O)OR⁷ group wherein R⁷ is other than H or a —C(O)N(R⁷)R⁸ group;
to a compound of formula (I) in which R³ comprises a —C(O)OH or C(O)O group;
by hydrolysis; or D. converting a compound of formula (I) wherein R¹ is L¹R¹⁰ where R¹⁰ is —N(R⁷)—C(O)OR⁸; to a compound of formula (I) wherein $R^{10}$ is —$NHR^7$;
by hydrolysis; or E. converting a compound of formula (I) wherein $R^1$ is $L^1R^{10}$, and $L^1$ comprises a moiety $Q^1$, $Q^2$ or $Q^3$ which is linked to $R^{10}$ via a ring nitrogen atom; and $R^{10}$ is $C(O)OR^7$; to a compound of formula (I) wherein $R^1$ is $L^1R^{10}$ and $R^{10}$ is H;
by hydrolysis; or F. converting a compound of formula (I) wherein $R^1$ is $L^1R^{10}$ and $R^{10}$ is —$NH_2$; to a compound of formula (I) wherein $R^1$ is $L^1R^{10}$ and $R^{10}$ is $N(R^7)R^8$ where $R^7$ is $CH_2$—$R^{7a}$ and $R^8$ is $CH_2$—$R^{8a}$ and one of $R^{7a}$ and $R^{8a}$ is $C_{1-11}$ alkyl optionally substituted with one or more halo or OH groups; and the other of $R^{7a}$ and $R^{8a}$ is H or $C_{1-11}$ alkyl optionally substituted with one or more halo or OH groups;
by reductive amination with an aldehyde, acetal or cyclic hemiacetal equivalent compound; or G. converting a compound of formula (I) wherein $R^1$ is $L^1R^{10}$; and $L^1$ comprises a moiety $Q^1$, $Q^2$ or $Q^3$ linked to $R^{10}$ via a ring nitrogen atom; and $R^{10}$ is H; to a compound of formula (I) wherein $R^1$ is $L^1R^{10}$; and $L^1$ comprises a moiety $Q^1$, $Q^2$ or $Q^3$ linked to a $Z^1$, $Z^2$ or $Z^3$ moiety via a ring nitrogen atom, wherein $Z^1$, $Z^2$ or $Z^3$ is $CH_2$-$C_{1-11}$ alkyl optionally substituted with one or more halo or OH groups; and $R^{10}$ is H;
by reductive amination with an aldehyde, acetal or cyclic hemiacetal equivalent compound; or H. converting a compound of formula (I) in which $R^1$ is $L^1R^{10}$ and $R^{10}$ is $NH_2$; to a compound of formula (I) in which $R^1$ is $L^1R^{10}$ and $R^{10}$ is —$NHC(=NR^9)N(R^8)_2$;
by reaction with a carboximidamide or a salt thereof; or I. Converting a compound of formula (I) in which $R^1$ is $C(O)OH$ to:

a compound of formula (I) in which $R^1$ is —$C(O)NR^{12}R^{13}$; or a compound of formula (I) in which $R^1$ is $L^1R^{10}$ and
$L^1$ is —$C(O)N(R^7)Z^1$—, —$C(O)N(R^7)Q^1$-, —$C(O)N(R^7)Z^1Q^1$-, —$C(O)N(R^7)Z^1Q^1Z^2$—, —$C(O)N(R^7)Q^1Z^1$—, —$C(O)N(R^7)Q^1Q^2$-, —$C(O)N(R^7)Q^1Q^2Z^1$—, —$C(O)N(R^7)Z^1Q^1Q^2Z^2$—, —$C(O)N(R^7)Z^1O(CH_2CH_2O)_nZ^2$— —$C(O)N(R^7)Z^1O(CH_2O)_nZ^2$—, —$C(O)N(R^7)Z^1Q^1Z^2N(R^8)Z^3$—, —$C(O)N(R^7)Z^1N(R^8)Z^2$—, —$C(O)N(R^7)Q^1Z^1N(R^8)Z^2$—, —$C(O)N(R^7)Z^1Q^{10}Q^2OQ^3$-, or —$C(O)N(R^7)Z^1Q^{10}Q^2OQ^3Z^2$; or $L^1$ is —$C(O)Q^1$-, —$C(O)Q^1Z^1$—, —$C(O)Q^1Q^2$-, —$C(O)Q^1Q^2Z^1$—, —$C(O)Q^1N(R^7)C(O)Z^1$—, —$C(O)Q^1N(R^7)C(O)Z^1Q^2$-, —$C(O)Q^1N(R^7)C(O)Z^1Q^2Q^3$- or —$C(O)Q^1NR(R^7)C(O)Z^1Q^2Z^2$—, wherein $Q^1$ is a heterocyclyl ring linked to the —$C(O)$ moiety via a ring nitrogen atom;
by reaction with an appropriate amine or ammonium salt.

22. A method for the treatment or prophylaxis of respiratory diseases and conditions, skin conditions or ocular conditions, the method comprising administering to a patient in need of such treatment an effective amount of a compound according to claim 1.

23. The method according to claim 22, wherein:
the respiratory diseases and conditions are selected from cystic fibrosis, chronic obstructive pulmonary disease (COPD), chronic bronchitis, emphysema, bronchiectasis, asthma, or primary ciliary dyskinesia;
the skin conditions are selected from psoriasis, atopic dermatitis, or ichthyosis; and
the ocular condition is dry eye disease.

24. A pharmaceutical composition comprising a compound according to claim 1 and a pharmaceutically acceptable excipient.

25. The pharmaceutical composition according to claim 24, wherein the pharmaceutical composition is formulated for nasal, bronchial (inhaled) or buccal administration as a dry powder for inhalation, an aerosol or a spray.

26. The pharmaceutical composition according to claim 24, further including an additional active agent selected from:
a β2 adrenoreceptor agonist;
an antihistamine;
dornase alpha;
a corticosteroid;
a leukotriene antagonist;
a CFTR repair therapy;
a TMEM16A potentiator; or an antibiotic.

27. A product comprising a compound according to claim 1 and an additional agent as a combined preparation for simultaneous, sequential or separate use in the treatment of a respiratory disease or condition, wherein the additional active agent is selected from:
a β2 adrenoreceptor agonist;
an antihistamine;
dornase alpha;
a corticosteroid;
a leukotriene antagonist; or an antibiotic.

28. The pharmaceutical composition according to claim 26, wherein:
the β2 adrenoreceptor agonist is selected from metaproterenol, isoproterenol, isoprenaline, albuterol, salbutamol, formoterol, salmeterol, indacaterol, terbutaline, orciprenaline, bitolterol mesylate or pirbuterol;
the antihistamine is a histamine $H_1$ receptor antagonist selected from loratadine, cetirizine, desloratadine, levocetirizine, fexofenadine, astemizole, azelastine, or chlorpheniramine, or a $H_4$ receptor antagonist;
the corticosteroid is selected from prednisone, prednisolone, flunisolide, triamcinolone acetonide, beclomethasone dipropionate, budesonide, fluticasone propionate mometasone furoate, or fluticasone furoate;
the leukotriene agonist is selected from montelukast or zafirlukast; and
the CFTR repair therapy is selected from ivacaftor, lumacaftor, or tezacaftor.

29. The product according to claim 27, wherein:
the β2 adrenoreceptor agonist is selected from metaproterenol, isoproterenol, isoprenaline, albuterol, salbutamol, formoterol, salmeterol, indacaterol, terbutaline, orciprenaline, bitolterol mesylate, or pirbuterol;
the antihistamine is a histamine $H_1$ receptor antagonist selected from loratadine, cetirizine, desloratadine, levocetirizine, fexofenadine, astemizole, azelastine, or chlorpheniramine; or a $H_4$ receptor antagonist;
the corticosteroid is selected from prednisone, prednisolone, flunisolide, triamcinolone acetonide, beclomethasone dipropionate, budesonide, fluticasone propionate mometasone furoate, or fluticasone furoate; and
the leukotriene agonist is selected from montelukast or zafirlukast.

30. The compound according to claim 1, wherein $X^-$ is selected from chloride, bromide, iodide, sulfate, nitrate, phosphate, formate, acetate, trifluoroacetate, fumarate, citrate, tartrate, oxalate, succinate, mandelate, methane sulfonate, or p-toluene sulfonate.

* * * * *